US010654884B2

(12) United States Patent
Cacatian et al.

(10) Patent No.: US 10,654,884 B2
(45) Date of Patent: May 19, 2020

(54) PURINE DERIVATIVES AS CD73 INHIBITORS FOR THE TREATMENT OF CANCER

(71) Applicant: Vitae Pharmaceuticals, Inc., Fort Washington, PA (US)

(72) Inventors: Salvacion Cacatian, Conshohocken, PA (US); David A. Claremon, Maple Glen, PA (US); Lanqi Jia, Horsham, PA (US); Angel Morales-Ramos, Blue Bell, PA (US); Suresh B. Singh, Kendall Park, NJ (US); Shankar Venkatraman, Lansdale, PA (US); Zhenrong Xu, Chalfont, PA (US); Yajun Zheng, Hockessin, DE (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 466 days.

(21) Appl. No.: 15/306,197

(22) PCT Filed: Apr. 23, 2015

(86) PCT No.: PCT/US2015/027235
§ 371 (c)(1),
(2) Date: Oct. 24, 2016

(87) PCT Pub. No.: WO2015/164573
PCT Pub. Date: Oct. 29, 2015

(65) Prior Publication Data
US 2017/0044203 A1   Feb. 16, 2017

Related U.S. Application Data

(60) Provisional application No. 62/051,529, filed on Sep. 17, 2014, provisional application No. 61/984,659, filed on Apr. 25, 2014.

(51) Int. Cl.
| C07H 19/16 | (2006.01) |
| C07H 19/06 | (2006.01) |
| C07D 473/36 | (2006.01) |
| C07D 473/40 | (2006.01) |
| C07D 405/04 | (2006.01) |
| C07D 473/34 | (2006.01) |
| A61K 31/517 | (2006.01) |
| A61K 31/675 | (2006.01) |
| A61K 31/7056 | (2006.01) |
| A61K 31/7072 | (2006.01) |
| A61K 31/7076 | (2006.01) |
| A61K 45/06 | (2006.01) |
| C07D 239/72 | (2006.01) |
| C07F 9/6512 | (2006.01) |
| C07F 9/6561 | (2006.01) |
| C07H 19/052 | (2006.01) |

(52) U.S. Cl.
CPC ............ *C07H 19/16* (2013.01); *A61K 31/517* (2013.01); *A61K 31/675* (2013.01); *A61K 31/7056* (2013.01); *A61K 31/7072* (2013.01); *A61K 31/7076* (2013.01); *A61K 45/06* (2013.01); *C07D 239/72* (2013.01); *C07D 405/04* (2013.01); *C07D 473/34* (2013.01); *C07D 473/36* (2013.01); *C07D 473/40* (2013.01); *C07F 9/65128* (2013.01); *C07F 9/65616* (2013.01); *C07H 19/052* (2013.01); *C07H 19/06* (2013.01)

(58) Field of Classification Search
CPC .. C07D 405/04; C07D 473/34; C07D 473/36; C07D 473/40; C07D 239/72; C07H 19/06; C07H 19/16; C07H 19/052; C07F 9/65128; C07F 9/65616; A61K 45/06; A61K 31/7076; A61K 31/7056; A61K 31/675; A61K 31/517; A61K 31/7072
See application file for complete search history.

(56) References Cited

U.S. PATENT DOCUMENTS

| 7,247,621 | B2 | 7/2007 | Zhi |
| 7,653,495 | B1 | 1/2010 | Murali |
| 8,019,557 | B2 | 9/2011 | Murali |
| 8,785,419 | B2 | 7/2014 | Murali |
| 8,956,824 | B2 | 2/2015 | Mui et al. |
| 2004/0023921 | A1 | 2/2004 | Zhi et al. |
| 2009/0156545 | A1* | 6/2009 | Hostetler ............ C07F 9/65586 514/47 |
| 2013/0052160 | A1 | 2/2013 | Zitvogel et al. |

(Continued)

FOREIGN PATENT DOCUMENTS

| WO | WO 2003/074083 | 9/2003 |
| WO | WO 2007/135195 | 11/2007 |

(Continued)

OTHER PUBLICATIONS

Debarge, Sebastien et al. "Design and Synthesis of a-Carboxy Phosphononucleosides" (2010) Americal Chemical Society, J. Org. Chem (2011) 76, 105-126.
Hladezuk, Isabelle et al. "Development of O—H insertion for the attachment of phosphonates to nucleosides; synthesis of a-carboxy phosphononucleosides" (2012) Tetrahedron 68, 1894-1909.
Hu, Xiao et al. "Novel synthetic RORy agonist compounds as a potential anti-tumor therapeutic approach" Society for Immunotherapy of Cancer, 29th Annual Meeting, Nov. 6-9, 2014, poster presentation, 1 pg.
Hu, Xiao et al. "Novel, Synthetic RORy Agonist Compounds as a Potential Anti-Cancer Approach" Society of Immunotherapy of Cancer, Annual Meeting, Nov. 6-9, 2014, poster/abstract, <https://lycera.com/publications> 1 pg.

(Continued)

*Primary Examiner* — Lawrence E Crane
(74) *Attorney, Agent, or Firm* — Atabak R. Royaee

(57) ABSTRACT

Provided are novel purine nucleoside/nucleotide analogues compounds, pharmaceutically acceptable salts thereof, and pharmaceutical compositions thereof, which are inhibitors of CD73 and are useful in the treatment of cancer.

14 Claims, No Drawings

(56) References Cited

U.S. PATENT DOCUMENTS

2013/0156790 A1    6/2013    Zitvogel

FOREIGN PATENT DOCUMENTS

| WO | WO 2012/031320 | 3/2012 |
|---|---|---|
| WO | WO 2014/153424 | 9/2014 |

OTHER PUBLICATIONS

STN Colombus—Registry Copyright Jun. 6, 2014 ACS on STN. 33 pgs.

Allard et al., "CD73-Generated Adenosine: Orchestrating the Tumor-Stroma Interplay to Promote Cancer Growth," *J Biomed Biotechnol.*, 2012:485156, Epub Oct. 16, 2012, 8 pages.

Allard et al., "Targeting CD73 and downstream adenosine receptor signaling in triple-negative breast cancer," *Expert Opin Ther Targets.*, 18(8):863-881, Epub May 6, 2014.

Antonioli et al.. "CD39 and CD73 in immunity and inflammation," Trends Mol Med., 19(6):355-367, Jun. 2013.

Antonioli et al., "Immunity, inflammation and cancer: a leading role for adenosine," *Nat Rev Cancer.*, 13(12):842-857 Dec. 2013.

Berge et al., "Pharmaceutical salts," *J Pharm Sci.*, 66(1):1-19, Jan. 1977.

Chatterjee et al., "Natural killer cells acquire CD73 expression upon exposure to mesenchymal stem cells," *Blood* 123(4):594-595, Jan. 23, 2014.

Cristalli et al., "Adenosine and 2-Chloroadenosine Deaza-Analogues as Adenosine Receptor Agonists1," *Nucleosides & Nucleotides*, 4( 5), 625-639, Epub Jan. 3, 2007.

Debarge et al., "Design and Synthesis of α-Carboxy Phosphononucleosides," *J. Org. Chem.*, 76(1):105-126, 2011.

Deghati et al., "Inhibition of nucloside transport By New analogues of nitrobenzylthioinosine," *Bioorganic & Medicinal Chemistry*, 11(6), 899-908, Mar. 2003.

Hladezuk et al., "Development of O-H insertion for the attachment of phosphonates to nucleosides; synthesis of a-carboxy phosphononucleosides," *Tetrahedrom.*, 68:1894-1909, Jan. 3, 2012.

Iqbal et al., "Identification of sulfonic acids as efficient ecto-50-nucleotidase inhibitors," *European J Med Chem.*, 70:685-697, Epub Oct. 28, 2013.

Jin et al., "CD73 on Tumor Cells Impairs Antitumor T-Cell Responses: A Novel Mechanism of Tumor-Induced Immune Suppression," *Cancer Res.*, 70:2245-2255, Epub Feb. 23, 2010.

New Syntheses of Diazo Compounds, Gerhard Maas, Angew. Chem. Int. Ed., 2009, 48, 8186.

Regateiro et al., "CD73 and adenosine generation in the creation of regulatory microenvironments," *Clin Exp Immunol.*, 171:1-7, 2012.

Remington's Pharmaceutical Science, 17th Ed., (Mack Publising Company, Easton, 1985), p. 1418.

Rockenbach et al., "NTPDase3 and ecto-5'-nucleotidase/CD73 are differentially expressed during mouse bladder cancer progression," *Purinergic Signal.*, 10(3):421-430, Epub Jan. 26, 2014.

Sorrentino et al., "The adenosinergic system in cancer: Key therapeutic target," *OncoImmunology.*, 2:1, e22448-1 and e22448-2, Jan. 2013.

Wang et al., "CD73 has distinct roles in nonhematopoietic and hematopoietic cells to promote tumor growth in mice," *J Clin Invest.*, 121(6):2371-2382, Jun. 2011.

Zhang, B., "CD73 promotes tumor growth and metastasis," *OncoImmunology.*, 1(1):67-70, Jan./Feb. 2012.

Zhang. B., "CD73: A Novel Target for Cancer Immunotherapy," *Cancer Res.* 70:6407-6411, Epub Aug. 3, 2010.

Zhang, B., "Opportunities and challenges for anti-CD73 cancer therapy," *Immunotherapy.*, 4(9):861-865, 2012.

International Preliminary Report on Patentability for International Application No. PCT/US2015/027235, dated Nov. 3, 2016, 9 pages.

International Search report and Written Opinion for International Application No. PCT/US2015/027235, dated Jul. 27, 2015, 13 pages.

Bean, Heather D. et al. "Glyoxylate as a Backbone Linkage for a Prebiotic Ancestor of RNA" (2006) Origins of Life and Evolution of Biospheres, vol. 36, 39-63.

Haselhorst, Thomas et al. "A 1H STD NMR spectroscopic investigation of sialylnucleoside mimetics as probes of CMP-Kdn synthetase" (2006) Glycoconj J, 23: 371-375.

\* cited by examiner

PURINE DERIVATIVES AS CD73 INHIBITORS FOR THE TREATMENT OF CANCER

CROSS-REFERENCE TO RELATED APPLICATIONS

This application is a 371 of PCT/US2015/027235 filed on Apr. 23, 2015, which claims the priority benefit of U.S. Provisional Application No. 62/051,529, filed on Sep. 17, 2014, and U.S. Provisional Application No. 61/984,659, filed on Apr. 25, 2014, the entire content of each of which is incorporated herein by reference.

TECHNICAL FIELD OF THE INVENTION

The present invention is directed to novel inhibitors of CD73, processes for their preparation, pharmaceutical compositions containing these inhibitors, and their use in the treatment of cancer and other diseases mediated by CD73.

BACKGROUND OF THE INVENTION

CD73 or ecto-5'-nucleotidase (5'-NT) is expressed in a number of tissues, is anchored to the cell membrane through a glycosylphosphatidylinositol (GPI) linkage, has ecto-enzyme activity and plays a role in signal transduction. The primary function of CD73 is to convert extracellular nucleotides (e.g., 5-AMP) to their corresponding nucleosides (e.g., adenosine). CD73 produces nucleosides, particularly adenosine, in the extracellular space, and is thought to modulate neuronal signaling, vascular perfusion, drug metabolism and immune responses, as well as to have anti-inflammatory and immunosuppressive capabilities.

Adenosine is an endogenous modulator of diverse physiological functions, including the cardiovascular system (as a vasodilator and cardiac depressor), the central nervous system (CNS) (inducing sedative, anxiolytic and antiepileptic effects), the respiratory system (inducing bronchoconstriction), the kidney (having biphasic action; inducing vasoconstriction at low concentrations and vasodilation at high doses), fat cells (inhibiting lipolysis), platelets (as an anti-aggregant), and the immune system, where extracellular adenosine acts on a variety of immune cells and mediates anti-inflammatory effects. Adenosine also promotes fibrosis (excess matrix production) in a variety of tissues.

CD73 is highly expressed on the surface of several types of cancer cells and immunosuppressive cells, including T regulator cells (Tregs) and myeloid-derived suppressor cells (MDSCs). ATP, released in high quantity from malignant cells succumbing to chemotherapy or other stressful conditions, is rapidly converted into adenosine, which accumulates in the tumor microenvironment. By activating adenosine receptors, intratumoral adenosine favors the escape of cancer cells from immune surveillance, hence promoting tumor progression. Targeting CD73 represents a potential strategy to increase the efficacy of anticancer therapy and offers new therapeutic strategies to limit tumor progression and treat a variety of cancers. Higher expression levels of CD73 are associated with tumor neovascularization, invasiveness, resistance to chemotherapy, and metastasis, and with shorter patient survival time in cancer, including breast cancer. CD73 inhibitors can be used to control tumor progression and metastasis.

Because inhibition of CD73 results in decreased adenosine, CD73 inhibitors can be used for the treatment of diseases or disorders mediated by adenosine and its actions on adenosine receptors, including $A_1$, $A_{2A}$, $A_{2B}$ and $A_3$. Thus, CD73 inhibitors can be used for enhancing immune responses, enhancing immunization, and increasing inflammation, as well as for treating a wide range of conditions, including neurological, neurodegenerative and CNS disorders and diseases, including depression and Parkinson's disease, cerebral and cardiac ischaemic diseases, sleep disorders, fibrosis, immune and inflammatory disorders, and cancer.

For reviews on the role of adenosine and CD73 in immunity, inflammation and cancer, see Antonioli, et al., 2013, Nature Rev., 13:842-857; Regateiro et al., 2012, Clin. Exp. Immunol., 171:1-7; Sorrentino et al., 2013, OncoImmunol., 2:e22448, doi:10.4161/onci.22448; and Allard et al., 2012, J. Biomed. Biotechnol., article ID 485156, 8 pages, doi:10.1155/2012/485156.

In light of the role that CD73 plays in disease pathogenesis, there is a need for new inhibitors of CD73 for the treatment of diseases including cancer.

SUMMARY OF THE INVENTION

The compounds described herein, and pharmaceutically acceptable compositions thereof, are effective inhibitors of CD73 which are useful for treating a variety of cancers and other diseases as further described herein.

Provided herein are CD73-inhibiting compounds of Formula I:

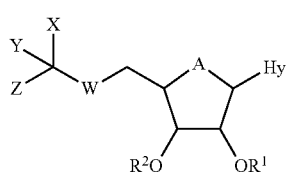

or pharmaceutically acceptable salts thereof, wherein the constituent variables are defined hereinbelow.

Further provided herein is a pharmaceutical composition comprising a compound of Formula I, or a pharmaceutically acceptable salt thereof, and at least one pharmaceutically acceptable carrier.

Further provided herein is a method of inhibiting CD73 comprising contacting CD73 with a compound of the invention, or a pharmaceutically acceptable salt thereof.

Further provided herein is a method of treating a disease such as cancer comprising administering to a patient a therapeutically effective amount of a compound of the invention, or a pharmaceutically acceptable salt thereof.

DETAILED DESCRIPTION

Compounds of the Invention

The present invention provides a compound of Formula I:

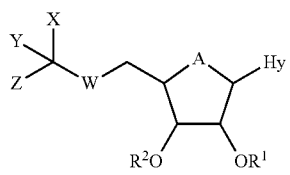

or a pharmaceutically acceptable salt thereof, wherein:

Hy is a monocyclic or bicyclic heterocycle of formula (i), (ii), (iii), (iv), or (v):

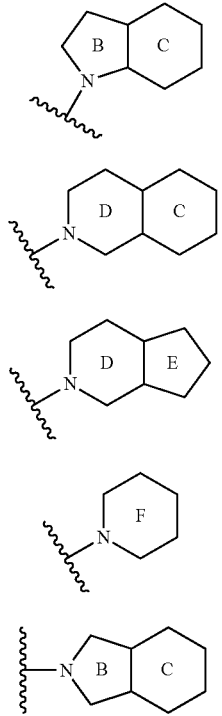

Ring B is a 5-membered heterocycloalkyl ring or a 5-membered heteroaryl ring, each optionally substituted by 1 or 2 substituents independently selected from oxo, $R^{N1}$, $R^{N2}$, $R^a$, $R^b$, $R^c$, $R^d$, $R^e$, and $R^z$;

Ring C is a 6-membered aryl ring, a 6-membered heteroaryl ring, a 6-membered cycloalkyl ring, or a 6-membered heterocycloalkyl ring, each optionally substituted by 1, 2, 3, or 4 substituents independently selected from oxo, $R^{N1}$, $R^{N2}$, $R^a$, $R^b$, $R^c$, $R^d$, $R^e$, and $R^z$;

Ring D is a 6-membered heterocycloalkyl ring optionally substituted by 1, 2, 3, or 4 substituents independently selected from oxo, $R^{N1}$, $R^{N2}$, $R^a$, $R^b$, $R^c$, $R^d$, $R^e$, and $R^z$;

Ring E is a 5-membered cycloalkyl ring, a 5-membered heterocycloalkyl ring, or a 5-membered heteroaryl ring, each optionally substituted by 1, 2, or 3 substituents independently selected from oxo, $R^{N1}$, $R^{N2}$, $R^a$, $R^b$, $R^c$, $R^d$, $R^e$, and $R^z$;

Ring F is a 6-membered heterocycloalkyl ring optionally substituted by 1, 2, 3, 4, or 5 substituents independently selected from oxo, $R^{N1}$, $R^{N2}$, $R^a$, $R^b$, $R^c$, $R^d$, $R^e$, and $R^z$;

A is O, S, $NR^f$, or $CH_2$;

W is O or S;

X is $C_{1-4}$ haloalkyl, —C(O)OR$^3$, —C(O)NR$^4$R$^5$, —CH$_2$OR$^3$, —S(O)$_2$R$^6$, —P(O)(OR$^7$)(OR$^8$), or a 5-6 membered heteroaryl group optionally substituted with 1, 2, or 3 substituents independently selected from halo, CN, OH, $C_{1-4}$ alkyl, $C_{1-4}$ alkoxy, $NH_2$, NH($C_{1-4}$ alkyl), N($C_{1-4}$ alkyl)$_2$, C(O)($C_{1-4}$ alkyl), C(O)NH$_2$, C(O)NH($C_{1-4}$ alkyl), C(O)N($C_{1-4}$ alkyl)$_2$, C(O)OH, and C(O)O($C_{1-4}$ alkyl);

Y is H, $Cy^1$, $C_{1-4}$ alkyl, or —C(O)OR$^9$, wherein said $C_{1-4}$ alkyl is optionally substituted by 1, 2, or 3 substituents independently selected from $Cy^1$, halo, $C_{1-4}$ haloalkyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$ R$^{b1}$, and S(O)$_2$NR$^{c1}$R$^{d1}$;

Z is —C(O)OR$^{10}$ or —P(O)(OR$^{11}$)(OR$^{12}$);

R$^1$ and R$^2$ are each independently selected from H, $C_{1-4}$ alkyl, —C(O)OR$^{13a}$, and —C(O)R$^{13b}$;

R$^3$ is H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl are each optionally substituted with 1, 2, 3, or 4 substituents independently selected from halo, $C_{1-4}$ alkyl, $C_{1-4}$ haloalkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$ R$^{b2}$, and S(O)$_2$NR$^{c2}$R$^{d2}$;

R$^4$ and R$^5$ are each independently selected from H, —NR$^A$R$^B$, —OR$^C$, $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl are each optionally substituted with 1, 2, 3, or 4 substituents independently selected from halo, $C_{1-4}$ alkyl, $C_{1-4}$ haloalkyl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$ R$^{b3}$, and S(O)$_2$NR$^{c3}$R$^{d3}$;

R$^6$ is $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl;

R$^7$ and R$^8$ are each independently selected from H and $C_{1-6}$ alkyl optionally substituted by 1, 2, or 3 substituents independently selected from halo, CN, OR$^{a4}$, SR$^{a4}$, C(O) R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O) NR$^{c4}$R$^{d4}$, NR$^{c4}$S(O)R$^{b4}$, NR$^{c4}$S(O)$_2$R$^{b4}$, NR$^{c4}$S(O)$_2$ NR$^{c4}$R$^{d4}$, S(O)R$^{b4}$, S(O)NR$^{c4}$R$^{d4}$, S(O)$_2$R$^{b4}$, and S(O)$_2$ NR$^{c4}$R$^{d4}$;

R$^9$ is H or $C_{1-4}$ alkyl;

R$^{10}$ is H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl are each optionally substituted with 1, 2, 3, or 4 substituents independently selected from halo, $C_{1-4}$ alkyl, $C_{1-4}$ haloalkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$;

$R^{11}$ and $R^{12}$ are each independently selected from H and $C_{1-6}$ alkyl optionally substituted by 1, 2, or 3 substituents independently selected from halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, and $S(O)_2NR^{c6}R^{d6}$;

each $R^{13a}$ is independently selected from H, $C_{1-4}$ alkyl, and phenyl;

each $R^{13b}$ is independently selected from H, $C_{1-4}$ alkyl, and phenyl;

$R^A$ is H or $C_{1-6}$ alkyl;

$R^B$ is $C_{1-6}$ alkyl or —$C(O)(C_{1-6}$ alkyl);

$R^C$ is H or $C_{1-6}$ alkyl;

$R^{N1}$ is $C_{1-6}$ alkyl, $C_{6-10}$ aryl, or 5-10 heteroaryl;

$R^{N2}$ is H, $C_{1-6}$ alkyl, $C_{6-10}$ aryl, or 5-10 heteroaryl;

$R^a$, $R^b$, $R^c$, and $R^d$ are each independently selected from $Cy^2$, H, halo, $C_{1-4}$ alkyl, $C_{1-4}$ haloalkyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)OR^{a7}$, $NR^{c7}C(O)NR^{c7}R^{d7}$, $NR^{c7}S(O)R^{b7}$, $NR^{c7}S(O)_2R^{b7}$, $NR^{c7}S(O)_2NR^{c7}R^{d7}$, $S(O)R^{b7}$, $S(O)NR^{c7}R^{d7}$, $S(O)_2R^{b7}$, and $S(O)_2NR^{c7}R^{d7}$, wherein said $C_{1-4}$ alkyl is optionally substituted by 1, 2, or 3 substituents independently selected from $Cy^2$, H, halo, $C_{1-4}$ haloalkyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)OR^{a7}$, $NR^{c7}C(O)NR^{c7}R^{d7}$, $NR^{c7}S(O)R^{b7}$, $NR^{c7}S(O)_2R^{b7}$, $NR^{c7}S(O)_2NR^{c7}R^{d7}$, $S(O)R^{b7}$, $S(O)NR^{c7}R^{d7}$, $S(O)_2R^{b7}$, and $S(O)_2NR^{c7}R^{d7}$;

$R^e$ and $R^z$ are each independently selected from H, halo, and $C_{1-4}$ alkyl;

$R^f$ is H, $C_{1-4}$ alkyl, or —$C(O)(C_{1-4}$ alkyl);

each $Cy^1$ and $Cy^2$ are independently selected from $C_{6-10}$ aryl, $C_{3-10}$ cycloalkyl, 5-10 membered heteroaryl, or 4-10 membered heterocycloalkyl, each of which is substituted with 1, 2, 3, or 4 substituents independently selected from halo, $C_{1-4}$ alkyl, $C_{1-4}$ haloalkyl, $C_{1-4}$ cyanoalkyl, CN, $NO_2$, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)OR^{a8}$, $NR^{c8}C(O)NR^{c8}R^{d8}$, $NR^{c8}S(O)R^{b8}$, $NR^{c8}S(O)_2R^{b8}$, $NR^{c8}S(O)_2NR^{c8}R^{d8}$, $S(O)R^{b8}$, $S(O)NR^{c8}R^{d8}$, $S(O)_2R^{b8}$, and $S(O)_2NR^{c8}R^{d8}$;

each $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, $R^{d4}$, $R^{a5}$, $R^{b5}$, $R^{c5}$, $R^{d5}$, $R^{a6}$, $R^{b6}$, $R^{c6}$, $R^{d6}$, $R^{a7}$, $R^{b7}$, $R^{c7}$, $R^{d7}$, $R^{a8}$, $R^{b8}$, $R^{c8}$, and $R^{d8}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- is optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a9}$, $SR^{a9}$, $C(O)R^{b9}$, $C(O)NR^{c9}R^{d9}$, $C(O)OR^{a9}$, $OC(O)R^{b9}$, $OC(O)NR^{c9}R^{d9}$, $NR^{c9}R^{d9}$, $NR^{c9}C(O)R^{b9}$, $NR^{c9}C(O)NR^{c9}R^{d9}$, $NR^{c9}C(O)OR^{a9}$, $S(O)R^{b9}$, $S(O)NR^{c9}R^{d9}$, $S(O)_2R^{b9}$, $NR^{c9}S(O)_2R^{b9}$, $NR^{c9}S(O)_2NR^{c9}R^{d9}$, and $S(O)_2NR^{c9}R^{d9}$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a9}$, $SR^{a9}$, $C(O)R^{b9}$, $C(O)NR^{c9}R^{d9}$, $C(O)OR^{a9}$, $OC(O)R^{b9}$, $OC(O)NR^{c9}R^{d9}$, $NR^{c9}R^{d9}$, $NR^{c9}C(O)R^{b9}$, $NR^{c9}C(O)NR^{c9}R^{d9}$, $NR^{c9}C(O)OR^{a9}$, $S(O)R^{b9}$, $S(O)NR^{c9}R^{d9}$, $S(O)_2R^{b9}$, $NR^{c9}S(O)_2R^{b9}$, $NR^{c9}S(O)_2NR^{c9}R^{d9}$, and $S(O)_2NR^{c9}R^{d9}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, $C_{1-4}$ alkyl, $C_{1-4}$ haloalkyl, $C_{1-4}$ cyanoalkyl, CN, $OR^{a9}$, $SR^{a9}$, $C(O)R^{b9}$, $C(O)NR^{c9}R^{d9}$, $C(O)OR^{a9}$, $OC(O)R^{b9}$, $OC(O)NR^{c9}R^{d9}$, $NR^{c9}R^{d9}$, $NR^{c9}C(O)R^{b9}$, $NR^{c9}C(O)NR^{c9}R^{d9}$, $NR^{c9}C(O)OR^{a9}$, $S(O)R^{b9}$, $S(O)NR^{c9}R^{d9}$, $S(O)_2R^{b9}$, $NR^{c9}S(O)_2R^{b9}$, $NR^{c9}S(O)_2NR^{c9}R^{d9}$, and $S(O)_2NR^{c9}R^{d9}$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a9}$, $SR^{a9}$, $C(O)R^{b9}$, $C(O)NR^{c9}R^{d9}$, $C(O)OR^{a9}$, $OC(O)R^{b9}$, $OC(O)NR^{c9}R^{d9}$, $NR^{c9}R^{d9}$, $NR^{c9}C(O)R^{b9}$, $NR^{c9}C(O)NR^{c9}R^{d9}$, $NR^{c9}C(O)OR^{a9}$, $S(O)R^{b9}$, $S(O)NR^{c9}R^{d9}$, $S(O)_2R^{b9}$, $NR^{c9}S(O)_2R^{b9}$, $NR^{c9}S(O)_2NR^{c9}R^{d9}$, and $S(O)_2NR^{c9}R^{d9}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, $C_{1-4}$ alkyl, $C_{1-4}$ haloalkyl, $C_{1-4}$ cyanoalkyl, CN, $OR^{a9}$, $SR^{a9}$, $C(O)R^{b9}$, $C(O)NR^{c9}R^{d9}$, $C(O)OR^{a9}$, $OC(O)R^{b9}$, $OC(O)NR^{c9}R^{d9}$, $NR^{c9}R^{d9}$, $NR^{c9}C(O)R^{b9}$, $NR^{c9}C(O)NR^{c9}R^{d9}$, $NR^{c9}C(O)OR^{a9}$, $S(O)R^{b9}$, $S(O)NR^{c9}R^{d9}$, $S(O)_2R^{b9}$, $NR^{c9}S(O)_2R^{b9}$, $NR^{c9}S(O)_2NR^{c9}R^{d9}$, and $S(O)_2NR^{c9}R^{d9}$;

or any $R^{c3}$ and $R^{d3}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a9}$, $SR^{a9}$, $C(O)R^{b9}$, $C(O)NR^{c9}R^{d9}$, $C(O)OR^{a9}$, $OC(O)R^{b9}$, $OC(O)NR^{c9}R^{d9}$, $NR^{c9}R^{d9}$, $NR^{c9}C(O)R^{b9}$, $NR^{c9}C(O)NR^{c9}R^{d9}$, $NR^{c9}C(O)OR^{a9}$, $S(O)R^{b9}$, $S(O)NR^{c9}R^{d9}$, $S(O)_2R^{b9}$, $NR^{c9}S(O)_2R^{b9}$, $NR^{c9}S(O)_2NR^{c9}R^{d9}$, and $S(O)_2NR^{c9}R^{d9}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, $C_{1-4}$ alkyl, $C_{1-4}$ haloalkyl, $C_{1-4}$ cyanoalkyl, CN, $OR^{a9}$, $SR^{a9}$, $C(O)R^{b9}$, $C(O)NR^{c9}R^{d9}$, $C(O)OR^{a9}$, $OC(O)R^{b9}$, $OC(O)NR^{c9}R^{d9}$, $NR^{c9}R^{d9}$, $NR^{c9}C(O)R^{b9}$, $NR^{c9}C(O)NR^{c9}R^{d9}$, $NR^{c9}C(O)OR^{a9}$, $S(O)R^{b9}$, $S(O)NR^{c9}R^{d9}$, $S(O)_2R^{b9}$, $NR^{c9}S(O)_2R^{b9}$, $NR^{c9}S(O)_2NR^{c9}R^{d9}$, and $S(O)_2NR^{c9}R^{d9}$;

or any $R^{c4}$ and $R^{d4}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a9}$, $SR^{a9}$, C(O)R$^{b9}$, C(O)NR$^{c9}$R$^{d9}$, C(O)OR$^{a9}$, OC(O)R$^{b9}$, OC(O)NR$^{c9}$R$^{d9}$, NR$^{c9}$R$^{d9}$, NR$^{c9}$C(O)R$^{b9}$, NR$^{c9}$C(O)NR$^{c9}$R$^{d9}$, NR$^{c9}$C(O)OR$^{a9}$, S(O)R$^{b9}$, S(O)NR$^{c9}$R$^{d9}$, S(O)$_2$R$^{b9}$, NR$^{c9}$S(O)$_2$R$^{b9}$, NR$^{c9}$S(O)$_2$NR$^{c9}$R$^{d9}$, and S(O)$_2$NR$^{c9}$R$^{d9}$, wherein said C$_{1-6}$ alkyl, C$_{3-7}$ cycloalkyl, 4-7 membered heterocycloalkyl, C$_{6-10}$ aryl, and 5-6 membered heteroaryl are optionally substituted by 1, 2, or 3 substituents independently selected from halo, C$_{1-4}$ alkyl, C$_{1-4}$ haloalkyl, C$_{1-4}$ cyanoalkyl, CN, OR$^{a9}$, SR$^{a9}$, C(O)R$^{b9}$, C(O)NR$^{c9}$R$^{d9}$, C(O)OR$^{a9}$, OC(O)R$^{b9}$, OC(O)NR$^{c9}$R$^{d9}$, NR$^{c9}$R$^{d9}$, NR$^{c9}$C(O)R$^{b9}$, NR$^{c9}$C(O)NR$^{c9}$R$^{d9}$, NR$^{c9}$C(O)OR$^{a9}$, S(O)R$^{b9}$, S(O)NR$^{c9}$R$^{d9}$, S(O)$_2$R$^{b9}$, NR$^{c9}$S(O)$_2$R$^{b9}$, NR$^{c9}$S(O)$_2$NR$^{c9}$R$^{d9}$, and S(O)$_2$NR$^{c9}$R$^{d9}$;

or any R$^{c5}$ and R$^{d5}$ together with the N atom to which they are attached form a 4-, 5-, 6-, or 7-membered heterocycloalkyl group optionally substituted with 1, 2, or 3 substituents independently selected from C$_{1-6}$ alkyl, C$_{3-7}$ cycloalkyl, 4-7 membered heterocycloalkyl, C$_{6-10}$ aryl, 5-6 membered heteroaryl, C$_{1-6}$ haloalkyl, halo, CN, OR$^{a9}$, SR$^{a9}$, C(O)R$^{b9}$, C(O)NR$^{c9}$R$^{d9}$, C(O)OR$^{a9}$, OC(O)R$^{b9}$, OC(O)NR$^{c9}$R$^{d9}$, NR$^{c9}$R$^{d9}$, NR$^{c9}$C(O)R$^{b9}$, NR$^{c9}$C(O)NR$^{c9}$R$^{d9}$, NR$^{c9}$C(O)OR$^{a9}$, S(O)R$^{b9}$, S(O)NR$^{c9}$R$^{d9}$, S(O)$_2$R$^{b9}$, NR$^{c9}$S(O)$_2$R$^{b9}$, NR$^{c9}$S(O)$_2$NR$^{c9}$R$^{d9}$, and S(O)$_2$NR$^{c9}$R$^{d9}$, wherein said C$_{1-6}$ alkyl, C$_{3-7}$ cycloalkyl, 4-7 membered heterocycloalkyl, C$_{6-10}$ aryl, and 5-6 membered heteroaryl are optionally substituted by 1, 2, or 3 substituents independently selected from halo, C$_{1-4}$ alkyl, C$_{1-4}$ haloalkyl, C$_{1-4}$ cyanoalkyl, CN, OR$^{a9}$, SR$^{a9}$, C(O)R$^{b9}$, C(O)NR$^{c9}$R$^{d9}$, C(O)OR$^{a9}$, OC(O)R$^{b9}$, OC(O)NR$^{c9}$R$^{d9}$, NR$^{c9}$R$^{d9}$, NR$^{c9}$C(O)R$^{b9}$, NR$^{c9}$C(O)NR$^{c9}$R$^{d9}$, NR$^{c9}$C(O)OR$^{a9}$, S(O)R$^{b9}$, S(O)NR$^{c9}$R$^{d9}$, S(O)$_2$R$^{b9}$, NR$^{c9}$S(O)$_2$R$^{b9}$, NR$^{c9}$S(O)$_2$NR$^{c9}$R$^{d9}$, and S(O)$_2$NR$^{c9}$R$^{d9}$;

or any R$^{c6}$ and R$^{d6}$ together with the N atom to which they are attached form a 4-, 5-, 6-, or 7-membered heterocycloalkyl group optionally substituted with 1, 2, or 3 substituents independently selected from C$_{1-6}$ alkyl, C$_{3-7}$ cycloalkyl, 4-7 membered heterocycloalkyl, C$_{6-10}$ aryl, 5-6 membered heteroaryl, C$_{1-6}$ haloalkyl, halo, CN, OR$^{a9}$, SR$^{a9}$, C(O)R$^{b9}$, C(O)NR$^{c9}$R$^{d9}$, C(O)OR$^{a9}$, OC(O)R$^{b9}$, OC(O)NR$^{c9}$R$^{d9}$, NR$^{c9}$R$^{d9}$, NR$^{c9}$C(O)R$^{b9}$, NR$^{c9}$C(O)NR$^{c9}$R$^{d9}$, NR$^{c9}$C(O)OR$^{a9}$, S(O)R$^{b9}$, S(O)NR$^{c9}$R$^{d9}$, S(O)$_2$R$^{b9}$, NR$^{c9}$S(O)$_2$R$^{b9}$, NR$^{c9}$S(O)$_2$NR$^{c9}$R$^{d9}$, and S(O)$_2$NR$^{c9}$R$^{d9}$, wherein said C$_{1-6}$ alkyl, C$_{3-7}$ cycloalkyl, 4-7 membered heterocycloalkyl, C$_{6-10}$ aryl, and 5-6 membered heteroaryl are optionally substituted by 1, 2, or 3 substituents independently selected from halo, C$_{1-4}$ alkyl, C$_{1-4}$ haloalkyl, C$_{1-4}$ cyanoalkyl, CN, OR$^{a9}$, SR$^{a9}$, C(O)R$^{b9}$, C(O)NR$^{c9}$R$^{d9}$, C(O)OR$^{a9}$, OC(O)R$^{b9}$, OC(O)NR$^{c9}$R$^{d9}$, NR$^{c9}$R$^{d9}$, NR$^{c9}$C(O)R$^{b9}$, NR$^{c9}$C(O)NR$^{c9}$R$^{d9}$, NR$^{c9}$C(O)OR$^{a9}$, S(O)R$^{b9}$, S(O)NR$^{c9}$R$^{d9}$, S(O)$_2$R$^{b9}$, NR$^{c9}$S(O)$_2$R$^{b9}$, NR$^{c9}$S(O)$_2$NR$^{c9}$R$^{d9}$, and S(O)$_2$NR$^{c9}$R$^{d9}$;

or any R$^{c7}$ and R$^{d7}$ together with the N atom to which they are attached form a 4-, 5-, 6-, or 7-membered heterocycloalkyl group optionally substituted with 1, 2, or 3 substituents independently selected from C$_{1-6}$ alkyl, C$_{3-7}$ cycloalkyl, 4-7 membered heterocycloalkyl, C$_{6-10}$ aryl, 5-6 membered heteroaryl, C$_{1-6}$ haloalkyl, halo, CN, OR$^{a9}$, SR$^{a9}$, C(O)R$^{b9}$, C(O)NR$^{c9}$R$^{d9}$, C(O)OR$^{a9}$, OC(O)R$^{b9}$, OC(O)NR$^{c9}$R$^{d9}$, NR$^{c9}$R$^{d9}$, NR$^{c9}$C(O)R$^{b9}$, NR$^{c9}$C(O)NR$^{c9}$R$^{d9}$, NR$^{c9}$C(O)OR$^{a9}$, S(O)R$^{b9}$, S(O)NR$^{c9}$R$^{d9}$, S(O)$_2$R$^{b9}$, NR$^{c9}$S(O)$_2$R$^{b9}$, NR$^{c9}$S(O)$_2$NR$^{c9}$R$^{d9}$, and S(O)$_2$NR$^{c9}$R$^{d9}$, wherein said C$_{1-6}$ alkyl, C$_{3-7}$ cycloalkyl, 4-7 membered heterocycloalkyl, C$_{6-10}$ aryl, and 5-6 membered heteroaryl are optionally substituted by 1, 2, or 3 substituents independently selected from halo, C$_{1-4}$ alkyl, C$_{1-4}$ haloalkyl, C$_{1-4}$ cyanoalkyl, CN, OR$^{a9}$, SR$^{a9}$, C(O)R$^{b9}$, C(O)NR$^{c9}$R$^{d9}$, C(O)OR$^{a9}$, OC(O)R$^{b9}$, OC(O)NR$^{c9}$R$^{d9}$, NR$^{c9}$R$^{d9}$, NR$^{c9}$C(O)R$^{b9}$, NR$^{c9}$C(O)NR$^{c9}$R$^{d9}$, NR$^{c9}$C(O)OR$^{a9}$, S(O)R$^{b9}$, S(O)NR$^{c9}$R$^{d9}$, S(O)$_2$R$^{b9}$, NR$^{c9}$S(O)$_2$R$^{b9}$, NR$^{c9}$S(O)$_2$NR$^{c9}$R$^{d9}$, and S(O)$_2$NR$^{c9}$R$^{d9}$;

or any R$^{c8}$ and R$^{d8}$ together with the N atom to which they are attached form a 4-, 5-, 6-, or 7-membered heterocycloalkyl group optionally substituted with 1, 2, or 3 substituents independently selected from C$_{1-6}$ alkyl, C$_{3-7}$ cycloalkyl, 4-7 membered heterocycloalkyl, C$_{6-10}$ aryl, 5-6 membered heteroaryl, C$_{1-6}$ haloalkyl, halo, CN, OR$^{a9}$, SR$^{a9}$, C(O)R$^{b9}$, C(O)NR$^{c9}$R$^{d9}$, C(O)OR$^{a9}$, OC(O)R$^{b9}$, OC(O)NR$^{c9}$R$^{d9}$, NR$^{c9}$R$^{d9}$, NR$^{c9}$C(O)R$^{b9}$, NR$^{c9}$C(O)NR$^{c9}$R$^{d9}$, NR$^{c9}$C(O)OR$^{a9}$, S(O)R$^{b9}$, S(O)NR$^{c9}$R$^{d9}$, S(O)$_2$R$^{b9}$, NR$^{c9}$S(O)$_2$R$^{b9}$, NR$^{c9}$S(O)$_2$NR$^{c9}$R$^{d9}$, and S(O)$_2$NR$^{c9}$R$^{d9}$, wherein said C$_{1-6}$ alkyl, C$_{3-7}$ cycloalkyl, 4-7 membered heterocycloalkyl, C$_{6-10}$ aryl, and 5-6 membered heteroaryl are optionally substituted by 1, 2, or 3 substituents independently selected from halo, C$_{1-4}$ alkyl, C$_{1-4}$ haloalkyl, C$_{1-4}$ cyanoalkyl, CN, OR$^{a9}$, SR$^{a9}$, C(O)R$^{b9}$, C(O)NR$^{c9}$R$^{d9}$, C(O)OR$^{a9}$, OC(O)R$^{b9}$, OC(O)NR$^{c9}$R$^{d9}$, NR$^{c9}$R$^{d9}$, NR$^{c9}$C(O)R$^{b9}$, NR$^{c9}$C(O)NR$^{c9}$R$^{d9}$, NR$^{c9}$C(O)OR$^{a9}$, S(O)R$^{b9}$, S(O)NR$^{c9}$R$^{d9}$, S(O)$_2$R$^{b9}$, NR$^{c9}$S(O)$_2$R$^{b9}$, NR$^{c9}$S(O)$_2$NR$^{c9}$R$^{d9}$, and S(O)$_2$NR$^{c9}$R$^{d9}$; and each R$^{a9}$, R$^{b9}$, R$^{c9}$, and R$^{d9}$ is independently selected from H, C$_{1-4}$ alkyl, C$_{1-4}$ haloalkyl, C$_{2-4}$ alkenyl, and C$_{2-4}$ alkynyl, wherein said C$_{1-4}$ alkyl, C$_{2-4}$ alkenyl, and C$_{2-4}$ alkynyl, is optionally substituted with 1, 2, or 3 substituents independently selected from OH, CN, amino, halo, C$_{1-4}$ alkyl, C$_{1-4}$ alkoxy, C$_{1-4}$ alkylthio, C$_{1-4}$ alkylamino, di(C$_{1-4}$ alkyl)amino, C$_{1-4}$ haloalkyl, and C$_{1-4}$ haloalkoxy;

wherein said compound is not:

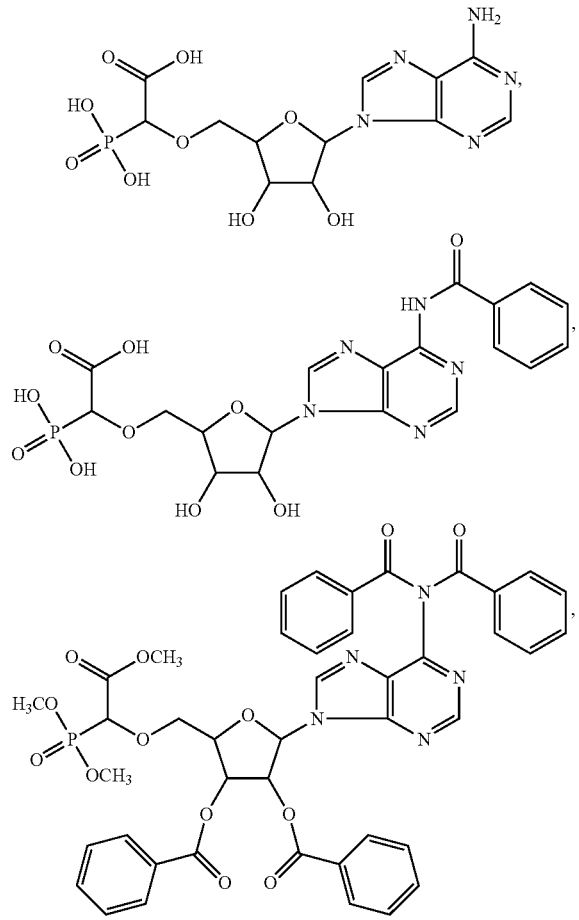

-continued
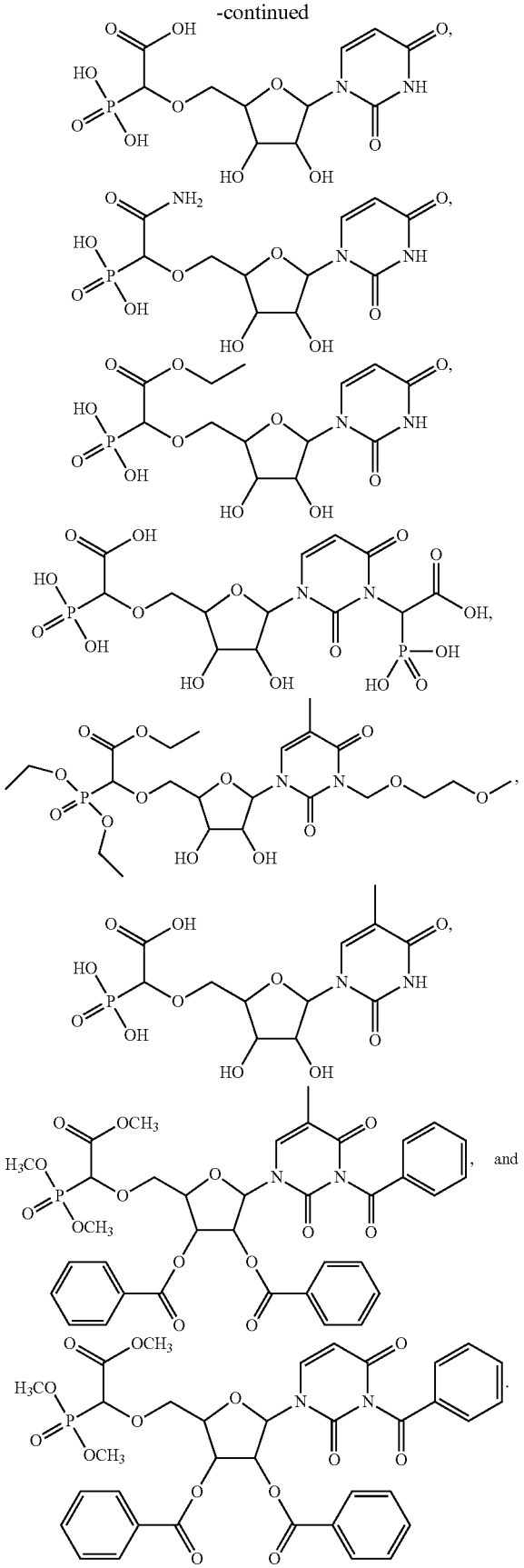
In some embodiments, Hy is a bicyclic heterocycle of formula (i):
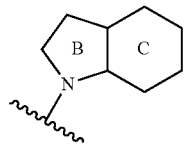
In some embodiments, Hy is selected from:
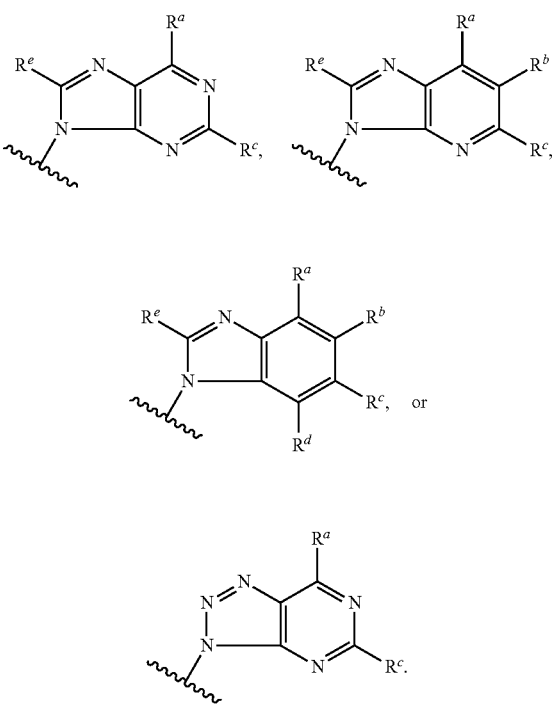
In some embodiments, Hy is:
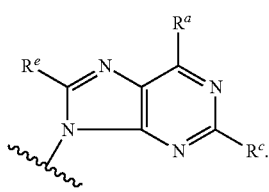
In some embodiments, Hy is:
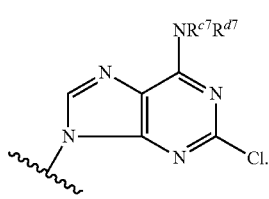

In some embodiments, Hy is:

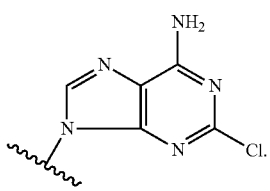 [SMILES: *n1cnc2c(N)nc(Cl)nc21]

In some embodiments, Hy is:

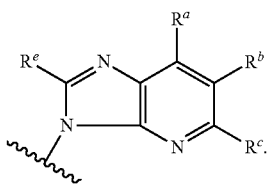

In some embodiments, Hy is:

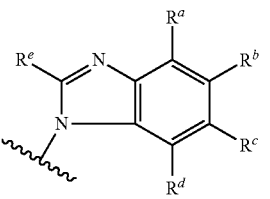

In some embodiments, Hy is:

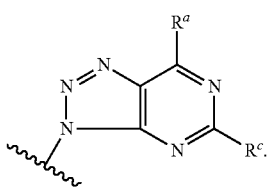

In some embodiments, Hy is a bicyclic heterocycle of formula (ii):

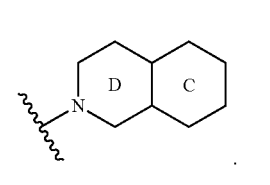

(ii)

In some embodiments, Hy is:

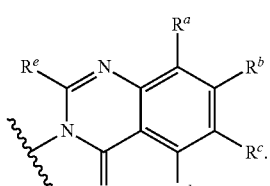

In some embodiments, Hy is a bicyclic heterocycle of formula (iii):

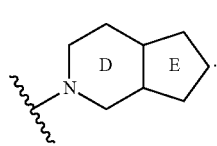

(iii)

In some embodiments, Hy is:

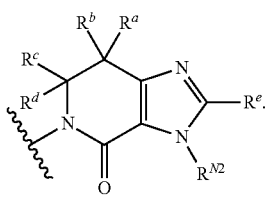

In some embodiments, Hy is a bicyclic heterocycle of formula (iv):

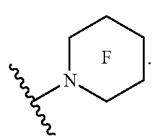

(iv)

In some embodiments, Hy is:

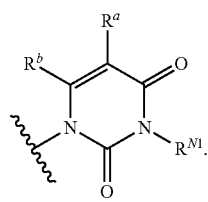

In some embodiments, Hy is:

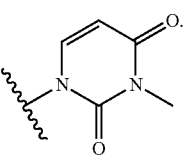 [SMILES: *n1ccc(=O)n(C)c1=O]

In some embodiments, Hy is a bicyclic heterocycle of formula (v):

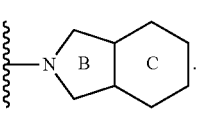

(v)

In some embodiments, Hy is:

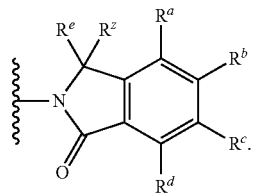

In some embodiments, A is O.
In some embodiments, A is S.
In some embodiments, A is NR$^f$.
In some embodiments, A is CH$_2$.
In some embodiments, W is O.
In some embodiments, W is S.
In some embodiments, R$^1$ and R$^2$ are both H.
In some embodiments, X is —C(O)OR$^3$, —C(O)NR$^4$R$^5$, —CH$_2$OR$^3$, —S(O)$_2$R$^6$, or a 5-membered heteroaryl group optionally substituted with halo, CN, OH, C$_{1-4}$ alkyl, C$_{1-4}$ alkoxy, NH$_2$, NH(C$_{1-4}$ alkyl), N(C$_{1-4}$ alkyl)$_2$, C(O)(C$_{1-4}$ alkyl), C(O)NH$_2$, C(O)NH(C$_{1-4}$ alkyl), C(O) N(C$_{1-4}$ alkyl)$_2$, C(O)OH, or C(O)O(C$_{1-4}$ alkyl).
In some embodiments, X is —C(O)OR$^3$.
In some embodiments, X is —C(O)OH or —C(O)O(CH$_2$CH$_3$).
In some embodiments, X is —C(O)O(CH$_2$CH$_3$).
In some embodiments, X is C$_{1-4}$ haloalkyl.
In some embodiments, X is —CF$_3$.
In some embodiments, Y is H or C$_{1-4}$ alkyl, wherein said C$_{1-4}$ alkyl is optionally substituted by Cy$^1$, OR$^{a1}$, or C(O)OR$^{a1}$.
In some embodiments, Y is H.
In some embodiments, Z is —C(O)OR$^{10}$.
In some embodiments, Z is —P(O)(OR$^{11}$)(OR$^{12}$).
In some embodiments, R$^3$ is H, C$_{1-6}$ alkyl, or C$_{6-10}$ aryl-C$_{1-4}$ alkyl.
In some embodiments, R$^3$ is H.
In some embodiments, R$^3$ is ethyl.
In some embodiments, R$^4$ and R$^5$ are each independently selected from H, —NR$^A$R$^B$, —OR$^C$, and C$_{1-6}$ alkyl.
In some embodiments, R$^6$ is C$_{1-6}$ alkyl.
In some embodiments, R$^9$ is H.
In some embodiments, R$^{11}$ and R$^{12}$ are each independently selected from H and C$_{1-4}$ alkyl.
In some embodiments, R$^{11}$ and R$^{12}$ are both H.
In some embodiments, R$^a$, R$^b$, R$^c$, and R$^d$ are each independently selected from Cy$^2$, H, halo, C$_{1-4}$ alkyl, C$_{1-4}$ haloalkyl, CN, OR$^{a7}$, SR$^{a7}$, NR$^{c7}$R$^{d7}$, and NR$^{c7}$C(O)R$^{b7}$, wherein said C$_{1-4}$ alkyl is optionally substituted by Cy$^2$ or NR$^{c7}$R$^{d7}$.
In some embodiments, R$^a$ is Cy$^2$, H, halo, C$_{1-4}$ alkyl, OR$^{a7}$, NR$^{c7}$R$^{d7}$, or NR$^{c7}$C(O)R$^{b7}$, wherein said C$_{1-4}$ alkyl is optionally substituted by Cy$^2$.
In some embodiments, R$^a$ is NR$^{c7}$R$^{d7}$.
In some embodiments, R$^a$ is NH$_2$.
In some embodiments, R$^b$ is H or halo.
In some embodiments, R$^c$ is Cy$^2$, halo, C$_{1-4}$ alkyl, C$_{1-4}$ haloalkyl, CN, OR$^{a7}$, SR$^{a7}$, C(O)R$^{b7}$, C(O)NR$^{c7}$R$^{d7}$, C(O)OR$^{a7}$, OC(O)R$^{b7}$, OC(O)NR$^{c7}$R$^{d7}$, NR$^{c7}$R$^{d7}$, NR$^{c7}$C(O)R$^{b7}$, NR$^{c7}$C(O)OR$^{a7}$, NR$^{c7}$C(O)NR$^{c7}$R$^{d7}$, NR$^{c7}$S(O)R$^{b7}$, NR$^{c7}$S(O)$_2$R$^{b7}$, NR$^{c7}$S(O)$_2$NR$^{c7}$R$^{d7}$, S(O)R$^{b7}$, S(O)NR$^{c7}$R$^{d7}$, S(O)$_2$R$^{b7}$, or S(O)$_2$NR$^{c7}$R$^{d7}$, wherein said C$_{1-4}$ alkyl is optionally substituted by 1, 2, or 3 substituents independently selected from Cy$^2$, H, halo, C$_{1-4}$ haloalkyl, CN, OR$^{a7}$, SR$^{a7}$, C(O)R$^{b7}$, C(O)NR$^{c7}$R$^{d7}$, C(O)OR$^{a7}$, OC(O)R$^{b7}$, OC(O)NR$^{c7}$R$^{d7}$, NR$^{c7}$R$^{d7}$, NR$^{c7}$C(O)R$^{b7}$, NR$^{c7}$C(O)OR$^{a7}$, NR$^{c7}$C(O)NR$^{c7}$R$^{d7}$, NR$^{c7}$S(O)R$^{b7}$, NR$^{c7}$S(O)$_2$R$^{b7}$, NR$^{c7}$S(O)$_2$NR$^{c7}$R$^{d7}$, S(O)R$^{b7}$, S(O)NR$^{c7}$R$^{d7}$, S(O)$_2$R$^{b7}$, and S(O)$_2$NR$^{c7}$R$^{d7}$.

In some embodiments, R$^c$ is Cy$^2$, H, halo, C$_{1-4}$ alkyl, C$_{1-4}$ haloalkyl, CN, OR$^{a7}$, or SR$^{a7}$, wherein said C$_{1-4}$ alkyl is optionally substituted by Cy$^2$ or NR$^{c7}$R$^{d7}$.
In some embodiments, R$^c$ is Cy$^2$, halo, C$_{1-4}$ alkyl, C$_{1-4}$ haloalkyl, CN, OR$^{a7}$, or SR$^{a7}$, wherein said C$_{1-4}$ alkyl is optionally substituted by Cy$^2$ or NR$^{c7}$R$^{d7}$.
In some embodiments, R$^c$ is halo.
In some embodiments, R$^c$ is Cl.
In some embodiments, R$^d$ is halo or CN.
In some embodiments, R$^e$ is H.
In some embodiments, R$^z$ is H.
In some embodiments, the compounds of the invention have Formula Ia:

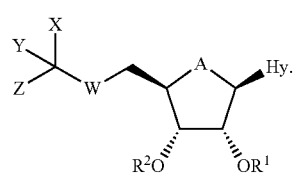

Ia

In some embodiments, the compounds of the invention have Formula IIa, IIb, IIc, IId, or IIe:

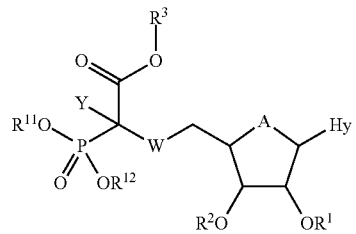

IIa

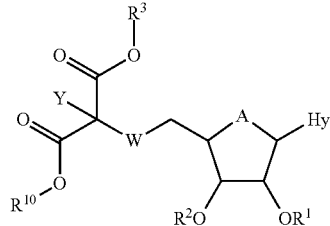

IIb

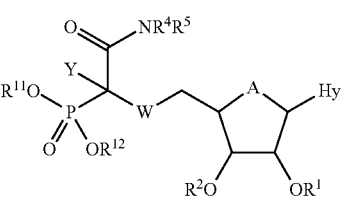

IIc

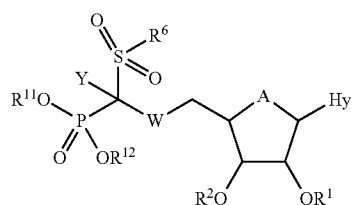

IId

In some embodiments, the compounds of the invention have Formula IIIa, IIIb, IIIc, IIId, or IIIe:

IIIa

IIIb

IIIc

IIId

IIIe

In some embodiments, the compounds of the invention have Formula IVa, IVb, IVc, IVd, or IVe:

IVa

IVb

IVc

IVd

IVe

In some embodiments, the compounds of the invention have Formula Va, Vb, Vc, Vd, or Ve:

Va

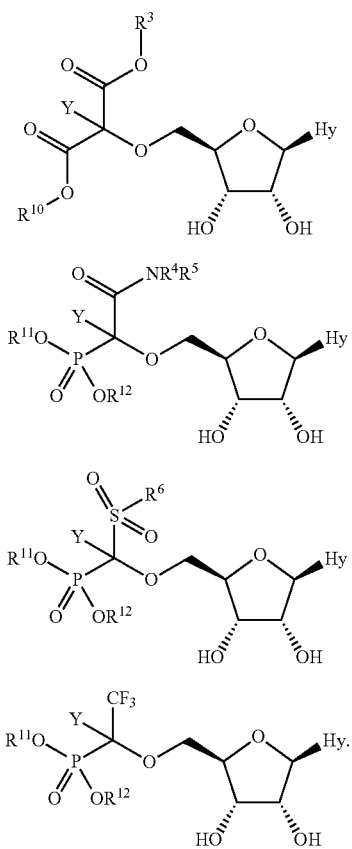

In some embodiments, the compounds of the invention have Formula IIa, IIb, IIc, IId, or IIe:

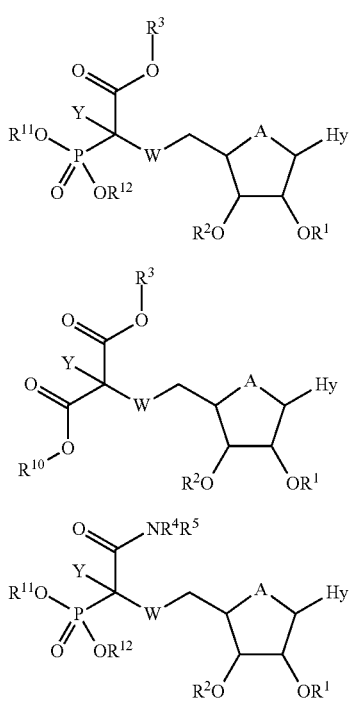

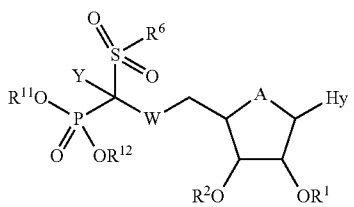

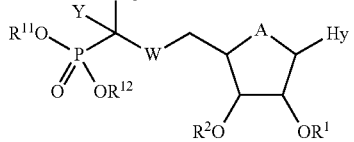

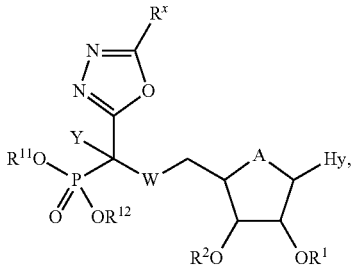

wherein $R^x$ is $C_{1-4}$ alkyl.

In some embodiments, the compounds of the invention have Formula IIa.

In some embodiments, the compounds of the invention have Formula IIb.

In some embodiments, the compounds of the invention have Formula IIc.

In some embodiments, the compounds of the invention have Formula IId.

In some embodiments, the compounds of the invention have Formula IIe.

In some embodiments, the compounds of the invention have Formula IIf.

In some embodiments, the compounds of the invention have Formula IIIa, IIIb, IIIc, IIId, IIIe, or IIIf:

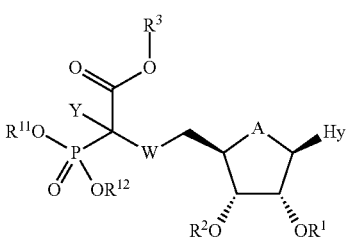

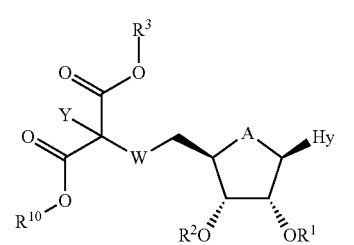

-continued

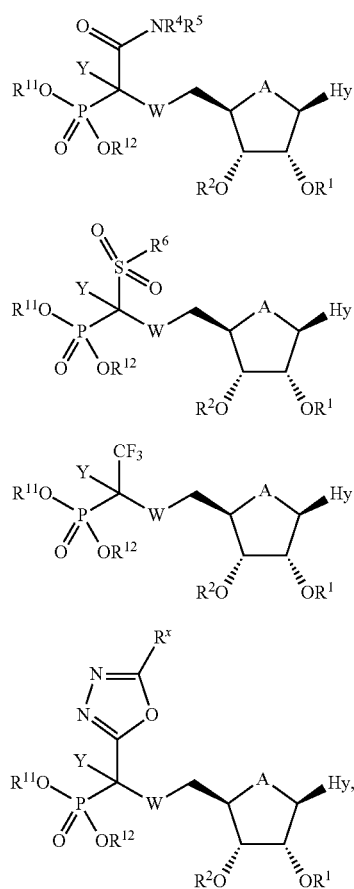

wherein $R^x$ is $C_{1-4}$ alkyl.

In some embodiments, the compounds of the invention have Formula IIIa.

In some embodiments, the compounds of the invention have Formula IIIb.

In some embodiments, the compounds of the invention have Formula IIIc.

In some embodiments, the compounds of the invention have Formula IIId.

In some embodiments, the compounds of the invention have Formula IIIe.

In some embodiments, the compounds of the invention have Formula IIIf.

In some embodiments, the compounds of the invention have Formula IVa, IVb, IVc, IVd, IVe, or IVf:

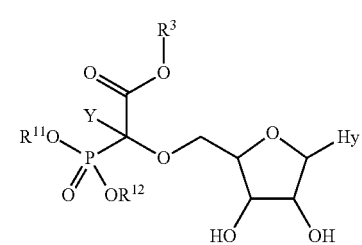

-continued

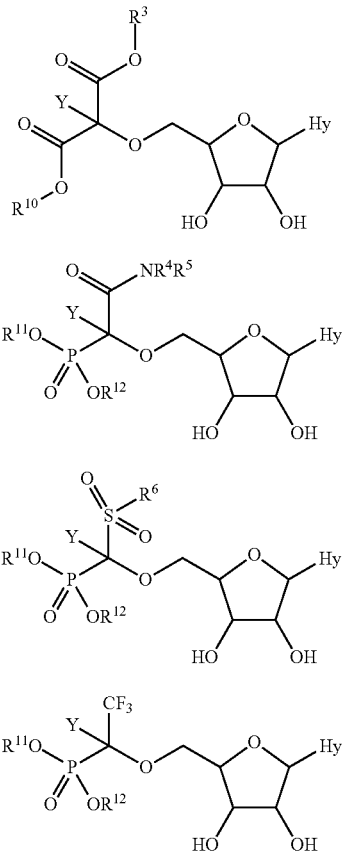

wherein $R^x$ is $C_{1-4}$ alkyl.

In some embodiments, the compounds of the invention have Formula IVa.

In some embodiments, the compounds of the invention have Formula IVb.

In some embodiments, the compounds of the invention have Formula IVc.

In some embodiments, the compounds of the invention have Formula IVd.

In some embodiments, the compounds of the invention have Formula IVe.

In some embodiments, the compounds of the invention have Formula IVf.

In some embodiments, the compounds of the invention have Formula Va, Vb, Vc, Vd, Ve, or Vf:

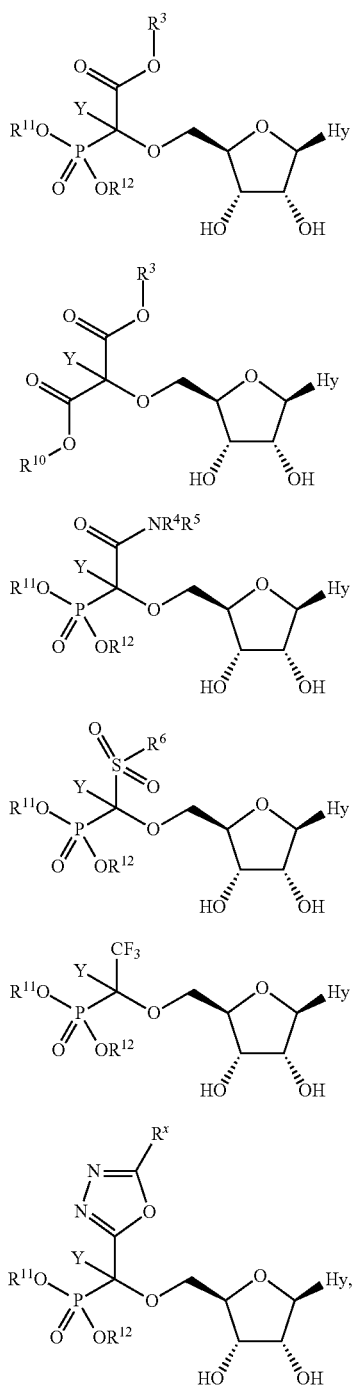

wherein $R^x$ is $C_{1-4}$ alkyl.

In some embodiments, the compounds of the invention have Formula Va.

In some embodiments, the compounds of the invention have Formula Vb.

In some embodiments, the compounds of the invention have Formula Vc.

In some embodiments, the compounds of the invention have Formula Vd.

In some embodiments, the compounds of the invention have Formula Ve.

In some embodiments, the compounds of the invention have Formula Vf.

In some embodiments, the compounds of the invention have Formula VIa, VIb, VIc, VId, VIe, or VIf:

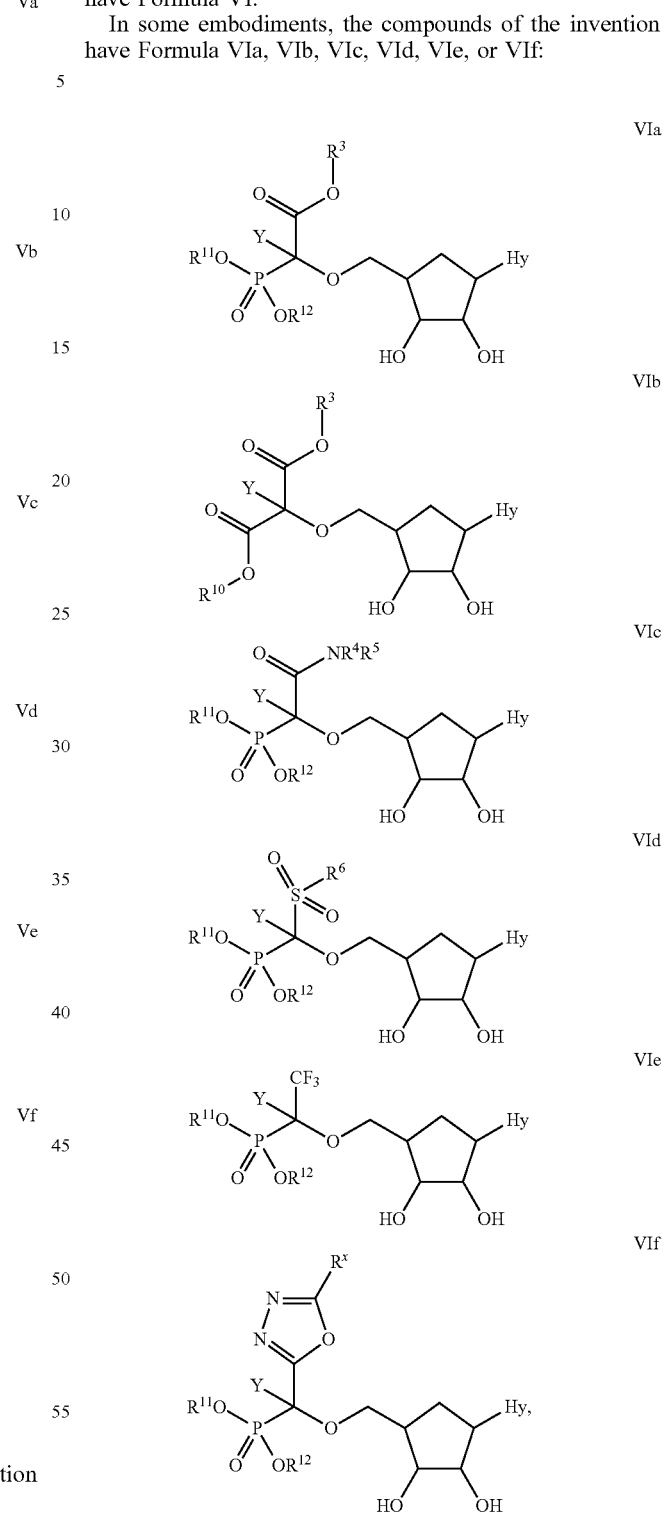

wherein $R^x$ is $C_{1-4}$ alkyl.

In some embodiments, the compounds of the invention have Formula VIa, VIb, or VIc.

In some embodiments, the compounds of the invention have Formula VIa.

In some embodiments, the compounds of the invention have Formula VIb.

In some embodiments, the compounds of the invention have Formula VIc.

In some embodiments, the compounds of the invention have Formula VId.

In some embodiments, the compounds of the invention have Formula VIe.

In some embodiments, the compounds of the invention have Formula VIf.

In some embodiments, the compounds of the invention have Formula VIIa, VIIb, VIIc, VIId, VIIe, or VIIf:

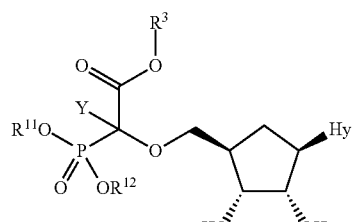
VIIa

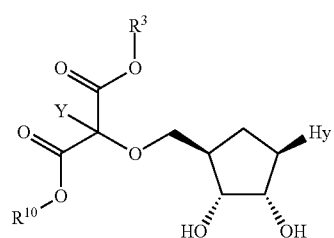
VIIb

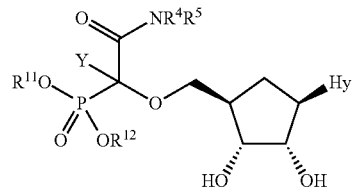
VIIc

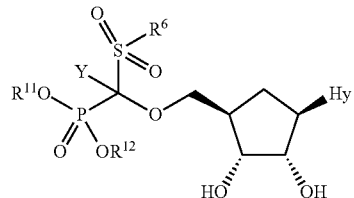
VIId

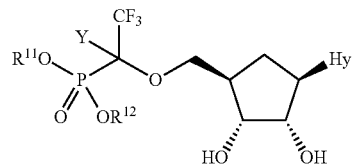
VIIe

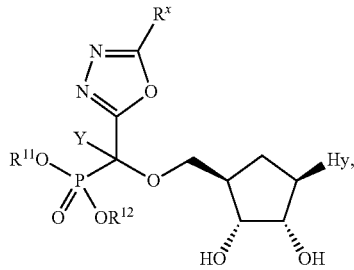
VIIf wherein $R^x$ is $C_{1-4}$ alkyl.

In some embodiments, the compounds of the invention have Formula VIIa, VIIb, or VIIc.

In some embodiments, the compounds of the invention have Formula VIIa.

In some embodiments, the compounds of the invention have Formula VIIb.

In some embodiments, the compounds of the invention have Formula VIIc.

In some embodiments, the compounds of the invention have Formula VIId.

In some embodiments, the compounds of the invention have Formula VIIe.

In some embodiments, the compounds of the invention have Formula VIIf.

In certain embodiments, the present invention provides the compound (1-((5-(6-amino-2-chloro-9H-purin-9-yl)-3,4-dihydroxytetrahydrofuran-2-yl)methoxy)-2-ethoxy-2-oxoethyl)phosphonic acid:

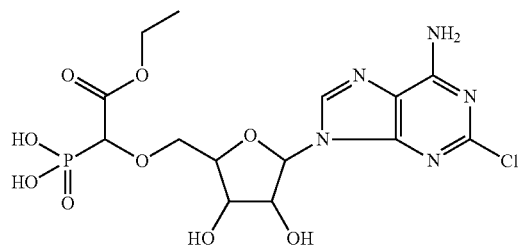 [SMILES: CCOC(=O)C(OCC1OC(n2cnc3c(N)nc(Cl)nc32)C(O)C1O)P(=O)(O)O]

or a pharmaceutically acceptable salt thereof.

In further embodiments, the present invention provides the compound (1-(((2R,3S,4R,5R)-5-(6-amino-2-chloro-9H-purin-9-yl)-3,4-dihydroxytetrahydrofuran-2-yl)methoxy)-2-ethoxy-2-oxoethyl)phosphonic acid:

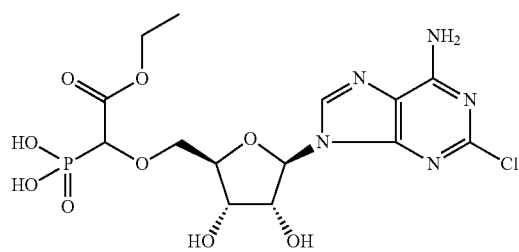

or a pharmaceutically acceptable salt thereof.

In further embodiments, the present invention provides the compound ((R)-1-(((2R,3S,4R,5R)-5-(6-amino-2-chloro-9H-purin-9-yl)-3,4-dihydroxytetrahydrofuran-2-yl)methoxy)-2-ethoxy-2-oxoethyl)phosphonic acid:

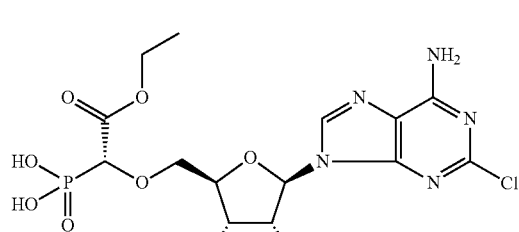

or a pharmaceutically acceptable salt thereof.

In further embodiments, the present invention provides the compound ((S)-1-(((2R,3S,4R,5R)-5-(6-amino-2-chloro-9H-purin-9-yl)-3,4-dihydroxytetrahydrofuran-2-yl)methoxy)-2-ethoxy-2-oxoethyl)phosphonic acid:

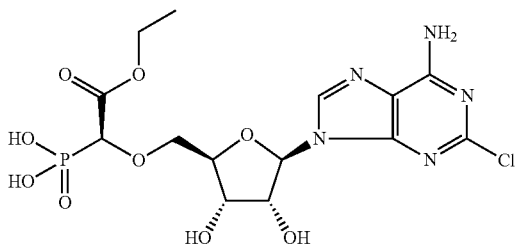

or a pharmaceutically acceptable salt thereof.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the phrase "optionally substituted" means unsubstituted or substituted. As used herein, the term "substituted" means that a hydrogen atom is removed and replaced by a substituent. It is to be understood that substitution at a given atom is limited by valency.

Throughout the definitions, the term "$C_{i-j}$" indicates a range which includes the endpoints, wherein i and j are integers and indicate the number of carbons. Examples include $C_{1-4}$, $C_{1-6}$, and the like.

The term "z-membered" (where z is an integer) typically describes the number of ring-forming atoms in a moiety where the number of ring-forming atoms is z. For example, piperidinyl is an example of a 6-membered heterocycloalkyl ring, pyrazolyl is an example of a 5-membered heteroaryl ring, pyridyl is an example of a 6-membered heteroaryl ring, and 1, 2, 3, 4-tetrahydro-naphthalene is an example of a 10-membered cycloalkyl group.

As used herein, the term "$C_{i-j}$ alkyl," employed alone or in combination with other terms, refers to a saturated hydrocarbon group that may be straight-chain or branched, having i to j carbons. In some embodiments, the alkyl group contains from 1 to 6 carbon atoms, or from 1 to 4 carbon atoms, or from 1 to 3 carbon atoms. Examples of alkyl moieties include, but are not limited to, chemical groups such as methyl, ethyl, n-propyl, isopropyl, n-butyl, s-butyl, and t-butyl.

As used herein, the term "$C_{i-j}$ alkoxy," employed alone or in combination with other terms, refers to a group of formula —O-alkyl, wherein the alkyl group has i to j carbons. Example alkoxy groups include methoxy, ethoxy, and propoxy (e.g., n-propoxy and isopropoxy). In some embodiments, the alkyl group has 1 to 3 carbon atoms.

As used herein, "$C_{i-j}$ alkenyl," employed alone or in combination with other terms, refers to an unsaturated hydrocarbon group having one or more double carbon-carbon bonds and having i to j carbons. In some embodiments, the alkenyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, "$C_{i-j}$ alkynyl," employed alone or in combination with other terms, refers to an unsaturated hydrocarbon group having one or more triple carbon-carbon bonds and having i to j carbons. Example alkynyl groups include, but are not limited to, ethynyl, propyn-1-yl, propyn-2-yl, and the like. In some embodiments, the alkynyl moiety contains 2 to 6 or 2 to 4 carbon atoms.

As used herein, the term "$C_{i-j}$ alkylamino," employed alone or in combination with other terms, refers to a group of formula —NH(alkyl), wherein the alkyl group has i to j carbon atoms. In some embodiments, the alkyl group has 1 to 6 or 1 to 4 carbon atoms.

As used herein, the term "di-$C_{i-j}$-alkylamino," employed alone or in combination with other terms, refers to a group of formula —N(alkyl)$_2$, wherein each of the two alkyl groups has, independently, i to j carbon atoms. In some embodiments, each alkyl group independently has 1 to 6 or 1 to 4 carbon atoms. In some embodiments, the dialkylamino group is —N($C_{1-4}$ alkyl)$_2$ such as, for example, dimethylamino or diethylamino.

As used herein, the term "$C_{i-j}$ alkylthio," employed alone or in combination with other terms, refers to a group of formula —S-alkyl, wherein the alkyl group has i to j carbon atoms. In some embodiments, the alkyl group has 1 to 6 or 1 to 4 carbon atoms. In some embodiments, the alkylthio group is $C_{1-4}$ alkylthio such as, for example, methylthio or ethylthio.

As used herein, the term "amino," employed alone or in combination with other terms, refers to a group of formula —NH$_2$.

As used herein, the term "aryl," employed alone or in combination with other terms, refers to a monocyclic or polycyclic (e.g., having 2, 3 or 4 fused rings) aromatic hydrocarbon, such as, but not limited to, phenyl, 1-naphthyl, 2-naphthyl, anthracenyl, phenanthrenyl, and the like. In some embodiments, aryl is $C_{6-10}$ aryl. In some embodiments, the aryl group is a naphthalene ring or phenyl ring. In some embodiments, the aryl group is phenyl.

As used herein, the term "$C_{i-j}$ cycloalkyl," employed alone or in combination with other terms, refers to a non-aromatic cyclic hydrocarbon moiety having i to j ring-forming carbon atoms, which may optionally contain one or more alkenylene groups as part of the ring structure. Cycloalkyl groups can include mono- or polycyclic (e.g., having 2, 3 or 4 fused rings) ring systems. Also included in the definition of cycloalkyl are moieties that have one or more aromatic rings fused (i.e., having a bond in common with) to the cycloalkyl ring, for example, benzo derivatives of cyclopentane, cyclopentene, cyclohexane, and the like. One or more ring-forming carbon atoms of a cycloalkyl group can be oxidized to form carbonyl linkages. In some embodiments, cycloalkyl is $C_{3-10}$ cycloalkyl, $C_{3-7}$ cycloalkyl, or $C_{5-6}$ cycloalkyl. Exemplary cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. Further exemplary cycloalkyl groups include cyclopropyl, cyclobutyl, cyclopentyl, and cyclohexyl.

As used herein, "$C_{i-j}$ haloalkoxy," employed alone or in combination with other terms, refers to a group of formula —O-haloalkyl having i to j carbon atoms. An example haloalkoxy group is OCF$_3$. An additional example haloalkoxy group is OCHF$_2$. In some embodiments, the haloalkoxy group is fluorinated only. In some embodiments, the alkyl group has 1 to 6 or 1 to 4 carbon atoms. In some embodiments, the haloalkoxy group is $C_{1-4}$ haloalkoxy.

As used herein, the term "halo," employed alone or in combination with other terms, refers to a halogen atom selected from F, Cl, I or Br. In some embodiments, "halo"

refers to a halogen atom selected from F, Cl, or Br. In some embodiments, the halo substituent is F.

As used herein, the term "$C_{i-j}$ haloalkyl," employed alone or in combination with other terms, refers to an alkyl group having from one halogen atom to 2s+1 halogen atoms which may be the same or different, where "s" is the number of carbon atoms in the alkyl group, wherein the alkyl group has i to j carbon atoms. In some embodiments, the haloalkyl group is fluorinated only. In some embodiments, the haloalkyl group is fluoromethyl, difluoromethyl, or trifluoromethyl. In some embodiments, the haloalkyl group is trifluoromethyl. In some embodiments, the alkyl group has 1 to 6 or 1 to 4 carbon atoms.

As used herein, the term "heteroaryl," employed alone or in combination with other terms, refers to a monocyclic or polycyclic (e.g., having 2, 3 or 4 fused rings) aromatic heterocyclic moiety, having one or more heteroatom ring members selected from nitrogen, sulfur and oxygen. In some embodiments, the heteroaryl group has 1, 2, 3, or 4 heteroatom ring members. In some embodiments, the heteroaryl group has 1, 2, or 3 heteroatom ring members. In some embodiments, the heteroaryl group has 1 or 2 heteroatom ring members. In some embodiments, the heteroaryl group has 1 heteroatom ring member. In some embodiments, the heteroaryl group is 5- to 10-membered or 5- to 6-membered. In some embodiments, the heteroaryl group is 5-membered. In some embodiments, the heteroaryl group is 6-membered. When the heteroaryl group contains more than one heteroatom ring member, the heteroatoms may be the same or different. The nitrogen atoms in the ring(s) of the heteroaryl group can be oxidized to form N-oxides. Example heteroaryl groups include, but are not limited to, pyridine, pyrimidine, pyrazine, pyridazine, pyrrole, pyrazole, azolyl, oxazole, isoxazole, thiazole, isothiazole, imidazole, furan, thiophene, triazole, tetrazole, thiadiazole, quinoline, isoquinoline, indole, benzothiophene, benzofuran, benzisoxazole, imidazo[1, 2-b]thiazole, purine, triazine. and the like.

As used herein, the term "heterocycloalkyl," employed alone or in combination with other terms, refers to a non-aromatic heterocyclic ring system, which may optionally contain one or more unsaturations as part of the ring structure, and which has at least one heteroatom ring member independently selected from nitrogen, sulfur and oxygen. In some embodiments, the heterocycloalkyl group has 1, 2, 3, or 4 heteroatom ring members. In some embodiments, the heterocycloalkyl group has 1, 2, or 3 heteroatom ring members. In some embodiments, the heterocycloalkyl group has 1 or 2 heteroatom ring members. In some embodiments, the heterocycloalkyl group has 1 heteroatom ring member. When the heterocycloalkyl group contains more than one heteroatom in the ring, the heteroatoms may be the same or different. Example ring-forming members include CH, $CH_2$, C(O), N, NH, O, S, S(O), and $S(O)_2$. Heterocycloalkyl groups can include mono- or polycyclic (e.g., having 2, 3 or 4 fused rings) ring systems, including spiro systems. Also included in the definition of heterocycloalkyl are moieties that have one or more aromatic rings fused (i.e., having a bond in common with) to the non-aromatic ring, for example, 1, 2, 3, 4-tetrahydro-quinoline, dihydrobenzofuran and the like. The carbon atoms or heteroatoms in the ring(s) of the heterocycloalkyl group can be oxidized to form a carbonyl, sulfinyl, or sulfonyl group (or other oxidized linkage) or a nitrogen atom can be quaternized. In some embodiments, heterocycloalkyl is 5- to 10-membered, 4- to 10-membered, 4- to 7-membered, 5-membered, or 6-membered. Examples of heterocycloalkyl groups include 1, 2, 3, 4-tetrahydro-quinoline, dihydrobenzofuran, azetidine, azepane, pyrrolidine, piperidine, piperazine, morpholine, thiomorpholine, and pyran.

The compounds described herein can be asymmetric (e.g., having one or more stereocenters). All stereoisomers, such as enantiomers and diastereoisomers, are intended unless otherwise indicated. Where a compound name or structure is silent with respect to the stereochemistry of a stereocenter, all possible configurations at the stereocenter are intended. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

When the compounds of the invention contain a chiral center, the compounds can be any of the possible stereoisomers. In compounds with a single chiral center, the stereochemistry of the chiral center can be (R) or (S). In compounds with two chiral centers, the stereochemistry of the chiral centers can each be independently (R) or (S) so the configuration of the chiral centers can be (R) and (R), (R) and (S); (S) and (R), or (S) and (S). In compounds with three chiral centers, the stereochemistry each of the three chiral centers can each be independently (R) or (S) so the configuration of the chiral centers can be (R), (R) and (R); (R), (R) and (S); (R), (S) and (R); (R), (S) and (S); (S), (R) and (R); (S), (R) and (S); (S), (S) and (R); or (S), (S) and (S).

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereoisomerically pure forms), 2-phenylglycinol, norephedrine, ephedrine, N-methylephedrine, cyclohexylethylamine, 1, 2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1, 2, 4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified (e.g., in the case of purine rings, unless otherwise indicated, when the compound name or structure has the 9H tautomer, it is understood that the 7H tautomer is also encompassed).

All compounds, and pharmaceutically acceptable salts thereof, can be found together with other substances such as water and solvents (e.g., hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in a compound of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in Remington's Pharmaceutical Sciences, 17$^{th}$ Ed., (Mack Publishing Company, Easton, 1985), p. 1418, Berge et al., J. Pharm. Sci., 1977, 66(1), 1-19, and in Stahl et al., Handbook of Pharmaceutical Salts: Properties, Selection, and Use, (Wiley, 2002).

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms.

"Racemate" or "racemic mixture" means a compound of equimolar quantities of two enantiomers, wherein such mixtures exhibit no optical activity; i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When a disclosed compound is named or depicted without indicating the stereochemistry of one or more stereocenters, each of the stereoisomers resulting from the possible stereochemistries at the undefined stereocenter(s) are intended to be encompassed. For example, if a stereocenter is not designated as R or S, then either or both are intended.

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable basic/cationic salts include, the sodium, potassium, calcium, magnesium, diethanolamine, n-methyl-D-glucamine, L-lysine, L-arginine, ammonium, ethanolamine, piperazine and triethanolamine salts.

Pharmaceutically acceptable acidic/anionic salts include, e.g., the acetate, benzenesulfonate, benzoate, bicarbonate, bitartrate, carbonate, citrate, dihydrochloride, gluconate, glutamate, glycollylarsanilate, hexylresorcinate, hydrobromide, hydrochloride, malate, maleate, malonate, mesylate, nitrate, salicylate, stearate, succinate, sulfate, tartrate, and tosylate.

The present invention further includes ester derivatives of the phosphonic acid compounds of the invention. For example, either or both of the hydroxyl groups of the phosphonic acid moiety can be esterified through routine synthetic methods to produce ester derivatives of the compounds of the invention. In some embodiment, the phosphonic acid esters can be alkyl esters (e.g., $C_{1-6}$ alkyl ester groups).

Specific examples of compounds of the invention are provided in the Examples. Pharmaceutically acceptable salts as well as the neutral forms of these compounds are included in the invention.

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in P. G. M. Wuts and T. W. Greene, *Protective Groups in Organic Synthesis*, 4th Ed., Wiley & Sons, Inc., New York (2006), which is incorporated herein by reference in its entirety.

Scheme I

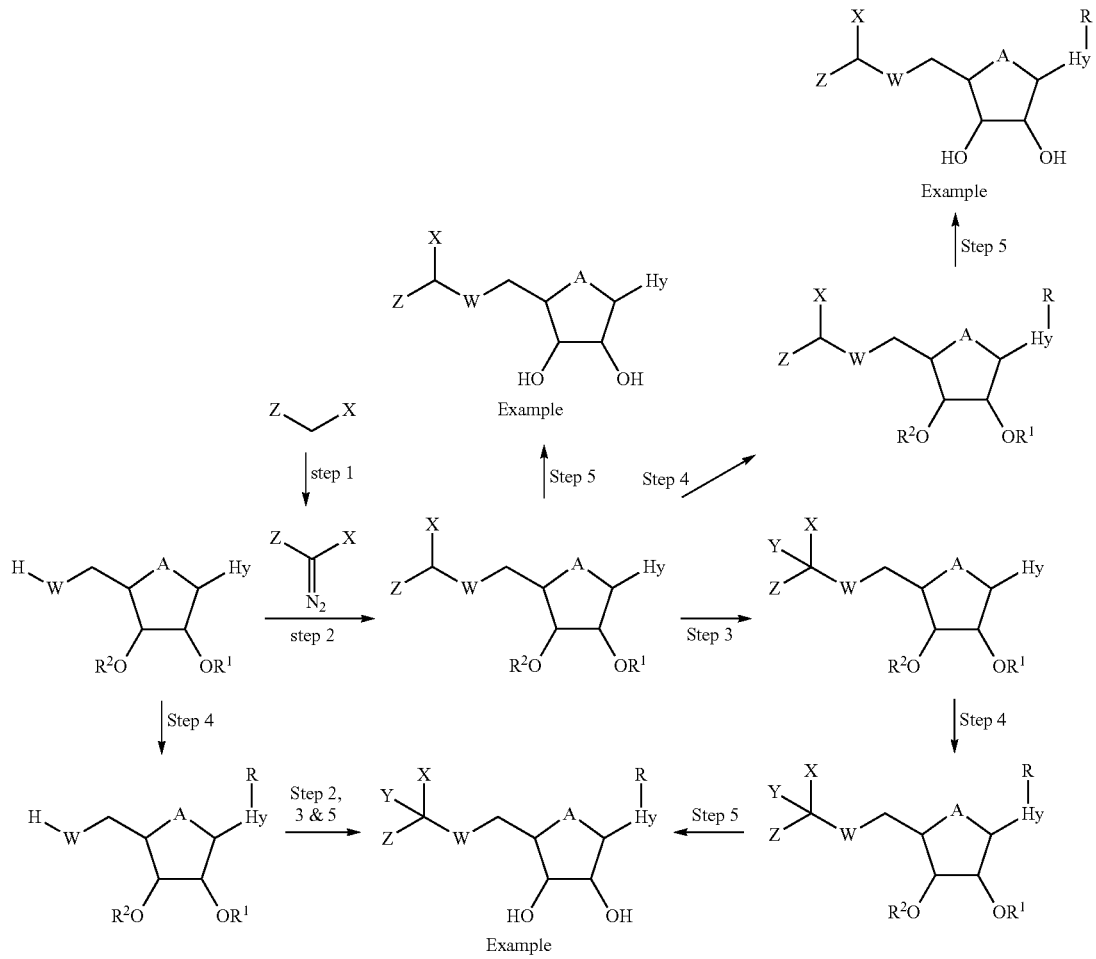

Example

In regard to Scheme I, the derivatives containing 5-(hydroxymethyl)-tetrahydrofuran-3,4-diol and 5-(hydroxymethyl)cyclopentane-1,2-diol substituted with various heterocycles at the 2-position are well known in literature. They are commercially available or can be synthesized by methods known in literature as referenced in, e.g., *Chemical Synthesis of Nucleoside Analogues* by Pedro Merino, 1st edition, John Wiley & Sons, 2013, and in other publications. The most common method of synthesis involves displacement of fully protected ribose with various heterocycles in the presence of Lewis acid in aprotic solvents. These reactions are well documented in the literature and illustrated in *Nucleosides & Nucleotides*, 4(5), 625-39; 1985 and in *Bioorganic & Medicinal Chemistry*, 11(6), 899-908; 2003. The most common method involves reaction of beta-D-ribofuranose 1,2,3,5-tetraacetate or tetrabenzoate with various basic protected or unprotected heterocycles such as 2-aminobenzimidazole, substituted purine, etc in the presence of Lewis acids such as tin tetrachloride, tetrafluroboroetherate etc., in solvents such as acetonitrile, dichloromethane, toluene etc. The corresponding 2-thiomethyl analogs can be synthesized from the above mentioned 2-hydroxymethyl analogs through numerous methods and are well documented in literature. The most common method of synthesizing these thiomethyl analogs is through Mitsunobu reaction as referenced in by Hughes, David L., *Organic Reactions*, (Hoboken, N.J., United States), 42, 1992. It is always prudent to protect various functional groups such as alcohols, amines, etc. through protecting groups compatible with the reactions sequence. The various protecting groups and their compatibility are well documented in Greene and Wuts, *Protective Groups in Organic Chemistry*, 2$^{nd}$ ed., John Wiley & Sons, 1991 and in subsequent editions. The most preferable protecting group for cis-diol is acetonide or diacetate or dibenzoate groups. Similarly, the amine of the nucleoside base or heterocycle can be protected with various protecting groups that are compatible with the reaction conditions and schemes. Most preferred protecting groups are tert butyloxycarbonyl or as benzoate protecting group for optimal reaction conditions.

Step 1

Synthesis of diazo compounds from active methylene compounds are well known in literature and are described in F. A. Carey, R. J. Sundberg, *Advanced Organic Chemistry*, 2$^{nd}$ edition, Plenum, 1983. Various active methylene compounds such a malonates or phosphonoacetates are well known in literature and can be synthesized from commercially available starting materials. They can be reacted with various diazo transfer reagents such arylsulfonylazide in the presence of inorganic or organic bases in aprotic solvents such as benzene, acetonitrile, THF, DMF, DCM etc. The diazo reagents are then isolated using various purification techniques and stored and handled carefully. They can also be synthesized from amine by dizotization reaction or from the ketone by reaction with hydrazines as described in New Syntheses of Diazo Compounds, Gerhard Maas, *Angew. Chem. Int. Ed.*, 2009, 48, 8186. The most preferred route involves reaction of phosphonoacetate or diethyl malonate with benzenesulfonyl azide or its analogs in presence of bases such as potassium carbonate or potassium tert-butoxide or NaH in solvents such as toluene, benzene, acetonitrile or THF at ambient temperature.

Step 2

The carbene insertion reaction is well known in literature and described in U. H. Brinke, *Advances in Carbene Chemistry*, Volume 3, Elsevier, 2001. These reactions are often carried out in inert atmosphere as catalyzed by various metal catalysts including rhodium or copper in aprotic solvent such as benzene, toluene or DCM. Various stereo selective syntheses can be achieved for such carbine insertion reaction in literature and can be utilized in this synthetic scheme. Alternatively, one can also use nucleophilic displacement of 2-bromo derivatives of active methylene compounds by alcohols, thiols, etc. in the presence of suitable bases such as triethyl amine or other amine bases or silver carbonate or other inorganic bases etc. The most preferred route involves reaction of 2-diazo phosphonoacetate or diazo malonate that is appropriately protected with protecting groups with alcohols in presence of rhodium acetate or copper triflate in toluene or in dichloromethane at optimal temperatures.

Step 3

The acidic proton in the intermediate from Step 2 can be further alkylated with various alkyl halides, aldehydes, acyl chloride etc. The alkylating agents can be a haloalkanes that are appropriately substituted with alkyl, aryl, or heterocycles. These alkylating agents can also be alkyl alcohols that are modified as tosylates, mesylates etc to form leaving groups. The alkylation is carried out in the presence of various bases such as cesium carbonate or LHMDS or NaH etc in aprotic solvents such as ethereal solvents diethyl ether, tetrahydrofuran (THF), tert-butyl-methyl ether, 1,4-dioxane, or THF or non-ether solvents such as DMF, DMSO etc. The choice of base and solvents are chosen to impart optimal alkylation conditions. Alkylation of activated methylenes is well described in literature is illustrated in F. A. Carey, R. J. Sundberg, *Advanced Organic Chemistry*, 2nd edition, Plenum, 1983 and in subsequent editions. The most preferred route of alkylation for these embodiments is NaH in THF or cesium carbonate in DMF or LDA in THF.

Step 4

The various heterocycles and bases in nucleosides can be further elaborated by various reactions (R=substituent). Such conversions are well described in Richard Larock, Comprehensive Organic Transformations, 4th edition, VCH Inc., 1989 and in subsequent editions. The nucleophilic displacement using amines and thiols can be carried out in protic or aprotic solvents at appropriate temperatures. The displacement with alcohols often requires the presence of base such as KOtBu or triethylamine or inorganic bases such as cesium carbonate. Alternatively, one can use metal mediated coupling such as Suzuki, Negishi, Stille Sonigishara or Heck reactions to impart alkyl and aryl groups, amines, alcohols, and thiols in the heterocyclic ring systems. Generally, Suzuki and Negishi couplings can be employed to introduce substituents in the heterocycle and in the bases of the nucleosides. Alternatively, one can employ these reactions with the starting material and then elaborate them through a series of steps to the final compounds.

Step 5

The intermediates from Steps 2-4 can be converted to final products by various deprotection methods. The deprotection methods are so chosen to maintain the integrity of the compound. Very often the initial step involves deprotection of phosphate protecting groups. This can be achieved by use of trimethylsilyl bromide in aprotic solvents such acetonitrile or dichloromethane at room temperature or under elevated conditions. Other methods can involve use of hydrogenation conditions to remove benzyl groups in phosphate moiety. This can be followed by deprotection of acid sensitive groups using strong acid in aprotic or in non protic solvents. The protecting groups are so chosen to maintain the integrity of the chirality and the sensitivity of deprotecting condition to the overall stability of the molecules. In the case of malonates and esters, the acid sensitive functional groups are removed first, followed by removal of acid protecting groups through base hydrolysis or through hydrogenation. The various protection and deprotection strategy for acids and phosphates are well known and described in detail in Greene and Wuts, *Protective Groups in Organic Chemistry*, 2nd edition, John Wiley & Sons, 1991 and in subsequent editions.

Uses, Formulations, and Administration

The compounds of the invention are useful as inhibitors of CD73 and, therefore, useful in the treatment of diseases, disorders, and conditions in which it is believed CD73 activity plays a role. Additionally, the compounds of the invention are useful as inhibitors of adenosine receptors such as, for example, the $A_{2A}$ receptor. Accordingly, the compounds of the invention are useful in the treatment of diseases, disorders, and conditions associated with activity of one or more adenosine receptors.

The present invention provides a method of treating a patient (e.g., a human) with cancer or a disorder mediated by CD73 comprising the step of administering to the patient an effective amount of the compound with any compound described herein, or a pharmaceutically acceptable salt or composition thereof.

The present invention further provides a method of treating a patient (e.g., a human) with a disorder mediated by CD73 using a composition comprising a compound disclosed herein and a pharmaceutically acceptable carrier, adjuvant, or vehicle. In certain embodiments, the amount of compound in the composition is such that it is effective as an inhibitor of CD73 in a biological sample or in a patient. In certain embodiments, the composition is formulated for administration to a patient in need of such composition. In some embodiments, the composition is formulated for oral administration to a patient.

The present invention provides a method of treating a patient (e.g., a human) with cancer or a disorder mediated by an adenosine receptor (e.g., $A_{2A}R$) comprising the step of administering to the patient an effective amount of the compound with any compound described herein, or a pharmaceutically acceptable salt or composition thereof.

The present invention further provides a method of treating a patient (e.g., a human) with a disorder mediated by an adenosine receptor (e.g., $A_{2A}R$) using a composition comprising a compound disclosed herein and a pharmaceutically acceptable carrier, adjuvant, or vehicle. In certain embodiments, the amount of compound in the composition is such that it is effective as an inhibitor of an adenosine receptor (e.g., $A_{2A}R$) in a biological sample or in a patient. In certain embodiments, the composition is formulated for administration to a patient in need of such composition. In some embodiments, the composition is formulated for oral administration to a patient.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a provided compound, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

Provided compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Pharmaceutically acceptable compositions provided herein may be formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

The amount of a compound of the invention that may be combined with carrier materials to produce a composition in a single dosage form will vary depending upon the patient to be treated and the particular mode of administration.

It should also be understood that a specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound in the composition will also depend upon the particular compound in the composition.

Compounds and compositions described herein are generally useful for the inhibition of CD73. Thus, in some embodiments, the present invention provides a method of inhibiting CD73. In further embodiments, the present invention provides a method of treating diseases or disorders mediated by CD73 in a subject, comprising administering a compound or composition of the invention to the subject. More particularly, the compounds and compositions described herein act as inhibitors of CD73. More particularly, the compounds and compositions described herein act to inhibit the anti-inflammatory activity and/or the immunosuppression activity of CD73. In further embodiments, the present invention provides a method of inhibiting the anti-inflammatory activity and/or the immunosuppression activity of CD73.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to prevent or delay their recurrence.

As used herein, the terms "prevention," "prevent," and "preventing" refer to prohibiting, hindering, or delaying onset of a disease, condition, or disorder in an individual who may be predisposed to the disease, condition, or disorder but does not yet experience or display the pathology or symptomatology of the disease.

Higher expression levels of CD73 are associated with tumor neovascularization, invasiveness, resistance to chemotherapy and metastasis, and with shorter patient survival time in cancer, including but not limited to breast cancer. Thus, the compounds of the invention can be useful in reducing tumor neovascularization, invasiveness, resistance to chemotherapy and metastasis, as well as to lengthen patient survival time in cancer patients, including but not limited to breast cancer patients. Accordingly, the CD73 inhibitors of the invention can be used to control tumor neovascularization, progression, resistance to chemotherapy and metastasis.

Diseases and conditions treatable according to the methods of the invention include, but are not limited to, cancer and other diseases or disorders mediated by CD73.

Diseases and conditions treatable according to the methods of the invention include, but are not limited to, cancer and other diseases or disorders mediated by one or more adenosine receptors (e.g., $A_{2A}R$).

The compounds according to the invention are believed to be effective against a broad range of cancers and tumor types, including, but not limited to, bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer.

In some embodiments, cancers that may be treated by the compounds, compositions and methods described herein include, but are not limited to, the following:

cardiac cancers, including, for example, sarcoma, e.g., angiosarcoma, fibrosarcoma, rhabdomyosarcoma, and liposarcoma; myxoma; rhabdomyoma; fibroma; lipoma and teratoma; lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma; gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel or colon, e.g., adenocarcinoma, tubular adenoma, villous adenoma, hamartoma, and leiomyoma; genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma; liver cancers, including, for example, hepatoma, e.g., hepatocellular carcinoma; cholangiocarcinoma; hepatoblastoma; angiosarcoma; hepatocellular adenoma; and hemangioma; bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors; nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiforme, oligodendroglioma, schwannoma, retinoblastoma, and congenital tumors; and cancers of the spinal cord, e.g., neurofibroma, meningioma, glioma, and sarcoma; gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa thecal cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma; hematologic cancers, including, for example, cancers of the blood, e.g., acute myeloid leukemia (AML), chronic myeloid leukemia (CML), acute lymphoblastic leukemia (ALL), chronic lymphoblastic leukemia, chronic lymphocytic leukemia, myeloproliferative diseases, multiple myeloma, and myelodysplastic syndrome, Hodgkin's lymphoma, non Hodgkin's lymphoma (malignant lymphoma) and Waldenstrom's macroglobulinemia; skin cancers, including, for example, malignant melanoma, basal cell carcinoma, squamous cell carcinoma, Kaposi's sarcoma, moles dysplastic nevi, lipoma, angioma, dermatofibroma, keloids, psoriasis; and adrenal gland cancers, including, for example, neuroblastoma.

Cancers may be solid tumors that may or may not be metastatic. Cancers may also occur, as in leukemia, as a diffuse tissue.

In particular embodiments, the diseases or disorders include cancer, more particularly breast cancer, triple-negative breast cancer, melanoma, renal cell carcinoma, colorectal carcinoma, pancreatic cancer, prostate cancer, ovarian cancer, gastric cancer, leukemia and lymphoma. Further cancers that can be treated with inhibitors of CD73 include bladder cancer, lung cancer, thyroid cancer, including papillary thyroid carcinoma, glioma, sarcoma, and liver cancer.

In some embodiments, the compounds of the invention can be used to overcome T-cell tolerance.

Compounds of the invention can also be used to increase or enhance an immune response, including increasing the immune response to an antigen; to improve immunization, including increasing vaccine efficacy; and to increase inflammation. In some embodiments, the compounds of the invention can be sued to enhance the immune response to vaccines including, but not limited, Listeria vaccines, oncolytic viral vaccines, and cancer vaccines such as GVAX® (granulocyte-macrophage colony-stimulating factor (GM-CF) gene-transfected tumor cell vaccine).

In one embodiment, compounds of the invention are used to enhance the immune response in an immunosuppressed subject, such as a subject infected with an immunodeficiency virus (e.g., HIV-1 or HIV-2). In another embodiment, compounds of the invention are used to enhance the immune response in a subject infected with a pathogen such as a bacterial, viral, or fungal pathogen, to facilitate destruction of the pathogen in the subject.

Immune deficiencies associated with immune deficiency diseases, immune suppressive medical treatment, acute and/or chronic infection, and aging can be treated using the compounds disclosed herein. Compounds of the invention can be used to stimulate the immune system of patients suffering from medical treatment or iatrogenically induced immune suppression, including those who have undergone bone marrow transplants, chemotherapy, and/or radiotherapy.

In other embodiments, compounds of the invention are used to increase or enhance an immune response to an antigen by providing adjuvant activity. In one embodiment, at least one antigen or vaccine is administered to a subject in conjunction with at least one compound of the invention to prolong an immune response to the antigen or vaccine. Therapeutic compositions are also provided which include at least one antigenic agent or vaccine component, including, but not limited to, viruses, bacteria, and fungi, or portions thereof, proteins, peptides, tumor-specific antigens, and nucleic acid vaccines, in combination with a compound of the invention.

Compounds of the invention can be used as antidepressants, to stimulate cognitive functions, and to improve motor impairment due to neurodegenerative diseases such as Parkinson's disease.

Compounds of the present invention can be used to treat infections, in particular infections caused by pathogens that exploit extonucleotidases in order to generate adenosine-rich environments to escape immune surveillance and infections associated with inflammation. Diseases and disorders treatable with compounds of the invention include infections, including but not limited to, parasitic, fungal, bacterial, and viral infections, including, but not limited to, *Leishmania, Trypanosoma, Toxoplasma, Trichomonas, Giardia, Candida, Legionella pneumophila, Staphylococcus aureus, Bacillus anthracis, Streptococcus sanguinis, Pseudomonas aeruginosa*, and AIDS. Compounds of the invention can be used to treat sepsis, decrease or inhibit bacterial growth, reduce inflammatory cytokine levels, and lessen organ injury.

Further diseases and disorders treatable with compounds of the invention include, but are not limited to, neurological, CNS, respiratory, neurodegenerative, inflammatory, cardiovascular, gastrointestinal, ophthalmologic, connective tissue, and renal diseases and disorders.

Diseases and disorders treatable with compounds of the invention also include, but are not limited to, AIDS, HIV infection, extra pyramidal syndrome (EPS), dystonia, primary (idiopathic) dystonia, akathisia, pseudoparkinsonism, tardive dyskinesia, restless leg syndrome (RLS), periodic limb movement in sleep (PLMS), attention deficit disorders, including attention deficit hyperactivity disorder (ADHD), depression, anxiety, cognitive function diseases, cognitive decline, Parkinson's disease, senile dementia, Alzheimer's disease, Huntington's disease, Wilson's disease, psychiatric disorders, Hallervorden-Spatz disease, progressive pallidal atrophy, cerebral ischemia, hemorrhagic stroke, neonatal ischemia and hypoxia, subarachnoid hemorrhage, traumatic brain injury, cardiac arrest, multiple sclerosis, diabetes, type II diabetes, diabetes mellitus, insulin resistance, risk of diabetes, epilepsy, asthma, chronic obstructive pulmonary disease (COPD), fibrosis, dermal fibrosis, hepatic fibrosis, liver fibrosis, pulmonary fibrosis, idiopathic pulmonary fibrosis, interstitial fibrosis, cystic fibrosis, emphysema, peritoneal fibrosis, cardiac fibrosis, myocardial fibrosis, endomyocardial fibrosis, atrial fibrosis, alcoholic fatty liver disease, fatty liver, hepatic steatosis, cirrhosis, hepatic cirrhosis, nonalcoholic fatty liver disease (NAFLD), nonalcoholic hepatosteatosis (NASH), mediastinal fibrosis, myelofibrosis, retroperitoneal fibrosis, progressive massive fibrosis, nephrogenic systemic fibrosis, Crohn's disease, keloids, hypertrophic scars, scleroderma, systemic sclerosis, arthrofibrosis, Peyronie's disease, priapism, Dupuytren's contracture, adhesive capsulitis, stroke, psychosis, psychoses of organic origin, dry eye disease, keratoconjunctivitis sicca, keratitis sicca, glaucoma, diabetic retinopathy, retinal ischemia, kidney disease, renal failure, and acute renal failure.

In some embodiments, diseases and disorders treatable with compounds of the invention are insulin resistance, diabetes and risk of diabetes. In some embodiments, compounds of the invention are used to reduce insulin resistance, reduce the risk of diabetes, decrease or inhibit statin-induced adenosine production, or reduce or decrease increases in blood glucose caused by a statin in a subject taking a statin. In some embodiments, compounds of the invention are used to treat diabetes in a subject taking a statin or to prevent diabetes in a subject taking a statin. Methods of the invention include decreasing, reducing, inhibiting, suppressing, limiting or controlling in the subject elevated blood glucose levels. In further aspects, methods of the invention include increasing, stimulating, enhancing, promoting, inducing or activating in the subject insulin sensitivity. Statins include, but are not limited to atorvastatin, cerivastatin, fluvastatin, lovastatin, mevastatin, pitavastatin, pravastatin, rousuvastatin and simvastatin.

In one embodiment, a human patient is treated with a compound of the present invention and a pharmaceutically acceptable carrier, adjuvant, or vehicle, wherein said compound is present in an amount to treat or ameliorate one or more of the diseases and conditions recited above.

The invention further relates to a combination therapy for treating or ameliorating a disease or a disorder described herein. In some embodiments, the combination therapy comprises administering at least one compound of the present invention in combination with one or more agents for treating or ameliorating cancer or diseases or disorders mediated by CD73. In some embodiments, the combination therapy comprises administering at least one compound of the present invention in combination with one or more agents for the treatment of cancer, including breast cancer, triple-negative breast cancer, melanoma, renal cell carcinoma, colorectal carcinoma, pancreatic cancer, prostate cancer, ovarian cancer, gastric cancer, leukemia and lymphoma.

The compounds according to the invention may also be used in combination with immunotherapies, including but not limited to cell-based therapies, antibody therapies and cytokine therapies, for the treatment of a disease or disorder disclosed herein.

In certain embodiments, compounds according to the invention are used in combination with one or more passive immunotherapies, including but not limited to naked monoclonal antibody drugs and conjugated monoclonal antibody drugs. Examples of naked monoclonal antibody drugs that can be used include, but are not limited to rituximab (Rituxan®), an antibody against the CD20 antigen; trastuzumab (Herceptin®), an antibody against the HER2 protein; alemtuzumab (Campath), an antibody against the CD52 antigen; cetuximab (Erbitux®), an antibody against the EGFR protein; and bevacizumab (Avastin®) which is an anti-angiogenesis inhibitor of VEGF protein.

Examples of conjugated monoclonal antibodies that can be used include, but are not limited to, radiolabeled antibody ibritumomab tiuxetan (Zevalin®); radiolabeled antibody tositumomab (Bexxar®); and immunotoxin gemtuzumab ozogamicin (Mylotarg®) which contains calicheamicin; BL22, an anti-CD22 monoclonal antibody-immunotoxin conjugate; radiolabeled antibodies such as OncoScint® and ProstaScint®; brentuximab vedotin (Adcetris®); ado-trastuzumab emtansine (Kadcyla®, also called TDM-1).

Further examples of therapeutic antibodies that can be used include, but are not limited to, REOPRO® (abciximab), an antibody against the glycoprotein IIb/IIIa receptor on platelets; ZENAPAX® (daclizumab) an immunosuppressive, humanized anti-CD25 monoclonal antibody; PANOREX™, a murine anti-17-IA cell surface antigen IgG2a antibody; BEC2, a murine anti-idiotype (GD3 epitope) IgG antibody; IMC-C225, a chimeric anti-EGFR IgG antibody; VITAXIN™ a humanized anti-αVβ3 integrin antibody; Campath 1H/LDP-03, a humanized anti CD52 IgG1 antibody; Smart M195, a humanized anti-CD33 IgG antibody; LYMPHOCIDE™, a humanized anti-CD22 IgG antibody; LYMPHOCIDE™ Y-90; Lymphoscan; Nuvion® (against CD3; CM3, a humanized anti-ICAM3 antibody; IDEC-114 a primatized anti-CD80 antibody; IDEC-131 a humanized anti-CD40L antibody; IDEC-151 a primatized anti-CD4 antibody; IDEC-152 a primatized anti-CD23 antibody; SMART anti-CD3, a humanized anti-CD3 IgG; 5G1.1, a humanized anti-complement factor 5 (C5) antibody; D2E7, a humanized anti-TNF-α antibody; CDP870, a humanized anti-TNF-α Fab fragment; IDEC-151, a primatized anti-CD4 IgG1 antibody; MDX-CD4, a human anti-CD4 IgG antibody; CD20-streptdavidin (+biotin-yttrium 90); CDP571, a humanized anti-TNF-α IgG4 antibody; LDP-02, a humanized anti-α4β7 antibody; OrthoClone OKT4A, a humanized anti-CD4 IgG antibody; ANTOVA™, a humanized anti-CD40L IgG antibody; ANTEGREN™, a humanized anti-VLA-4 IgG antibody; and CAT-152, a human anti-TGF-$β_2$ antibody.

In certain embodiments, compounds according to the invention are used in combination with one or more targeted immunotherapies containing toxins but not an antibody, including but not limited to denileukin diftitox (Ontak®), IL-2 linked to diphtheria toxin.

The compounds according to the invention may also be used in combination with adjuvant immunotherapies for the treatment of a disease or disorder disclosed herein. Such adjuvant immunotherapies include, but are not limited to, cytokines, such as granulocyte-macrophage colony-stimulating factor (GM-CSF), granulocyte-colony stimulating factor (G-CSF), macrophage inflammatory protein (MIP)-1-alpha, interleukins (including IL-1, IL-2, IL-4, IL-6, IL-7, IL-12, IL-15, IL-18, IL-21, and IL-27), tumor necrosis factors (including TNF-alpha), and interferons (including IFN-alpha, IFN-beta, and IFN-gamma); aluminum hydroxide (alum); Bacille Calmette-Guérin (BCG); Keyhole limpet hemocyanin (KLH); Incomplete Freund's adjuvant (IFA); QS-21; DETOX; Levamisole; and Dinitrophenyl (DNP), and combinations thereof, such as, for example, combinations of interleukins, for example IL-2, with other cytokines, such as IFN-alpha.

In certain embodiments, compounds according to the invention are used in combination with vaccine therapy, including but not limited to autologous and allogeneic tumor cell vaccines, antigen vaccines (including polyvalent antigen vaccines), dendritic cell vaccines, and viral vaccines.

In another embodiment, the present disclosure comprises administering to a subject with an immunosensitive cancer an effective amount of a compound of the invention and one or more additional anti-cancer therapies selected from: surgery, anti-cancer agents/drugs, biological therapy, radiation therapy, anti-angiogenesis therapy, immunotherapy, adoptive transfer of effector cells, gene therapy or hormonal therapy. Examples of anti-cancer agents/drugs are described below.

In some embodiments, the anti-cancer agents/drug is, for example, adriamycin, aactinomycin, bleomycin, vinblastine, cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride; palbociclib; Yervoy® (ipilimumab); Mekinist™ (trametinib); peginterferon alfa-2b, recombinant interferon alfa-2b; Sylatron™ (peginterferon alfa-2b); Tafinlar® (dabrafenib); Zelboraf® (vemurafenib); or nivolumab.

The compounds according to the present invention can be administered in combination with existing methods of treating cancers, for example by chemotherapy, irradiation, or surgery. Thus, there is further provided a method of treating cancer comprising administering an effective amount of a compound of the invention, or a pharmaceutically acceptable salt form thereof, to a subject in need of such treatment, wherein an effective amount of at least one additional cancer chemotherapeutic agent is administered to the subject. Examples of suitable cancer chemotherapeutic agents include any of: abarelix, ado-trastuzumab emtansine, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, emtansine, epirubicin, eribulin, erlotinib, estramustine, etoposide phosphate, etoposide, everolimus, exemestane, fentanyl citrate, filgrastim, floxuridine, fludarabine, fluorouracil, fruquintinib, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, ixabepilone, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, paclitaxel albumin-stabilized nanoparticle formulation, pamidronate, panitumumab, pegaspargase, pegfilgrastim, pemetrexed disodium, pentostatin, pertuzuma, pipobroman, plicamycin, procarbazine, quinacrine, rasburicase, rituximab, sorafenib, streptozocin, sulfatinib, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, volitinib, vorinostat, and zoledronate.

In particular embodiments, compounds according to the invention are used in combination with one or more anticancer agent selected from methotrexate, paclitaxel albumin-stabilized nanoparticle formulation, ado-trastuzumab emtansine, eribulin, doxorubicin, fluorouracil, everolimus, anastrozole, pamidronate disodium, exemestane, capecitabine, cyclophosphamide, docetaxel, epirubicin, toremifene, fulvestrant, letrozole, gemcitabine, gemcitabine hydrochloride, goserelin acetate, trastuzumab, ixabepilone, lapatinib ditosylate, megestrol acetate, tamoxifen citrate, pamidronate disodium, palbociclib, and pertuzumab for the treatment of breast cancer.

Other anti-cancer agents/drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; andrographolide; angiogenesis inhibitors; antagonist D; antagonist G; antarelix; anti-dorsalizing morphogenetic protein-1; antiandrogen; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors; castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclin-dependent kinase inhibitors; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitors; microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; zanoterone; zilascorb; zinostatin stimalamer; 5-fluorouracil; and leucovorin.

In some embodiments, the anti-cancer agent/drug is an agent that stabilizes microtubules. As used herein, a "microtubulin stabilizer" means an anti-cancer agent/drug which acts by arresting cells in the G2-M phases due to stabilization of microtubules. Examples of microtubulin stabilizers include ACLITAXEL® and Taxol® analogues. Additional examples of microtubulin stabilizers include without limitation the following marketed drugs and drugs in development: Discodermolide (also known as NVP-XX-A-296); Epothilones (such as Epothilone A, Epothilone B, Epothilone C (also known as desoxyepothilone A or dEpoA); Epothilone D (also referred to as KOS-862, dEpoB, and desoxyepothilone B); Epothilone E; Epothilone F; Epothilone B N-oxide; Epothilone A N-oxide; 16-aza-epothilone B; 21-aminoepothilone B (also known as BMS-310705); 21-hydroxyepothilone D (also known as Desoxyepothilone F and dEpoF), 26-fluoroepothilone); FR-182877 (Fujisawa, also known as WS-9885B), BSF-223651 (BASF, also known as ILX-651 and LU-223651); AC-7739 (Ajinomoto, also known as AVE-8063A and CS-39.HCl); AC-7700 (Ajinomoto, also known as AVE-8062, AVE-8062A, CS-39-L-Ser.HCl, and RPR-258062A); Fijianolide B; Laulimalide; Caribaeoside; Caribaeolin; Taccalonolide; Eleutherobin; Sarcodictyin; Laulimalide; Dictyostatin-1; Jatrophane esters; and analogs and derivatives thereof.

In another embodiment, the anti-cancer agent/drug is an agent that inhibits mictotubules. As used herein, a "microtubulin inhibitor" means an anti-cancer agent which acts by inhibiting tubulin polymerization or microtubule assembly. Examples of microtubulin inhibitors include without limitation the following marketed drugs and drugs in development: Erbulozole (also known as R-55104); Dolastatin 10 (also known as DLS-10 and NSC-376128); Mivobulin isethionate (also known as CI-980); Vincristine; NSC-639829; ABT-751 (Abbot, also known as E-7010); Altorhyrtins (such as Altorhyrtin A and Altorhyrtin C); Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9); Cemadotin hydrochloride (also known as LU-103793 and NSC-D-669356); Auristatin PE (also known as NSC-654663); Soblidotin (also known as TZT-1027), LS-4559-P (Pharmacia, also known as LS-4577); LS-4578 (Pharmacia, also known as LS-477-P); LS-4477 (Pharmacia), LS-4559 (Pharmacia); RPR-112378 (Aventis); Vincristine sulfate; DZ-3358 (Daiichi); GS-164 (Takeda); GS-198 (Takeda); KAR-2 (Hungarian Academy of Sciences); SAH-49960 (Lilly/Novartis); SDZ-268970 (Lilly/Novartis); AM-97 (Armad/Kyowa Hakko); AM-132 (Armad); AM-138 (Armad/Kyowa Hakko); IDN-5005 (Indena); Cryptophycin 52 (also known as LY-355703); Vitilevuamide; Tubulysin A; Canadensol; Centaureidin (also known as NSC-106969); T-138067 (Tularik, also known as T-67, TL-138067 and TI-138067); COBRA-1 (Parker Hughes Institute, also known as DDE-261 and WHI-261); H10 (Kansas State University); H16 (Kansas State University); Oncocidin A1 (also known as BTO-956 and DIME); DDE-313 (Parker Hughes Institute); SPA-2 (Parker Hughes Institute); SPA-1 (Parker Hughes Institute, also known as SPIKET-P); 3-IAABU (Cytoskeleton/Mt. Sinai School of Medicine, also known as MF-569); Narcosine (also known as NSC-5366); Nascapine, D-24851 (Asta Medica), A-105972 (Abbott); Hemiasterlin; 3-BAABU (Cytoskeleton/Mt. Sinai School of Medicine, also known as MF-191); TMPN (Arizona State University); Vanadocene acetylacetonate; T-138026 (Tularik); Monsatrol; Inanocine (also known as NSC-698666); 3-IAABE (Cytoskeleton/Mt. Sinai School of Medicine); A-204197 (Abbott); T-607 (Tularik, also known as T-900607); RPR-115781 (Aventis); Eleutherobins (such as Desmethyleleutherobin, Desaetyleleutherobin, Isoeleutherobin A, and Z-Eleutherobin); Halichondrin B; D-64131 (Asta Medica); D-68144 (Asta Medica); Diazonamide A; A-293620 (Abbott); NPI-2350 (Nereus); TUB-245 (Aventis); A-259754 (Abbott); Diozostatin; (−)-Phenylahistin (also known as NSCL-96F037); D-68838 (Asta Medica); D-68836 (Asta Medica); Myoseverin B; D-43411 (Zentaris, also known as D-81862); A-289099 (Abbott); A-318315 (Abbott); HTI-286 (also known as SPA-110, trifluoroacetate salt) (Wyeth); D-82317 (Zentaris); D-82318 (Zentaris); SC-12983 (NCI); Resverastatin phosphate sodium; BPR-0Y-007 (National Health Research Institutes); SSR-250411 (Sanofi); Combretastatin A4; eribulin (Halaven®); and analogs and derivatives thereof.

In further embodiments, compounds according to the invention are used in combination with one or more alkylating agents, antimetabolites, natural products, or hormones.

Examples of alkylating agents useful in the methods of the invention include but are not limited to, nitrogen mustards (e.g., mechloroethamine, cyclophosphamide, chlorambucil, melphalan, etc.), ethylenimine and methylmelamines (e.g., hexamethylmelamine, thiotepa), alkyl sulfonates (e.g., busulfan), nitrosoureas (e.g., carmustine, lomustine, semustine, streptozocin, etc.), or triazenes (decarbazine, etc.).

Examples of antimetabolites useful in the methods of the invention include but are not limited to folic acid analog (e.g., methotrexate), or pyrimidine analogs (e.g., fluorouracil, floxouridine, cytarabine), and purine analogs (e.g., mercaptopurine, thioguanine, pentostatin). Examples of natural products useful in the methods of the invention include but are not limited to vinca alkaloids (e.g., vinblastin, vincristine), epipodophyllotoxins (e.g., etoposide, teniposide), antibiotics (e.g., actinomycin D, daunorubicin, doxorubicin, bleomycin, plicamycin, mitomycin) or enzymes (e.g., L-asparaginase).

Examples of hormones and antagonists useful for the treatment of cancer include but are not limited to adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), and gonadotropin releasing hormone analog (e.g., leuprolide).

Other agents that can be used in combination with the compounds of the invention for the treatment of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), and adrenocortical suppressant (e.g., mitotane, aminoglutethimide). Other anti-cancer agents/drugs that can be used in combination with the compounds of the invention include, but are not limited to, liver X receptor (LXR) modulators, including LXR agonists and LXR beta-selective agonists; aryl hydrocarbon receptor (AhR) inhibitors; inhibitors of the enzyme poly ADP ribose polymerase (PARP), including olaparib, iniparib, rucaparib, veliparib; inhibitors of vascular endothelial growth factor (VEGF) receptor tyrosine kinases, including cediranib; programmed cell death protein 1 (PD-1) inhibitors, including nivolumab (Bristol-Myers Squibb Co.) and pembrolizumab (Merck & Co., Inc.; MK-3475); MEK inhibitors, including cobimetinib; B-Raf enzyme inhibitors, including vemurafenib; cytotoxic T lymphocyte antigen (CTLA-4) inhibitors, including tremelimumab; programmed death-ligand 1 (PD-L1) inhibitors, including MEDI4736 (AstraZeneca); inhibitors of the Wnt pathway; inhibitors of epidermal growth factor receptor (EGFR) including AZD9291 (AstraZeneca), erlotinib, gefitinib, panitumumab, and cetuximab; adenosine A2A receptor inhibitors; adenosine A2B receptor inhibitors; and Wnt pathway inhibitors.

The compounds of the invention can be used in combination with one or more therapeutic strategies including immune checkpoint inhibitors, including inhibitors of PD-1 and CTLA-4.

In some embodiments, the compounds of the invention can be used in combination with one or more agent that activates, enhances or agonizes the retinoic acid receptor-related orphan receptor gamma (RORγ) for treating or ameliorating cancer or diseases or disorders mediated by CD73. In some embodiments, the combination therapy comprises administering at least one compound of the present invention in combination with one or more RORγ agonist for the treatment of cancer, including breast cancer, triple-negative breast cancer, melanoma, renal cell carcinoma, colorectal cancer, pancreatic cancer, prostate cancer, ovarian cancer, gastric cancer, leukemia and lymphoma.

Compounds of the invention can be used in combination with one or more other agents or therapies for the treatment of Parkinson's disease, including, but not limited to, adenosine A2A receptors antagonists such as ATL-444, istradefylline (KW-6002), MSX-3, preladenant (SCH-420814), SCH-58261, SCH-412348, SCH-442416, ST-1535, caffeine, VER-6623, VER-6947, VER-7835, vipadenant (BIIB-014), ZM-241385, ASP5854, and tozadenant (SYN115); dopamine; L-dopa (levodopa); DOPA decarboxylase (DDC) inhibitors such as carbidopa; levodopa combined with carbidopa (Sinemet®, Atamet®); dopamine agonists such as pramipexole (Mirapex®), ropinirole (Requip®), rotigotine (Neupro®), and apomorphine (Apokyn®); monoamine oxidase B (MAO-B) inhibitors, including selegiline (Eldepryl®, Zelapar®) and rasagiline (Azilect®); catechol O-methyltransferase (COMT) inhibitors, including Entacapone (Comtan®) and tolcapone (Tasmar®); anticholinergics, including benztropine (Cogentin®) and trihexyphenidyl; amantadine; and deep brain stimulation.

In some embodiments, the combination therapy comprises administering at least one compound of the invention in combination with one or more compound selected from the group of, for example, beta secretase (BACE1) inhibitors; gamma-secretase inhibitors; amyloid aggregation inhibitors (e.g., ELND-005); directly or indirectly acting neuroprotective and/or disease-modifying substances; anti-oxidants (e.g., vitamin E or ginkolide); anti-inflammatory substances (e.g., Cox inhibitors, NSAIDs); HMG-CoA reductase inhibitors (statins); acetylcholinesterase inhibitors (e.g., donepezil, rivastigmine, tacrine, galantamine, memantine; tacrine); NMDA receptor antagonists (e.g., memantine); AMPA receptor agonists; AMPA receptor positive modulators, AMPAkines, monoamine receptor reuptake inhibitors, substances modulating the concentration or release of neurotransmitters; substances inducing the secretion of growth hormone (e.g., ibutamoren mesylate and capromorelin); CB-1 receptor antagonists or inverse agonists; antibiotics (e.g., minocyclin or rifampicin); PDE2, PDE4, PDE5, PDE9, PDE10 inhibitors, GABAA receptor inverse agonists, GABAA receptor antagonists, nicotinic receptor agonists or partial agonists or positive modulators, alpha4beta2 nicotinic receptor agonists or partial agonists or positive modulators, alpha7 nicotinic receptor agonists or partial agonists or positive modulators; histamine H3 antagonists, 5 HT-4 agonists or partial agonists, 5HT-6 antagonists, alpha2-adrenoreceptor antagonists, calcium antagonists, muscarinic receptor M1 agonists or partial agonists or positive modulators, muscarinic receptor M2 antagonists, muscarinic receptor M4 antagonists, metabotropic glutamate-receptor 5 positive modulators, antidepressants, such as citalopram, fluoxetine, paroxetine, sertraline and trazodone; anxiolytics, such as lorazepam and oxazepam; antiphychotics, such as aripiprazole, clozapine, haloperidol, olanzapine, quetiapine, risperidone and ziprasidone, and other substances that modulate receptors or enzymes in a manner such that the efficacy and/or safety of the compounds according to the invention is increased and/or unwanted side effects are reduced.

Combination therapy includes e.g., co-administration of a compound of the invention and one or more other pharmaceutically active agent; sequential administration of a compound of the invention and one or more other agent; administration of a composition containing a compound of the invention and one or more other agent; or simultaneous administration of separate compositions containing a compound of the invention and one or more other agent.

The invention further provides a method of treating a subject, such as a human, suffering from one of the above-mentioned disorders or diseases.

The invention further relates to the use of provided compounds for the production of pharmaceutical compositions which are employed for the treatment and/or prophylaxis and/or amelioration of the diseases and disorders mentioned herein.

Compounds or compositions described herein may be administered using any amount and any route of administration effective for treating or lessening the severity of one or more of the diseases and conditions described herein. The exact amount required will vary from subject to subject, depending on the species, age, and general condition of the subject, the severity of the infection, disease or disorder, the particular agent, its mode of administration, and the like. Provided compounds are preferably formulated in unit dosage form for ease of administration and uniformity of dosage. The expression "unit dosage form" as used herein refers to a physically discrete unit of agent appropriate for the patient to be treated. It will be understood, however, that the total daily usage of the compounds and compositions of the present disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this disclosure can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, provided compounds may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

The term "biological sample", as used herein, includes, without limitation, cell cultures or extracts thereof, biopsied material obtained from a mammal or extracts thereof, and blood, saliva, urine, feces, semen, tears, or other body fluids or extracts thereof.

The amount of both a compound of the invention and an additional therapeutic agent (in those compositions which comprise an additional therapeutic agent as described above) that may be combined with the carrier materials to produce a single dosage form will vary depending upon the host treated and the particular mode of administration.

In those compositions which comprise an additional therapeutic agent, that additional therapeutic agent and the provided compound may act synergistically. Therefore, the amount of additional therapeutic agent in such compositions will be less than that required in a monotherapy utilizing only that therapeutic agent.

The amount of additional therapeutic agent present in the compositions of this disclosure will be no more than the amount that would normally be administered in a composition comprising that therapeutic agent as the only active agent.

EXAMPLES

As depicted in the Examples below, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Microwave reactions were carried out in CEM reactor using discovery SP system. Where NMR data are presented, spectra were obtained in Varian-400 (400 MHz). Spectra are reported as ppm downfield from tetramethylsilane with number of proton, multiplicities and, in certain instances, coupling constants indicated parenthetically along with reference to deuterated solvent. Compounds were also purified by ISCO flash chromatography system utilizing standard methods described in the manual.

Compounds were purified by the acidic preparative HPLC methods described below.

RP HPLC Method A:

Mobile phase A: water with 0.1% TFA; Mobile phase B: ACN with 0.1% TFA; Flow rate: 20 mL/min; Detection: UV 220 nm/254 nm; Column: Luna 5µ $C_{18}$ (2) 250×21.20 mm column; Column temperature: 30° C.

| Time in min | % A | % B |
| --- | --- | --- |
| 0.0 | 90 | 10 |
| 3.5 | 90 | 10 |
| 12.20 | 50 | 50 |
| 14.5 | 10 | 90 |
| 13.7 | 90 | 10 |

RP HPLC Method B:

Mobile phase A: water with 0.1% TFA; Mobile phase B: ACN with 0.1% TFA; Flow rate: 25 mL/min; Detection: UV 220 nm/254 nm; Column: C-18 Synergi Max-RP 150*30 mm*4 µm; Column temperature: 30° C.

| Time in min | % A | % B |
| --- | --- | --- |
| 0.0 | 90 | 10 |
| 12.00 | 60 | 40 |
| 12.20 | 10 | 90 |
| 13.5 | 90 | 10 |

LCMS data were obtained by utilizing the following chromatographic conditions:

LCMS Method 1

HPLC System: Waters ACQUITY; Column: Waters ACQUITY CSH™ C18 1.7 µM. Guard column: Waters Assy. Frit, 0.2 µM, 2.1 mm; Column tem: 40° C.

Mobile Phase: A: TFA: Water (1:1000, v:v) Mobile phase B: TFA: ACN (1:1000, v:v); Flow Rate: 0.65 mL/min; Injection Volume: 2 µL; Acquisition time: approximately 1.5 minute.

| Gradient Program | |
|---|---|
| Time (min) | B % |
| 0 | 10 |
| 2.0 | 90 |
| 2.20 | 10 |

Mass Spectrometer: Waters SQD; Ionization: Positive Electrospray Ionization (ESI); Mode Scan (100-1400 m/z in every 0.2 second); ES Capillary Voltage: 3.5 kV; ES Cone Voltage: 25 v.

Source Temperature: 120° C.; Desolvation Temperature: 500° C.; Desolvation Gas Flow: Nitrogen Setting 650 (L/h); Cone Gas Flow: Nitrogen Setting 50 (L/h).

LCMS Method 2

HPLC system: HPLC System: Waters ACQUITY; Column: Waters ACQUITY CSH™ C18 1.7 µM. Guard column: Waters Assy. Frit, 0.2 µM, 2.1 mm; Column temp: 40° C.

Mobile Phase: A—Formic Acid:Water (1:1000, v:v); Mobile Phase B—Formic Acid:ACN (1:1000, v:v).

| Gradient Program | |
|---|---|
| Time (min) | B % |
| 0 | 5 |
| 4.8 | 95 |
| 5.0 | 95 |
| 5.21 | 5 |

Flow Rate: 0.65 mL/min; Injection Volume: 2 µL; Acquisition time: approximately 5.5 minute.

Mass Spectrometer: Waters SQD; Ionization: Positive Electrospray Ionization (ESI); Mode Scan (100-1400 m/z in every 0.2 second); ES Capillary Voltage: 3.5 kV; ES Cone Voltage: 25 v. Source Temperature: 120° C.; Desolvation Temperature: 500° C.; Desolvation Gas Flow: Nitrogen Setting 650 (L/h); Cone Gas Flow: Nitrogen Setting 50 (L/h).

LCMS Method 3

HPLC system: HPLC System: Waters ACQUITY; Column: Waters ACQUITY CSH™ C18 1.7 µM. Guard column: Waters Assy. Frit, 0.2 µM, 2.1 mm; Column temp: 40° C.

Mobile Phase: A—Formic Acid:Water (1:1000, v:v); Mobile Phase B—Formic Acid:ACN (1:1000, v:v).

| Gradient Program | |
|---|---|
| Time (min) | B % |
| 0 | 5 |
| 5 | 15 |
| 15.0 | 95 |
| 15.2 | 5 |

Flow Rate: 0.65 mL/min; Injection Volume: 2 µL; Acquisition time: approximately 15.2 minute.

Mass Spectrometer: Waters SQD; Ionization: Positive Electrospray Ionization (ESI); Mode Scan (100-1400 m/z in every 0.2 second); ES Capillary Voltage: 3.5 kV; ES Cone Voltage: 25 v. Source Temperature: 120° C.; Desolvation Temperature: 500° C.; Desolvation Gas Flow: Nitrogen Setting 650 (L/h); Cone Gas Flow: Nitrogen Setting 50 (L/h).

The racemic compounds were separated by the following supercritical fluid chromatography methods.

Method A

Instrument: Thar SFC 80; Column: AD 250 mm*30 mm, 5 µm; Mobile phase: A: Supercritical $CO_2$, B: IPA (0.05% DEA), A: B=80:20 at 60 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm.

Method B:

Instrument: SFC MG2; Column: OJ 250 mm*30 mm, 5 µm; Mobile phase: A: Supercritical $CO_2$, B: MeOH (0.05% DEA), A:B=90:10 at 70 mL/min; Column Temp: 38° C.; Nozzle Pressure: 100 Bar Nozzle Temp: 60° C.; Evaporator Temp: 20° C.; Trimmer Temp: 25° C.; Wavelength: 220 nm.

The invention is illustrated by the following examples, in which the following abbreviations may be employed:

| Abbreviation | Meaning |
|---|---|
| ACN | Acetonitrile |
| Al(Me)$_3$ | Trimethyl aluminium |
| Boc$_2$O | Tert butoxy carbonyl anhydride |
| BzCl | Benzoyl chloride |
| brine | Saturated aqueous NaCl |
| CbzOSu | Carbobenzyloxysuccinate |
| DCM | Methylene chloride (dichloromethane) |
| DIEA | Diisopropylethyl amine |
| DMA | Dimethyl acetamide |
| DMF | Dimethyl formamide |
| dppf | 1,1-Bis(diphenylphosphino)ferrocene |
| Et$_3$N | Triethylamine |
| EtOAc | Ethyl acetate |
| EtOH | Ethanol |
| gm | Gram |
| h | Hour(s) |
| HATU | 1-[Bis(dimethylamino)methylene]-1H-1,2,3-triazolo[4,5-b]pyridinium 3-oxid hexafluorophosphate |
| HBTU | 2-(1H-Benzotriazole-1-yl)-1,1,3,3-tetramethyluronium hexafluorophosphate |
| HPLC | High performance liquid chromatography |
| Im | Imidazole |

-continued

| Abbreviation | Meaning |
|---|---|
| LiHMDS | Lithium hexadimethylsilane |
| LCMS | Liquid chromatography-mass spectrometry |
| min | Minute(s) |
| MeNH$_2$•HCl | Methyl amine hydrocholoride |
| MeOH | Methanol |
| MeI | Methyl iodide |
| Me | Methyl |
| mL | Milliliters |
| mmol | Millimoles |
| mg | Milligram |
| NaHMDS | Sodium hexamethyldisilazide |
| NaOMe | Sodium methoxide |
| p-ABSA | Para-acetamido-benzenesulfonyl azide |
| Pd(OAc)$_2$ | Palladium (II) acetate |
| PdCl$_2$(PPh$_3$)$_2$ | Bistriphenylphosphine dichloropalladium(ii) |
| PdCl$_2$dppf | [1,1-bis(diphenylphosphino)ferrocene] dichloropalladium(ii) |
| Pd(PPh$_3$)$_4$ | Triphenylphosphine terakis palladium (0) |
| Prep-TLC | Preparative thin layer chrmatography |
| Rh$_2$(OAc)$_4$ | Rhodium(II) acetate dimer |
| RP | Reverse phase |
| RT | Room temperature |
| SFC | Super critical fluid chromatography |
| $t_R$ | Retention time in LCMS |
| t-BuOK | Potassium tert butoxide |
| TBAF | Tetra butyl ammonium fluoride |
| TBDMS | tert Butyl dimethyl silyl |
| TBDMSCl | tert Butyl dimethyl silyl chloride |
| TBDPSCl | tert Butyl diphenyl silyl chloride |
| TEA | Triethylamine |
| TFA | Trifluoroacetic acid |
| THF | Tetrahydrofuran |
| TLC | Thin layer chromatography |
| TMSBr | Bromo trimethylsilane |
| TsN3 | Tosyl azide |
| v | Volume |
| XPhos | Dicyclohexyphosphino-2',4',6'-triiso-propyl-1,1'-biphenyl |
| ZnMeCl | Methyl chlorozinc |

Example 1, Isomer 1: ((R)-1-(((2R,3S,4R,5R)-5-(6-amino-2-chloro-9H-purin-9-yl)-3,4-dihydroxytetra-hydrofuran-2-yl)methoxy)-2-ethoxy-2-oxoethyl) phosphonic Acid and Example 1, Isomer 2: ((S)-1-(((2R,3S,4R,5R)-5-(6-amino-2-chloro-9H-purin-9-yl)-3,4-dihydroxytetra-hydrofuran-2-yl)methoxy)-2-ethoxy-2-oxoethyl) phosphonic Acid Example 1, Isomer 1

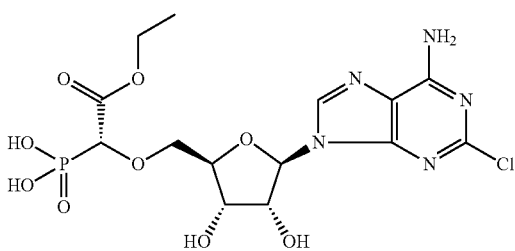 [SMILES: CCOC(=O)C(OC[C@H]1O[C@@H](n2cnc3c(N)nc(Cl)nc32)[C@H](O)[C@@H]1O)P(=O)(O)O]

Example 1, Isomer 2

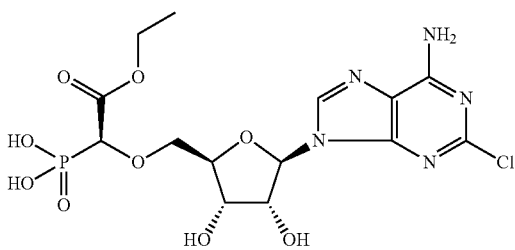 [SMILES: CCOC(=O)[C@@H](OC[C@H]1O[C@@H](n2cnc3c(N)nc(Cl)nc32)[C@H](O)[C@@H]1O)P(=O)(O)O]

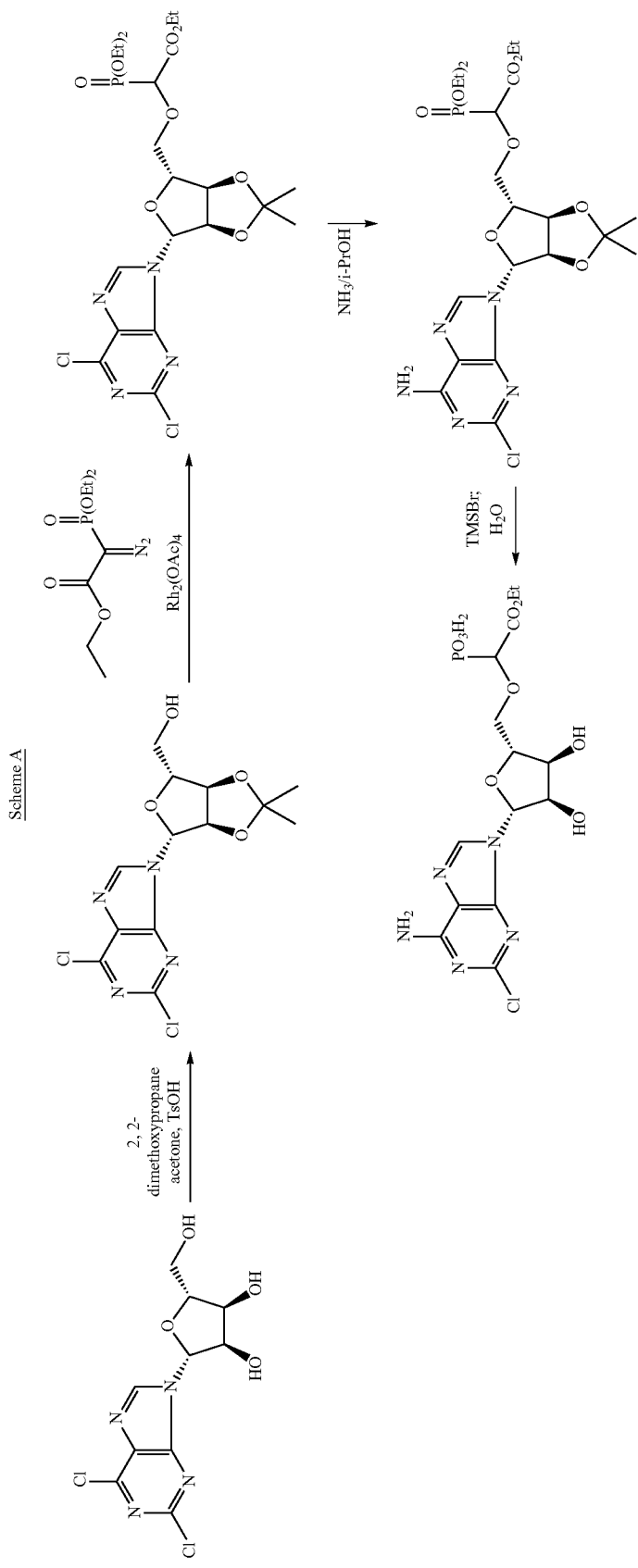

Step 1: ((3aR,4R,6R,6aR)-6-(2,6-dichloro-9H-purin-9-yl)-2,2-dimethyltetrahydrofuro[3,4-d][1,3]dioxol-4-yl)methanol A mixture of (2R,3R,4S,5R)-2-(2,6-dichloro-9H-purin-9-yl)-5-(hydroxymethyl)-tetrahydrofuran-3,4-diol (15.05 g, 46.9 mmol, Chemshuttle, USA, Cat #417), 2,2-dimethoxypropane (60 mL), and p-toluenesulfonic acid monohydrate (11.16 g) in acetone (460 mL) was stirred at RT for 16 h. Sodium bicarbonate (15.56 g) and water (300 mL) were added and stirred for 2 h. The resulting mixture was extracted with ethyl acetate (3×500 mL). The combined organic phase was dried over $Na_2SO_4$ and solvents were evaporated under reduced pressure. The residue was purified by chromatography on silica gel (330 g column eluted with 0→4% methanol in DCM over 60 min) to afford 15.93 g (94%) of ((3aR,4R,6R,6aR)-6-(2,6-dichloro-9H-purin-9-yl)-2,2-dimethyltetrahydrofuro[3,4-d][1,3]dioxol-4-yl)methanol as a solid. LCMS Method 1: $t_R$=1.21 min, m/z 361, 363 (MH$^+$).

Step 2: ethyl 2-(((3aR,4R,6R,6aR)-6-(2,6-dichloro-9H-purin-9-yl)-2,2-dimethyltetrahydrofuro[3,4-d][1,3]dioxol-4-yl)methoxy)-2-(diethoxyphosphoryl)acetate To a solution of ((3aR,4R,6R,6aR)-6-(2,6-dichloro-9H-purin-9-yl)-2,2-dimethyltetrahydrofuro[3,4-d][1,3]dioxol-4-yl)methanol (8.63 g, 23.9 mmol 1) and ethyl 2-diazo-2-(diethoxyphosphoryl)acetate (8.59 g, 34.3 mmol) in benzene (400 mL) was added 0.1030 g (0.233 mmol) of rhodium acetate dimer. The reaction mixture was degassed and then heated at 100° C. and stirred at that temperature for 18 h under nitrogen. The solution was cooled to RT, the solvent was evaporated under reduced pressure, the residue was purified by chromatography on silica gel (330 g column eluted with 30 to 80% ethyl acetate/hexanes over 60 min) to give 10.86 g (78%) of ethyl 2-(((3aR,4R,6R,6aR)-6-(2,6-dichloro-9H-purin-9-yl)-2,2-dimethyltetrahydrofuro[3,4-d][1,3]dioxol-4-yl)methoxy)-2-(diethoxyphosphoryl)acetate. LCMS Method 1: $t_R$=1.52 min, m/z 583, 585 (MH$^+$).

Step 3: ethyl 2-(((3aR,4R,6R,6aR)-6-(6-amino-2-chloro-9H-purin-9-yl)-2,2-dimethyltetrahydrofuro[3,4-d][1,3]dioxol-4-yl)methoxy)-2-(diethoxyphosphoryl)acetate To a solution of ethyl 2-(((3aR,4R,6R,6aR)-6-(2,6-dichloro-9H-purin-9-yl)-2,2-dimethyltetrahydrofuro[3,4-d][1,3]dioxol-4-yl)methoxy)-2-(diethoxyphosphoryl)acetate (4.97 g, 8.5 mmol) in dry THF (250 mL) was added 150 mL of 2.0 M ammonia in 2-propanol. The reaction mixture was vigorously stirred at RT for 3 d. The solvents were removed under reduced pressure at RT, the residue was purified by chromatography on silica gel (330 g column eluted with 0 to 5% methanol in DCM over 60 min) to afford 4.19 g (87%) of ethyl 2-(((3aR,4R,6R,6aR)-6-(6-amino-2-chloro-9H-purin-9-yl)-2,2-dimethyltetrahydrofuro[3,4-d][1,3]dioxol-4-yl)methoxy)-2-(diethoxyphosphoryl)acetate, which was further purified by reverse-phase HPLC (Phenomenex® Luna 5μ $C_{18}$ (2) 250×21.20 mm column, 10% $CH_3CN/H_2O$, 0.1% $CF_3COOH$ over 1.5 min, 10% to 90% $CH_3CN/H_2O$, 0.1% $CF_3COOH$ over 12 min, and then 90% $CH_3CN/H_2O$, 0.1% $CF_3COOH$ over 4 min, flow rate 20 mL/min) to give ethyl 2-(((3aR,4R,6R,6aR)-6-(6-amino-2-chloro-9H-purin-9-yl)-2,2-dimethyltetrahydrofuro[3,4-d][1,3]dioxol-4-yl)methoxy)-2-(diethoxyphosphoryl)acetate as TFA salt. LCMS Method 1: $t_R$=1.26 min, m/z 564, 566 (MH$^+$).

Step 4: (1-(((2R,3S,4R,5R)-5-(6-amino-2-chloro-9H-purin-9-yl)-3,4-dihydroxytetrahydrofuran-2-yl)methoxy)-2-ethoxy-2-oxoethyl)phosphonic Acid To a solution of ethyl 2-(((3aR,4R,6R,6aR)-6-(6-amino-2-chloro-9H-purin-9-yl)-2,2-dimethyltetrahydrofuro[3,4-d][1,3]dioxol-4-yl)methoxy)-2-(diethoxyphosphoryl)acetate TFA salt (2.57 g, 3.79 mmol) in dry $CH_3CN$ (80 mL) was added 8 mL of bromotrimethylsilane. The reaction mixture was stirred at RT for 22 h and then quenched with 12 mL of water and allowed to stir at RT for 4 h. The reaction mixture was treated with 12 mL of ammonium hydroxide. After an additional 2 h, the solvents were removed under reduced pressure at RT to give 8.82 g of crude product, which was purified by reverse-phase HPLC (Phenomenex® Luna 5μ $C_{18}$ (2) 250×21.20 mm column, 10% $CH_3CN/H_2O$, 0.1% $CF_3COOH$ over 3.5 min, 10% to 50% $CH_3CN/H_2O$, 0.1% $CF_3COOH$ over 12 min, 50% to 90% $CH_3CN/H_2O$, 0.1% $CF_3COOH$ over 0.5 min, and then 90% $CH_3CN/H_2O$, 0.1% $CF_3COOH$ over 2 min, flow rate 20 mL/min) to separate two diastereomers, and the more polar isomer (believed to be the R isomer; Isomer 1) 0.69 g (31%) and the less polar isomer (believed to be the S isomer; Isomer 2) 0.85 g (38%) were isolated.

More polar isomer (Isomer 1): LCMS Method 3: $t_R$=1.42 min, m/z 468, 470 (MH$^+$); $^1$H NMR ($D_2O$, 400 MHz) δ 9.00 (s, 1H), 5.92 (d, J=4.1 Hz, 1H), 4.57 (t, J=4.5 Hz, 1H), 4.41 (t, J=5.0 Hz, 1H), 4.29 (d, J=18.2 Hz, 1H), 4.22-4.20 (m, 1H), 4.09 (q, J=7.2 Hz, 2H), 3.88 (dd, J=11.1, 2.3 Hz, 1H), 3.72 (dd, J=11.1, 3.2 Hz, 1H), 1.09 (t, J=7.2 Hz, 3H); $^{31}$P NMR ($D_2O$, 162 MHz) δ 9.48 (s).

Less polar isomer (Isomer 2): LCMS Method 3: $t_R$=1.79 min, m/z 468, 470 (MH$^+$); $^1$H NMR ($D_2O$, 400 MHz) δ 9.26 (s, 1H), 5.96 (d, J=3.8 Hz, 1H), 4.58 (t, J=4.4 Hz, 1H), 4.42 (t, J=5.0 Hz, 1H), 4.27 (d, J=18.2 Hz, 1H), 4.24-4.22 (m, 1H), 4.13 (q, J=7.2 Hz, 2H), 3.87 (dd, J=11.0, 2.2 Hz, 1H), 3.70 (dd, J=10.8, 2.3 Hz, 1H), 1.11 (t, J=7.2 Hz, 3H); $^{31}$P NMR ($D_2O$, 162 MHz) δ 9.21 (s).

Example 2: (2-(((2R,3S,4R,5R)-5-(2-chloro-6-(methylamino)-9H-purin-9-yl)-3,4-dihydroxytetrahydrofuran-2-yl)methoxy)-2-methylmalonic Acid)

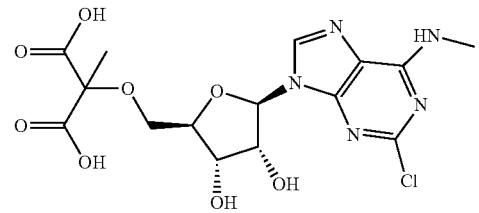 [SMILES: CNc1nc(Cl)nc2c1ncn2[C@@H]1O[C@H](COC(C)(C(=O)O)C(=O)O)[C@@H](O)[C@H]1O]

Scheme B

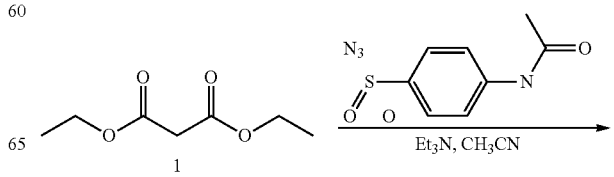

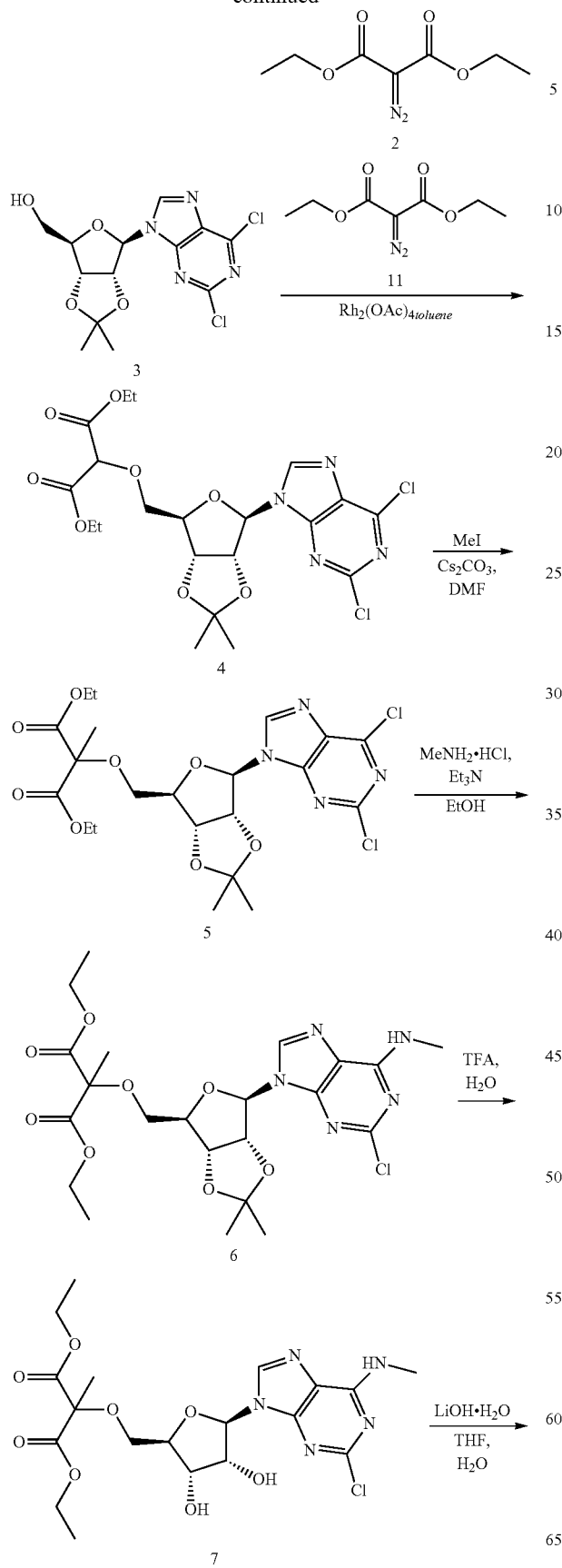

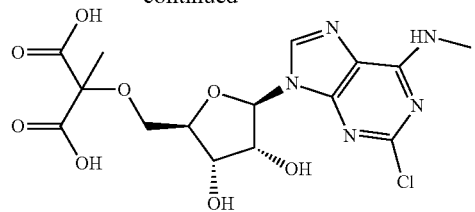

Example 2: Step 1. Diethyl 2-diazomalonate (2)

p-ABSA (899 mg, 3.75 mmol) and Et$_3$N (472 mg, 79.5 mmol) were added to a solution of diethyl malonate (500 mg, 3.12 mmol) in ACN (10 mL) and stirred at RT for 14 h. After which time, the reaction mixture was filtered and the filtrate was concentrated in vacuo and purified by column chromatography on silica gel (petroleum ether:ethyl acetate=10:1) to give diethyl 2-diazomalonate (2) as a yellow oil (400 mg). $^1$H NMR: (CDCl3): δ 4.24-4.34 (m, 4H), 1.28-1.33 (t, J=7.2 Hz, 3H).

Step 2: Diethyl 2-(((3aR,4R,6R,6aR)-6-(2,6-dichloro-9H-purin-9-yl)-2,2-dimethyltetrahydrofuro[3,4-d][1,3]dioxol-4-yl)methoxy)malonate (4)

Compound 2 (500 mg, 2.68 mmol) and Rh$_2$(OAc)$_4$ (88.2 mg, 0.2 mmol) were added to a solution of ((3aR,4R,6R,6aR)-6-(2,6-dichloro-9H-purin-9-yl)-2,2-dimethyltetrahydrofuro[3,4-d][1,3]dioxol-4-yl)methanol (3) (742 mg, 2.06 mmol) in toluene (10 mL) under a N$_2$ atmosphere and stirred overnight at 95-100° C. under N$_2$. The reaction mixture was concentrated in vacuo to dryness and the residue was purified by column chromatography on silica gel (petroleum ether:ethyl acetate=10:1 to 1:1) to give compound 4 as a colorless oil (530 mg). $^1$H NMR: (CDCl$_3$): δ 8.83 (s, 1H), 6.31-6.32 (d, J=3.2 Hz, 1H), 5.20-5.23 (m, 1H), 5.10-5.15 (m, 1H), 4.58-4.59 (m, 1H), 4.49 (s, 1H), 4.24-4.30 (m, 4H), 3.80-3.90 (d, J=2.0 Hz, 1H), 3.65-3.75 (m, 1H), 1.65 (s, 3H), 1.43 (s, 3H), 1.25-1.31 (m, 6H).

Step 3: Diethyl 2-(((3aR,4R,6R,6aR)-6-(2,6-dichloro-9H-purin-9-yl)-2,2-dimethyltetrahydrofuro[3,4-d][1,3]dioxol-4-yl)methoxy)-2-methylmalonate (5)

To a solution of compound 4 (50 mg, 0.096 mmol) in DMF (3 mL) was added Cs$_2$CO$_3$ (62.9 mg, 0.19 mmol) and the reaction was stirred at RT for 30 min. MeI (27.2 mg, 0.19 mmol) was added at RT and the reaction was stirred for 16 h, after which time, water (10 mL) was added. The product was extracted with EtOAc (10 mL×3). The combined organic layers were washed with brine (15 mL), dried over anhydrous Na$_2$SO$_4$, filtered, concentrated and purified by chromatography column on silica gel (petroleum ether:ethyl acetate=10:1 to 2:1) to afford compound 5 as an oil (45 mg). $^1$H NMR: (CDCl$_3$): δ 8.83 (s, 1H), 6.29-6.31 (d, J=3.2 Hz, 1H), 5.17-5.19 (m, 1H), 5.09-5.12 (m, 1H), 4.58-4.59 (d, J=1.6 Hz, 1H), 4.15-4.30 (m, 4H), 3.83-3.84 (m, 1H), 3.68-3.69 (m, 1H), 2.0 (s, 3H), 1.66 (s, 3H), 1.30 (s, 3H), 1.22-1.28 (m, 6H).

Step 4: Diethyl 2-(((3aR,4R,6R,6aR)-6-(2-chloro-6-(methylamino)-9H-purin-9-yl)-2,2-dimethyltetrahydrofuro[3,4-d][1,3]dioxol-4-yl)methoxy)-2-methylmalonate (6)

To a solution of compound 5 (100 mg, 0.19 mmol) in EtOH (2 mL) was added MeNH$_2$.HCl (19 mg, 0.28 mmol)

and TEA (38.4 mg, 0.38 mmol) and the reaction was stirred at RT for 16 h. It was concentrated and crude material was directly purified by silica gel chromatography on (petroleum ether:ethyl acetate=10:1 to 2:1) to afford compound 6 as an oil (70 mg). $^1$H NMR: (CDCl$_3$): δ 8.26 (s, 1H), 6.19-6.21 (d, J=3.2 Hz, 1H), 5.90-6.00 (m, 1H), 5.12-5.17 (m, 2H), 4.45-4.55 (m, 1H), 4.15-4.35 (m, 4H), 3.84-3.88 (m, 1H), 3.70-3.73 (m, 1H), 3.16 (s, 3H), 1.60-1.63 (m, 3H), 1.38 (s, 3H), 1.22-1.29 (m, 6H).

Step 5: (Diethyl 2-(((2R,3S,4R,5R)-5-(2-chloro-6-(methylamino)-9H-purin-9-yl)-3,4-dihydroxytetrahydrofuran-2-yl)methoxy)-2-methylmalonate) (7)

To a solution of compound 6 (100 mg, 0.19 mmol) in TFA (2 mL) and DCM (1 mL) was added H$_2$O (1 mL). The resulting mixture was stirred at RT for 2 h. The reaction mixture was concentrated in vacuo to dryness to afford residue. The residue was purified by column chromatography on silica gel (petroleum ether:ethyl acetate=10:1 to 1:1) to give compound 7 as a white solid (28.6 mg). LCMS Method 2: $t_R$=2.81 min, m/z=488.0/490.0 ((M+H)$^+$ chlorine isotopes). $^1$H NMR: (CD$_3$OD): δ 8.54 (s, 1H), 6.02-6.38 (d, J=5.4 Hz, 1H), 4.68-4.70 (t, J=4.8 Hz, 1H), 4.39-4.40 (m, 1H), 4.23-4.39 (m 5H), 3.81-3.82 (m, 1H), 3.74-3.76 (m, 1H), 3.07 (s, 2H), 1.69 (s, 3H), 1.22-1.29 (m, 6H).

Step 6: (Example 2) (2-(((2R,3S,4R,5R)-5-(2-chloro-6-(methylamino)-9H-purin-9-yl)-3,4-dihydroxytetrahydrofuran-2-yl)methoxy)-2-methylmalonic Acid)

To a solution of crude compound 7 (diethyl 2-(((2R,3S, 4R,5R)-5-(2-chloro-6-(methylamino)-9H-purin-9-yl)-3,4-dihydroxytetrahydrofuran-2-yl)methoxy)-2-methylmalonate) (80 mg, crude) in THF (2 mL) and H$_2$O (2 mL) was added LiOH.H$_2$O (11.33 mg, 0.49 mmol). The mixture was stirred at RT for 16 h. The reaction mixture was adjusted to pH=6 by 4M HCl, The reaction mixture was concentrated in vacuo to dryness to afford crude product as an oil. The residue was purified by RP HPLC Method B to afford the title compound as a white solid (12.5 mg). LCMS Method 3: $t_R$=2.71 min, m/z=432.1/434.1 ((M+H)$^+$ chlorine isotopes). $^1$H NMR: (CD$_3$OD): δ 8.59 (s, 1H), 5.98-6.00 (d, J=4.0 Hz, 1H), 4.63-4.67 (t, J=4.8 Hz, 1H), 4.40-4.50 (m, 1H), 4.20-4.25 (d, J=3.6 Hz, 1H), 3.81-3.86 (m, 1H), 3.72-3.76 (m, 1H), 3.06 (s, 3H), 1.59 (s, 3H).

Example 3: 2-(((2R,3S,4R,5R)-5-(6-amino-2-chloro-9H-purin-9-yl)-3,4-dihydroxytetrahydrofuran-2-yl)methoxy)malonic acid

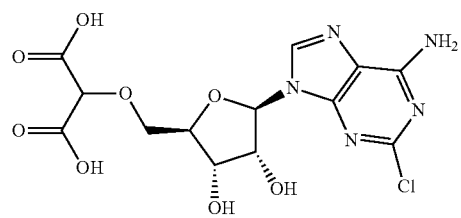 [SMILES: Nc1nc(Cl)nc2c1ncn2[C@@H]1O[C@H](COC(C(=O)O)C(=O)O)[C@@H](O)[C@H]1O]

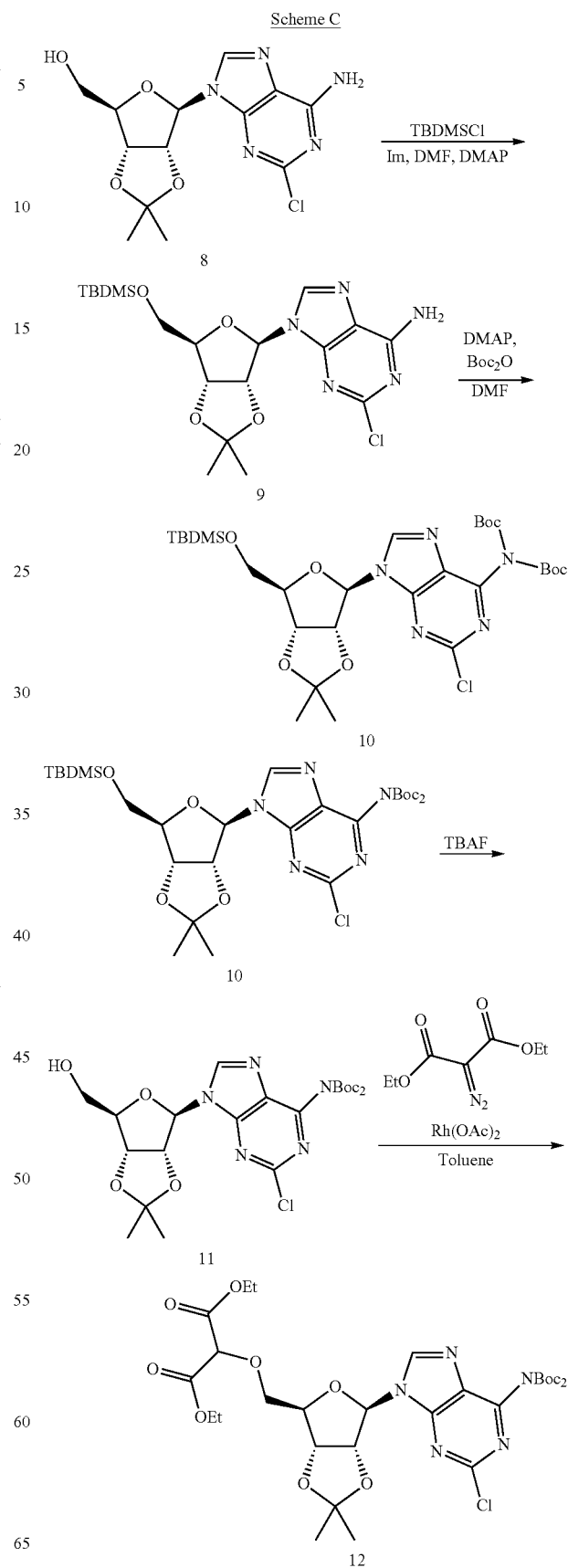

Scheme C

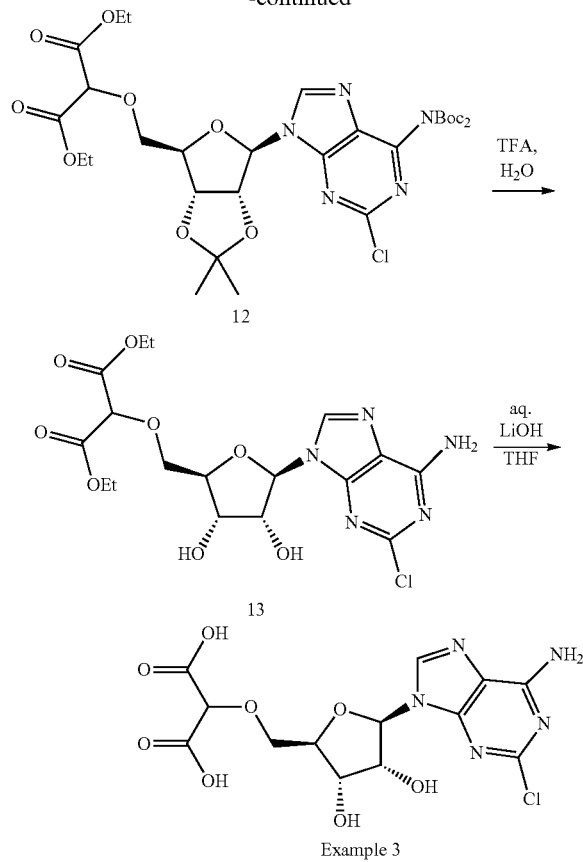

Example 3

Step 1. 5'-O-tert-butyldimethylsilyl-2'-3'-O-isopropylidene-2-chloro-adenosine (9)

Imidazole (57.1 mmol) was added in one portion to ((3aR,4R,6R,6aR)-6-(6-amino-2-chloro-9H-purin-9-yl)-2,2-dimethyltetrahydrofuro[3,4-d][1,3]dioxol-4-yl)methanol (22.9 mmol) in dry DMF (70 mL) under an argon atmosphere at 0° C. Then TBDMSCl (27.4 mmol) was added in portions over 30 min and the mixture was stirred for 2 h at 0° C. and overnight at RT. The reaction mixture was evaporated in vacuo and the resulting solid was taken up in 2:1 ethyl acetate/water (300 mL). The aqueous layer was extracted with EtOAc (100 mL) and the combined organic layers were washed with water (100 mL), brine (50 mL) and dried over $Na_2SO_4$. Evaporation resulted in compound 9 as a white sticky solid (70%). $^1$H NMR (CDCl$_3$) δ: 8.25 (s, 1H), 6.17 (d, J=2.5 Hz, 1H), 5.19 (dd, J=2.5 Hz, 6.1 Hz, 1H), 4.91 (dd, J=2.2 Hz, 6.1 Hz, 1H), 4.46 (dd, J=3.3 Hz, 5.8 Hz, 1H), 3.89 (dd, J=3.4 Hz, 11.4 Hz, 1H), 3.77 (dd, J=3.7 Hz, 11.4 Hz, 1H), 1.62 (s, 3H), 1.40 (s, 3H), 0.81 (s, 9H). LCMS Method 2: $t_R$=3.2 min, m/z: 456.2, [M+H]$^+$.

Step 2: N6, N6-bis-Boc-5'-O-tert-butyldimethylsilyl-2'-3'-O-isopropylidene-2-chloro-adenosine (10)

Compound 9 (23.1 mmol), 4-(N,N-dimethylamino)pyridine (2.5 mmol), and TEA (50 mmol) were dissolved in dry DMF (160 mL) under an argon atmosphere at 0° C. Boc$_2$O (10.8 g, 49 mmol) was dissolved in dry DMF (5 mL) and added to the solution dropwise. The reaction mixture was allowed to stir at 0° C. for one h and overnight at RT. Evaporation under vacuum and subsequent purification by column chromatography (hexane/ethyl acetate 4:1 to 1:1), yielded compound 10 as a white solid (73%). $^1$H NMR (CDCl$_3$) δ: 8.31 (s, 1H), 6.23 (d, J=2.6 Hz, 1H), 5.20 (dd, J=2.1 Hz, 6.1 Hz, 1H), 4.93 (dd, J=2.5 Hz, 6.1 Hz, 1H), 4.42 (dd, J=3.7 Hz, 6.3 Hz, 1H), 3.87 (dd, J=3.7 Hz, 11.3 Hz, 1H), 3.76 (dd, J=3.9, Hz, 11.3 Hz, 1H), 1.62 (s, 3H),, 1.41 (s, 18H), 1.39 (s, 3H), 0.85 (s, 9H), 0.00 (s, 6H). LCMS Method 2: $t_R$=4.2 min: m/z 656.3, [M+H]$^+$

Step 3: N6,N6-bis-Boc-2'-3'-O-isopropylidene-2-chloro-adenosine (11)

Compound 10 (21.0 mmol) was dissolved in dry THF (120 mL) under an argon atmosphere. TBAF trihydrate (31.5 mL, 1M solution in THF) was added dropwise to the solution and stirred overnight. The reaction mixture was evaporated to dryness and subsequently purified by column chromatography (hexane/ethyl acetate 2:1 to hexane/ethyl acetate 1:3) to yield compound 11 as a white solid (91%). $^1$H NMR (CDCl3) δ: 8.16 (s, 1H), 5.96 (d, J=4.7 Hz, 1H), 5.20 (t, J=5.3 Hz, 1H), 5.11 (dd, J=1.2 Hz, 6.0 Hz, 1H), 4.53 (s, 1H), 3.97 (dd, J=1.4 Hz, 11.2 Hz, 1H), 3.80 (dd, J=2.0 Hz, 12.6 Hz, 1H), 1.64 (s, 3H), 1.46 (s, 18H), 1.38 (s, 3H).

Step 4: Diethyl 2-(((3aR,4R,6R,6aR)-6-(2,chloro, N6, N6-bis-Boc-9H-purin-9-yl)-2,2-dimethyltetrahydrofuro[3,4-d][1,3]dioxol-4-yl)methoxy)malonate (12)

To a solution of compound 11 (742.9 mg, 2.06 mmol) in toluene (10 mL) was added diethyl 2-diazomalonate (500 mg, 2.68 mmol) and Rh$_2$(OAc)$_4$ (88.2 mg, 0.2 mmol) under N$_2$ atmosphere. The resulting mixture was stirred overnight at 95-100° C. under N$_2$. The reaction mixture was concentrated in vacuo to dryness. The residue was purified by column chromatography on silica gel (petroleum ether:ethyl acetate=10:1 to 1:1) to give compound 12 as a colorless oil (530 mg). $^1$H NMR: (CDCl$_3$): δ 8.83 (s, 1H), 6.31-6.32 (d, J=3.2 Hz, 1H), 5.20-5.23 (m, 1H), 5.10-5.15 (m, 1H), 4.58-4.59 (m, 1H), 4.49 (s, 1H), 4.24-4.30 (m, 4H), 3.80-3.90 (d, J=2.0 Hz, 1H), 3.65-3.75 (m, 1H), 1.65 (s, 3H), 1.43 (s, 3H), 1.25-1.31 (m, 6H).

Step 5: (Example 3) 2-(((2R,3S,4R,5R)-5-(6-amino-2-chloro-9H-purin-9-yl)-3,4-dihydroxytetrahydrofuran-2-yl)methoxy)malonic acid The above intermediate was subjected to Steps 5 & 6 of Example 2 to yield the title compound which was purified by RP HPLC Method B. LCMS Method 3: $t_R$=1.3 min, m/z=404.1/406.1 ((M+H)$^+$ chlorine isotopes). $^1$H NMR: (CD$_3$OD): δ 8.59 (s, 1H), 5.98-6.00 (d, J=4.0 Hz, 1H), 4.72-4.76 (m, 1H), 4.63-4.67 (t, J=4.8 Hz, 1H), 4.40-4.50 (m, 1H), 4.20-4.25 (d, J=3.6 Hz, 1H), 3.81-3.86 (m, 1H), 3.72-3.76 (m, 1H).

Example 4: 2-(((2R,3S,4R,5R)-5-(6-amino-2-chloro-9H-purin-9-yl)-3,4-dihydroxytetrahydrofuran-2-yl)methoxy)-2-(4-fluorobenzyl)malonic acid

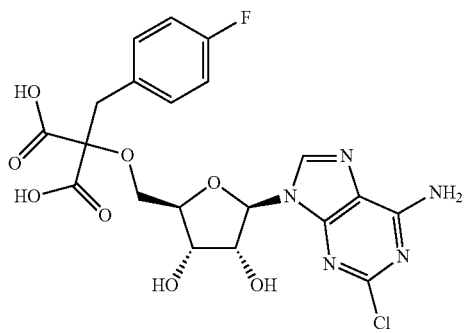 [SMILES: Nc1nc(Cl)nc2c1ncn2[C@@H]1O[C@H](COC(Cc2ccc(F)cc2)(C(=O)O)C(=O)O)[C@@H](O)[C@H]1O]

This compound was synthesized according to Example 2. In Step 3, 4-fluorobenzyl bromide was used instead of MeI. In Step 4, ammonia was used instead of methyl amine. The final compound was purified by RP HPLC Method B. LCMS Method 3: $t_R$=3.65 min, m/z=512.5, 514.5 (M+H)$^+$, $^1$H NMR (CD$_3$OD) δ 8.59 (bs, 1H), 7.22 (bm, 2H), 6.86 (bm, 2H), 5.97 (m, 1H), 4.60 (m, 1H), 4.39 (m, 1H), 4.22 (m, 1H), 3.81 (m, 1H), 3.69 (m, 1H), 3.25 (bs, 2H) ppm. $^{19}$F NMR (CD$_3$OD, 376 MHz) δ 77.1 ppm.

Example 5: 2-(((2R,3S,4R,5R)-5-(6-amino-2-chloro-9H-purin-9-yl)-3,4-dihydroxytetrahydrofuran-2-yl)methoxy)-2-(methoxymethyl)malonic acid

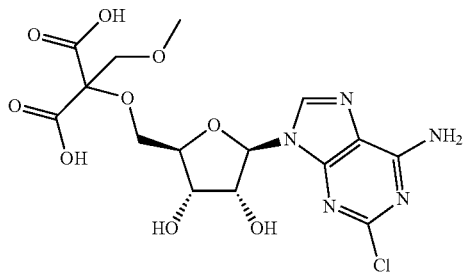 [SMILES: COCC(OC[C@H]1O[C@@H](n2cnc3c(N)nc(Cl)nc32)[C@H](O)[C@@H]1O)(C(=O)O)C(=O)O]

This compound was synthesized according to Example 2. In Step 3, methoxymethyl chloride was used instead of methyl iodide. In Step 4, ammonia was used instead of methyl amine. The final compound was purified by RP HPLC Method B. LCMS Method 3: $t_R$=3.65 min $t_R$=1.13 min, m/z=448.5, 450.5 (M+H)$^+$. $^1$H NMR (D$_2$O) δ 8.93 (s, 1H), 6.08 (d, 1H), 4.81 (m, 1H), 4.58 (m, 1H), 4.40 (m, 1H), 4.01 (s, 2H), 3.94 (dd, 1H), 3.83 (dd, 1H), 3.39 (s, 3H).

Example 6: 2-(((2R,3S,4R,5R)-5-(6-amino-2-chloro-9H-purin-9-yl)-3,4-dihydroxytetrahydrofuran-2-yl)methoxy)-2-((benzyloxy)methyl)malonic acid

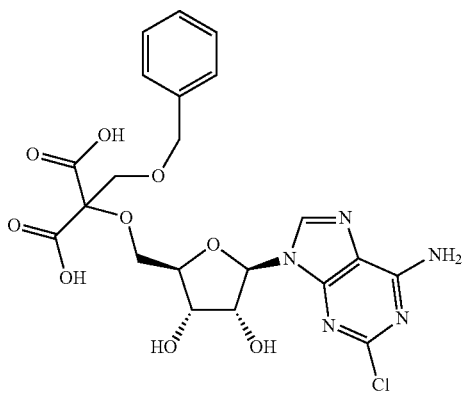 [SMILES: Nc1nc(Cl)nc2c1ncn2[C@@H]1O[C@H](COC(COCc2ccccc2)(C(=O)O)C(=O)O)[C@@H](O)[C@H]1O]

This compound was synthesized according to Example 2. In Step 3, benzyloxymethyl chloride was used instead of methyl iodide. In Step 4, ammonia was used instead of methyl amine. The final compound was purified by RP HPLC Method B. LCMS Method 3: $t_R$=3.90 min in 16 min chromatography, m/z=524.4, 526.4 (M+H)$^+$. $^1$H NMR (CD$_3$OD) δ 8.90 (s, 1H), 7.21 (m, 5H), 6.07 (d, 1H), 4.90 (m, 1H), 4.57 (bs, 2H), 4.43 (m, 1H), 4.25 (m, 1H), 4.04 (bs, 2H), 3.83 (dd, 1H), 3.70 (dd, 1H).

Example 7: 2-(((2R,3S,4R,5R)-5-(6-amino-2-chloro-9H-purin-9-yl)-3,4-dihydroxytetrahydrofuran-2-yl)methoxy)-2-benzylmalonic acid

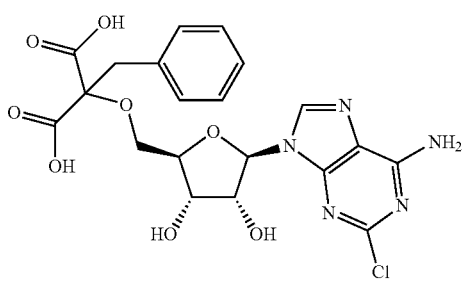 [SMILES: Nc1nc(Cl)nc2c1ncn2[C@@H]1O[C@H](COC(Cc2ccccc2)(C(=O)O)C(=O)O)[C@@H](O)[C@H]1O]

This compound was synthesized according to Example 2. In Step 3, benzyl bromide was used instead of methyl iodide. In Step 4, ammonia was used instead of methyl amine. The final compound was purified by RP HPLC Method B. LCMS Method 3: $t_R$=3.43 min, m/z=494.5, 496.5 (M+H)$^+$, $^1$H NMR (CD$_3$OD) δ 8.50 (s, 1H), 7.23 (m, 2H), 7.16 (m, 3H), 6.01 (d, 1H), 4.71 (m, 1H), 4.28 (m, 2H), 4.00 (dd, 1H), 3.79 (dd, 1H), 3.41 (bs, 2H).

Example 8: 2-(((2R,3S,4R,5R)-5-(6-amino-9H-purin-9-yl)-3,4-dihydroxytetrahydrofuran-2-yl)methoxy)malonic acid

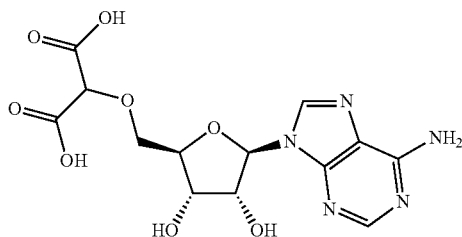 [SMILES: Nc1ncnc2c1ncn2[C@@H]1O[C@H](COC(C(=O)O)C(=O)O)[C@@H](O)[C@H]1O]

This compound was synthesized according to Example 3. ((3aR,4R,6R,6aR)-6-(6-amino-9H-purin-9-yl)-2,2-dimethyltetrahydrofuro[3,4-d][1,3]dioxol-4-yl)methanol was used as starting material. The final compound was purified by RP HPLC Method B. LCMS Method 3: $t_R$=0.98 min, m/z=370.3 (M+H)$^+$, $^1$H NMR (D$_2$O) δ 8.80 (s, 1H), 8.43 (s, 1H), 6.20 (d, 1H), 4.87 (m, 1H), 4.59 (m, 1H), 4.59 (s, 1H), 4.40 (m, 1H), 3.90 (m, 2H).

Example 9: ((R)-2-(((2R,3S,4R,5R)-5-(6-amino-2-chloro-9H-purin-9-yl)-3,4-dihydroxytetrahydrofuran-2-yl)methoxy)-1-ethoxy-1-oxopropan-2-yl) phosphonic Acid and Example 9a: ((S)-2-(((2R,3S,4R,5R)-5-(6-amino-2-chloro-9H-purin-9-yl)-3,4-dihydroxytetrahydrofuran-2-yl)methoxy)-1-ethoxy-1-oxopropan-2-yl) phosphonic Acid Example 9

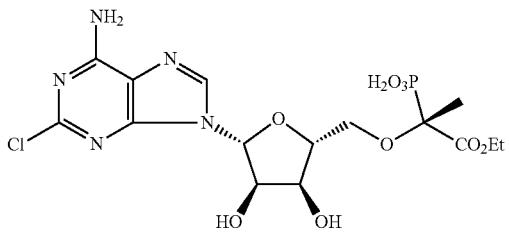

Example 9a

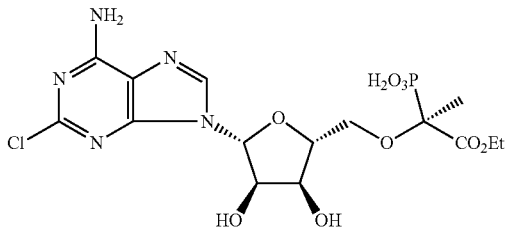

Scheme D

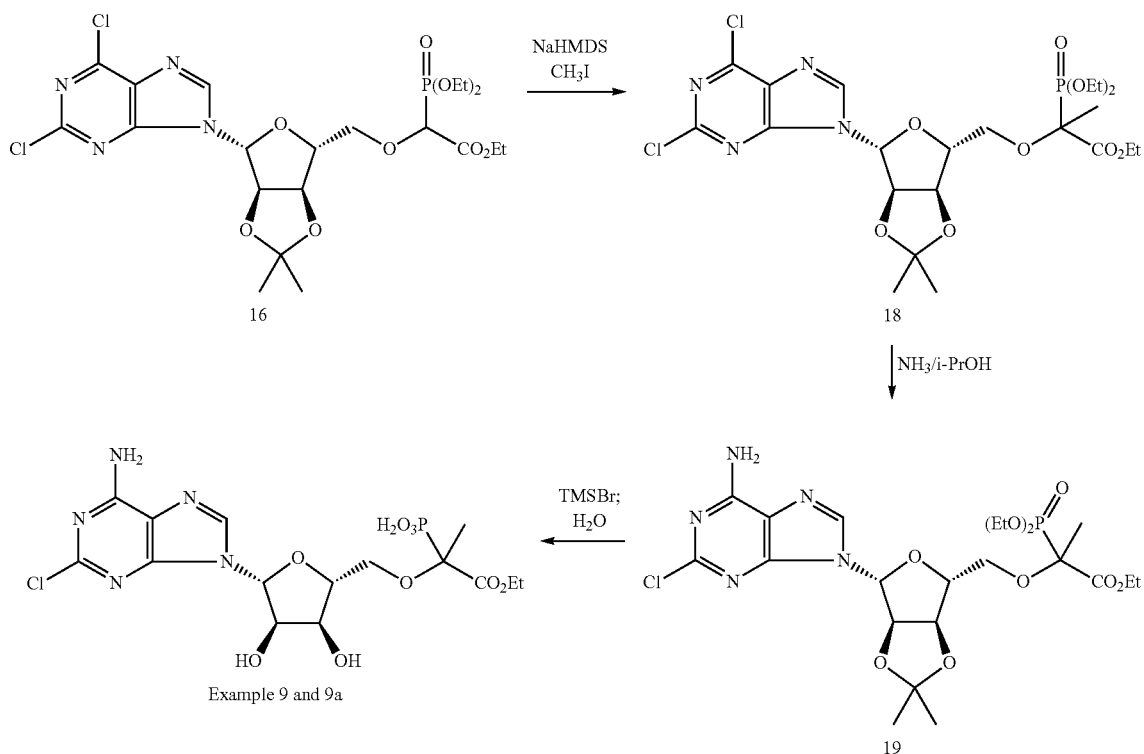

Step 1: Ethyl 2-(((3aR,4R,6R,6aR)-6-(2,6-dichloro-9H-purin-9-yl)-2,2-dimethyltetrahydrofuro[3,4-d][1,3]dioxol-4-yl)methoxy)-2-(diethoxyphosphoryl)propanoate (18)

NaHMDS (1.0 M in THF, 2 mL, 2 mmol) was added dropwise to a solution of compound 18 (0.4946 g, 0.85 mmol) in THF (8 mL) at −78° C. under nitrogen. The resulting solution was stirred at −78° C. for 30 min and then MeI (0.5 mL) was added. After an additional 1 h at −78° C., the reaction mixture was stirred in an ice bath for 3 h and then quenched with saturated NH$_4$Cl. The organic product was extracted with EtOAc (25 mL) and dried over Na$_2$SO$_4$. The solvent was evaporated under reduced pressure, the residue was purified by chromatography on silica gel (40 g column eluted with 30 to 80% ethyl acetate/hexanes over 40 min) to give of compound 18 (0.1128 g). LCMS Method 1: $t_R$=1.59 min, m/z=597, 599 (M+H)$^+$.

Step 2: Ethyl 2-(((3aR,4R,6R,6aR)-6-(6-amino-2-chloro-9H-purin-9-yl)-2,2-dimethyltetrahydrofuro[3,4-d][1,3]dioxol-4-yl)methoxy)-2-(diethoxyphosphoryl)propanoate (19)

A solution of NH$_3$ in 2-propanol (5 mL of 2.0 M) was added to a solution of compound 18 (0.1128 g, 0.19 mmol) in dry THF (8 mL) and stirred for 3 d at RT. The solvents were removed under reduced pressure at RT, the residue was purified by chromatography on silica gel (40 g column eluted with 0 to 5% methanol in DCM over 40 min) to afford compound 19 (0.076 g). LCMS Method 1: $t_R$=1.33 min, m/z=578, 580 (M+H$^+$).

Step 3: (Examples 9 and 9a) ((R)-2-(((2R,3S,4R,5R)-5-(6-amino-2-chloro-9H-purin-9-yl)-3,4-dihydroxytetrahydrofuran-2-yl)methoxy)-1-ethoxy-1-oxopropan-2-yl)phosphonic acid and ((S)-2-(((2R,3S,4R,5R)-5-(6-amino-2-chloro-9H-purin-9-yl)-3,4-dihydroxytetrahydrofuran-2-yl)methoxy)-1-ethoxy-1-oxopropan-2-yl)phosphonic Acid Title compounds were prepared from ethyl 2-(((3aR,4R,6R,6aR)-6-(6-amino-2-chloro-9H-purin-9-yl)-2,2-dimethyltetrahydrofuro[3,4-d][1,3]dioxol-4-yl)methoxy)-2-(diethoxyphosphoryl)propanoate (0.0760 g) according to Example 1, Step 3. The final compound was purified by RP HPLC Method A to separate two diastereomers. After the two fractions were evaporated under reduced pressure at RT, the residue was dissolved in 50 mL of distilled water and then lyophilized to yield TFA salt to yield the 1$^{st}$ eluting isomer, which corresponds to Example 9 and the 2$^{nd}$ eluting isomer which corresponds to Example 9a.

Example 9, LCMS Method 3: $t_R$=1.91 min, m/z=482, 484 (M+H$^+$).

Example 9a, LCMS Method 3: $t_R$=2.09 min, m/z=482, 484 (M+H$^+$).

Example 10: ((R)-(((2R,3S,4R,5R)-5-(6-amino-2-chloro-9H-purin-9-yl)-3,4-dihydroxytetrahydrofuran-2-yl)methoxy)(methylsulfonyl)methyl)phosphonic Acid and

Example 10a: ((S)-(((2R,3S,4R,5R)-5-(6-amino-2-chloro-9H-purin-9-yl)-3,4-dihydroxytetrahydrofuran-2-yl)methoxy)(methylsulfonyl)methyl)phosphonic Acid

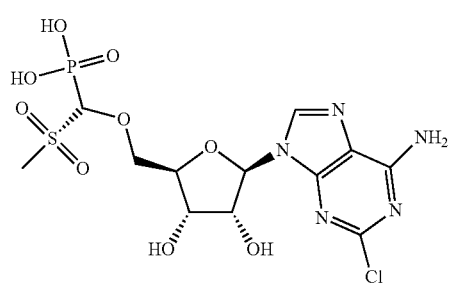

Example 10

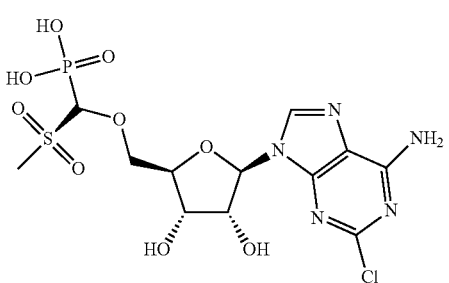

Example 10a

Scheme E

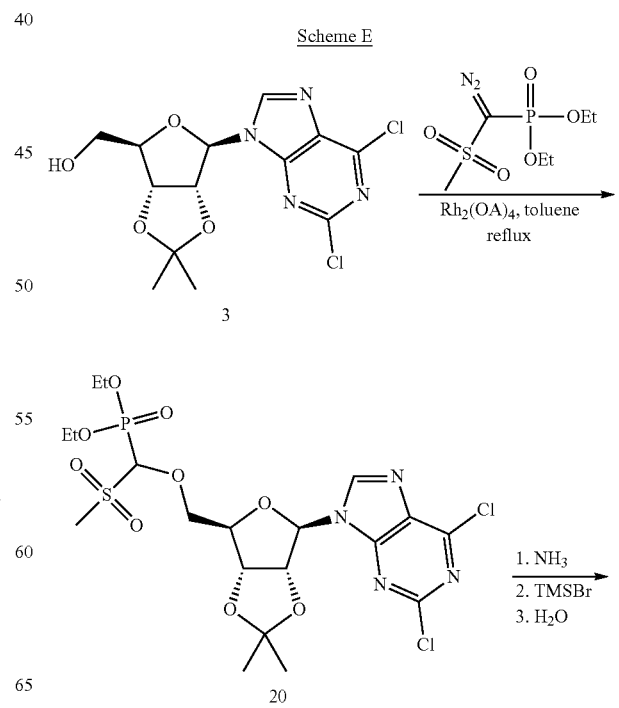

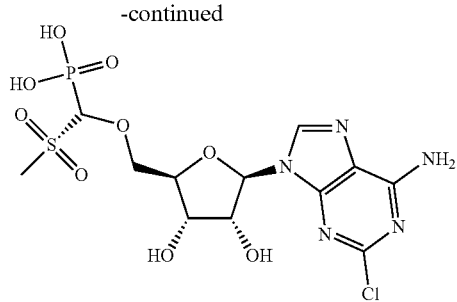

Example 10

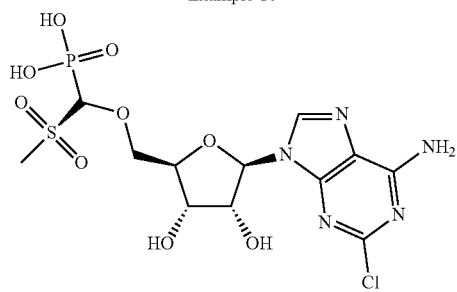

Example 10a

Step 1: Diethyl ((((3aR,4R,6R,6aR)-6-(2,6-dichloro-9H-purin-9-yl)-2,2 dimethyltetrahydrofuro[3,4-d][1,3]dioxol-4-yl)methoxy)(methylsulfonyl)methyl) phosphonate (20)

Rh$_2$(OAc)$_4$ (19 mg, 0.042 mmol) was added to a solution of compound 3 (150 mg, 0.42 mmol) and diethyl (diazo(methylsulfonyl)methyl) phosphonate (215 mg, 0.84 mmol) in toluene (5 mL) under N$_2$ at RT. The mixture was stirred overnight at 90-95° C. The mixture was concentrated in vacuo to afford crude product, which was purified by column chromatography on silica gel (petroleum ether:ethyl acetate=1:4) to afford compound 20 (150 mg) as a colorless oil. LCMS Method 1: $t_R$=0.99 min, m/z=589.1/591.1 ((M+H)$^+$ chlorine isotopes). $^1$H NMR: (CDCl$_3$): δ 8.38-8.49 (m, 1H), 6.18 (m, 1H), 5.27-5.29 (m, 1H), 5.06-5.14 (m, 1H), 4.18-4.48 (m, 8H), 3.04-3.07 (d, J=14.8 Hz, 3H), 1.64 (s, 3H), 1.28-1.40 (m, 10H).

Step 2: (Example 10) ((R)-(((2R,3S,4R,5R)-5-(6-amino-2-chloro-9H-purin-9-yl)-3,4-dihydroxytetrahydrofuran-2-yl)methoxy)(methylsulfonyl)methyl) phosphonic acid and (Example 10a) ((S)-(((2R,3S,4R,5R)-5-(6-amino-2-chloro-9H-purin-9-yl)-3,4-dihydroxytetrahydrofuran-2-yl)methoxy)(methylsulfonyl)methyl)phosphonic Acid The title compounds were synthesized from the above intermediate 20 utilizing Steps 2 and 3 as described in Example 1. The final compound was purified by RP HPLC Method A to separate two diastereomers. After the two fractions were evaporated under reduced pressure at RT, the residue was dissolved in 50 mL of distilled water and then lyophilized to yield TFA salt to yield the 1$^{st}$ eluting isomer, which corresponds to Example 10 and the 2$^{nd}$ eluting isomer which corresponds to Example 10a.

Example 10: LCMS Method 3: $t_R$=1.10 min, m/z=474 (M+H)$^+$.

Example 10a: LCMS Method 3: $t_R$=1.24 min, m/z=474 (M+H)$^+$.

Example 11: ((S)-(((2R,3S,4R,5R)-5-(6-amino-2-chloro-9H-purin-9-yl)-3,4-dihydroxytetrahydrofuran-2-yl)methoxy)(ethylsulfonyl)methyl)phosphonic Acid and Example 11a: ((R)-(((2R,3S,4R,5R)-5-(6-amino-2-chloro-9H-purin-9-yl)-3,4-dihydroxytetrahydrofuran-2-yl)methoxy)(ethylsulfonyl)methyl)phosphonic Acid Example 11

Example 11a

Scheme F

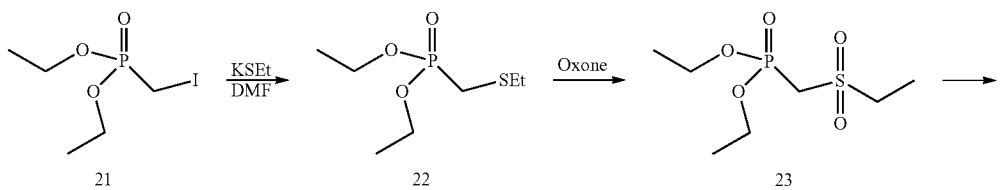

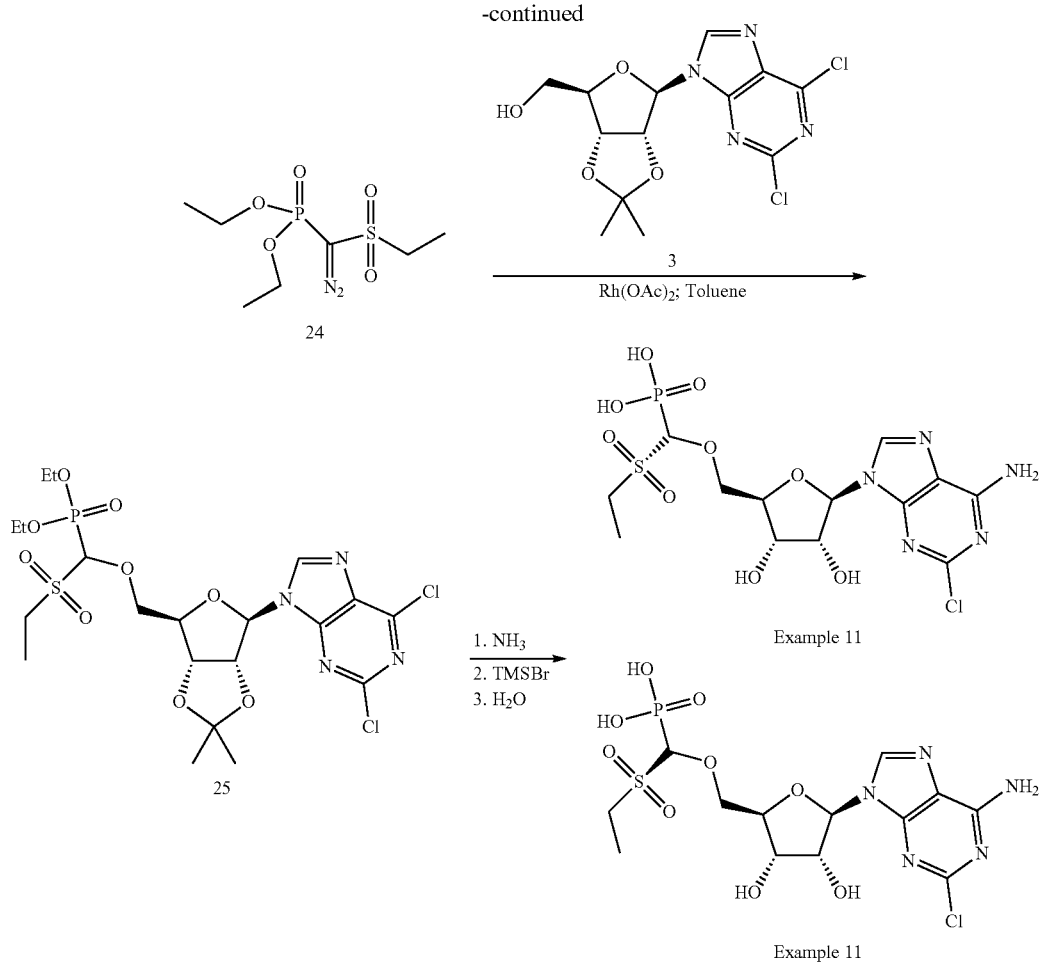

Example 11

This compound was synthesized according to Example 1. In Step 1, diethyl (diazo(propylsulfonyl)methyl) phosphonate was used instead of ethyl 2-diazo-2-(diethoxyphosphoryl)acetate. The diethyl (diazo(propylsulfonyl)methyl)phosphonate was synthesized as described below.

Step 1: S-((diethoxyphosphoryl)methyl ethanethioate (22)

To a solution of diethyl (iodomethyl)phosphonate (12.0 g, 45.7 mmol) in DMF (150 mL) was added potassium ethanethioate (10.4 g, 91.4 mmol). The resulting mixture was stirred at RT overnight. After 14 h, the reaction mixture was diluted with water (200 mL) and extracted with EtOAc (3×150 mL). The combined organic layers were washed with brine (3×450 mL), dried over anhydrous $Na_2SO_4$ and concentrated in vacuo to give crude S-((diethoxyphosphoryl)methyl) ethanethioate as a black oil which was used for the next step without purification. $^1$H NMR: (CDCl$_3$): δ 4.12-4.16 (q, J=6.8 Hz, 4H), 3.21-3.25 (d, J=14.0 Hz, 2H), 2.39 (d, J=0.8 Hz, 3H), 1.31-1.34 (t, J=6.8 Hz, 6H).

Step 2: Diethyl ((ethylsulfonyl)methyl)phosphonate (23)

To a solution of compound 21 (2.0 g, 8.8 mmol) in MeOH/H$_2$O (160 mL, 1:1) was added Oxone® monopersulfate (8.7 g, 14.1 mmol) and the reaction was stirred overnight at RT. After 14 h, the reaction mixture was diluted with water (50 mL) and extracted ethyl acetate (3×100 mL). The organic layer was washed with brine (2×80 mL), dried over Na$_2$SO$_4$, filtered and concentrated in vacuo to give compound 23 (1.9 g, 84%) as a yellow oil. $^1$H NMR: (CDCl$_3$): δ 4.19-4.27 (m, 4H), 3.51-3.56 (d, J=16.8 Hz, 2H), 3.28-3.33 (m, 2H), 1.84-1.95 (m, 2H), 1.34-1.38 (t, J=7.2 Hz, 6H), 1.07-1.11 (t, J=7.2 Hz, 3H).

Step 3: Diethyl (diazo(propylsulfonyl)methyl)phosphonate (24)

To a solution of compound 23 (1.5 g, 6.6 mmol) in ACN (40 mL) was added TsN$_3$ (1.3 g, 6.6 mmol) and K$_2$CO$_3$ (912 mg, 6.6 mmol) and stirred overnight at RT. After 16 h, the reaction mixture was filtered and the filtrate was concentrated in vacuo. The residue was purified by column chromatography on silica gel (petroleum ether:ethyl acetate=1:1) to give compound 24 as a yellow oil (850 mg). $^1$H NMR: (CDCl$_3$): δ 4.19-4.27 (m, 4H), 3.51-3.56 (d, J=16.8 Hz, 2H), 3.28-3.33 (m, 2H), 1.84-1.95 (m, 2H), 1.34-1.38 (t, J=7.2 Hz, 6H), 1.07-1.11 (t, J=7.2 Hz, 3H).

Step 4: (Example 11) ((S)-(((2R,3S,4R,5R)-5-(6-amino-2-chloro-9H-purin-9-yl)-3,4-dihydroxytetrahydrofuran-2-yl)methoxy)(ethylsulfonyl)methyl)phosphonic acid and (Example 11a) ((R)-(((2R,3S,4R,5R)-5-(6-amino-2-chloro-9H-purin-9-yl)-3,4-dihydroxytetrahydrofuran-2-yl)methoxy)(ethylsulfonyl)methyl)phosphonic Acid The title compounds were synthesized from the above intermediate according to Example 1. The product was purified by RP HPLC Method A to separate two diastereomers. After the two fractions were evaporated under reduced pressure at RT, the residue was dissolved in 50 mL of distilled water and then lyophilized to yield TFA salt to yield the $1^{st}$ eluting isomer, which is Example 11 and the $2^{nd}$ eluting isomer which is Example 11a.

Example 11: LCMS Method 3: $t_R$=1.17 min, m/z=488, 490 (M+H)$^+$.

Example 11a: LCMS Method 3: $t_R$=1.42 min, m/z=488, 490 (M+H)$^+$.

Example 12: ((R)-(((2R,3S,4R,5R)-5-(6-amino-2-chloro-9H-purin-9-yl)-3,4-dihydroxytetrahydrofuran-2-yl)methoxy)(propylsulfonyl)methyl)phosphonic Acid and Example 12a: ((S)-(((2R,3S,4R,5R)-5-(6-amino-2-chloro-9H-purin-9-yl)-3,4-dihydroxytetrahydrofuran-2-yl)methoxy)(propylsulfonyl)methyl)phosphonic Acid

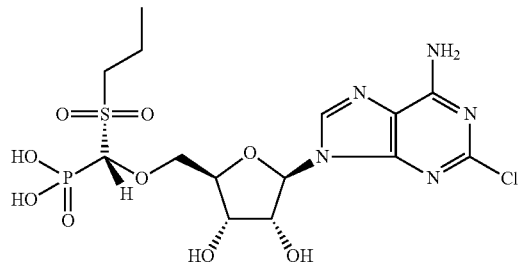
Example 12

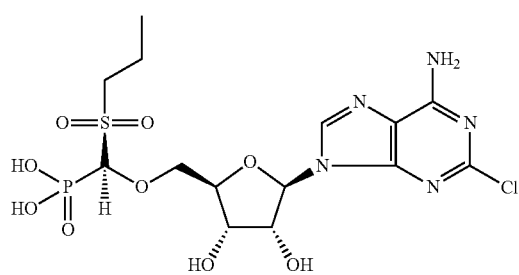
Example 12a

These compounds were synthesized according to Example 1. In Step 1, diethyl (diazo(n-propylsulfonyl)methyl)phosphonate was used instead of diethyl (diazo(methylsulfonyl)methyl)phosphonate. Diethyl (diazo(n-propylsulfonyl)methyl)phosphonate was synthesized by the method described for diethyl (diazo(ethylsulfonyl)methyl)phosphonate in Example 11. The final compound was purified by RP HPLC Method A to separate two diastereomers. After the two fractions were evaporated under reduced pressure at RT, the residue was dissolved in 50 mL of distilled water and then lyophilized to yield TFA salt to yield the $1^{st}$ eluting isomer, which is Example 12 and the $2^{nd}$ eluting isomer which is Example 12a Example 12: LCMS Method 2: $t_R$=1.54 min, m/z=502 (M+H)$^+$.

Example 12a: LCMS Method 2: $t_R$=1.79 min, m/z=502 (M+H)$^+$.

Example 13: ((R)-(((2R,3S,4R,5R)-5-(6-amino-2-chloro-9H-purin-9-yl)-3,4-dihydroxytetrahydrofuran-2-yl)methoxy)(isobutylsulfonyl)methyl)phosphonic Acid and Example 13a: ((S)-(((2R,3S,4R,5R)-5-(6-amino-2-chloro-9H-purin-9-yl)-3,4-dihydroxytetrahydrofuran-2-yl)methoxy)(isobutylsulfonyl)methyl)phosphonic Acid

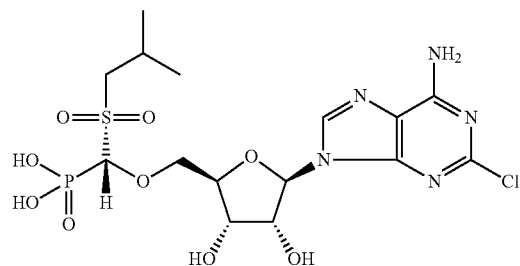
Example 13

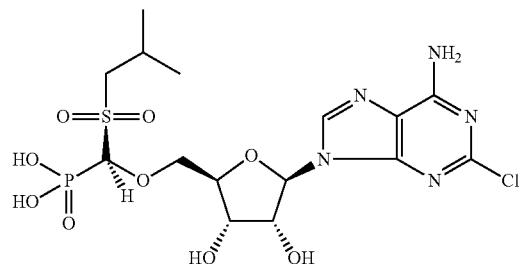
Example 13a

These compounds were prepared according to Example 1. In Step 1, diethyl (diazo(isopropylsulfonyl)methyl)phosphonate was used instead of diethyl (diazo(methylsulfonyl)methyl)phosphonate. Diethyl (diazo(isopropylsulfonyl)methyl)phosphonate was synthesized by the method described for diethyl (diazo(ethylsulfonyl)methyl)phosphonate in Example 11. The compounds were purified by RP HPLC Method A to separate two diastereomers. After the two fractions were evaporated under reduced pressure at RT, the residue was dissolved in 50 mL of distilled water and then lyophilized to yield TFA salt to yield the $1^{st}$ eluting isomer, which is Example 13 and the $2^{nd}$ eluting isomer which is Example 13a.

Example 13: LCMS Method 2: $t_R$=1.76 min, m/z=516 (M+H)$^+$.

Example 13a: LCMS Method 2: $t_R$=1.94 min, m/z=516 (M+H)$^+$.

Example 14: ((R)-1-(((2R,3S,4R,5R)-5-(6-amino-2-chloro-9H-purin-9-yl)-3,4-dihydroxytetrahydrofuran-2-yl)methoxy)-2-isobutoxy-2-oxoethyl)phosphonic Acid and Example 14a: ((S)-1-(((2R,3S,4R,5R)-5-(6-amino-2-chloro-9H-purin-9-yl)-3,4-dihydroxytetrahydrofuran-2-yl)methoxy)-2-isobutoxy-2-oxoethyl)phosphonic Acid Example 15: ((R)-1-(((2R,3S,4R,5R)-5-(6-amino-2-chloro-9H-purin-9-yl)-3,4-dihydroxytetrahydrofuran-2-yl)methoxy)-2-(tert-butoxy)-2-oxoethyl) phosphonic Acid and Example 15a: ((S)-1-(((2R,3S,4R,5R)-5-(6-amino-2-chloro-9H-purin-9-yl)-3,4-dihydroxytetrahydrofuran-2-yl)methoxy)-2-(tert-butoxy)-2-oxoethyl) phosphonic Acid

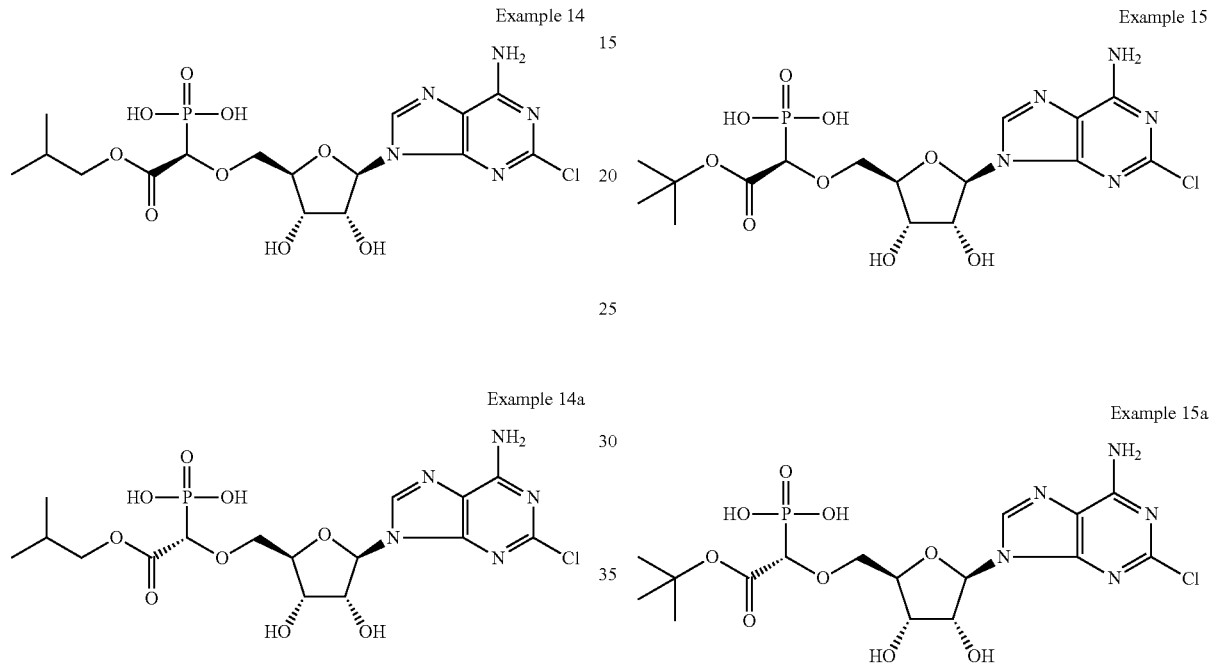

These compounds were prepared as described in Example 1, starting with isobutyl 2-diazo-2-(diethoxyphosphoryl)acetate instead of ethyl 2-diazo-2-(diethoxyphosphoryl)acetate. The final compound was purified by RP HPLC Method A to separate two diastereomers. After the two fractions were evaporated under reduced pressure at RT, the residue was dissolved in 50 mL of distilled water and then lyophilized to yield TFA salt to yield the 1$^{st}$ eluting isomer, which is Example 14 and the 2$^{nd}$ eluting isomer which is Example 14a.

Example 14: LCMS Method 2: $t_R$=1.91 min, m/z=496 (M+H)$^+$. $^1$H NMR (D$_2$O) δ 8.58 (s, 1H), 5.85 (d, 1H), 4.61 (m, 1H), 4.29 (d, 1H), 4.21 (s, 1H), 4.07 (s, 1H), 3.86 (m, 2H), 3.72 (m, 2H), 1.86 (m, 1H), 0.88 (d, 6H). $^{31}$P NMR (D$_2$O) δ 10.13.

Example 14a: LCMS Method 2: $t_R$=2.02 min, m/z=496 (M+H)$^+$. $^1$H NMR (D$_2$O) δ 8.56 (s, 1H), 5.86 (d, 1H), 4.62 (m, 1H), 4.33 (d, 1H), 4.22 (s, 1H), 4.09 (s, 1H), 3.88 (m, 2H), 3.74 (m, 2H), 1.86 (m, 1H), 0.87 (d, 6H). $^{31}$P NMR (D$_2$O) δ 10.33.

These compounds were prepared according to Example 1 starting with tert butyl 2-diazo-2-(dimethoxyphosphoryl) acetate instead of ethyl 2-diazo-2-(diethoxyphosphoryl)acetate. The final compound was purified by was purified by RP HPLC Method A to separate two diastereomers. After the two fractions were evaporated under reduced pressure at RT, the residue was dissolved in 50 mL of distilled water and then lyophilized to yield TFA salt to yield the 1$^{st}$ eluting isomer, which is Example 15 and the 2$^{nd}$ eluting isomer which is Example 15a.

Example 15: ((R)-1-(((2R,3S,4R,5R)-5-(6-amino-2-chloro-9H-purin-9-yl)-3,4-dihydroxytetrahydro furan-2-yl) methoxy)-2-(tert-butoxy)-2-oxoethyl)phosphonic acid TFA salt. LCMS Method 2: $t_R$=1.83 min, m/z=496 (M+H)$^+$. $^1$H NMR (CD$_3$OD) δ 8.67 (s, 1H), 6.02 (d, 1H), 4.66 (m, 1H), 4.45 (m, 1H), 4.28 (d, 1H, 18 Hz), 4.22 (m, 1H), 3.92 (m, 1H), 3.82 (m, 1H), 1.49 (s, 9H). $^{31}$P NMR (CD$_3$OD) δ 12.16. $^{19}$F NMR (CD$_3$OD) δ −77.36.

Example 15a: ((S)-1-(((2R,3S,4R,5R)-5-(6-amino-2-chloro-9H-purin-9-yl)-3,4-dihydroxytetrahydro furan-2-yl) methoxy)-2-(tert-butoxy)-2-oxoethyl)phosphonic acid, TFA salt. LCMS Method 2: $t_R$=1.98 min, m/z=496 (M+H)$^+$. $^1$H NMR (CD$_3$OD) δ 8.96 (s, 1H), 6.05 (d, 1H), 4.64 (m, 1H), 4.44 (m, 1H), 4.28 (d, 1H, 18 Hz), 4.24 (m, 1H), 3.96 (m, 1H), 3.80 (m, 1H), 1.50 (s, 9H). $^{31}$P NMR (CD$_3$OD) δ 12.21. $^{19}$F NMR (CD$_3$OD) δ −77.59.

Example 16: ((R)-1-(((2R,3S,4R,5R)-5-(6-amino-2-chloro-9H-purin-9-yl)-3,4-dihydroxytetrahydrofuran-2-yl)methoxy)-2-(benzyloxy)-2-oxoethyl) phosphonic Acid and Example 16a: ((S)-1-(((2R,3S,4R,5R)-5-(6-amino-2-chloro-9H-purin-9-yl)-3,4-dihydroxytetrahydrofuran-2-yl)methoxy)-2-(benzyloxy)-2-oxoethyl) phosphonic Acid Example 17: ((R)-1-(((2R,3S,4R,5R)-5-(6-amino-2-chloro-9H-purin-9-yl)-3,4-dihydroxytetrahydrofuran-2-yl)methoxy)-2-(isobutylamino)-2-oxoethyl) phosphonic Acid and Example 17a: ((S)-1-(((2R,3S,4R,5R)-5-(6-amino-2-chloro-9H-purin-9-yl)-3,4-dihydroxytetrahydrofuran-2-yl)methoxy)-2-(isobutylamino)-2-oxoethyl) phosphonic Acid

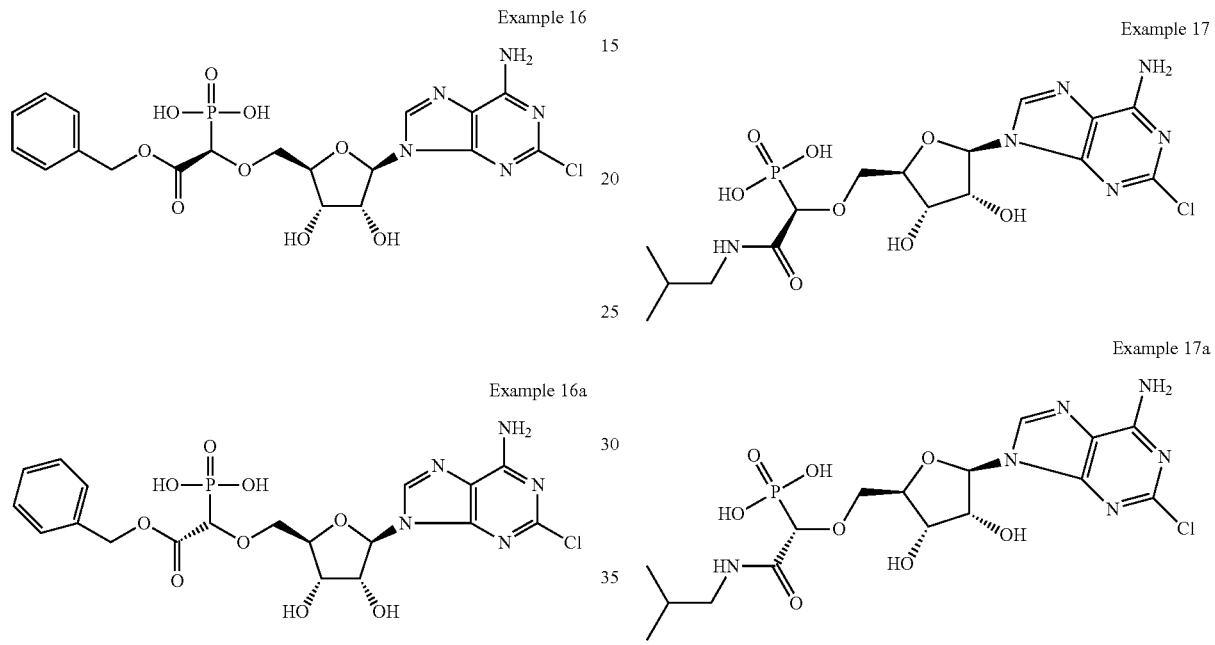

These compounds were prepared according to Example 1 starting with benzyl 2-diazo-2-(dimethoxyphosphoryl)acetate instead of ethyl 2-diazo-2-(diethoxyphosphoryl)acetate. The final compound was purified by was purified by RP HPLC Method A to separate two diastereomers. After the two fractions were evaporated under reduced pressure at RT, the residue was dissolved in 50 mL of distilled water and then lyophilized to yield TFA salt to yield the 1$^{st}$ eluting isomer, which is Example 16 and the 2$^{nd}$ eluting isomer which is Example 16a.

Example 16: LCMS Method 2: $t_R$=1.98 min, m/z=530 (M+H$^+$). $^1$H NMR (CD$_3$OD) δ 9.02 (s, 1H), 7.34-7.16 (m, 5H), 6.01 (d, 1H), 5.23 (m, 2H), 4.60 (m, 1H), 4.52 (d, 1H), 4.50 (m, 1H), 4.23 (s, 1H), 4.08 (m, 1H), 3.84 (m, 1H). $^{31}$P NMR (CD$_3$OD) δ 11.45. $^{19}$F NMR (CD$_3$OD) δ −77.52.

Example 16a: LCMS Method 2: $t_R$=2.05 min, m/z=530 (M+H$^+$). $^1$H NMR (CD$_3$OD) δ 9.68 (s, 1H), 7.25 (d, 2H), 7.09-6.99 (m, 3H), 6.02 (d, 1H), 5.46 (d, 1H), 5.16 (d, 1H), 4.55 (m, 1H), 4.52 (d, 1H), 4.45 (m, 1H), 4.29 (d, 1H), 4.09 (m, 1H), 3.86 (d, 1H). $^{31}$P NMR (CD$_3$OD) δ 11.45.

Scheme G

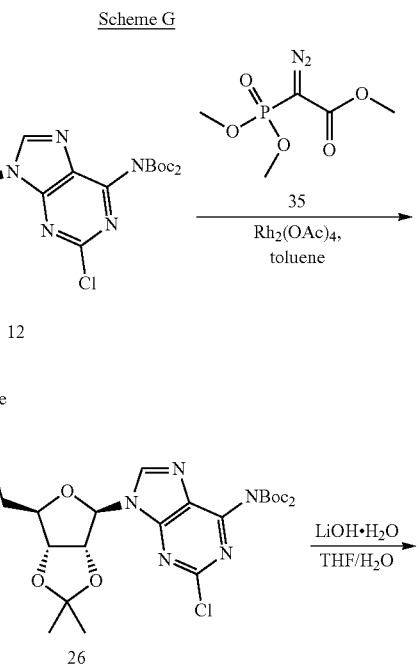

-continued

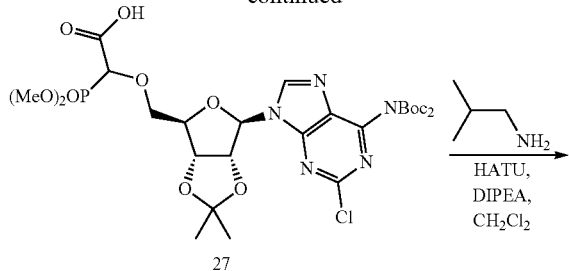

27

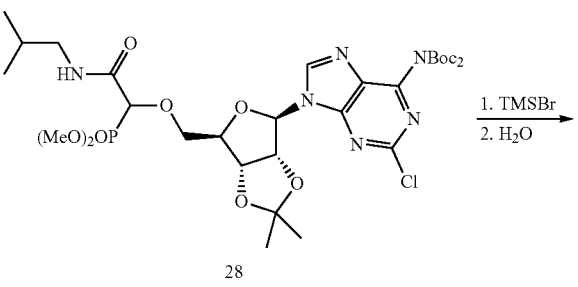

28

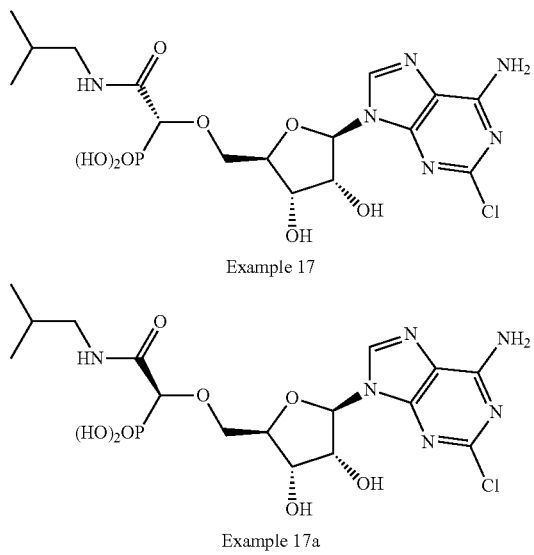

Example 17

Example 17a

Step 1: N,N di tert-butyl carboxylate-methyl 2-(((3aR,4R,6R,6aR)-6-(6-amino-2-chloro-9H-purin-9-yl)-2,2-dimethyltetrahydrofuro[3,4-d][1,3]dioxol-4-yl)methoxy)-2-(dimethoxyphosphoryl)acetate (26)

Compound 26 was prepared analogously to Step 1 of Example 1 from N,N-di-tert-butyl carboxylate 9-((3aR,4R,6R,6aR)-6-((hydroxymethyl)-2,2-dimethyltetrahydrofuro[3,4-d][1,3]dioxol-4-yl)-2-chloro-9H-purin-6-amine) (2 g, 3.7 mmol) with methyl 2-diazo-2-(dimethoxyphosphoryl)acetate (1.15 g, 5.54 mmol) yielding a colorless oil (1.5 gm) which was used for next step directly. $^1$H NMR: (CDCl$_3$): δ 8.58-8.62 (d, J=16.0 Hz, 1H), 6.26 (d, J=3.2 Hz, 1H), 5.09-5.18 (m, 2H), 4.35-4.47 (m, 2H), 3.62-3.87 (m, 11H), 1.28-1.64 (m, 24H).

Step 2: N,N di tert-butyl carboxylate-2-(((3aR,4R,6R,6aR)-6-(6-amino-2-chloro-9H-purin-9-yl)-2,2-dimethyltetrahydrofuro[3,4-d][1,3]dioxol-4-yl)methoxy)-2-(dimethoxyphosphoryl) acetic acid (27)

LiOH.H$_2$O (41 mg, 0.96 mmol) in H$_2$O (0.25 mL) was added to a solution of compound 26 (350 mg, 0.48 mmol) in THF (5 mL). The resulting mixture was stirred at RT for 1 h. The reaction mixture was adjusted by HCl (1N) to pH=7.0 and concentrated in vacuo to remove THF. The mixture was extracted with EtOAc (2×20 mL). The organic layers were concentrated in vacuo to give compound 27 (280 mg) and used directly for next step. LCMS Method 2: $t_R$=0.82 min; m/z=708.0/710.1 ((M+H)$^+$ chlorine isotopes).

Step 3: N,N di tert-butyl carboxylate-dimethyl (1-(((3aR,4R,6R,6aR)-6-(6-amino-2-chloro-9H-purin-9-yl)-2,2-dimethyltetrahydrofuro[3,4-d][1,3]dioxol-4-yl)methoxy)-2-(isobutylamino)-2-oxoethyl) phosphonate (28)

To a solution of compound 27 (250 mg, 0.35 mmol) in DCM (15 mL) was added isobutylamine (52 mg, 0.71 mmol), HATU (270 mg, 0.71 mmol) and DIEA (226 mg, 1.75 mmol). The resulting mixture was stirred overnight at RT. After 14 h, the reaction mixture was diluted with water (15 mL) and extracted with DCM (3×20 mL). The organic layers were combined and concentrated in vacuo to dryness. The residue was purified by preparative TLC (EtOAc) to give compound 28 as a white solid. LCMS Method 2: $t_R$=1.22 min; m/z=763.3/765.3 ((M+H)$^+$ chlorine isotopes) $^1$H NMR: (CDCl$_3$): δ 8.37-8.39 (d, J=5.6 Hz, 1H), 6.65-6.75 (m, 1H), 6.19-6.24 (m, 1H), 5.10-5.24 (m, 2H), 4.43-4.45 (m, 1H), 4.20-4.30 (m, 1H), 3.85-4.05 (m, 8H), 2.90-3.11 (m, 3H), 1.73 (s, 3H), 1.46-1.48 (m, 18H), 1.40 (s, 3H), 0.81-0.82 (m, 6H).

Step 4: (Example 17) ((S)-1-(((2R,3S,4R,5R)-5-(6-amino-2-chloro-9H-purin-9-yl)-3,4-dihydroxytetrahydrofuran-2-yl)methoxy)-2-(isobutylamino)-2-oxoethyl)phosphonic acid and (Example 17a) ((S)-1-(((2R,3S,4R,5R)-5-(6-amino-2-chloro-9H-purin-9-yl)-3,4-dihydroxytetrahydrofuran-2-yl)methoxy)-2-(isobutylamino)-2-oxoethyl)phosphonic Acid The compounds were prepared according to Step 3 of Example 1. The final compound was purified by RP HPLC Method A to separate the two diastereomers. After the two fractions were evaporated under reduced pressure at RT, the residue was dissolved in 50 mL of distilled water and then lyophilized to yield the TFA salt; the 1$^{st}$ eluting isomer corresponding to Example 17 and the 2$^{nd}$ eluting isomer corresponding to Example 17a.

Example 17: LCMS Method 3: $t_R$=1.94 min, m/z=495, 497 (M+H$^+$).

Example 17a: LCMS Method 3: $t_R$=2.42 min, m/z=495, 497 (M+H$^+$).

Example 18: ((R)-1-(((2R,3S,4R,5R)-5-(6-amino-2-chloro-9H-purin-9-yl)-3,4-dihydroxytetrahydrofuran-2-yl)methoxy)-2-(ethylamino)-2-oxoethyl) phosphonic Acid and Example 18a: ((S)-1-(((2R,3S,4R,5R)-5-(6-amino-2-chloro-9H-purin-9-yl)-3,4-dihydroxytetrahydrofuran-2-yl)methoxy)-2-(ethylamino)-2-oxoethyl) phosphonic Acid Example 19: ((R)-1-(((2R,3S,4R,5R)-5-(6-amino-2-chloro-9H-purin-9-yl)-3,4-dihydroxytetrahydrofuran-2-yl)methoxy)-2-(tert-butylamino)-2-oxoethyl) phosphonic Acid and Example 19a: ((S)-1-(((2R,3S,4R,5R)-5-(6-amino-2-chloro-9H-purin-9-yl)-3,4-dihydroxytetrahydrofuran-2-yl)methoxy)-2-(tert-butylamino)-2-oxoethyl) phosphonic Acid

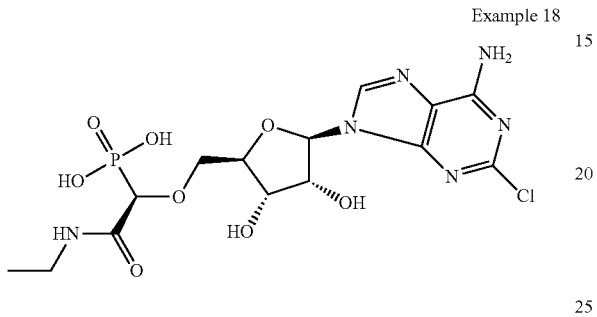

Example 18

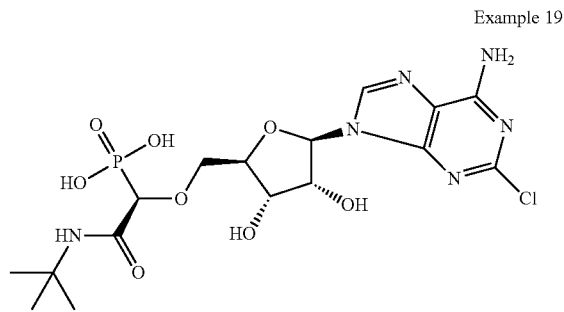

Example 19

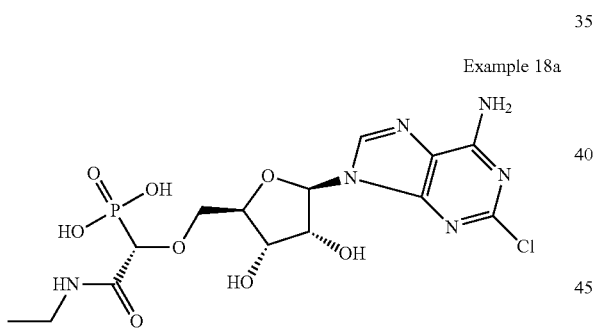

Example 18a

Example 19a

These compounds were prepared according to Example 17. In Step 3, ethyl amine was used instead of isobutyl amine. The final compound was purified by RP HPLC Method A to separate the two diastereomers. After the two fractions were evaporated under reduced pressure at RT, the residue was dissolved in 50 mL of distilled water and then lyophilized to yield the TFA salt; the $1^{st}$ eluting isomer corresponding to Example 18 and the $2^{nd}$ eluting isomer corresponding to Example 18a.

Example 18: LCMS Method 1: $t_R$=1.12 min, m/z=563, 565 (M+H$^+$).

Example 18a: LCMS Method 1: $t_R$=1.32 min, m/z=563, 565 (M+H$^+$).

The compounds were prepared according to Example 17. In Step 3, tert-butyl amine was used instead of isobutylamine. The final compound was purified by RP HPLC Method A to separate the two diastereomers. After the two fractions were evaporated under reduced pressure at RT, the residue was dissolved in 50 mL of distilled water and then lyophilized to yield the TFA salt; the $1^{st}$ eluting isomer corresponding to Example 19 and the $2^{nd}$ eluting isomer corresponding to Example 19a.

Example 19: LCMS Method 3: $t_R$=1.94, m/z=495, 497 (M+H$^+$).

Example 19a: LCMS Method 3: $t_R$=2.68 min, m/z=495, 497 (M+H$^+$).

Example 20: (2-(2-acetylhydrazinyl)-1-(((2R,3S,4R,5R)-5-(6-amino-2-chloro-9H-purin-9-yl)-3,4-dihydroxytetrahydrofuran-2-yl)methoxy)-2-oxoethyl)phosphonic Acid

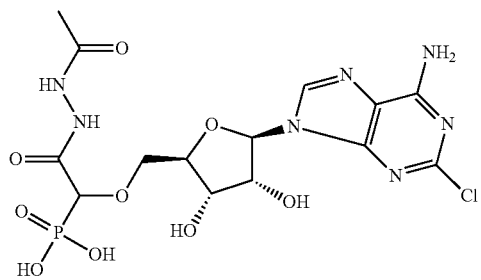 [SMILES: CC(=O)NNC(=O)C(OC[C@H]1O[C@@H](n2cnc3c(N)nc(Cl)nc32)[C@H](O)[C@@H]1O)P(=O)(O)O]

The title compound was prepared according to Example 18. In Step 3, N-acetyl hydrazide was used instead of isobutyl amine. The crude product was purified by RP HPLC Method A and isolated as mixture of diastereomers.

Example 20: LCMS Method 2: $t_R$=0.98 min, m/z=496 (M+H)$^+$.

Example 21: ((R)-(((2R,3S,4R,5R)-5-(6-amino-2-chloro-9H-purin-9-yl)-3,4-dihydroxytetrahydrofuran-2-yl)methoxy)(5-methyl-1,3,4-oxadiazol-2-yl)methyl)phosphonic acid and

Example 21a: ((S)-(((2R,3S,4R,5R)-5-(6-amino-2-chloro-9H-purin-9-yl)-3,4-dihydroxytetrahydrofuran-2-yl)methoxy)(5-methyl-1,3,4-oxadiazol-2-yl)methyl)phosphonic acid Example 21

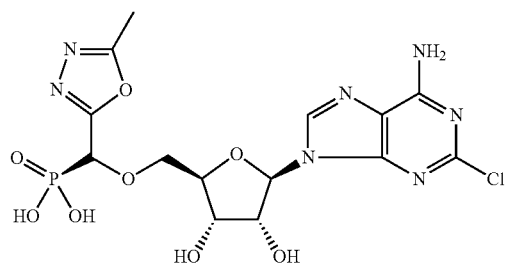

Example 21a

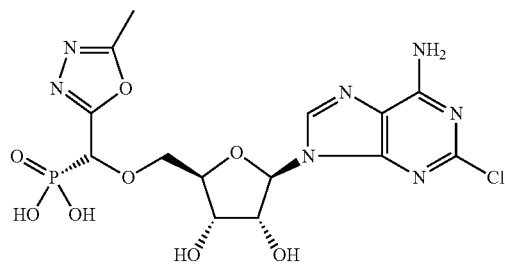

Scheme H

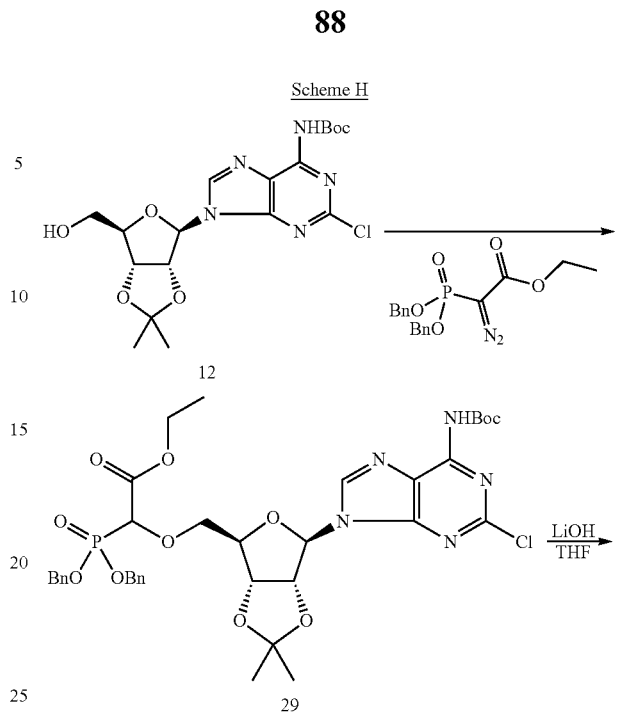

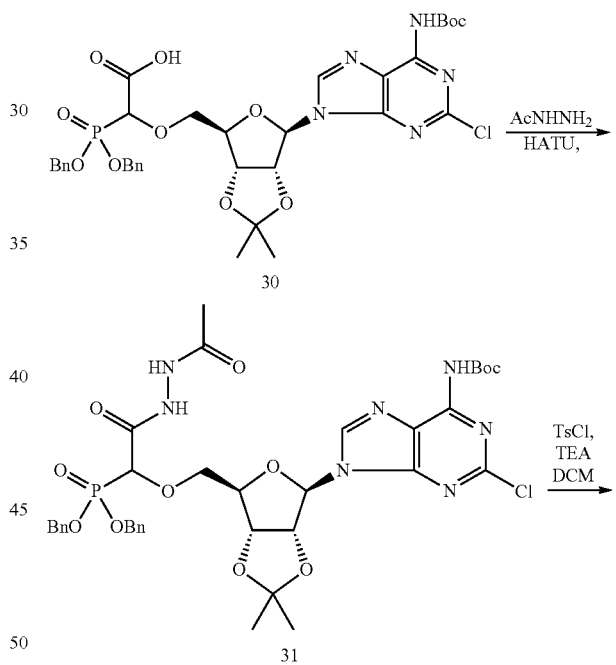

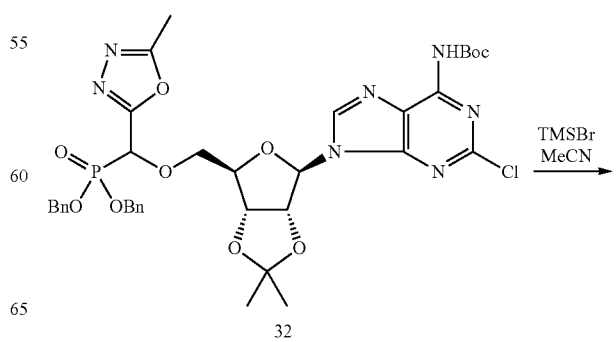

-continued

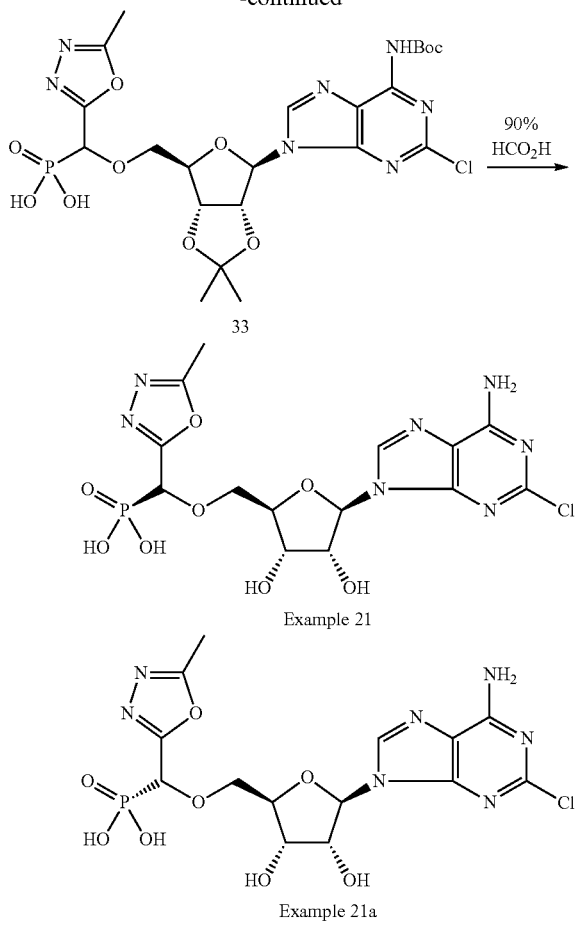

33

Example 21

Example 21a

Step 1: tert-Butyl (9-((3aR,4R,6R,6aR)-6-((2-(2-acetylhydrazinyl)-1-(bis(benzyloxy)phosphoryl)-2-oxoethoxy)methyl)-2,2-dimethyltetrahydrofuro[3,4-d][1,3]dioxol-4-yl)-2-chloro-9H-purin-6-yl)carbamate (31)

Compound 31 was synthesized from compound 12 and ethyl 2-(bis(benzyloxy)phosphoryl)-2-diazoacetate according to Example 20.

Step 2: Preparation of tert-butyl (9-((3aR,4R,6R,6aR)-6-(((bis(benzyloxy)phosphoryl)(5-methyl-1,3,4-oxadiazol-2-yl)methoxy)methyl)-2,2-dimethyltetrahydrofuro[3,4-d][1,3]dioxol-4-yl)-2-chloro-9H-purin-6-yl)carbamate (32)

To a solution of compound 31 (72.5 mg, 0.089 mmol) in DCM (3 mL) was added TEA (74 µL, 0.53 mmol), followed by TsCl (20 mg, 0.11 mmol). The mixture was stirred overnight at RT. The reaction mixture was purified by silica gel chromatography using hexane-EtOAc as an eluent to yield compound 32 (52.9 mg). LCMS Method 2: $t_R$=1.68 min, m/z=798 (M+H$^+$).

Step 3: Preparation of (((((3aR,4R,6R,6aR)-6-(6-((tert-butoxycarbonyl)amino)-2-chloro-9H-purin-9-yl)-2,2-dimethyltetrahydrofuro[3,4-d][1,3]dioxol-4-yl)methoxy)(5-methyl-1,3,4-oxadiazol-2-yl)methyl)phosphonic acid (33)

TMSBr (52 µL, 0.34 mmol) was added to a solution of compound 32, (52.9 mg, 0.066 mmol) in anhydrous ACN (3 mL) under N$_2$ atmosphere. The mixture was stirred at RT for 1 h. Volatile components were removed in vacuo to afford crude product as light brown foam. The crude product was used for next step without further purification. LCMS Method 2: $t_R$=2.13 min, m/z=618 (M+H$^+$).

Step 4: Preparation of Example 21 and 21a: ((R)-(((2R,3S,4R,5R)-5-(6-amino-2-chloro-9H-purin-9-yl)-3,4-dihydroxytetrahydrofuran-2-yl)methoxy)(5-methyl-1,3,4-oxadiazol-2-yl)methyl)phosphonic acid and ((S)-(((2R,3S,4R,5R)-5-(6-amino-2-chloro-9H-purin-9-yl)-3,4-dihydroxytetrahydrofuran-2-yl)methoxy)(5-methyl-1,3,4-oxadiazol-2-yl)methyl) phosphonic Acid The above crude product was dissolved in 90% HCO$_2$H (1.5 mL). The mixture was stirred at RT for 3.5 h. Solvents were removed under reduced pressure and the residue was purified was purified by RP HPLC Method A to separate two diastereomers. After the two fractions were evaporated under reduced pressure at RT, the residue was dissolved in 50 mL of distilled water and then lyophilized to yield the TFA salt; the 1$^{st}$ eluting isomer corresponding to Example 21 (6.2 mg) and the 2$^{nd}$ eluting isomer corresponding to Example 21a (6.3 mg).

Example 21: LCMS Method 2: $t_R$=1.20 min, 478 (M+H)$^+$.
Example 21a: LCMS Method 2: $t_R$=1.50 min, 478 (M+H)$^+$.

Example 22: ((R)-1-(((2R,3S,4R,5R)-5-(2-chloro-6-(cyclopropylamino)-9H-purin-9-yl)-3,4-dihydroxytetrahydrofuran-2-yl)methoxy)-2-ethoxy-2-oxoethyl)phosphonic Acid and Example 22a: ((S)-1-(((2R,3S,4R,5R)-5-(2-chloro-6-(cyclopropylamino)-9H-purin-9-yl)-3,4-dihydroxytetrahydrofuran-2-yl)methoxy)-2-ethoxy-2-oxoethyl)phosphonic Acid

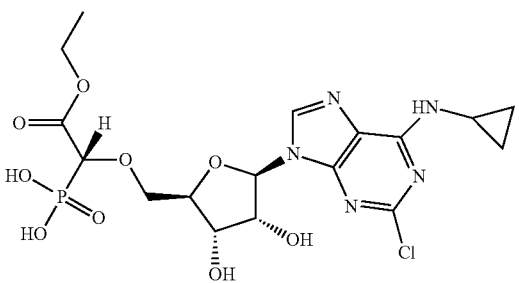

Example 22

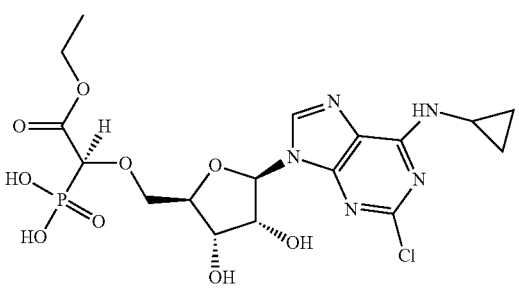

Example 22a

Scheme I

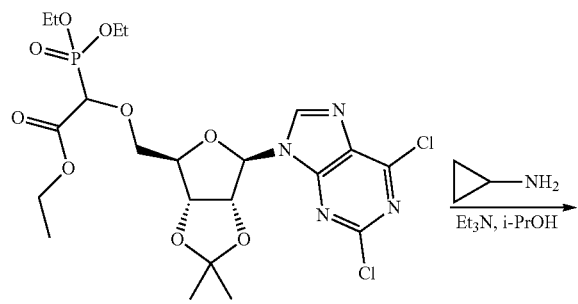

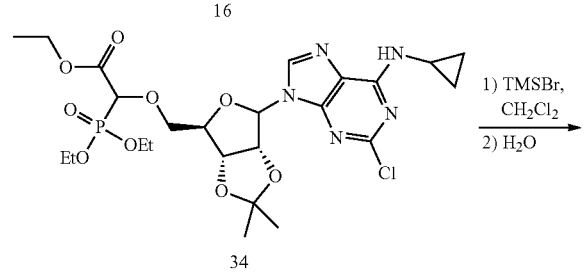

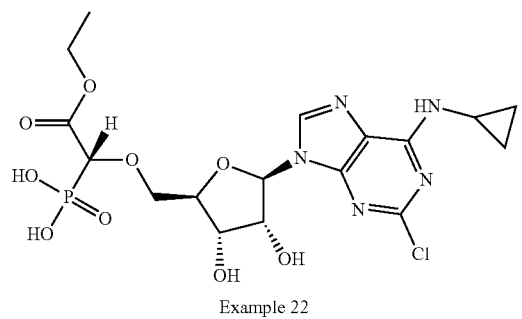

Example 22

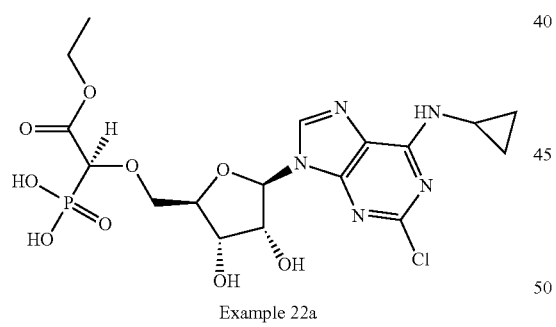

Example 22a

Step 1: Ethyl 2-(((3aR,4R,6R,6aR)-6-(2-chloro-6-(cyclopropylamino)-9H-purin-9-yl)-2,2-dimethyltetrahydrofuro[3,4-d][1,3]dioxol-4-yl)methoxy)-2-(diethoxyphosphoryl)acetate (34)

Compound 16 was treated with 1 eq. of cyclopropyl amine and triethylamine in isoproponal as solvent and stirred overnight at RT. The solvents were removed under reduced pressure and the crude product was purified on silical gel with DCM and MeOH as solvent. The compound 34 eluted with 3% MeOH in DCM. LCMS Method 2: $t_R$=0.794 min, m/z=604.1/606.1 (M+H$^+$).

Step 2: (Example 22) ((S)-1-(((2R,3S,4R,5R)-5-(2-chloro-6-(cyclopropylamino)-9H-purin-9-yl)-3,4-dihydroxytetrahydrofuran-2-yl)methoxy)-2-ethoxy-2-oxoethyl)phosphonic acid) & (Example 22a) (((R)-1-(((2R,3S,4R,5R)-5-(2-chloro-6-(cyclopropylamino)-9H-purin-9-yl)-3,4-dihydroxytetrahydrofuran-2-yl)methoxy)-2-ethoxy-2-oxoethyl)phosphonic Acid To a solution of compound 34 (70 mg, 0.12 mmol) in DCM (2.5 mL) was added TMSBr (178 mg, 153 μL) and was stirred overnight at RT. After 14 h, the reaction mixture was quenched with 2 drops of water. The resulted mixture was concentrated in vacuo to dryness. The residue was purified by RP HPLC Method B to give the 1$^{st}$ eluting isomer as Example 22 (9.3 mg) and the 2$^{nd}$ eluting isomer as Example 22a (6.6 mg) as a white solid.

Example 22: LCMS Method 1: $t_R$: 0.86 min, m/z=508.1, 510.1 (M+H$^+$). $^1$H NMR (D$_2$O): δ 8.61 (s, 1H), 5.98-5.99 (d, J=5.6 Hz, 1H), 4.75-4.80 (m, 1H), 4.43-4.47 (t, J=4.4 Hz, 1H), 4.24-4.31 (m, 2H), 4.09-4.15 (q, J=7.2 Hz, 2H), 3.85-3.95 (m, 1H), 3.65-3.75 (m, 1H), 2.83 (s, 1H), 1.11-1.15 (t, J=7.2 Hz, 3H), 0.85-0.88 (m, 2H), 0.63-0.67 (m, 2H).

Example 22a: LCMS Method 1: $t_R$: 0.99 min, m/z=508.1, 510.1 (M+H$^+$). $^1$H NMR (D$_2$O): δ 8.61 (s, 1H), 5.98-5.99 (d, J=5.6 Hz, 1H), 4.75-4.80 (m, 1H), 4.43-4.47 (t, J=4.4 Hz, 1H), 4.24-4.31 (m, 2H), 4.09-4.15 (q, J=7.2 Hz, 2H), 3.85-3.95 (m, 1H), 3.65-3.75 (m, 1H), 2.83 (s, 1H), 1.11-1.15 (t, J=7.2 Hz, 3H), 0.85-0.88 (m, 2H), 0.63-0.67 (m, 2H).

Example 23: ((R)-1-(((2R,3S,4R,5R)-5-(2-chloro-6-(methylamino)-9H-purin-9-yl)-3,4-dihydroxytetrahydrofuran-2-yl)methoxy)-2-ethoxy-2-oxoethyl) phosphonic acid and Example 23a: ((S)-1-(((2R,3S,4R,5R)-5-(2-chloro-6-(methylamino)-9H-purin-9-yl)-3,4-dihydroxytetrahydrofuran-2-yl)methoxy)-2-ethoxy-2-oxoethyl) phosphonic Acid

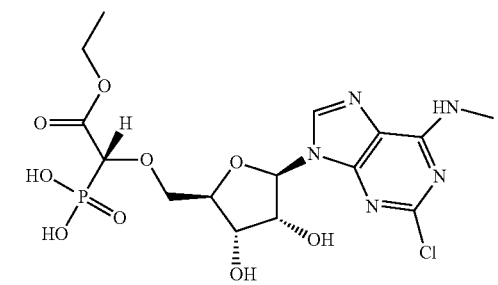

Example 23

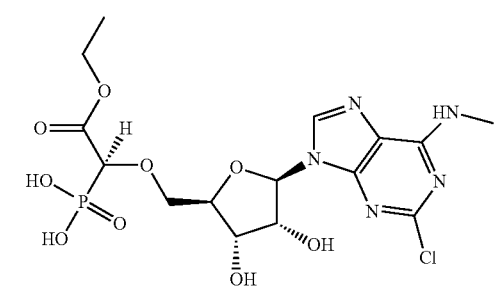

Example 23a

These compounds were prepared according to Example 22. Methyl amine was used instead of cyclopropylmethyl amine. in Step 1. The final compound was purified by RP HPLC Method B to give the 1st eluting isomer as Example 23 and the 2nd eluting isomer as Example 23a as a white solid Example 23: LCMS Method 3: $t_R$=2.02 min, m/z=482, 484 (M+H$^+$).

Example 23a: LCMS Method 3: $t_R$=2.46 min, m/z=482, 484 (M+H$^+$).

Example 24: ((R)-1-(((2R,3S,4R,5R)-5-(6-(benzy-lamino)-2-chloro-9H-purin-9-yl)-3,4-dihydroxytetrahydrofuran-2-yl)methoxy)-2-ethoxy-2-oxoethyl) phosphonic Acid and Example 24a: ((S)-1-(((2R,3S,4R,5R)-5-(6-(benzy-lamino)-2-chloro-9H-purin-9-yl)-3,4-dihydroxytetrahydrofuran-2-yl)methoxy)-2-ethoxy-2-oxoethyl) phosphonic Acid Example 25: ((R)-1-(((2R,3S,4R,5R)-5-(2-chloro-6-(cyclopentylamino)-9H-purin-9-yl)-3,4-dihydroxytetrahydrofuran-2-yl)methoxy)-2-ethoxy-2-oxoethyl)phosphonic Acid and Example 25a: ((S)-1-(((2R,3S,4R,5R)-5-(2-chloro-6-(cyclopentylamino)-9H-purin-9-yl)-3,4-dihydroxytetrahydrofuran-2-yl)methoxy)-2-ethoxy-2-oxoethyl)phosphonic Acid

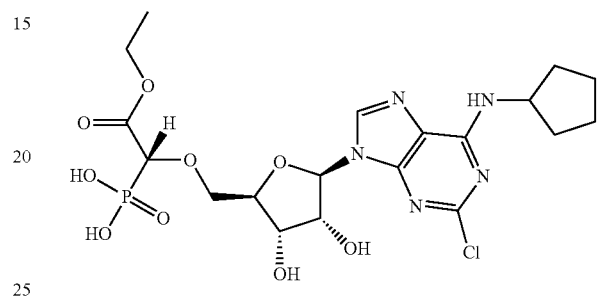

Example 25

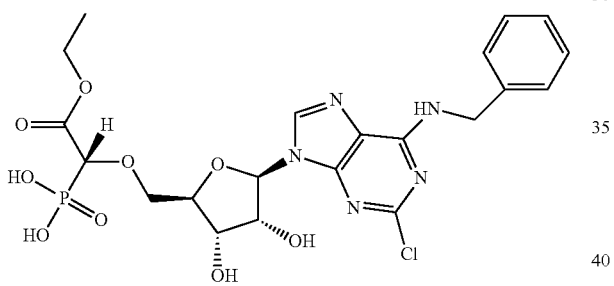

Example 24

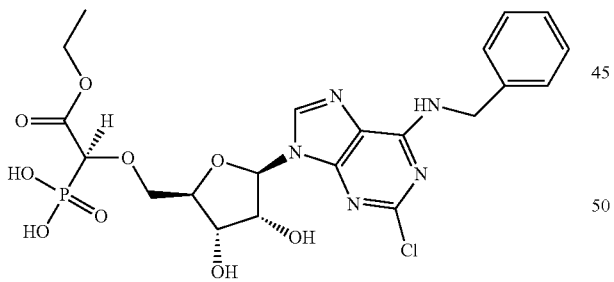

Example 24a

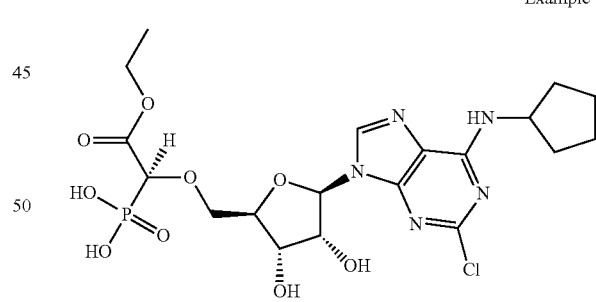

Example 25a

The compounds were prepared according to Example 22. Benzyl amine was used instead of cyclopropylmethyl amine. The final compound was purified by RP HPLC Method B to give the 1st eluting isomer as Example 24 and the 2nd eluting isomer as Example 24a as a white solid Example 24: LCMS Method 3: $t_R$=4.42 min, m/z=558, 560 (M+H$^+$).

Example 24a: LCMS Method 3: $t_R$=4.79 min, m/z=558, 560 (M+H$^+$).

The compounds were prepared according to Example 22. Benzyl amine was used instead of cyclopropylmethyl amine. The final compound was purified by RP HPLC Method B to give the 1st eluting isomer as Example 25 and the 2nd eluting isomer as Example 25a as a white solid.

Example 25: LCMS Method 3: $t_R$=4.20 min, m/z=536, 538 (M+H$^+$).

Example 25a: LCMS Method 3: $t_R$=4.61 min, m/z=536, 538 (M+H$^+$).

Example 26: ((R)-1-(((2R,3S,4R,5R)-5-(2-chloro-6-(1H-imidazol-1-yl)-9H-purin-9-yl)-3,4-dihydroxytetrahydrofuran-2-yl)methoxy)-2-ethoxy-2-oxoethyl) phosphonic Acid and Example 26a: ((S)-1-(((2R,3S,4R,5R)-5-(2-chloro-6-(1H-imidazol-1-yl)-9H-purin-9-yl)-3,4-dihydroxytetrahydrofuran-2-yl)methoxy)-2-ethoxy-2-oxoethyl)phosphonic Acid Example 26

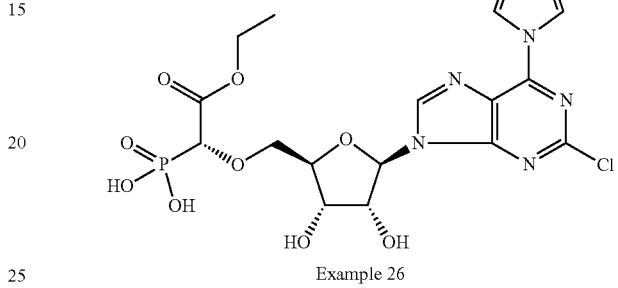

Example 26a

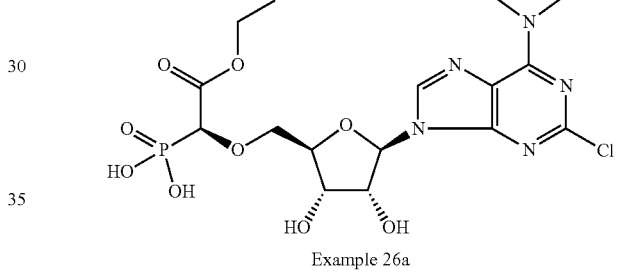

Scheme J

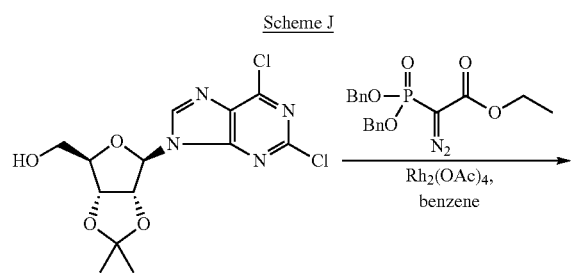

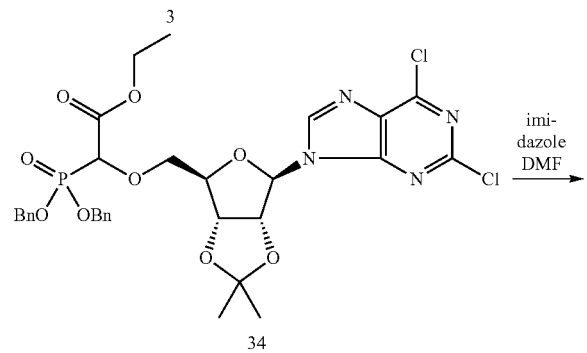

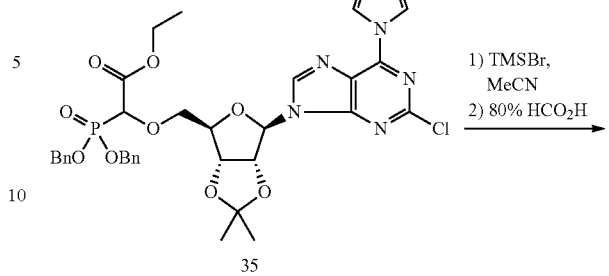

Step 1: Preparation of ethyl 2-(bis(benzyloxy)phosphoryl)-2-(((3aR,4R,6R,6aR)-6-(2,6-dichloro-9H-purin-9-yl)-2,2-dimethyltetrahydrofuro[3,4-d][1,3]dioxol-4-yl)methoxy)acetate (34)

Ethyl 2-(bis(benzyloxy)phosphoryl)-2-diazoacetate (2.386 g, 6.38 mmol) was added to a solution of ((3aR,4R,6R,6aR)-6-(2,6-dichloro-9H-purin-9-yl)-2,2-dimethyltetrahydrofuro[3,4-d][1,3]dioxol-4-yl)methanol (3, 2.095 g, 5.80 mmol 1) and $Rh_2(OAc)_4$ (51 mg, 0.116 mmol) in benzene (72 mL) under $N_2$ atmosphere and refluxed for 16 h, cooled and washed with $H_2O$. The separated organic layer was dried over anhydrous $Na_2SO_4$, and filtered, and evaporated to dryness. The residue was purified by silica gel chromatography to yield compound 34 (2.95 g). LCMS Method 1: $t_R$=1.80 min, m/z=707 (M+H$^+$).

Step 2: Preparation of ethyl 2-(bis(benzyloxy)phosphoryl)-2-(((3aR,4R,6R,6aR)-6-(2-chloro-6-(1H-imidazol-1-yl)-9H-purin-9-yl)-2,2-dimethyltetrahydrofuro[3,4-d][1,3]dioxol-4-yl)methoxy)acetate (35)

A mixture of compound 34 (48 mg, 0.068 mmol), Im (23 mg, 0.34 mmol), and KI (50 mg, 0.3 mmol) in DMF (2 mL) was stirred overnight at RT. DMF was removed in vacuo to yield the crude product 35, which was used in the next step without further purification.

Step 3: Preparation of ((R)-1-(((2R,3S,4R,5R)-5-(2-chloro-6-(1H-imidazol-1-yl)-9H-purin-9-yl)-3,4-dihydroxytetrahydrofuran-2-yl)methoxy)-2-ethoxy-2-oxoethyl)phosphonic acid and ((S)-1-(((2R,3S,4R,5R)-5-(2-chloro-6-(1H-imidazol-1-yl)-9H-purin-9-yl)-3,4-dihydroxytetrahydrofuran-2-yl)methoxy)-2-ethoxy-2-oxoethyl)phosphonic Acid TMSBr (0.1 mL) was added to a solution of crude product 35 in anhydrous ACN (3 mL) and stirred at RT for 5 min before volatile components was removed under reduced pressure. 80% HCO$_2$H (1 mL) was added to the residue and stirred overnight. The final compound was purified by RP HPLC Method B to give the 1$^{st}$ eluting isomer as Example 26 (2.73 mg) and the 2$^{nd}$ eluting isomer as Example 26a (2.71 mg) as a white solid were isolated as TFA salts.

Example 26: LCMS Method 2: $t_R$=1.83 min, m/z=519 (M+H$^+$).

Example 26a: LCMS Method 2: $t_R$=1.94 min, m/z=519 (M+H$^+$).

Example 27: ((R)-1-(((2R,3S,4R,5R)-5-(2-chloro-6-ethoxy-9H-purin-9-yl)-3,4-dihydroxytetrahydrofuran-2-yl)methoxy)-2-ethoxy-2-oxoethyl)phosphonic Acid and Example 27a: ((S)-1-(((2R,3S,4R,5R)-5-(2-chloro-6-ethoxy-9H-purin-9-yl)-3,4-dihydroxytetrahydrofuran-2-yl)methoxy)-2-ethoxy-2-oxoethyl)phosphonic Acid

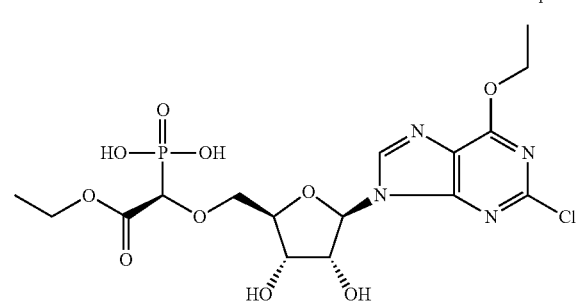
Example 27

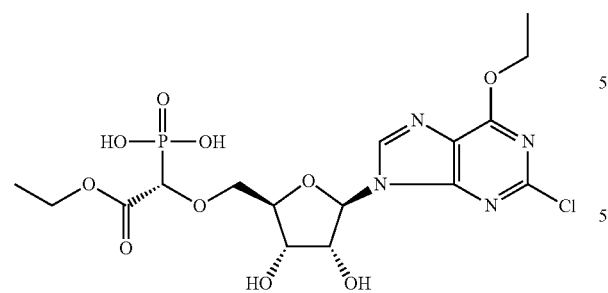
Example 27a

These compounds were synthesized according to Example 20. Sodium ethoxide in ethanol was used instead of cyclopropylmethyl amine. The final compound was purified by RP HPLC Method B to give the 1$^{st}$ eluting isomer as Example 27 and the 2$^{nd}$ eluting isomer as Example 27a which were isolated as TFA salts.

Example 27: LCMS Method 2: $t_R$=2.05 min, m/z=497 (M+H$^+$). $^1$H NMR (D$_2$O) δ 8.78 (s, 1H), 5.93 (d, 1H), 4.59 (m, 3H), 4.26 (d, 1H), 4.19 (m, 1H), 4.11 (m, 3H), 3.71 (m, 2H), 1.40 (m, 3H), 1.16 (m, 3H). $^{31}$P NMR (D$_2$O) δ 10.04. $^{19}$F NMR (D$_2$O) δ −74.81.

Example 27a: LCMS Method 2: $t_R$=2.16 min, m/z=497 (M+H$^+$). $^1$H NMR (D$_2$O) δ 8.78 (s, 1H), 5.93 (d, 1H), 4.58 (m, 3H), 4.28 (d, 1H), 4.21 (m, 1H), 4.11 (m, 3H), 3.71 (m, 2H), 1.40 (m, 3H), 1.17 (m, 3H). $^{31}$P NMR (D$_2$O) δ 10.13. $^{19}$F NMR (D$_2$O) δ −74.80.

Example 28: ((R)-1-(((2R,3S,4R,5R)-5-(2-chloro-6-methyl-9H-purin-9-yl)-3,4-dihydroxytetrahydrofuran-2-yl)methoxy)-2-ethoxy-2-oxoethyl)phosphonic Acid and Example 28a: ((S)-1-(((2R,3S,4R,5R)-5-(2-chloro-6-methyl-9H-purin-9-yl)-3,4-dihydroxytetrahydrofuran-2-yl)methoxy)-2-ethoxy-2-oxoethyl)phosphonic Acid

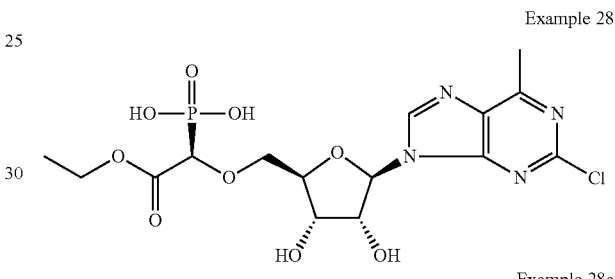
Example 28

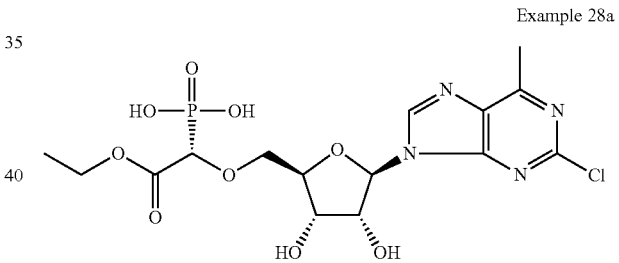
Example 28a

Scheme K1

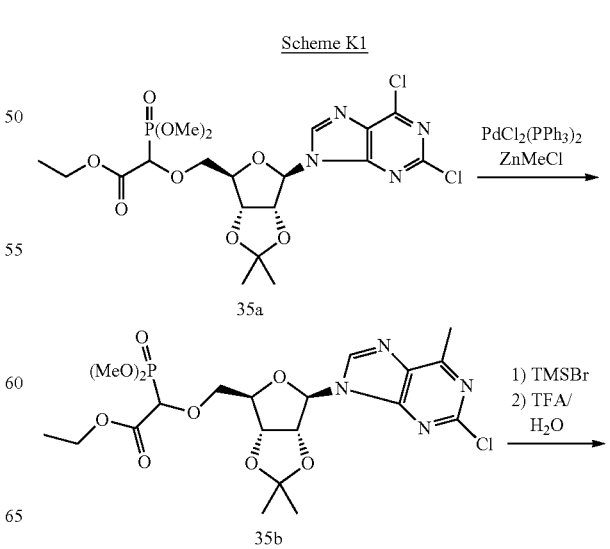

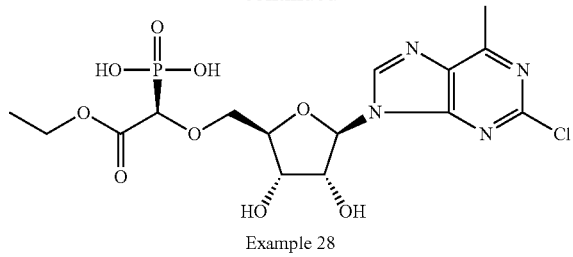

Example 28

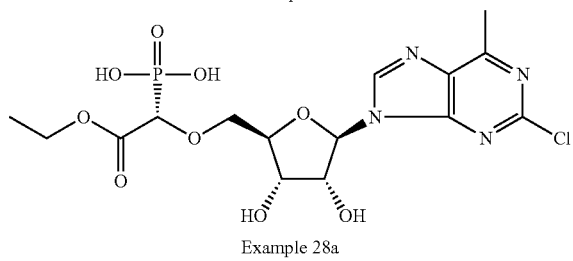

Example 28a

Step 1: Ethyl 2-(((3aR,4R,6R,6aR)-6-(2,6-dichloro-9H-purin-9-yl)-2,2-dimethyltetrahydrofuro[3,4-d][1,3]dioxol-4-yl)methoxy)-2-(dimethoxyphosphoryl)acetate (35a)

Compound 35a was synthesized by the method of Step 1 of Example 1 starting from compound 3 and ethyl 2-diazo-2-(dimethoxyphosphoryl)acetate. LCMS Method 1: 555.1 (M+H⁺).

Step 2: Compound 35b

A solution of compound 35a (200 mg, 0.34 mmol) and PdCl$_2$(PPh$_3$)$_2$ (12 mg, 0.17 mmol) in THF (3.7 mL) was evacuated and flushed with N$_2$ three times, followed by the addition of ZnMeCl (0.20 µL, 2M THF) and stirred overnight at 80° C. The reaction appeared 50% complete and an additional PdCl$_2$(PPh$_3$)$_2$ (12 mg, 0.17 mmol) and ZnMeCl (0.20 µL, 2M THF) was added and heated at 80° C. for 4 h. The reaction was cooled to RT and quenched with saturated NH$_4$Cl. The reaction was extracted with EtOAc and organic layer was dried over brine, Na$_2$SO$_4$, and the solvent evaporated. The crude material was purified flash column chromatography utilizing hexane-EtOAc as an eluent to afford ethyl 2-(((3aR,4R,6R,6aR)-6-(2-chloro-6-methyl-9H-purin-9-yl)-2,2-dimethyltetrahydrofuro[3,4-d][1,3]dioxol-4-yl)methoxy)-2-(dimethoxyphosphoryl)acetate (35b, 54 mg).

Step 3: (Example 28) ((R)-1-(((2R,3S,4R,5R)-5-(2-chloro-6-methyl-9H-purin-9-yl)-3,4-dihydroxytetrahydrofuran-2-yl)methoxy)-2-ethoxy-2-oxoethyl)phosphonic acid and (Example 28a) ((S)-1-(((2R,3S,4R,5R)-5-(2-chloro-6-methyl-9H-purin-9-yl)-3,4-dihydroxytetrahydrofuran-2-yl)methoxy)-2-ethoxy-2-oxoethyl)phosphonic Acid Compound 35b was converted to the compounds of Examples 28 and 28a as described in Step 3 of Example 1.

The final compound was purified by RP HPLC Method B to give the 1$^{st}$ eluting isomer as Example 28 and the 2$^{nd}$ eluting isomer as Example 28a which were isolated as TFA salts.

Example 28: LCMS Method 2: t$_R$=1.68 min, m/z=467 (M+H⁺). $^1$H NMR (CD$_3$OD) δ 8.97 (s, 1H), 6.15 (d, 1H), 4.75 (m, 1H), 4.48 (m, 1H), 4.41 (d, 1H), 4.25 (m, 3H), 3.96 (m, 1H), 3.83 (m, 1H), 2.77 (s, 1H), 1.29 (s, 3H). $^{31}$P NMR (CD$_3$OD) δ 11.46. $^{19}$F NMR (CD$_3$OD) δ −77.36.

Example 28a: LCMS Method 2: t$_R$=1.87 min, m/z=467 (M+H⁺). $^1$H NMR (CD$_3$OD) δ 9.14 (s, 1H), 6.16 (d, 1H), 4.74 (m, 1H), 4.46 (m, 1H), 4.40 (d, 1H), 4.27 (m, 3H), 3.96 (m, 1H), 3.83 (m, 1H), 2.77 (s, 1H), 1.29 (s, 3H). $^{31}$P NMR (CD$_3$OD) δ 11.69. $^{19}$F NMR (CD$_3$OD) δ −77.51.

Example 29: ((R)-2-(((2R,3S,4R,5R)-5-(2-chloro-6-(ethylamino)-9H-purin-9-yl)-3,4-dihydroxytetrahydrofuran-2-yl)methoxy)-1-ethoxy-1-oxopropan-2-yl)phosphonic Acid and Example 29a: ((S)-2-(((2R,3S,4R,5R)-5-(2-chloro-6-(ethylamino)-9H-purin-9-yl)-3,4-dihydroxytetrahydrofuran-2-yl)methoxy)-1-ethoxy-1-oxopropan-2-yl)phosphonic Acid

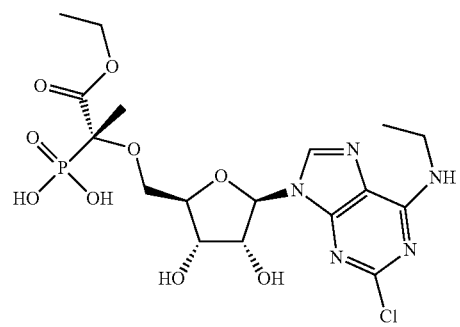

Example 29

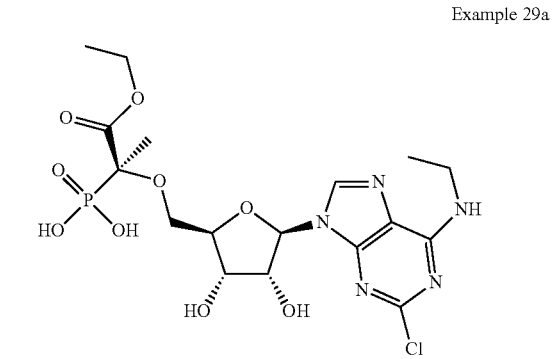

Example 29a

Scheme K2

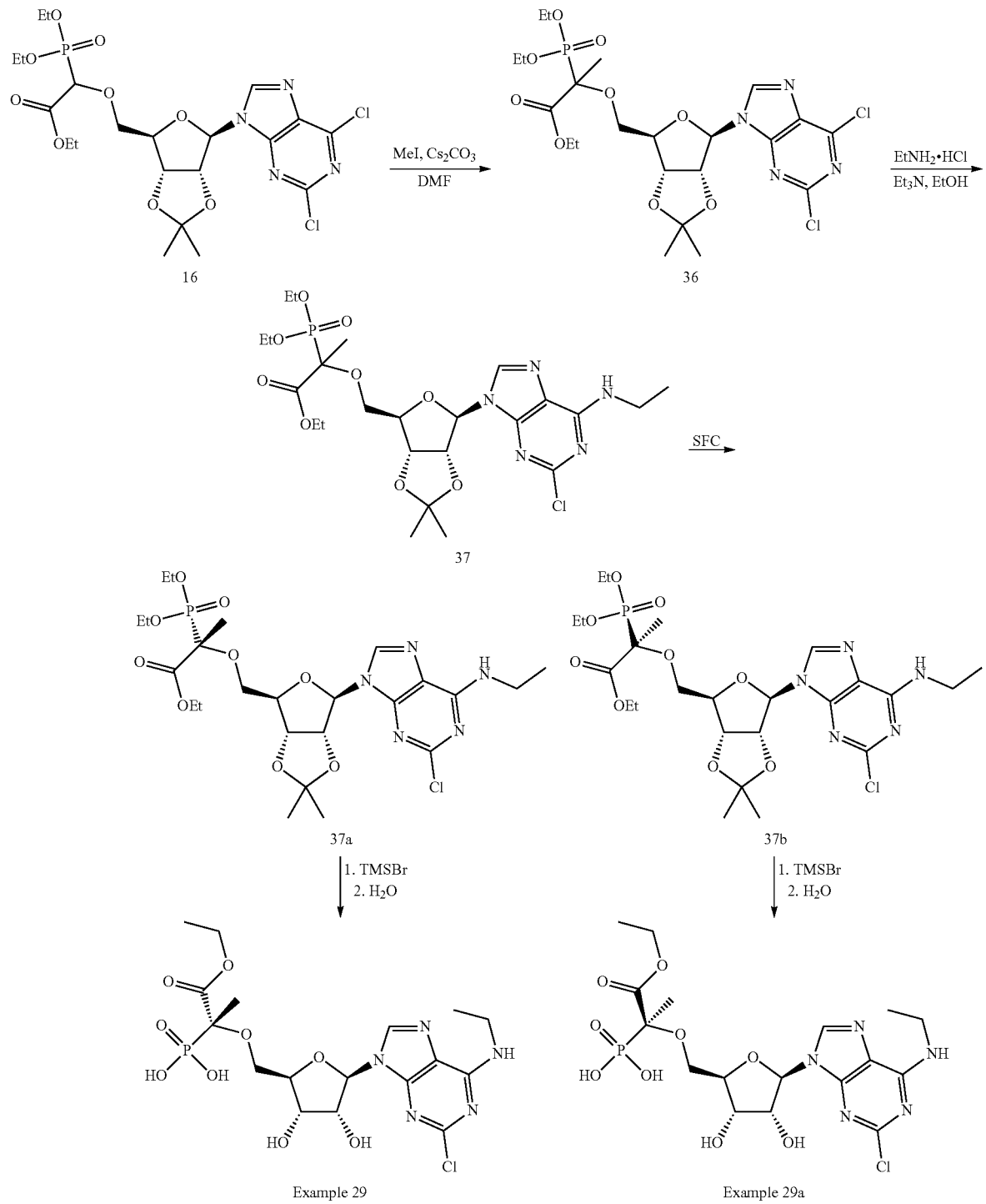

Step 1: Ethyl 2-(((3aR,4R,6R,6aR)-6-(2,6-dichloro-9H-purin-9-yl)-2,2-dimethyltetrahydrofuro[3,4-d][1,3]dioxol-4-yl)methoxy)-2-(diethoxyphosphoryl)propanoate (36)

Cs$_2$CO$_3$ (332 mg, 1.02 mmol) was added to a solution of compound 16 (300 mg, 0.51 mmol) in DMF (5 mL). After 10 min, MeI (365 mg, 2.57 mmol) was added to the above solution and stirred at RT overnight. H$_2$O (10 mL) was added, and product was extracted with EtOAc (3×10 mL). The combined organic layers were washed with brine, dried over Na$_2$SO$_4$, filtered and concentrated to afford crude product 36. The residue was purified by column chromatography on silica gel (petroleum ether:ethyl acetate=1:4) to afford compound 36 (ethyl 2-(((3aR,4R,6R,6aR)-6-(2,6-dichloro-9H-purin-9-yl)-2,2-dimethyltetrahydrofuro[3,4-d][1, 3]dioxol-4-yl)methoxy)-2-(diethoxyphosphoryl)propanoate) as a yellow oil (200 mg). LCMS Method 2: $t_R$: 1.170 min, m/z=597.1/599.2 (M+H$^+$) (chlorine isotopes).

Step 2: (Ethyl 2-(((3aR,4R,6R,6aR)-6-(2-chloro-6-aminoethyl-9H-purin-9-yl)-2,2-dimethyltetrahydrofuro[3,4-d][1,3]dioxol-4-yl)methoxy)-2-(diethoxyphosphoryl)propanoate) (37)

This compound was synthesized according to Step 4 of Example 1 from compound 36 (200 mg, 0.33 mmol) to afford compound 37 as a colorless oil. Yield: 200 mg (98%) LCMS Method 2 $t_R$ value: 0.841 min, (M+H)$^+$=606.1/608.1 (chlorine isotopes). The mixture was separated by preparative SFC method 1 to afford compound 37a (87.5 mg) and compound 37b (83 mg).

Compound 37a: LC MS Method 2: $t_R$: 0.837 min; m/z: = 606.1/608.1 (M+H$^+$) (chlorine isotopes) $^1$H NMR: (CDCl$_3$): δ 8.21 (s, 1H), 6.14-6.16 (d, J=2.8 Hz, 1H), 5.87 (s, 1H), 5.14-5.18 (m, 2H), 4.45-4.50 (m, 1H), 4.15-4.26 (m, 6H), 3.90-3.95 (d, J=4.0 Hz, 1H), 3.60-3.80 (m, 3H), 1.60-1.70 (m, 6H), 1.25-1.40 (m, 15H).

Compound 37b: LCMS Method 2: $t_R$: 0.845 min, m/z=606.1/608.1 (M+H$^+$) (chlorine isotopes) $^1$H NMR: (CDCl$_3$): δ 8.12 (s, 1H), 6.12-6.13 (d, J=2.4 Hz, 1H), 5.93 (s, 1H), 5.14-5.18 (m, 2H), 4.49-4.52 (m, 1H), 4.19-4.27 (m, 6H), 3.90-3.95 (m, 1H), 3.84-3.86 (d, J=4.4 Hz, 1H), 3.55-3.75 (m, 2H), 1.60-1.64 (m, 6H), 1.21-1.38 (m, 15H).

Step 3: Example 29: ((S)-2-(((2R,3S,4R,5R)-5-(2-chloro-6-(ethylamino)-9H-purin-9-yl)-3,4-dihydroxytetrahydrofuran-2-yl)methoxy)-1-ethoxy-1-oxopropan-2-yl)phosphonic acid and Example 29a: ((S)-2-(((2R,3S,4R,5R)-5-(2-chloro-6-(ethylamino)-9H-purin-9-yl)-3,4-dihydroxytetrahydrofuran-2-yl)methoxy)-1-ethoxy-1-oxopropan-2-yl)phosphonic Acid The compounds of Example 29 (derived from compound 37a) and Example 29a (derived from compound 37b) were prepared according to the methods of Example 1, Step 3.

Example 29: LCMS Method 3: $t_R$=3.22 min, m/z 510.3, 512.3 (M+H$^+$); $^1$H NMR (D$_2$O) δ 8.78 (s, 1H), 6.05 (d, 1H), 4.82 (m, 1H), 4.60 (m, 1H), 4.38 (m, 1H), 4.20 (m, 2H), 3.95 (dd, 1H), 3.72 (dd, 1H), 3.59 (b, 2H), 1.63 (d, 3H), 1.27 (t, 3H), 1.21 (t, 3H) ppm.; $^{31}$P NMR (D$_2$O, 162 MHz) δ 12.9 (s).

Example 29a: LCMS Method 3: $t_R$=3.38 min, m/z 510.4, 512.4 (M+H$^+$); $^1$H NMR (D$_2$O) δ 9.22 (bs, 1H), 6.10 (d, 1H), 4.75 (m, 1H), 4.58 (m, 1H), 4.39 (m, 1H), 4.21 (m, 2H), 3.90 (dd, 1H), 3.78 (dd, 1H), 3.59 (b, 2H), 1.64 (d, 3H), 1.27 (t, 3H), 1.19 (t, 3H) ppm.; $^{31}$P NMR (D$_2$O, 162 MHz) δ 13.2 (s).

Example 30: ((R)-1-(((2R,3S,4R,5R)-3,4-dihydroxy-5-(3-methyl-2,4-dioxo-3,4-dihydropyrimidin-1(2H)-yl)tetrahydrofuran-2-yl)methoxy)-2-ethoxy-2-oxoethyl)phosphonic Acid and Example 30a: ((S)-1-(((2R,3S,4R,5R)-3,4-dihydroxy-5-(3-methyl-2,4-dioxo-3,4-dihydropyrimidin-1(2H)-yl)tetrahydrofuran-2-yl)methoxy)-2-ethoxy-2-oxoethyl)phosphonic Acid Example 30

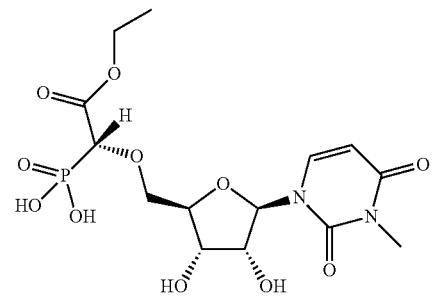

Example 30a

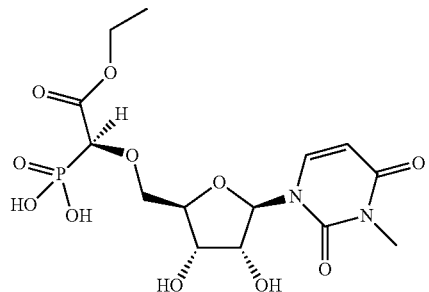

These compounds were synthesized from 1-((3aR,4R,6R,6aR)-6-(hydroxymethyl)-2,2-dimethyltetrahydrofuro[3,4-d][1,3]dioxol-4-yl)-3-methylpyrimidine-2,4(1H,3H)-dione and ethyl 2-diazo-2-(dimethoxyphosphoryl)acetate as described in Example 1, skipping Step 2. The final compound was purified by RP HPLC Method B to give 1$^{st}$ eluting isomer Example 30 and 2$^{nd}$ eluting isomer Example 30a as TFA salts.

Example 30: ((R)-1-(((2R,3S,4R,5R)-3,4-dihydroxy-5-(3-methyl-2,4-dioxo-3,4-dihydropyrimidin-1(2H)-yl)tetrahydrofuran-2-yl)methoxy)-2-ethoxy-2-oxoethyl)phosphonic acid LCMS Method 2: $t_R$=1.13 min, m/z=425 (M+H$^+$). $^1$H NMR (DMSO) δ 7.95 (d, 1H), 5.74 (d, 1H), 5.54 (d, 1H), 4.19-3.77 (m, 6H), 3.65-3.90 (m, 2H), 3.00 (s, 3H), 1.05 (m, 3H). $^{31}$P NMR (DMSO) δ 10.73. $^{19}$F NMR (DMSO) δ −74.63.

Example 30a: ((S)-1-(((2R,3S,4R,5R)-3,4-dihydroxy-5-(3-methyl-2,4-dioxo-3,4-dihydropyrimidin-1(2H)-yl)tetrahydrofuran-2-yl)methoxy)-2-ethoxy-2-oxoethyl)phosphonic acid LCMS Method 2: $t_R$=1.35 min, m/z=425 (M+H$^+$). $^1$H NMR (DMSO) δ 8.21 (d, 1H), 5.86 (d, 1H), 5.64 (d, 1H), 4.25 (d, 1H), 4.16-4.09 (m, 3H), 4.06 (m, 1H), 4.00 (m, 1H), 3.66 (m, 2H), 3.14 (m, 3H), 1.17 (m, 3H). $^{31}$P NMR (DMSO) δ 10.94. $^{19}$F NMR (DMSO) δ −74.34.

Example 31: (1-(((2R,3S,4R,5R)-3,4-dihydroxy-5-(3-methyl-2,4-dioxo-3,4-dihydropyrimidin-1(2H)-yl)tetrahydrofuran-2-yl)methoxy)-2-(methylamino)-2-oxoethyl)phosphonic Acid

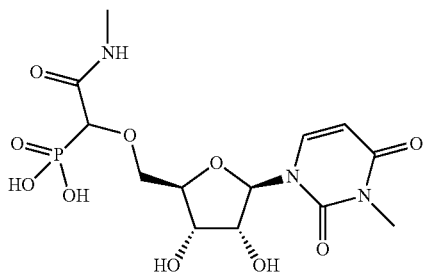 [SMILES: CNC(=O)C(OC[C@H]1O[C@@H](n2ccc(=O)n(C)c2=O)[C@H](O)[C@@H]1O)P(=O)(O)O]

This compound was synthesized according to Example 17, starting with 1-((3aR,4R,6R,6aR)-6-(hydroxymethyl)-2,2-dimethyltetrahydrofuro[3,4-d][1,3]dioxol-4-yl)-3-methylpyrimidine-2,4(1H,3H)-dione instead of N,N-di-tert-butyl carboxylate 9-((3aR,4R,6R,6aR)-6-((hydroxymethyl)-2,2-dimethyltetrahydrofuro[3,4-d][1,3]dioxol-4-yl)-2-chloro-9H-purin-6-amine). In Step 3, methylamine was used instead of isobutyl amine. The final compound was purified by RP HPLC Method B and isolated as mixture of diastereomers and as TFA salt.

Example 31: (1-(((2R,3S,4R,5R)-3,4-dihydroxy-5-(3-methyl-2,4-dioxo-3,4-dihydropyrimidin-1(2H)-yl)tetrahydrofuran-2-yl)methoxy)-2-(ethylamino)-2-oxoethyl)phosphonic acid. LCMS Method 2: $t_R$=1.05 min, m/z=410 (M+H$^+$). $^1$H NMR (DMSO) δ 8.14 (d, 1H), 8.06 (d, 1H), 7.63 (m, 2H), 5.88 (m, 2H), 5.73 (m, 1H), 5.39 (m, 2H), 4.17-4.00 (m, 8H), 3.18 (m, 3H), 4.06 (s, 6H), 2.66 (m, 6H). $^{19}$F NMR (DMSO) δ −74.431.

Example 32: (1-(((2R,3S,4R,5R)-3,4-dihydroxy-5-(3-methyl-2,4-dioxo-3,4-dihydropyrimidin-1(2H)-yl)tetrahydrofuran-2-yl)methoxy)-2-(ethylamino)-2-oxoethyl)phosphonic Acid

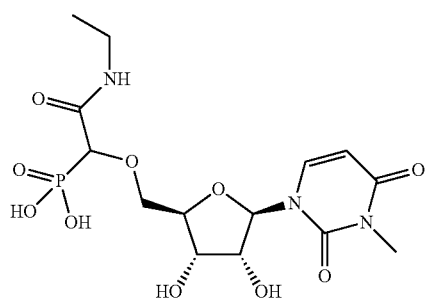 [SMILES: CCNC(=O)C(OC[C@H]1O[C@@H](n2ccc(=O)n(C)c2=O)[C@H](O)[C@@H]1O)P(=O)(O)O]

This compound was synthesized according to Example 17, starting with 1-((3aR,4R,6R,6aR)-6-(hydroxymethyl)-2,2-dimethyltetrahydrofuro[3,4-d][1,3]dioxol-4-yl)-3-methylpyrimidine-2,4(1H,3H)-dione instead of N,N-di-tert-butyl carboxylate 9-((3aR,4R,6R,6aR)-6-((hydroxymethyl)-2,2-dimethyltetrahydrofuro[3,4-d][1,3]dioxol-4-yl)-2-chloro-9H-purin-6-amine). In Step 3, ethylamine was used instead of isobutyl amine. The final compound was purified by RP HPLC Method B and isolated as a mixture of diastereomers as a TFA salt.

Example 32: (1-(((2R,3S,4R,5R)-3,4-dihydroxy-5-(3-methyl-2,4-dioxo-3,4-dihydropyrimidin-1(2H)-yl)tetrahydrofuran-2-yl)methoxy)-2-(ethylamino)-2-oxoethyl)phosphonic acid. LCMS Method 2: $t_R$=1.13 min, m/z=424 (M+H$^+$). $^1$H NMR (DMSO) δ 8.13 (d, 1H), 8.05 (d, 1H), 7.59 (s, 2H), 5.87 (s, 2H), 5.72 (m, 2H), 5.36 (br m, 1H), 4.15-4.00 (m, 8H), 3.17 (s, 6H), 1.022 (s, 6H). $^{31}$P NMR (DMSO) δ 12.28, 12.05. $^{19}$F NMR (DMSO) δ −73.55.

Example 33: (2-(tert-butoxy)-1-(((2R,3S,4R,5R)-5-(2,6-dimethoxy-9H-purin-9-yl)-3,4-dihydroxytetrahydrofuran-2-yl)methoxy)-2-oxoethyl)phosphonic Acid and

Example 33a: 2-(((2R,3S,4R,5R)-5-(2,6-dimethoxy-9H-purin-9-yl)-3,4-dihydroxytetrahydrofuran-2-yl)methoxy)-2-phosphonoacetic acid Example 33

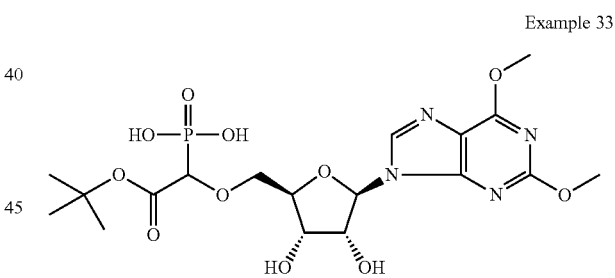

Example 33a

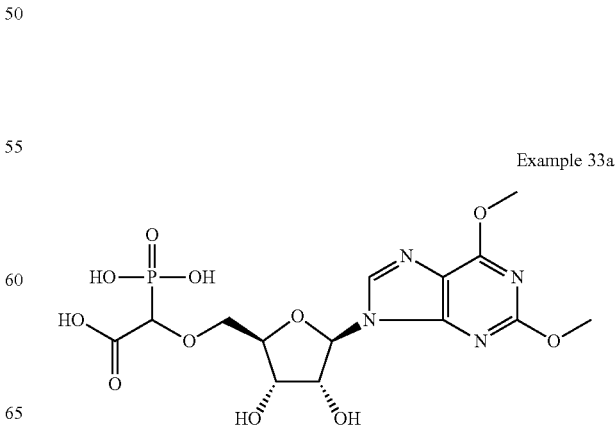

Scheme M

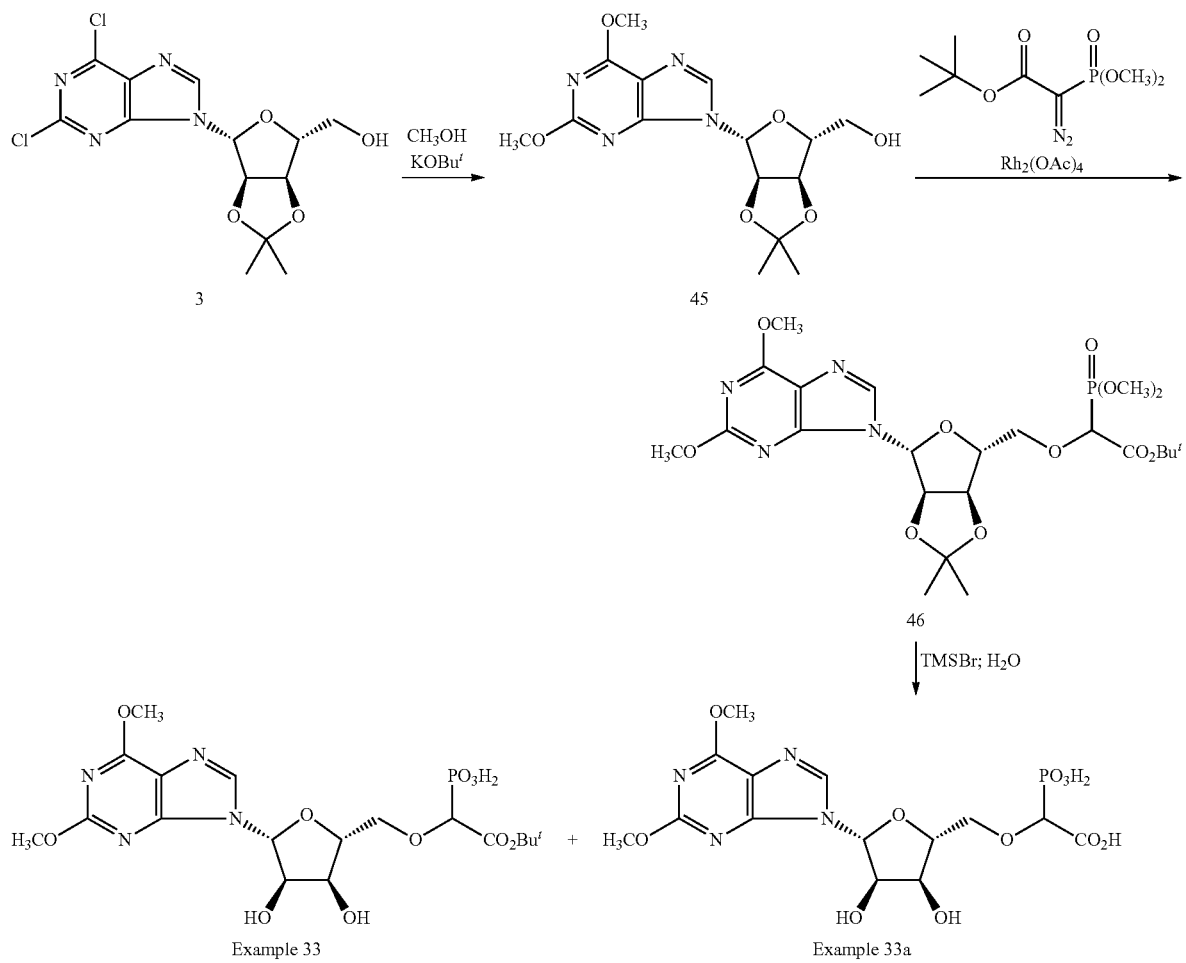

Step 1: ((3aR,4R,6R,6aR)-6-(2,6-dimethoxy-9H-purin-9-yl)-2,2-dimethyltetrahydrofuro[3,4-d][1,3]dioxol-4-yl)methanol (45)

KOBu$^t$ (1.61 g, 14.3 mmol) was added to a solution of compound 3 (0.5076 g, 1.4 mmol) in MeOH (30 mL) and stirred for 4 h at 100° C. After cooling to RT, the solvent was evaporated in vacuo, the residue was purified by chromatography on silica gel (80 g column eluted with 0 to 5% methanol in DCM over 40 min) to give compound 45 as a foam. LCMS Method 1: $t_R$=1.02 min, m/z 353 (MH$^+$).

Step 2: tert-butyl 2-(((3aR,4R,6R,6aR)-6-(2,6-dimethoxy-9H-purin-9-yl)-2,2-dimethyltetrahydrofuro[3,4-d][1,3]dioxol-4-yl)methoxy)-2-(dimethoxyphosphoryl)acetate (46)

Rhodium acetate dimer (0.0137 g, 0.031 mmol) was added to a solution of compound 45 (0.3302 g, 0.94 mmol) and tert-butyl 2-diazo-2-(dimethoxyphosphoryl)acetate (0.4390 g, 1.75 mmol) in benzene (25 mL) and then the reaction was stirred for 16 h at 100° C. under nitrogen. After cooling to RT, the solvent was evaporated under reduced pressure, the residue was purified by chromatography on silica gel (40 g column eluted with 30 to 80% EtOAc/hexanes over 30 min) to give compound 46 (0.2920 g). LCMS Method 1: $t_R$=1.34 min, m/z 575 (MH$^+$).

Step 3: 2-(((2R,3S,4R,5R)-5-(2,6-dimethoxy-9H-purin-9-yl)-3,4-dihydroxytetrahydrofuran-2-yl)methoxy)-2-phosphonoacetic acid and (2-(tert-butoxy)-1-(((2R,3S,4R,5R)-5-(2,6-dimethoxy-9H-purin-9-yl)-3,4-dihydroxytetrahydrofuran-2-yl)methoxy)-2-oxoethyl)phosphonic Acid To a solution of tert-butyl 2-(((3aR,4R,6R,6aR)-6-(2,6-dimethoxy-9H-purin-9-yl)-2,2-dimethyltetrahydrofuro[3,4-d][1,3]dioxol-4-yl)methoxy)-2-(dimethoxyphosphoryl)acetate (0.1570 g, 0.273 mmol) in dry CH$_3$CN (8 mL) was added 2 mL of bromotrimethylsilane. The reaction mixture was stirred at RT for 17 h and then quenched with water (3 mL). After stirring at RT for 9 h, the reaction mixture was treated with NH$_4$OH (3 mL). After an additional 14 h, the solvents were removed under reduced pressure at RT and the residue was purified by RP HPLC Method A to afford two products as mixture of diastereomers, which were dissolved in 5 mL of distilled water and then lyophilized to yield the title products.

Example 33 (mixture of diastereomers): 2-(((2R,3S,4R,5R)-5-(2,6-dimethoxy-9H-purin-9-yl)-3,4-dihydroxytetrahydrofuran-2-yl)methoxy)-2-phosphonoacetic acid: LCMS Method 3: $t_R$=1.31 min, m/z 451 (M+H$^+$).

Example 33a (mixture of diastereomers): (2-(tert-butoxy)-1-(((2R,3S,4R,5R)-5-(2,6-dimethoxy-9H-purin-9-yl)-3,4-dihydroxytetrahydrofuran-2-yl)methoxy)-2-oxoethyl)phosphonic acid: LCMS Method 3: $t_R$=2.61, m/z 507 (M+H$^+$).

Example 34: ((R)-1-(((2R,3S,4R,5R)-5-(2-chloro-6-(ethylamino)-9H-purin-9-yl)-3,4-dihydroxytetrahydrofuran-2-yl)methoxy)-2-(ethylamino)-2-oxoethyl)phosphonic Acid and Example 34a: ((S)-1-(((2R,3S,4R,5R)-5-(2-chloro-6-(ethylamino)-9H-purin-9-yl)-3,4-dihydroxytetrahydrofuran-2-yl)methoxy)-2-(ethylamino)-2-oxoethyl)phosphonic Acid Example 34

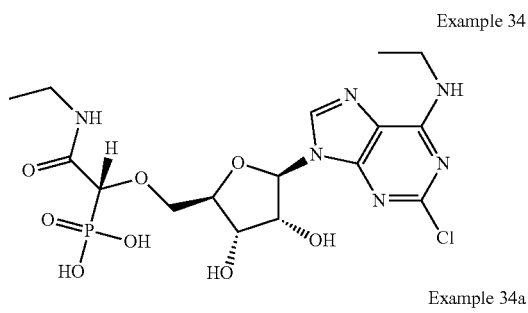

Example 34a

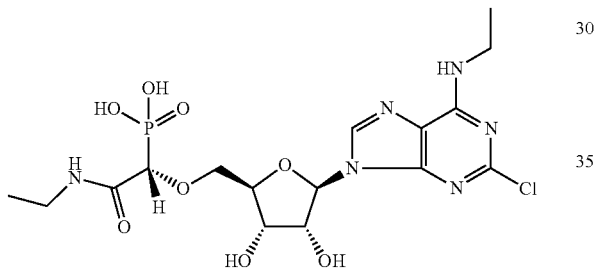

The title compounds were synthesized from compound 16 by treating with ethyl amine in EtOH under microwave conditions. The resulting crude product was further elaborated as described in Step 3 of Example 1. The final compounds were purified by RP HPLC Method B to give 1$^{st}$ eluting isomer Example 34 and 2$^{nd}$ eluting isomer Example 34a as TFA salts Example 34 LCMS Method 2: $t_R$=1.83 min, m/z=495 (M+H$^+$). $^1$H NMR (D$_2$O) δ 8.47 (s, 1H), 8.33 (s, 1H), 7.45 (s, 1H), 5.83 (d, 1H), 4.58 (m, 1H), 4.20 (m, 1H), 4.07 (ap s, 1H), 3.96 (d, 1H), 3.68 (ap s, 2H), 3.43 (m, 2H), 3.02 (m, 2H), 1.15 (m, 3H), 0.87 (m, 3H). $^{31}$P NMR (D$_2$O) δ 11.2. $^{19}$F NMR (D$_2$O) δ −75.82.

Example 34a. LCMS Method 2: $t_R$=1.91 min, m/z=495 (M+H$^+$). $^1$H NMR (D$_2$O) δ 8.48 (s, 1H), 8.33 (m, 1H), 7.43 (m, 1H), 5.83 (d, 1H), 4.56 (m, 1H), 4.20 (m, 1H), 4.07 (m, 1H), 4.03 (d, 1H), 3.70 (ap s, 2H), 3.44 (m, 2H), 3.13-2.99 (m, 2H), 1.15 (m, 3H), 0.91 (m, 3H). $^{31}$P NMR (D$_2$O) δ 12.31. $^{19}$F NMR (D$_2$O) δ −74.8.

Example 35: (1-(((2R,3S,4R,5R)-5-(6-amino-9H-purin-9-yl)-3,4-dihydroxytetrahydrofuran-2-yl)methoxy)-2-(hydroxyamino)-2-oxoethyl)phosphonic Acid

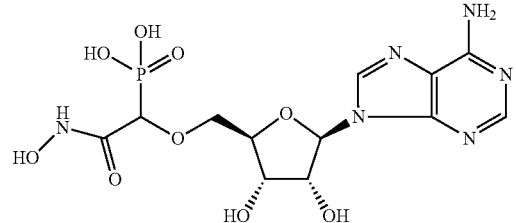 [SMILES: Nc1ncnc2c1ncn2[C@@H]1O[C@H](COC(C(=O)NO)P(=O)(O)O)[C@@H](O)[C@H]1O]

Scheme N

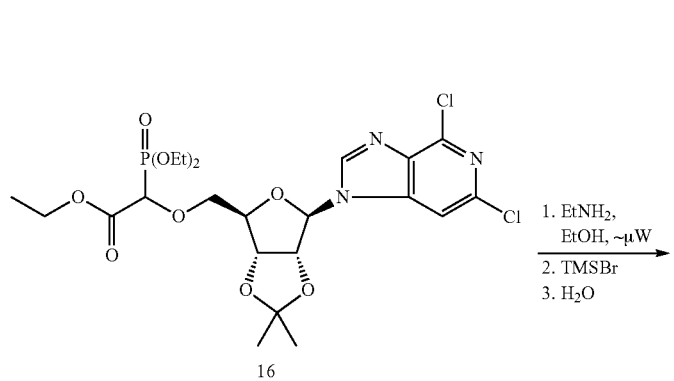

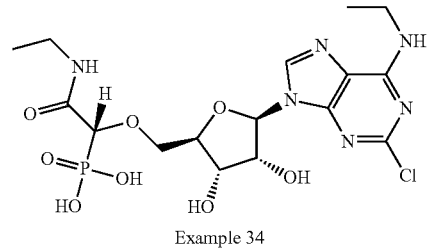

Example 34

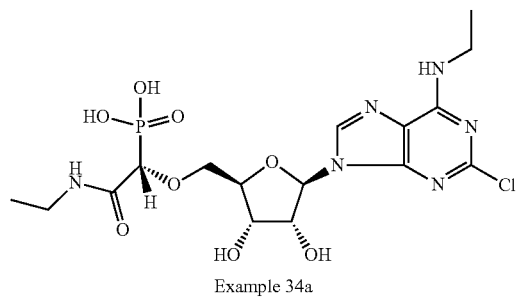

Example 34a

Scheme O

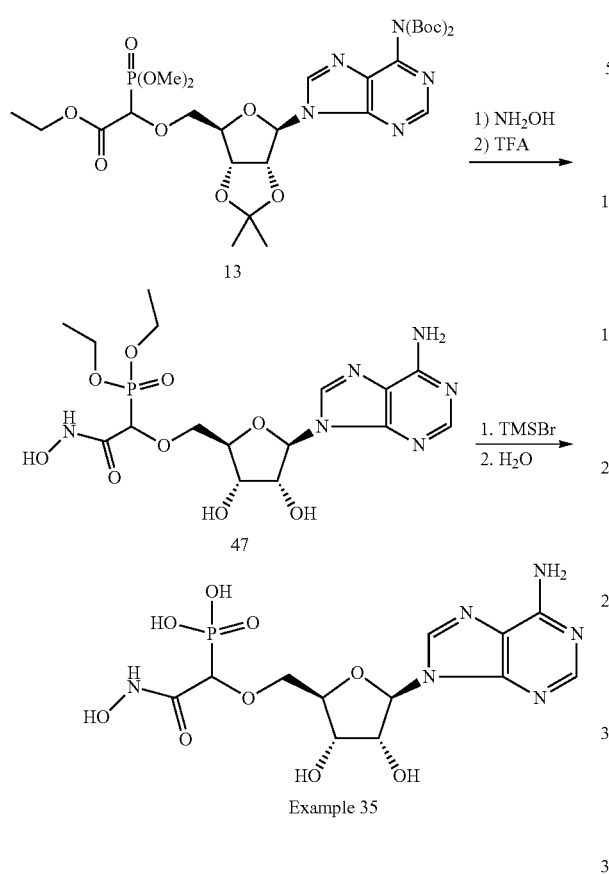

Example 35

Step 1: Compound 47

An aqueous solution of NH$_2$OH (50%, 1 mL) was added to a solution of compound 13 (157 mg, 0.22 mmol) in THF (2 mL) and stirred overnight at RT. The reaction was diluted with EtOAc and dried over Na$_2$SO$_4$. The crude material was treated with excess TFA and monitored until the reaction was complete. The final compound was purified by RP HPLC Method B and isolated as mixture of diastereomers as a TFA salt. Diethyl (1-(((2R,3S,4R,5R)-5-(6-amino-9H-purin-9-yl)-3,4-dihydroxytetrahydro furan-2-yl)methoxy)-2-(hydroxyamino)-2-oxoethyl)phosphonate (47). LCMS Method 2: $t_R$=1.20 min, m/z=477 (M+H$^+$). $^1$H NMR (CD$_3$OD) δ 8.76 (s, 1H), 8.64 (s, 1H), 8.38 (ap d, 2H), 6.10 (m, 2H), 4.70 (m, 2H), 4.23-4.37 (m, 4H), 4.26-4.18 (m, 10H), 3.99-3.83 (m, 4H), 1.33 (m, 12H). $^{31}$P NMR (CD$_3$OD) δ 16.95, 16.81. $^{19}$F NMR (CD$_3$OD) δ 77.61

Step 2. (1-(((2R,3S,4R,5R)-5-(6-amino-9H-purin-9-yl)-3,4-dihydroxytetrahydrofuran-2-yl)methoxy)-2-(hydroxyamino)-2-oxoethyl)phosphonic Acid The title compound was synthesized from compound 47 according to Example 1, Step 3. LCMS Method 2: $t_R$=0.94 min, m/z=421 (M+H$^+$).

Example 36: ((R)-1-(((2R,3S,4R,5R)-5-(6-benzamido-2-chloro-9H-purin-9-yl)-3,4-dihydroxytetrahydrofuran-2-yl)methoxy)-2-ethoxy-2-oxoethyl) phosphonic Acid and

Example 36a: ((S)-1-(((2R,3S,4R,5R)-5-(6-benzamido-2-chloro-9H-purin-9-yl)-3,4-dihydroxytetrahydrofuran-2-yl)methoxy)-2-ethoxy-2-oxoethyl) phosphonic Acid

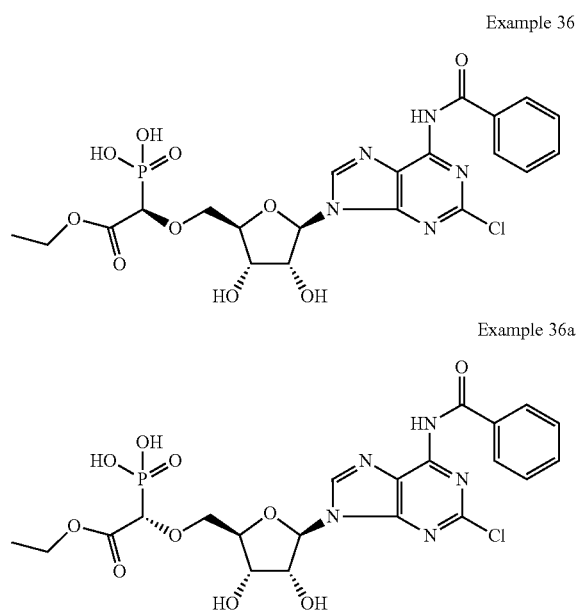

Example 36

Example 36a

Scheme P

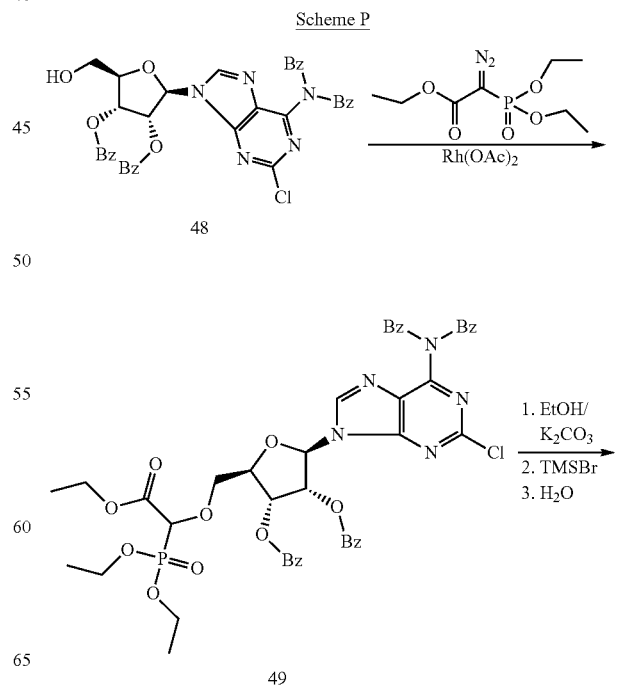

113
-continued

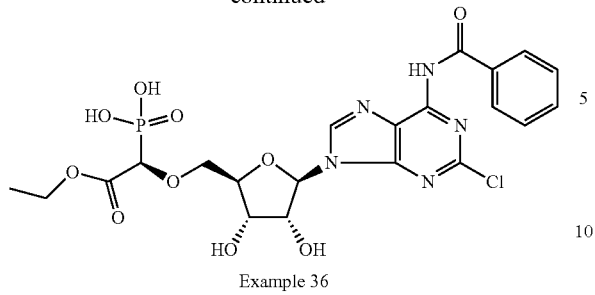

Example 36

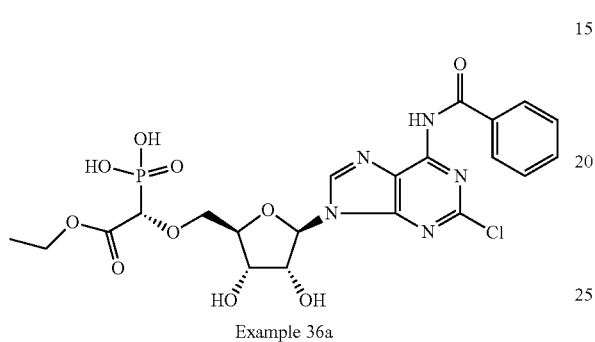

Example 36a

The title compounds were synthesized from (2R,3R,4R,5R)-2-(6-(N-benzoylbenzamido)-2-chloro-9H-purin-9-yl)-5-(hydroxymethyl)tetrahydrofuran-3,4-diyl dibenzoate, which was reacted with triethyl diazophophonoacetate as described in Step 1 of Example 1. The crude intermediate was then treated with 10 mole % of K$_2$CO$_3$ in EtOH overnight at RT. The solution was filtered and the crude material was further treated as described in Step 3 of Example 1. The final compound was purified by RP HPLC Method B to give 1$^{st}$ eluting isomer Example 36 and 2$^{nd}$ eluting isomer Example 36a, isolated as TFA salts.

Example 36: ((R)-1-(((2R,3S,4R,5R)-5-(6-benzamido-2-chloro-9H-purin-9-yl)-3,4-dihydroxytetrahydrofuran-2-yl)methoxy)-2-ethoxy-2-oxoethyl)phosphonic acid. LCMS Method 2: t$_R$=2.05 min, m/z=572 (M+H$^+$). $^1$H NMR (CD$_3$OD) δ 9.54 (s, 1H), 8.10 (d, 2H), 7.70 (m, 1H), 7.59 (m, 2H), 6.25 (d, 1H), 4.78 (m, 1H), 4.61 (m, 1H), 4.32 (m, 4H), 3.99 (d, 1H), 3.84 (d, 1H), 1.32 (m, 3H). $^{31}$P NMR (CD$_3$OD) δ 11.45. $^{19}$F NMR (CD$_3$OD) δ −76.97.

Example 36a: ((S)-1-(((2R,3S,4R,5R)-5-(6-benzamido-2-chloro-9H-purin-9-yl)-3,4-dihydroxytetrahydro furan-2-yl)methoxy)-2-ethoxy-2-oxoethyl)phosphonic acid. LCMS Method 2: t$_R$=2.13 min, m/z=572 (M+H$^+$). $^1$H NMR (CD$_3$OD) δ 8.10 (m, 2H), 7.71 (m, 1H), 7.61 (m, 2H), 6.21 (m, 1H), 4.60 (m, 2H), 4.28 (m4H), 3.87 (m, 2H), 1.35 (m, 3H). $^{31}$P NMR (CD$_3$OD) δ 11.46. $^{19}$F NMR (CD$_3$OD) δ −76.91.

114

Example 37: ((R)-1-(((2S,3R,4S,5S)-5-(6-amino-2-methyl-9H-purin-9-yl)-3,4-dihydroxytetrahydrofuran-2-yl)methoxy)-2-ethoxy-2-oxoethyl)phosphonic Acid and Example 37a: ((S)-1-(((2S,3R,4S,5S)-5-(6-amino-2-methyl-9H-purin-9-yl)-3,4-dihydroxytetrahydrofuran-2-yl)methoxy)-2-ethoxy-2-oxoethyl)phosphonic Acid

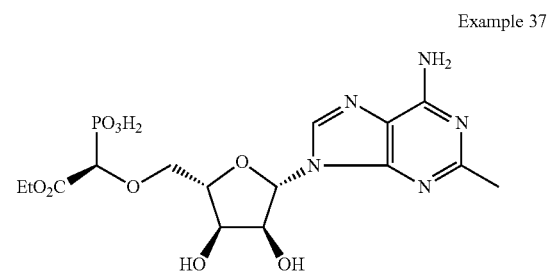

Example 37

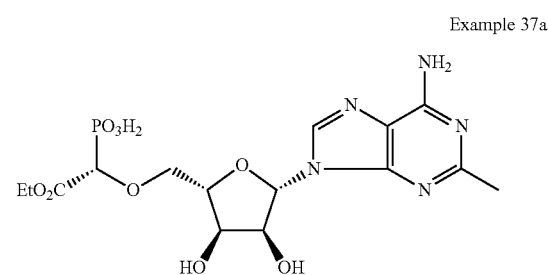

Example 37a

Scheme Q1

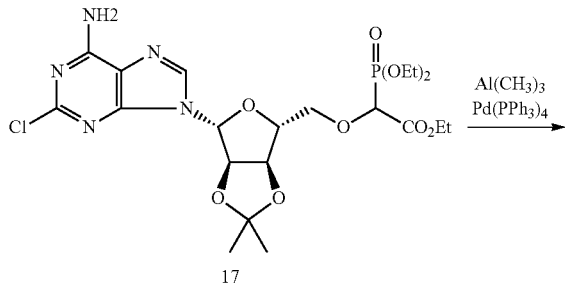

17

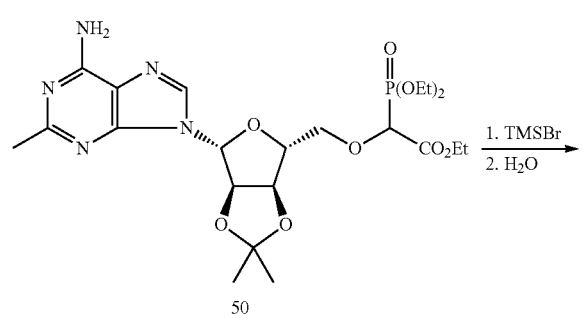

50

-continued

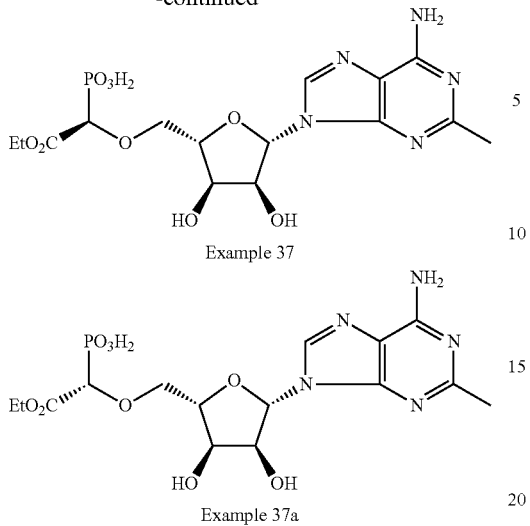

Example 37

Example 37a

Step 1: Ethyl 2-(((3aR,4R,6R,6aR)-6-(6-amino-2-methyl-9H-purin-9-yl)-2,2-dimethyltetrahydrofuro[3,4-d][1,3]dioxol-4-yl)methoxy)-2-(diethoxyphosphoryl)acetate (50)

A mixture of compound 17 (0.0780 g, 0.14 mmol), Pd(PPh$_3$)$_4$ (0.0270 g, 0.0233 mmol), and Al(CH$_3$)$_3$ (2.0 M in heptane, 1 mL, 2 mmol) in THF (5 mL) was stirred for 21 h at 75° C. The reaction mixture was cooled to RT and quenched with sat. NaHCO$_3$ (2 mL), extracted with DCM, dried over Na$_2$SO$_4$. After the solvents were evaporated under reduced pressure, the residue was purified by chromatography on silica gel (40 g column, eluted with 0 to 10% methanol in DCM over 40 min) to afford compound 50 (47 mg). LCMS Method 2: $t_R$=0.90 min, m/z 544 (M+H$^+$).

Step 2

(1-(((2R,3S,4R,5R)-5-(6-amino-2-methyl-9H-purin-9-yl)-3,4-dihydroxytetrahydrofuran-2-yl)methoxy)-2-ethoxy-2-oxoethyl)phosphonic acid was prepared from ethyl 2-(((3aR,4R,6R,6aR)-6-(6-amino-2-methyl-9H-purin-9-yl)-2,2-dimethyltetrahydrofuro[3,4-d][1,3]dioxol-4-yl)methoxy)-2-(diethoxyphosphoryl)acetate (0.0474 g) by the method described in Step 3 of Example 1. The final compound was purified by RP HPLC Method B to give 1$^{st}$ eluting isomer Example 37 and 2$^{nd}$ eluting isomer Example 37a, as TFA salts.

Example 37: LCMS Method 3: $t_R$=1.05 min, m/z 448 (M+H$^+$).

Example 37a: LCMS Method 3: $t_R$=1.17 min, m/z 448 (M+H$^+$).

Example 38: 2-(((2R,3S,4R,5R)-5-(2,6-dimethyl-9H-purin-9-yl)-3,4-dihydroxytetrahydrofuran-2-yl)methoxy)-2-phosphonoacetic acid

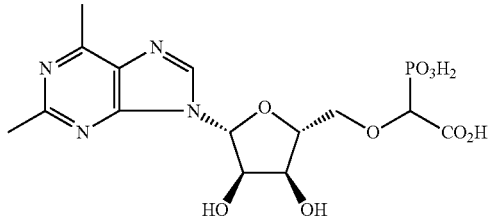

Scheme Q2

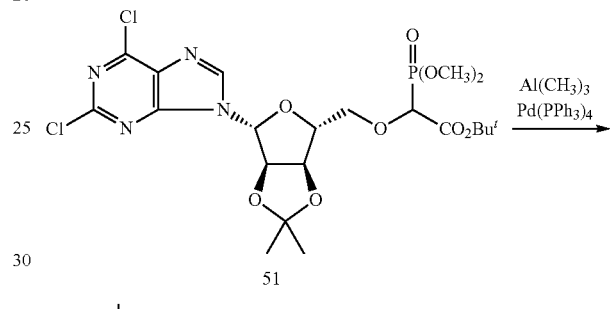

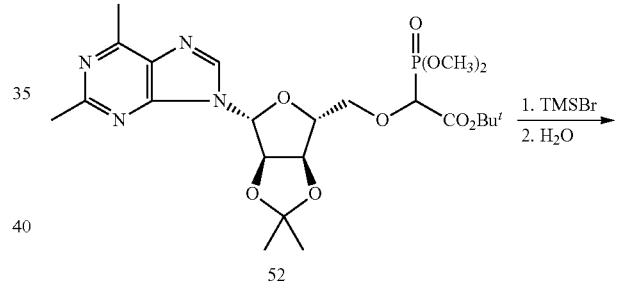

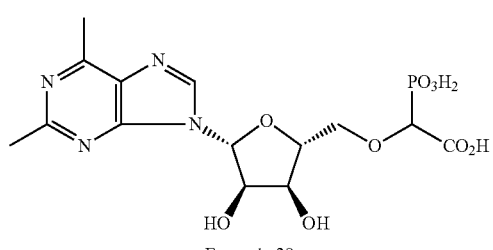

Example 38

Step 1: tert-Butyl 2-(dimethoxyphosphoryl)-2-(((3aR,4R,6R,6aR)-6-(2,6-dichloro-9H-purin-9-yl)-2,2-dimethyltetrahydrofuro[3,4-d][1,3]dioxol-4-yl)methoxy)acetate (51)

Compound 51 was synthesized from compound 3 and tert-butyl 2-diazo-2-(dimethoxyphosphoryl)acetate by the method described in Step 1 of Example 1. LCMS Method 1: $t_R$=1.17 min, m/z 482.2 (M+H$^+$).

Step 2. tert-butyl 2-(dimethoxyphosphoryl)-2-(((3aR,4R,6R,6aR)-6-(2,6-dimethyl-9H-purin-9-yl)-2,2-dimethyltetrahydrofuro[3,4-d][1,3]dioxol-4-yl)methoxy)acetate (52)

A mixture of compound 51 (0.1605 g, 0.275 mmol), Pd(PPh₃)₄ (0.0228 g, 0.0197 mmol), and Al(CH₃)₃ (2.0 M in heptane, 1.4 mL, 2.8 mmol) in THF (5 mL) was stirred for 21 h at 75° C. The reaction mixture was cooled to RT and then quenched with sat. NaHCO₃ (3 mL), extracted with DCM, dried over Na₂SO₄. After the solvents were removed in vacuo, the residue was purified by chromatography on silica gel (40 g column eluted with 0 to 10% methanol in DCM over 40 min) to afford 0.0582 g of tert-butyl 2-(dimethoxyphosphoryl)-2-(((3aR,4R,6R,6aR)-6-(2,6-dimethyl-9H-purin-9-yl)-2,2-dimethyltetrahydrofuro[3,4-d][1,3]dioxol-4-yl)methoxy)acetate. LCMS Method 1: $t_R$=1.06 min, m/z 543 (M+H⁺).

Step 3: 2-(((2R,3S,4R,5R)-5-(2,6-dimethyl-9H-purin-9-yl)-3,4-dihydroxytetrahydrofuran-2-yl)methoxy)-2-phosphonoacetic acid. (Example 38)

TMSBr (1 mL) was added to a solution of compound 52 (0.0582 g, 0.11 mmol) in dry ACN (3 mL) and stirred for 24 h at RT and quenched with water (2 mL). After stirring at RT for 3 d, the reaction mixture was treated with aq. NH₄OH (2 mL). After an additional 2 h, the solvents were removed in vacuo at RT and the residue was purified by RP HPLC Method A to afford 2-(((2R,3S,4R,5R)-5-(2,6-dimethyl-9H-purin-9-yl)-3,4-dihydroxytetrahydrofuran-2-yl)methoxy)-2-phosphonoacetic acid, which was dissolved in 5 mL of distilled water and then lyophilized as a mixture of diastereomers. LCMS Method 3: $t_R$=1.02 min, m/z=419 (M+H⁺).

Example 39: ((R)-1-(((2R,3S,4R,5R)-5-(6-amino-2-benzyl-9H-purin-9-yl)-3,4-dihydroxytetrahydrofuran-2-yl)methoxy)-2-ethoxy-2-oxoethyl)phosphonic Acid and

Example 39a: ((S)-1-(((2R,3S,4R,5R)-5-(6-amino-2-benzyl-9H-purin-9-yl)-3,4-dihydroxytetrahydrofuran-2-yl)methoxy)-2-ethoxy-2-oxoethyl)phosphonic Acid Example 39

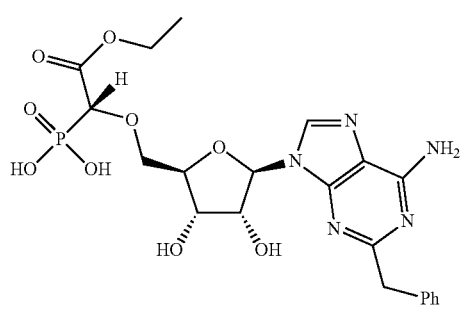

Example 39a

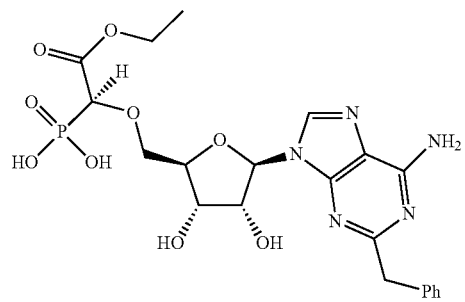

Scheme R

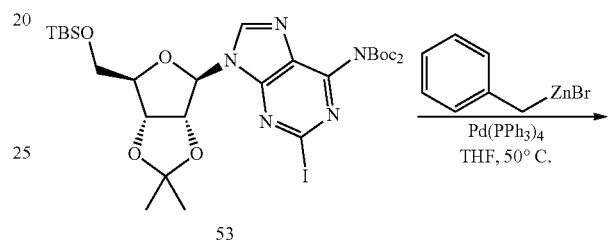

53

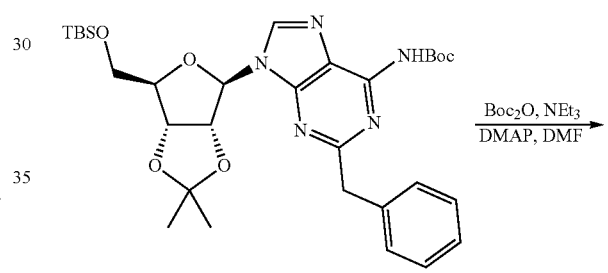

54

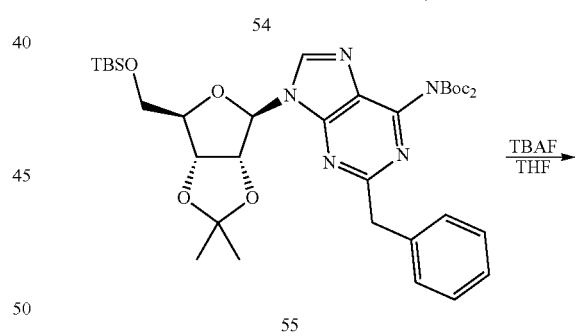

55

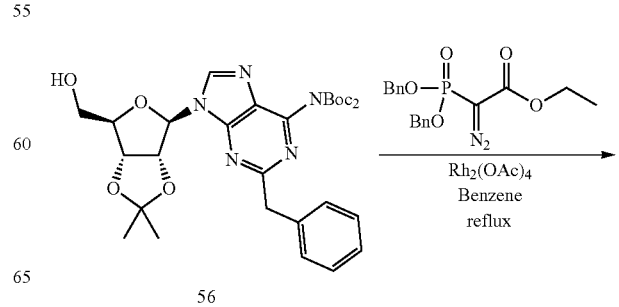

56

-continued

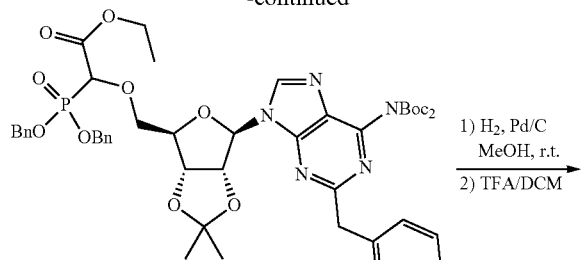

57

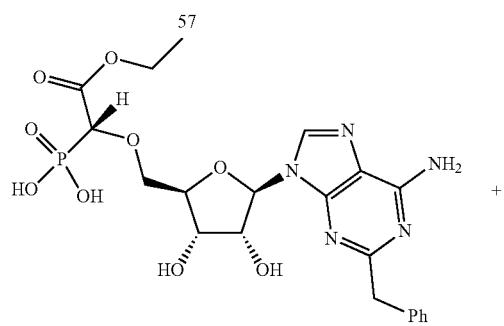

Example 39

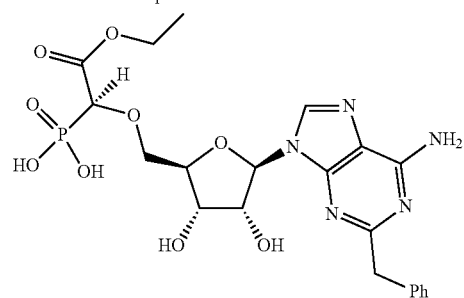

Example 39a

Step 1: tert-Butyl (2-benzyl-9-((3aR,4R,6R,6aR)-6-(((tert-butyldimethylsilyl)oxy)methyl)-2,2-dimethyl-tetrahydrofuro[3,4-d][1,3]dioxol-4-yl)-9H-purin-6-yl) carbamate (54)

N6, N6-bis-Boc-5'-O-tert-butyldimethylsilyl-2'-3'-O-isopropylidene-2-iodo-adenosine (53, 203 mg, 0.27 mmol) was synthesized from 2-iodo-adenosine as described by Smith, C., et. al. Angew. Chem. Int. Ed. 2011, 50(39), pp. 9200. To a degassed solution of compound 53 in THF (1.8 mL) was added benzyl zinc bromide (1.63 mL, 0.5 M in THF, 0.82 mmol) followed by Pd(PPh$_3$)$_4$ (16 mg, 0.01 mmol), and the reaction was heated to 50° C. until completion as monitored by LCMS Method 1. The mixture was cooled to RT and partitioned between EtOAc and 0.5 M HCl. The organic phase was washed with water, brine, successively and dried over Na$_2$SO$_4$. The crude material 54 was purified by flash chromatography using hexane/EtOAc as eluent, yielding compound 54 as colorless oil (139 mg).

Step 2: N6, N6-bis-Boc-5'-O-tert-butyldimethylsilyl-2'-3'-O-isopropylidene-2-benzyl-adenosine (55)

This reaction was set up as describe in Step 1 (above) using compound 54 (130 mg, 1.0 eq.), DMAP (0.1 eq.), Boc$_2$O (1.3 eq.), TEA (1.0 eq.) in DMF, yielding the desired bis-Boc product (55, 132 mg) as a colorless oil. LCMS Method 2: $t_R$=2.06 min, m/z=712.4 (M+H$^+$).

Step 3: N6,N6-bis-Boc-2'-3'-O-isopropylidene-2-benzyl-adenosine (56)

To a solution of compound 55 (132 mg, 0.19 mmol) in THF (2 mL) was added TBAF (0.28 mL, 1M in THF, 0.28 mmol), and the reaction was allowed to stir at RT for 3 h. The volatiles were removed in vacuo and the crude purified by flash chromatography using hexane-EtOAc as an eluent, yielding compound 56 (120 mg) as a colorless oil. LCMS Method 1: $t_R$=1.67 min, m/z=598.4 (M+H$^+$).

Step 4: Compound 57

Rh$_2$(OAc)$_4$ (2 mg, 0.005 mmol) was added to a solution of compound 56 (120 mg, 0.19 mmol) and ethyl 2-(bis(benzyloxy)phosphoryl)-2-diazoacetate (113 mg, 0.30 mmol) in benzene (2 mL). The reaction mixture was refluxed overnight. The volatiles were removed under vacuum and the crude purified by flash chromatography using hexane/EtOAc as eluent, yielding compound 57 (130 mg) as a colorless oil. LCMS Method 1: $t_R$=2.06 min, m/z=712.4 (M+H$^+$).

Step 5: ((R)-1-(((2R,3S,4R,5R)-5-(6-amino-2-benzyl-9H-purin-9-yl)-3,4-dihydroxytetrahydrofuran-2-yl)methoxy)-2-ethoxy-2-oxoethyl)phosphonic acid and ((S)-1-(((2R,3S,4R,5R)-5-(6-amino-2-benzyl-9H-purin-9-yl)-3,4-dihydroxytetrahydrofuran-2-yl)methoxy)-2-ethoxy-2-oxoethyl)phosphonic Acid Pd/C (7 mg) was added to a solution of compound 57 (65 mg, 0.069 mmol) in MeOH (5 mL) and stirred for 1 h at RT. The mixture was filtered over Celite, then the filtrate was concentrated and the crude was dissolved in DCM (2 mL) and TFA (1 mL). After 2 h at RT, water (3 drops) was added and the reaction was allowed to stir for an additional h at RT. The volatiles were removed under vacuum and the crude was purified by RP HPLC Method B to give 1$^{st}$ eluting isomer Example 39 (7 mg) and 2$^{nd}$ eluting isomer Example 39a (7.7 mg) as colorless oils.

Example 39: LCMS Method 3: $t_R$=2.27 min, m/z=524.5 (M+H$^+$); $^1$H NMR (CD$_3$OD) δ 8.66 (s, 1H), 7.36 (d, 2H), 7.19 (t, 2H), 7.11 (t, 1H), 5.96 (d, 1H), 4.39 (m, 1H), 4.32 (d, 1H), 4.11-4.28 (m, 6H), 3.99 (m, 1H), 3.63 (dd, 1H), 1.21 (t, 3H) ppm.; $^{31}$P NMR (CD$_3$OD) δ 9.74 (bs).

Example 39a: LCMS Method 3: $t_R$=3.13 min, m/z=524.5 (M+H$^+$); $^1$H NMR (CD$_3$OD) δ 9.04 (s, 1H), 7.19-7.45 (m, 5H), 6.16 (m, 1H), 4.42-4.19 (m, 8H), 3.84 (m, 1H), 3.77 (dd, 1H), 1.21 (bs, 3H) ppm.; $^{31}$P NMR (CD$_3$OD) δ 10.99 (bs).

Example 40: ((R)-1-(((2R,3S,4R,5R)-5-(6-amino-2-phenyl-9H-purin-9-yl)-3,4-dihydroxytetrahydrofuran-2-yl)methoxy)-2-ethoxy-2-oxoethyl)phosphonic Acid and Example 40a: ((S)-1-(((2R,3S,4R,5R)-5-(6-amino-2-phenyl-9H-purin-9-yl)-3,4-dihydroxytetrahydrofuran-2-yl)methoxy)-2-ethoxy-2-oxoethyl)phosphonic Acid

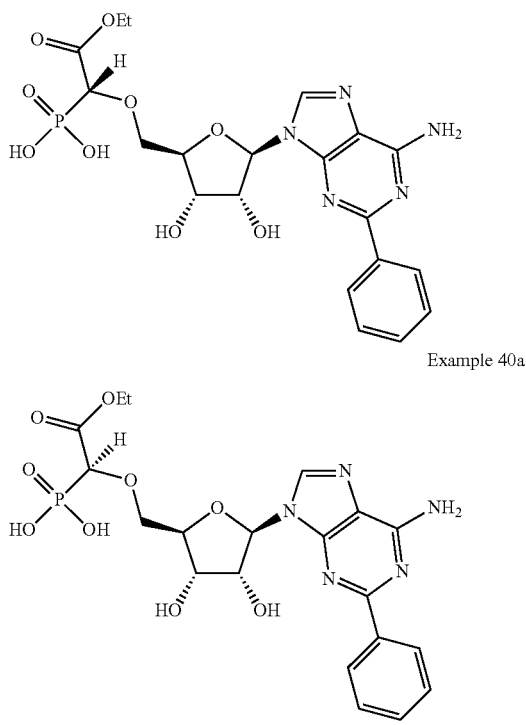

Example 40

Example 40a

The title compounds were synthesized by the method described in Example 39. In Step 3, the following procedure was carried out. To a degassed solution of N6,N6-bis-Boc-2'-3'-O-isopropylidene-2-iodo-adenosine (192 mg, 0.30 mmol), phenyl boronic acid (55 mg, 0.45 mmol) and $K_2CO_3$ (210 mg, 1.52 mmol) in dioxane/$H_2O$ (3 mL; 4:1) was added Pd(PPh$_3$)$_4$ (17 mg, 0.01 mmol). The reaction was heated to 100° C. overnight. After cooling to RT, the mixture was filtered through a pad of Celite and the filtrate was concentrated under vacuum. The crude material was purified by flash chromatography using hexane-EtOAc as eluent yielding tert-butyl (9-((3aR,4R,6R,6aR)-6-(((tert-butyldimethylsilyl)oxy)methyl)-2,2-dimethyltetrahydrofuro[3,4-d][1,3]dioxol-4-yl)-2-phenyl-9H-purin-6-yl)carbamate as a colorless oil (84 mg). This compound was further elaborated as described in Step 5 of Example 39. The final product was purified by RP HPLC Method B to give 1$^{st}$ eluting isomer Example 40 and 2$^{nd}$ eluting isomer Example 40a.

Example 40: LCMS Method 3: $t_R$=3.85 min, m/z=546.5 (M+H$^+$); $^1$H NMR (CD$_3$OD) δ 9.62 (s, 1H), 7.80 (d, 2H), 6.90 (m, 1H), 6.21 (bs, 1H), 4.55-4.67 (m, 3H), 4.28 (m, 3H), 4.17 (d, 1H), 3.89 (d, 1H), 1.33 (t, 3H) ppm. $^{31}$P NMR (CD$_3$OD) δ 10.88 (bs).

Example 40a: LCMS Method 3: $t_R$=4.28 min, m/z=546.4 (M+H$^+$); $^1$H NMR (CD$_3$OD) δ 9.77 (s, 1H), 7.86 (m, 2H), 7.03 (m, 1H), 6.23 (m, 1H), 4.83 (m, 1H), 4.52 (m, 1H), 4.41 (d, 1H), 4.22-4.35 (m, 3H), 4.01 (m, 1H), 3.82 (m, 1H), 1.22 (m, 3H) ppm. $^{31}$P NMR (CD$_3$OD) δ 10.48 (bs).

Example 41: ((R)-1-(((2R,3S,4R,5R)-5-(6-amino-2-(3,5-difluorophenyl)-9H-purin-9-yl)-3,4-dihydroxytetrahydrofuran-2-yl)methoxy)-2-ethoxy-2-oxoethyl)phosphonic Acid and Example 41a: ((S)-1-(((2R,3S,4R,5R)-5-(6-amino-2-(3,5-difluorophenyl)-9H-purin-9-yl)-3,4-dihydroxytetrahydrofuran-2-yl)methoxy)-2-ethoxy-2-oxoethyl)phosphonic Acid

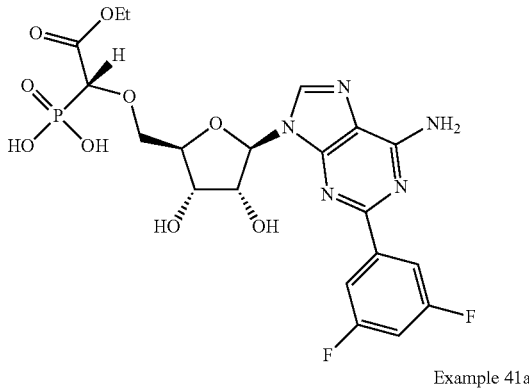

Example 41

Example 41a

The title compounds were synthesized by the method described in Example 40. In Step 3, 3,5-difluoro phenylboronic acid was utilized instead of phenylboronic acid. The final product was purified by RP HPLC Method B to give 1$^{st}$ eluting isomer Example 41 and 2$^{nd}$ eluting isomer Example 41a.

Example 41: LCMS Method 3: $t_R$=3.85 min, m/z=546.5 (M+H$^+$); $^1$H NMR (CD$_3$OD, 400 MHz) δ 9.62 (s, 1H), 7.80 (d, 2H), 6.90 (m, 1H), 6.21 (bs, 1H), 4.55-4.67 (m, 3H), 4.28 (m, 3H), 4.17 (d, 1H), 3.89 (d, 1H), 1.33 (t, 3H) ppm. $^{31}$P NMR (CD$_3$OD) δ 10.88 (bs).

Example 41a: LCMS Method 3: $t_R$=4.28 min, m/z=546.4 (M+H$^+$); $^1$H NMR (CD$_3$OD, 400 MHz) δ 9.77 (s, 1H), 7.86 (m, 2H), 7.03 (m, 1H), 6.23 (m, 1H), 4.83 (m, 1H), 4.52 (m, 1H), 4.41 (d, 1H), 4.22-4.35 (m, 3H), 4.01 (m, 1H), 3.82 (m, 1H), 1.22 (m, 3H) ppm. $^{31}$P NMR (CD$_3$OD) δ 10.48 (bs).

Example 42: ((R)-1-(((2R,3S,4R,5R)-5-(6-amino-2-(trifluoromethyl)-9H-purin-9-yl)-3,4-dihydroxytetrahydrofuran-2-yl)methoxy)-2-ethoxy-2-oxoethyl) phosphonic Acid and

Example 42a: ((S)-1-(((2R,3S,4R,5R)-5-(6-amino-2-(trifluoromethyl)-9H-purin-9-yl)-3,4-dihydroxytetrahydrofuran-2-yl)methoxy)-2-ethoxy-2-oxoethyl) phosphonic Acid

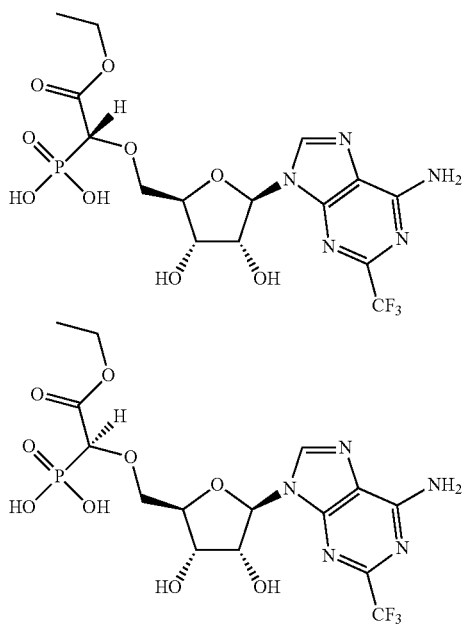

The title compounds were synthesized by the method described in Example 39. The following procedure was utilized in Step 3. (1,10-Phenanthroline)(trifluoromethyl)copper(I) (125 mg, 0.40 mmol) was added to a solution of N6,N6-bis-Boc-5'-O-tert-butyldimethylsilyl-2'-3'-O-isopropylidene-2-iodo-adenosine (200 mg, 0.27 mmol) in DMF (1.1 mL) and stirred overnight at RT. The mixture was diluted with diethyl ether and filtered through a pad of Celite. The combined filtrate was washed with 0.5M HCl, saturated aq. NaHCO₃, brine and dried over sodium sulfate. This crude was purified by flash chromatography yielding tert-butyl (9-((3aR,4R,6R,6aR)-6-(((tert-butyldimethylsilyl)oxy)methyl)-2,2-dimethyltetrahydrofuro[3,4-d][1,3]dioxol-4-yl)-2-(trifluoromethyl)-9H-purin-6-yl)carbamate (125 mg) as a colorless oil. This compound was further elaborated as described in Steps 4 & 5 of Example 39. The final product was purified by RP HPLC Method B to give 1$^{st}$ eluting isomer Example 42 and 2$^{nd}$ eluting isomer Example 42a.

Example 42: LCMS Method 3: $t_R$=2.28 min, m/z 502.4 (M+H$^+$); $^1$H NMR (D$_2$O, 400 MHz) δ 8.88 (s, 1H), 6.19 (d, 1H), 4.89, (t, 1H), 4.57 (t, 1H), 4.39 (m, 1H), 4.37 (d, 1H), 4.18 (q, 2H), 4.01 (dd, 1H), 3.90 (dd, 1H), 1.20 (t, 3H) ppm. $^{31}$P NMR (D$_2$O, 162 MHz) δ 8.71 (s).

Example 42a: LCMS Method 3: $t_R$=2.75 min, m/z 502.4 (M+H$^+$); $^1$H NMR (D$_2$O, 400 MHz) δ 9.08 (s, 1H), 6.22 (d, 1H), 4.84 (t, 1H), 4.62 (t, 1H), 4.39 (m, 1H), 4.37 (d, 1H), 4.22 (q, 2H), 3.97 (dd, 1H), 3.85 (dd, 1H), 1.22 (t, 3H) ppm. $^{31}$P NMR (D$_2$O, 162 MHz) δ 8.40 (bs).

Example 43: (1-(((2R,3S,4R,5R)-5-(6-amino-2-(methylthio)-9H-purin-9-yl)-3,4-dihydroxytetrahydrofuran-2-yl)methoxy)-2-ethoxy-2-oxoethyl)phosphonic Acid

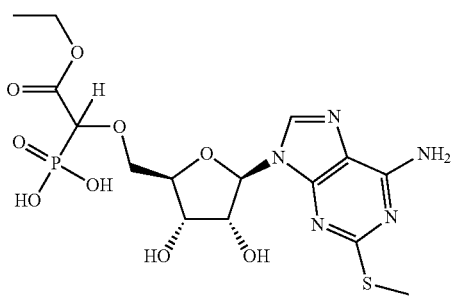 [SMILES: CCOC(=O)C(OC[C@H]1O[C@@H](n2cnc3c(N)nc(SC)nc32)[C@H](O)[C@@H]1O)P(=O)(O)O]

The title compound was synthesized from ((3aR,4R,6R,6aR)-6-(6-amino-2-(methylthio)-9H-purin-9-yl)-2,2-dimethyltetrahydrofuro[3,4-d][1,3]dioxol-4-yl)methanol by the method described in Example 1. The final product was purified by RP HPLC Method B and isolated as mixture of diastereomers and as TFA salt.

Example 43 (mixt. of diastereomers): (1-(((2R,3S,4R,5R)-5-(6-amino-2-(methylthio)-9H-purin-9-yl)-3,4-dihydroxytetrahydro furan-2-yl)methoxy)-2-ethoxy-2-oxoethyl) phosphonic acid LCMS Method 2: $t_R$=1.16 min, m/z=480 (M+H$^+$). $^1$H NMR (CD$_3$OD) δ 9.02 (s), 6.11 (d), 5.98 (d), 4.69 (t), 4.5 (t), 4.4 (d), 4.33 (m), 4.25 (m), 4.12 (m), 3.98 (m), 3.82 (m), 2.62 (s), 2.60 (s), 1.29 (t). $^{31}$P NMR (CD$_3$OD) δ 11.45, 10.70. $^{19}$F NMR (CD$_3$OD) δ −77.44.

Example 44: ((R)-1-(((2R,3S,4R,5R)-5-(6-amino-2-(ethylthio)-9H-purin-9-yl)-3,4-dihydroxytetrahydrofuran-2-yl)methoxy)-2-ethoxy-2-oxoethyl)phosphonic acid and

Example 44a: ((S)-1-(((2R,3S,4R,5R)-5-(6-amino-2-(ethylthio)-9H-purin-9-yl)-3,4-dihydroxytetrahydrofuran-2-yl)methoxy)-2-ethoxy-2-oxoethyl)phosphonic Acid Example 44

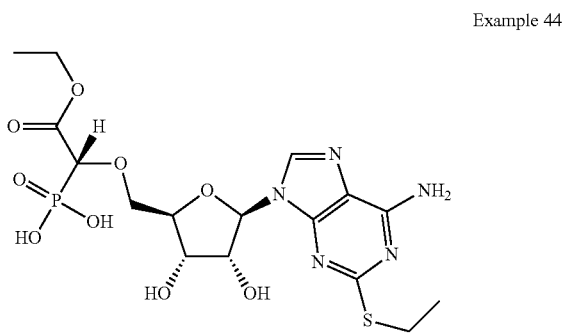

Example 44a

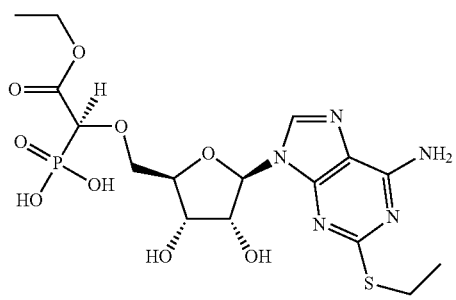

The title compounds were synthesized from ((3aR,4R,6R,6aR)-6-(6-amino-2-(ethylthio)-9H-purin-9-yl)-2,2-dimethyltetrahydrofuro[3,4-d][1,3]dioxol-4-yl)methanol by the method described in Example 1. The final product was purified by RP HPLC Method B to give 1$^{st}$ eluting isomer Example 44 and 2$^{nd}$ eluting isomer Example 44a.

Example 44: LCMS Method 2: $t_R$=1.83 min, m/z=494 (M+H$^+$). $^1$H NMR (CD$_3$OD) δ 8.91 (s, 1H), 5.99 (d, 1H, 5 Hz), 4.60 (m, 1H), 4.42 (m, 1H), 4.30 (d, 1H, 18 Hz), 4.17 (m, 3H), 3.89 (m, 1H), 3.72 (m, 1H), 3.14 (m, 2H), 1.33 (m, 3H), 1.21 (m, 3H).

Example 44a: LCMS Method 2: $t_R$=1.94 min, m/z=494 (M+H$^+$). $^1$H NMR (CD$_3$OD) δ 9.22 (s, 1H), 6.04 (s, 1H), 4.45 (s, 1H), 4.26 (d, 1H, 18 Hz), 4.17 (m, 1H), 4.10 (m, 2H), 3.81 (d, 1H), 3.71 (d, 1H), 1.35 (m, 3H), 1.12 (m, 3H).

Example 45a

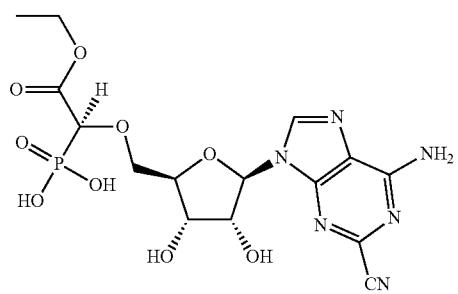

The title compounds were synthesized by the method described in Example 39. In Step 3, ZnCN$_2$ was utilized instead of benzyl zinc bromide. The final product was purified by RP HPLC Method B to give 1$^{st}$ eluting isomer Example 45 and 2$^{nd}$ eluting isomer Example 45a.

Example 45 LCMS Method 2: $t_R$=1.57 min, m/z=459 (M+H$^+$). $^1$H NMR (CD$_3$OD) δ 8.82 (s, 1H), 6.09 (d, 1H), 4.70 (m, 1H), 4.47 (m, 1H), 4.40 (d, 1H, 18 Hz), 4.25 (m, 3H), 3.94 (m, 1H), 3.84 (m, 1H), 1.29 (s, 3H). $^{31}$P NMR (CD$_3$OD) δ 11.45. $^{19}$F NMR (CD$_3$OD) δ -77.42.

Example 45a LCMS Method 2: $t_R$=1.59 min, m/z=459 (M+H$^+$). $^1$H NMR (CD$_3$OD) δ 8.87 (s, 1H), 6.00 (d, 1H), 4.60 (m, 1H), 4.35 (m, 1H), 4.31 (d, 1H), 4.16 (m, 3H), 3.87 (m, 1H), 3.73 (m, 1H), 1.18 (s, 3H). $^{31}$P NMR (CD$_3$OD) δ 11.46. $^{19}$F NMR (CD$_3$OD) δ -77.74.

Example 45: ((R)-1-(((2R,3S,4R,5R)-5-(6-amino-2-cyano-9H-purin-9-yl)-3,4-dihydroxytetrahydrofuran-2-yl)methoxy)-2-ethoxy-2-oxoethyl)phosphonic Acid and Example 45a: ((S)-1-(((2R,3S,4R,5R)-5-(6-amino-2-cyano-9H-purin-9-yl)-3,4-dihydroxytetrahydrofuran-2-yl)methoxy)-2-ethoxy-2-oxoethyl)phosphonic Acid Example 46: ((R)-1-(((2R,3S,4R,5R)-5-(6-amino-2-isobutyl-9H-purin-9-yl)-3,4-dihydroxytetrahydrofuran-2-yl)methoxy)-2-ethoxy-2-oxoethyl)phosphonic Acid and Example 46a: ((S)-1-(((2R,3S,4R,5R)-5-(6-amino-2-isobutyl-9H-purin-9-yl)-3,4-dihydroxytetrahydrofuran-2-yl)methoxy)-2-ethoxy-2-oxoethyl)phosphonic Acid Example 45

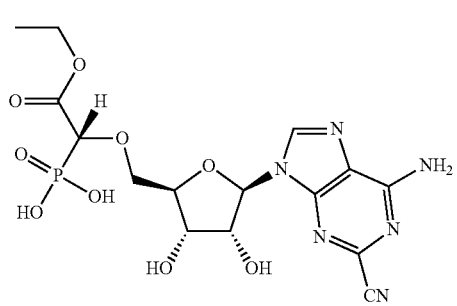

Example 46

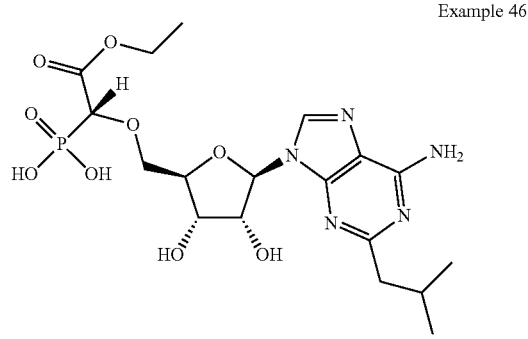

Example 46a

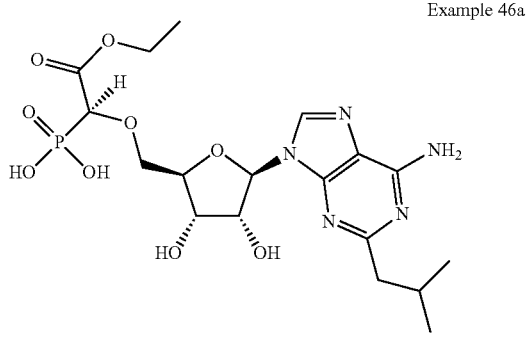

The title compounds were synthesized by the method described in Example 39. In Step 3, isobutyl zinc bromide was used instead of benzyl zinc bromide. The final product was purified by RP HPLC Method B to give 1$^{st}$ eluting isomer Example 46 and 2$^{nd}$ eluting isomer Example 46a as colorless oils.

Example 46: LCMS Method 3: $t_R$=2.13 min, m/z=490.4 (M+H$^+$); $^1$H NMR (D$_2$O) δ 8.73 (s, 1H), 6.18 (d, 1H), 4.85 (t, 1H), 4.57 (t, 1H), 4.38 (m, 1H), 4.34 (d, 1H), 4.22 (q, 2H), 3.98 (dd, 1H), 3.83 (dd, 1H), 2.80 (d, 2H), 2.21 (m, 1H), 1.22 (t, 3H), 1.00 (d, 6H) ppm. $^{31}$P NMR (D$_2$O, 162 MHz) δ 8.45 (s).

Example 46a: LCMS Method 3: $t_R$=2.65 min, m/z=490.3 (M+H$^+$); $^1$H NMR (D$_2$O) δ 8.89 (s, 1H), 6.19 (d, 1H), 4.87 (t, 1H), 4.60 (t, 1H), 4.39 (m, 1H), 4.34 (d, 1H), 4.24 (q, 2H), 3.96 (dd, 1H), 3.82 (dd, 1h), 2.80 (d, 2H), 2.21 (m, 1H), 1.23 (t, 3H), 1.00 (d, 6H) ppm. $^{31}$P NMR (D$_2$O, 162 MHz) δ 8.36 (bs).

Example 47: 2-(((2R,3S,4R,5R)-5-(6-amino-2-chloro-9H-purin-9-yl)-3,4-dihydroxytetrahydrofuran-2-yl)methoxy)-2-(4-chlorobenzyl)malonic acid

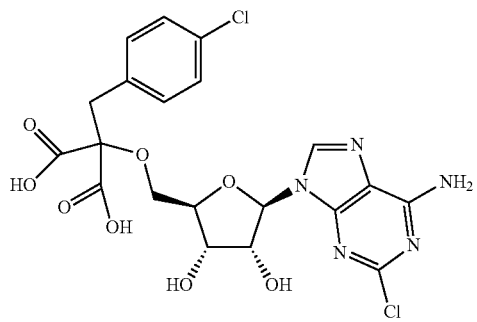 [SMILES: Nc1nc(Cl)nc2c1ncn2[C@@H]1O[C@H](COC(Cc2ccc(Cl)cc2)(C(=O)O)C(=O)O)[C@@H](O)[C@H]1O]

The title compound was synthesized by the method described in Example 2. In Step 2, 4-chloro benzylbromide was used. In Step 3, ammonia was used. The final product was purified by RP HPLC Method B to give Example 47.

Example 47: LCMS Method 2: $t_R$=1.17; 528.2 & 530.2 (M+H$^+$).

Example 48: 2-(((2R,3S,4R,5R)-5-(6-amino-2-chloro-9H-purin-9-yl)-3,4-dihydroxytetrahydrofuran-2-yl)methoxy)-2-(4-cyanobenzyl)malonic acid

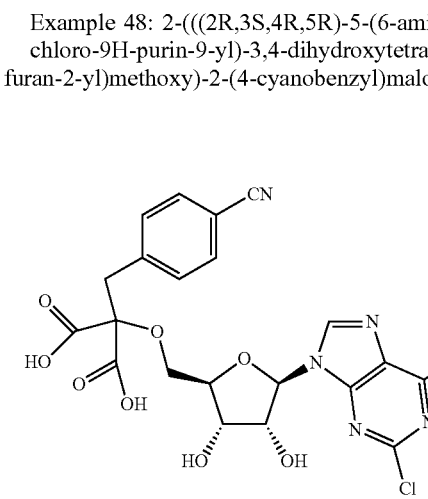

The title compound was synthesized by the method described in Example 2. In Step 2, 4-cyano benzylbromide was used. In Step 3, ammonia was used. The final product was purified by RP HPLC Method B to give Example 48 as a TFA salt.

Example 48: LCMS Method 2: $t_R$=1.17 min; 519.2 & 521.2 (M+H$^+$).

Example 49: ((R)-1-(((2R,3S,4R,5R)-5-(6-amino-2-(oxazol-2-yl)-9H-purin-9-yl)-3,4-dihydroxytetrahydrofuran-2-yl)methoxy)-2-ethoxy-2-oxoethyl)phosphonic Acid and Example 49a: ((S)-1-(((2R,3S,4R,5R)-5-(6-amino-2-(oxazol-2-yl)-9H-purin-9-yl)-3,4-dihydroxytetrahydrofuran-2-yl)methoxy)-2-ethoxy-2-oxoethyl)phosphonic Acid Example 49

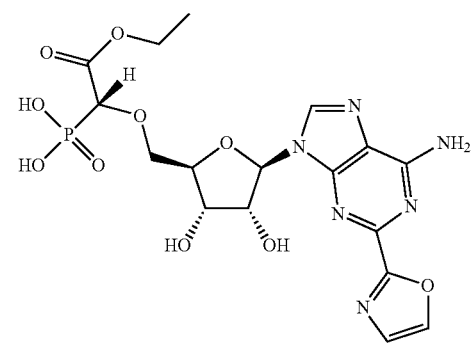

Example 49a

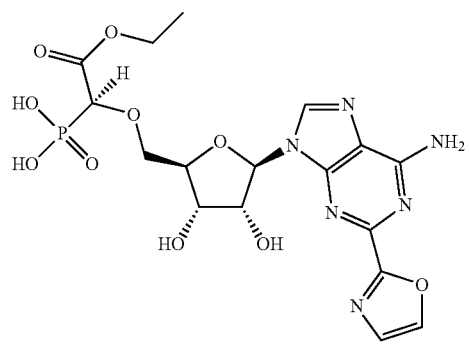

The title compounds were synthesized by the method described in Example 39. The following procedure was utilized in Step 3. To a degassed solution of N6, N6-bis-Boc-5'-O-tert-butyldimethylsilyl-2'-3'-O-isopropylidene-2-iodo-adenosine (200 mg, 0.27 mmol) in DMF (2.6 mL) was added Pd(PPh$_3$)$_4$ (15 mg, 0.013 mmol) and 2-(tributylstannyl)oxazole (0.013 mmol) and the reaction mixture was heated overnight at 100° C. DMF was removed in vacuo. The crude was used as such for the subsequent reactions. The final product was purified by RP HPLC Method B to give 1$^{st}$ eluting isomer Example 49 and 2$^{nd}$ eluting isomer Example 49a.

Example 49: LCMS Method 3: $t_R$=1.65 min, m/z=501.3 (M+H$^+$); $^1$H NMR (D$_2$O) δ 8.77 (s, 1H), 8.11 (s, 1H), 7.43 (s, 1H), 6.23 (d, 1H), 5.00 (t, 1H), 4.56 (t, 1H), 4.42 (m, 1H), 4.37 (d, 1H), 4.09 (q, 2H), 4.00 (m, 2H), 1.17 (t, 3H) ppm. $^{31}$P NMR (D$_2$O) δ 8.67 (s).

Example 49a: LCMS Method 3: $t_R$=2.22 min, m/z=501.3 (M+H$^+$); $^1$H NMR (D$_2$O) δ 8.93 (s, 1H), 8.09 (s, 1H), 7.43 (s, 1H), 6.24 (d, 1H), 4.95 (t, 1H), 4.62 (t, 1H), 4.41 (m, 1H), 4.37 (d, 1H), 4.21 (q, 2H), 3.90-4.01 (m, 2H), 1.22 (t, 3H) ppm. $^{31}$P NMR (CD$_3$OD) δ 8.52 (bs).

Example 50: ((R)-1-(((2R,3S,4R,5R)-5-(6-amino-2-cyclopropyl-9H-purin-9-yl)-3,4-dihydroxytetrahydrofuran-2-yl)methoxy)-2-ethoxy-2-oxoethyl)phosphonic acid and Example 50a: ((S)-1-(((2R,3S,4R,5R)-5-(6-amino-2-cyclopropyl-9H-purin-9-yl)-3,4-dihydroxytetrahydrofuran-2-yl)methoxy)-2-ethoxy-2-oxoethyl)phosphonic Acid

Example 50

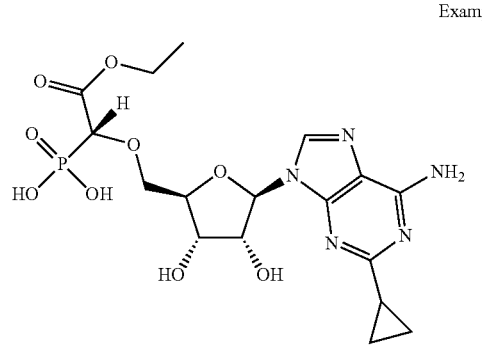

Example 50a

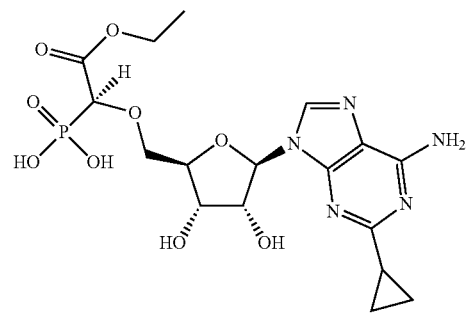

The title compounds were synthesized by the method described in Example 39. In Step 3, cyclopropyl zinc bromide was used instead of benzyl zinc bromide. The final product was purified by RP HPLC Method B to give 1$^{st}$ eluting isomer Example 50 and 2$^{nd}$ eluting isomer Example 50a.

Example 50: LCMS Method 3: $t_R$=1.28 min, m/z=474.4 (M+H$^+$); $^1$H NMR (D$_2$O) δ 8.60 (s, 1H), 6.10 (d, 1H), 4.86 (t, 1H), 4.51 (t, 1H), 4.37 (m, 1H), 4.32 (d, 1H), 4.21 (q, 2H), 3.93 (dd, 1H), 3.82 (dd, 1H), 2.19 (m, 1H), 1.28 (d, 4H), 1.22 (t, 3H) ppm. $^{31}$P NMR (D$_2$O) δ 8.61 (s).

Example 50a: LCMS Method 3: $t_R$=2.07 min, m/z=474.3 (M+H$^+$); $^1$H NMR (D$_2$O) δ 8.77 (s, 1H), 6.14 (d, 1H), 4.84 (t, 1H), 4.58 (t, 1H), 4.38 (m, 1H), 4.35 (d, 1H), 4.23 (q, 2H), 3.93 (dd, 1H), 3.81 (dd, 1h), 2.19 (m, 1H), 1.26 (m, 4H), 1.22 (t, 3H) ppm. $^{31}$P NMR (D$_2$O) δ 8.35 (s).

Example 51: ((R)-1-(((2R,3S,4R,5R)-5-(6-amino-2-((R)-oxazolidin-2-yl)-9H-purin-9-yl)-3,4-dihydroxytetrahydrofuran-2-yl)methoxy)-2-ethoxy-2-oxoethyl)phosphonic Acid and Example 51a: ((R)-1-(((2R,3S,4R,5R)-5-(6-amino-2-((S)-oxazolidin-2-yl)-9H-purin-9-yl)-3,4-dihydroxytetrahydrofuran-2-yl)methoxy)-2-ethoxy-2-oxoethyl)phosphonic Acid and Example 51b: ((1S)-1-(((2R,3S,4R,5R)-5-(6-amino-2-(oxazolidin-2-yl)-9H-purin-9-yl)-3,4-dihydroxytetrahydrofuran-2-yl)methoxy)-2-ethoxy-2-oxoethyl) phosphonic Acid

Example 51

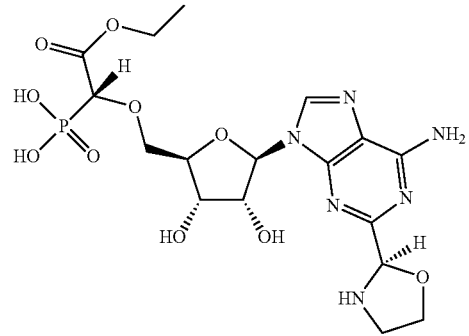

-continued

Example 51a

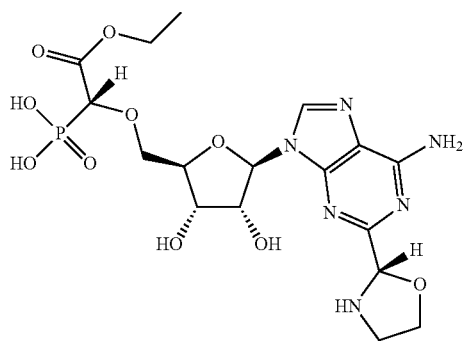

Example 51b

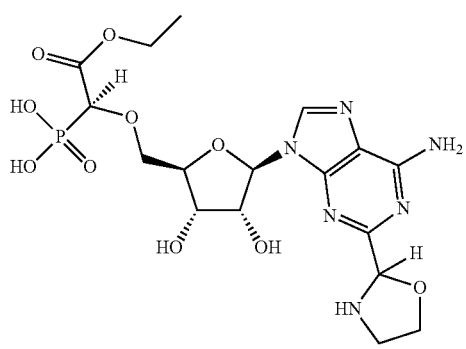

(mixture of diastreomers)

The title compounds were synthesized by the method described in Example 49. In Step 5, the hydrogenation was carried out in MeOH for 4 hrs. The final products were isolated by reverse phase chromatography as described in Example 49. The final product was purified by RP HPLC Method B to give $1^{st}$ eluting isomer Example 51 and $2^{nd}$ eluting isomer Example 51a and third eluting isomer as Example 51b. Example 51b was found to be a mixture of diastereomers.

Example 51: LCMS Method 3: $t_R$=1.02 min, m/z=505.4 (M+H$^+$); $^1$H NMR (D$_2$O) δ 8.78 (s, 1H), 6.15 (d, 1H), 4.76 (t, 1H), 4.59 (m, 2H), 4.42 (t, 1H), 4.24 (m, 1H), 4.21 (d, 1H), 4.12 (q, 2H), 3.84 (dd, 1H), 3.76 (dd, 1H), 3.34 (q, 2H), 1.16 (t, 3H) ppm. $^{31}$P NMR (D$_2$O) δ 8.49 (s).

Example 51a: LCMS Method 3: $t_R$=1.55 min, m/z=505.4 (M+H$^+$); $^1$H NMR (D$_2$O) δ 8.76 (s, 1H), 6.12 (d, 1H), 4.75 (t, 1H), 4.42 (t, 1H), 4.24 (m, 1H), 4.21 (d, 1H), 4.08 (q, 2H), 3.84 (m, 1H), 3.75 (dd, 1H), 3.35 (q, 2H), 1.17 (t, 3H) ppm. $^{31}$P NMR (D$_2$O) δ 8.49 (s).

Example 51b: LCMS Method 3: $t_R$=1.12 min and 1.93 min, m/z=505.4 (M+H$^+$); $^1$H NMR (D$_2$O) δ 9.00 (s, 1H), 6.16 (d, 1H), 4.69 (t, 1H), 4.62 (m, 2H), 4.46 (t, 1H), 4.25 (m, 1H), 4.16, q, 2H), 3.82 (m, 1H), 3.72 (m, 1H), 3.33 (q, 2H), 1.12 (t, 3H) ppm. $^{31}$P NMR (D$_2$O) δ 8.39 (s).

Example 52: ((S)-1-(((2R,3S,4R,5R)-5-(6-amino-2-fluoro-9H-purin-9-yl)-3,4-dihydroxytetrahydrofuran-2-yl)methoxy)-2-ethoxy-2-oxoethyl)phosphonic Acid and Example 52a: ((R)-1-(((2R,3S,4R,5R)-5-(6-amino-2-fluoro-9H-purin-9-yl)-3,4-dihydroxytetrahydrofuran-2-yl)methoxy)-2-ethoxy-2-oxoethyl)phosphonic Acid Example 52

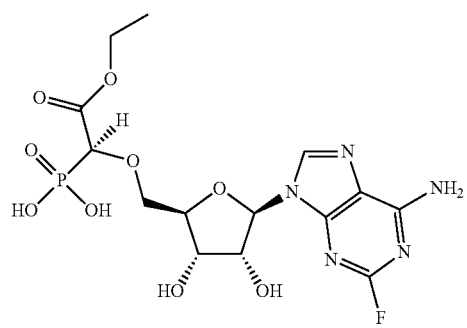

Example 52a

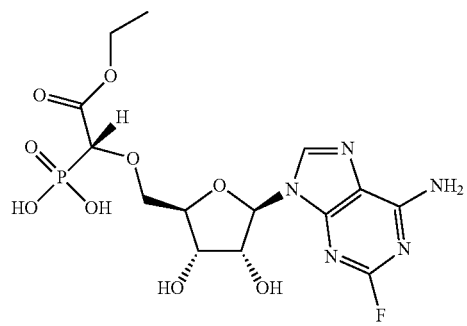

The title compounds were synthesized from ((3aR,4R,6R,6aR)-6-(6-amino-2-fluoro-9H-purin-9-yl)-2,2-dimethyltetrahydrofuro[3,4-d][1,3]dioxol-4-yl)methano 1 as described in Example 1. The final product was purified by RP HPLC Method B to give $1^{st}$ eluting isomer Example 52 and $2^{nd}$ eluting isomer Example 52a.

Example 52: LCMS Method 3: $t_R$=1.27 min, m/z=452.4 (M+H$^+$); $^1$H NMR (D$_2$O) δ 8.85 (s, 1H), 6.00 (d, 1H), 4.70 (m, 1H), 4.50 (t, 1H), 4.24-4.35 (m, 2H), 4.18 (q, 2H), 3.92 (dd, 1H), 3.79 (dd, 1H), 1.19 (t, 3H) ppm. $^{31}$P NMR (D$_2$O) δ 8.66 (s).

Example 52a: LCMS Method 3: $t_R$=1.67 min, m/z=452.4 (M+H$^+$); $^1$H NMR (D$_2$O) δ 9.11 (s, 1H), 6.02 (d, 1H), 4.73 (m, 1H), 4.51 (t, 1H), 4.27-4.31 (m, 2H), 4.20 (q, 2h), 3.91 (dd, 1H), 3.78 (dd, 1H), 1.18 (t, 3H) ppm. $^{31}$P NMR (D$_2$O) δ 8.53 (bs).

133

Example 53: (R)-2-(((2R,3S,4R,5R)-5-(6-amino-2-fluoro-9H-purin-9-yl)-3,4-dihydroxytetrahydrofuran-2-yl)methoxy)-2-phosphonoacetic Acid and Example 53a: (S)-2-(((2R,3S,4R,5R)-5-(6-amino-2-fluoro-9H-purin-9-yl)-3,4-dihydroxytetrahydrofuran-2-yl)methoxy)-2-phosphonoacetic acid Example 53

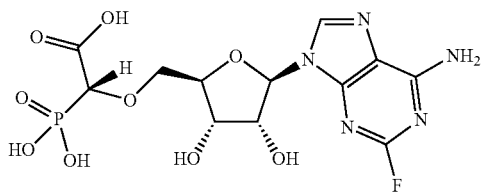

Example 53a

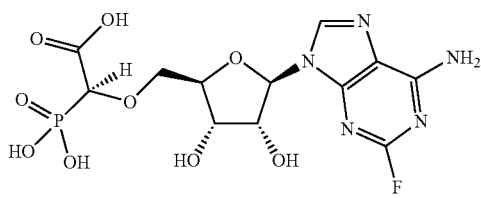

The title compounds were synthesized by the method described in Example 20. The final compounds were purified by RP HPLC Method B and isolated as a TFA salt.

Example 53: LCMS Method 3: $t_R$=1.27 min, m/z=424.4 (M+H$^+$); $^1$H NMR (D$_2$O) δ 8.85 (s, 1H), 6.00 (d, 1H), 4.70 (m, 1H), 4.50 (t, 1H), 4.24-4.35 (m, 2H), 3.92 (dd, 1H), 3.79 (dd, 1H),) ppm. $^{31}$P NMR (D$_2$O) δ 8.66 (s).

Example 53a: LCMS Method 3: $t_R$=1.67 min, m/z=424.2 (M+H$^+$); $^1$H NMR (D$_2$O) δ 9.11 (s, 1H), 6.02 (d, 1H), 4.73 (m, 1H), 4.51 (t, 1H), 4.27-4.31 (m, 2H), 3.91 (dd, 1H), 3.78 (dd, 1H), ppm. $^{31}$P NMR (D$_2$O) δ 8.53 (bs).

Example 54: (1-(((2R,3S,4R,5R)-5-(6-amino-2-cyano-9H-purin-9-yl)-3,4-dihydroxytetrahydrofuran-2-yl)methoxy)-2-(tert-butoxy)-2-oxoethyl)phosphonic Acid and Example 54a: ((R)-1-(((2R,3S,4R,5R)-5-(6-amino-2-cyano-9H-purin-9-yl)-3,4-dihydroxytetrahydrofuran-2-yl)methoxy)-2-(tert-butoxy)-2-oxoethyl) phosphonic Acid and Example 54b: ((S)-1-(((2R,3S,4R,5R)-5-(6-amino-2-cyano-9H-purin-9-yl)-3,4-dihydroxytetrahydrofuran-2-yl)methoxy)-2-(tert-butoxy)-2-oxoethyl) phosphonic Acid Example 54

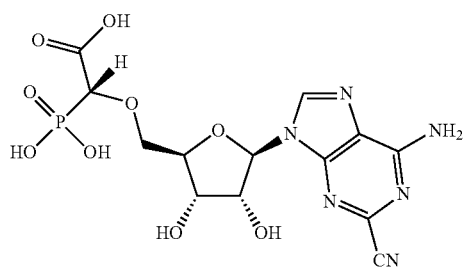

134

Example 54a

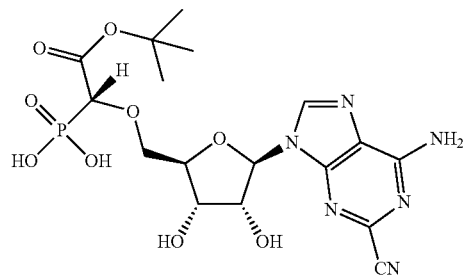

Example 54b

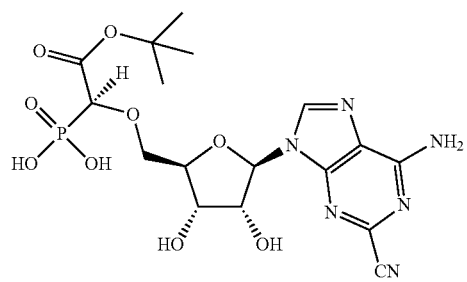

Scheme S

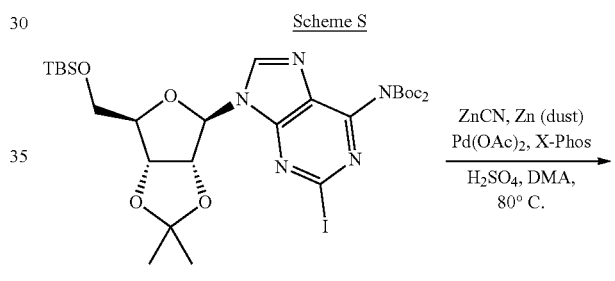

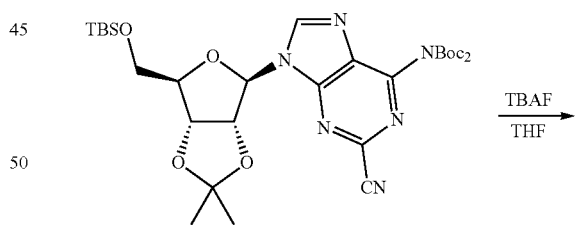

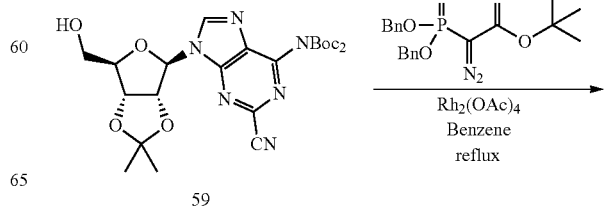

-continued

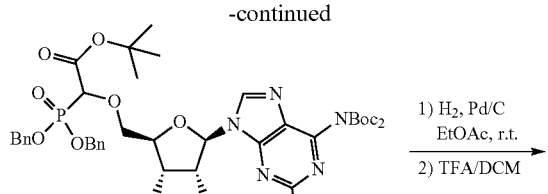

60

1) H₂, Pd/C EtOAc, r.t.
2) TFA/DCM

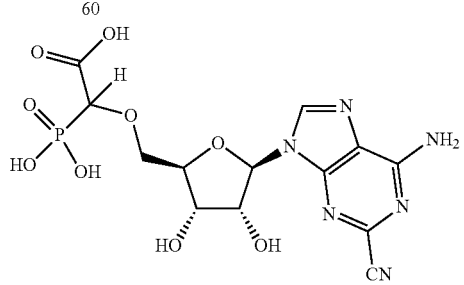

Example 54

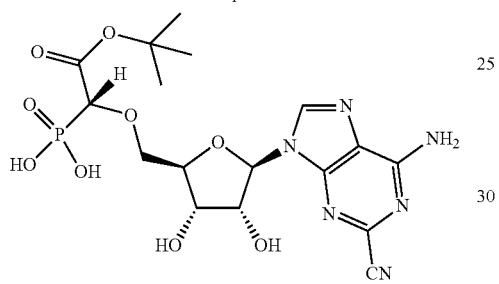

Example 54a

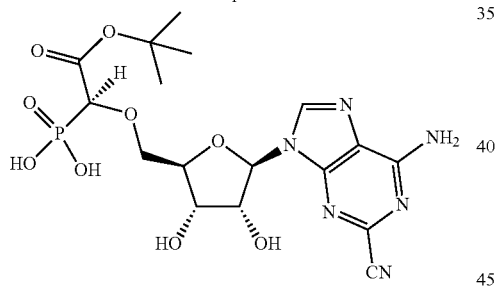

Example 54b

Step 1: N6, N6-bis-Boc-5'-O-tert-butyldimethylsilyl-2'-3'-O-isopropylidene-2-cyano-adenosine (58)

To a degassed solution of N6, N6-bis-Boc-5'-O-tert-butyldimethylsilyl-2'-3'-O-isopropylidene-2-iodo-adenosine (53, 500 mg, 0.67 mmol), zinc dust (2 mg, 0.03 mmol), and zinc cyanide (47 mg, 0.40 mmol) in DMA (3.3 mL) was added conc. H₂SO₄ (667 μL (0.05 eq.) and the reaction was heated for 5 min at 80° C., then an aged (30 min) solution of Pd(OAc)₂ (25 mg), X-Phos (100 mg) and H₂SO₄ conc. (17 μL) in DMA (5 mL) was added to the previous mixture. The reaction was heated overnight at 80° C. The volatiles were removed in vacuo and the crude purified by flash chromatography on silica gel using hexane-EtOAc as an eluent, yielding the compound 58 (255 mg) as a colorless oil. This compound was further elaborated according to Steps 2-4 as described in Example 39. The final product was purified by RP HPLC Method B to give 1ˢᵗ eluting isomer Example 54 as a mixture of diastereomers and 2ⁿᵈ eluting isomer Example 54b and 3ʳᵈ eluting isomer Example 54a.

Example 54: LCMS Method 3: $t_R$=3.20 min, m/z=431.1 (M+H⁺).

Example 54a: LCMS Method 3: $t_R$=2.43 min; m/z=487.6 (M+H⁺); ¹H NMR (D₂O) δ 8.83 (s, 1H), 6.11 (d, 1H), 4.82 (m, 1H), 4.53 (t, 1H), 4.38 (m, 1H), 4.25 (d, 1H), 3.99 (dd, 1H), 3.84 (dd, 1H), 1.39 (s, 9H) ppm. ³¹P NMR (D₂O) δ 9.92 (s).

Example 54b: LCMS Method 3: $t_R$=3.20 min; m/z=487.6 (M+H⁺); ¹H NMR (D₂O) δ 8.97 (s, 1H), 6.16 (d, 1H), 4.82 (m, 1H), 4.59 (m, 1H), 4.39 (m, 1H), 4.20 (d, 1H), 3.93 (dd, 1H), 3.81 (dd, 1H), 1.21 (s, 9H) ppm. ³¹P NMR (D₂O) δ 8.82 (s).

Example 55: ((R)-1-(((2R,3S,4R,5R)-5-(6-amino-2-(aminomethyl)-9H-purin-9-yl)-3,4-dihydroxytetrahydrofuran-2-yl)methoxy)-2-(tert-butoxy)-2-oxoethyl)phosphonic Acid and Example 55a: ((S)-1-(((2R,3S,4R,5R)-5-(6-amino-2-(aminomethyl)-9H-purin-9-yl)-3,4-dihydroxytetrahydrofuran-2-yl)methoxy)-2-(tert-butoxy)-2-oxoethyl)phosphonic Acid Example 55

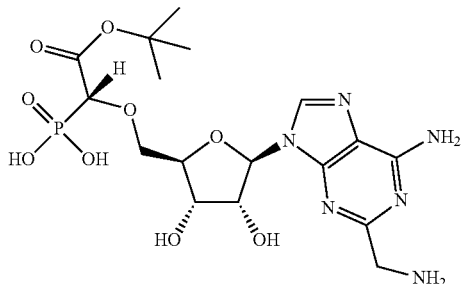

Example 55a

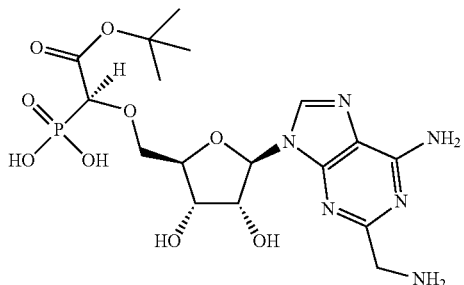

Scheme T

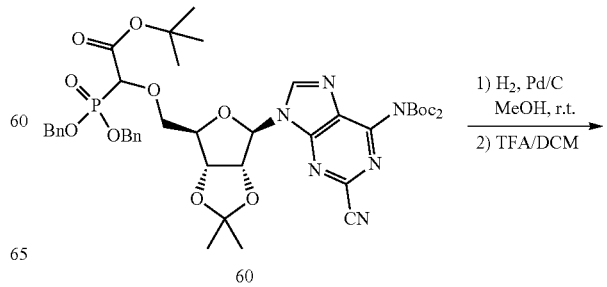

60

1) H₂, Pd/C MeOH, r.t.
2) TFA/DCM

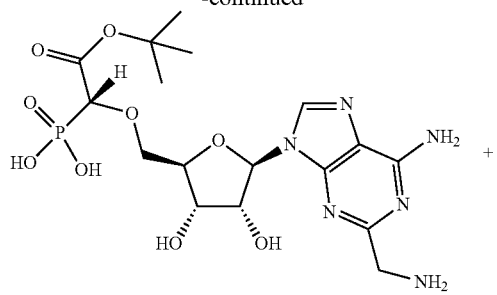

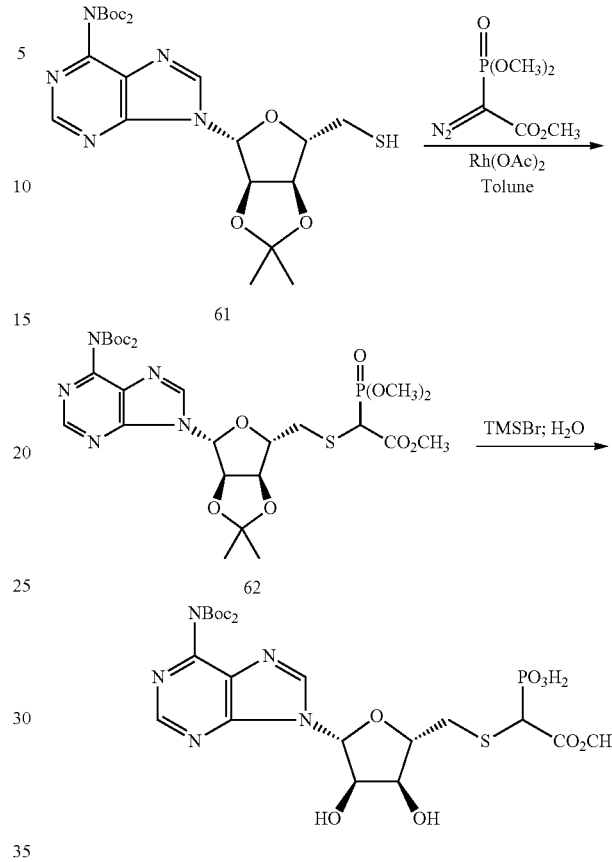

Scheme U

61

62

The title compounds were synthesized by the method described in Example 39. In Step 5, MeOH was used for hydrogenation which was carried out for 4 h. The final product was purified by RP HPLC Method B to give $1^{st}$ eluting isomer Example 55 (2.0 mg) and $2^{nd}$ eluting isomer Example 55a (3.2 mg) as white solids.

Example 55: LCMS Method 3: $t_R$=1.10, m/z=491.6 (M+H$^+$); $^1$H NMR (D$_2$O, 400 MHz) δ 8.91 (s, 1H), 6.20 (d, 1h), 4.91 (t, 1H), 4.59 (t, 1H), 4.42 (s, 2H), 4.37 (m, 1H), 4.21 (d, 1H), 3.96 (dd, 1H), 3.82 (dd, 1H), 1.22 (s, 9H) ppm. $^{31}$P NMR (D$_2$O, 162 MHz) δ 9.05 (s).

Example 55a: LCMS Method 3: $t_R$=1.55 min, m/z=491.6 (M+H$^+$); $^1$H NMR (D$_2$O) δ 9.14 (s, 1H), 6.23 (d, 1H), 4.85 (t, 1H), 4.60 (t, 1H), 4.44 (s, 2H), 4.40 (m, 1H), 4.22 (d, 1H), 3.98 (dd, 1H), 3.80 (dd, 1H), 1.24 (s, 9H) ppm. $^{31}$P NMR (D$_2$O) δ 8.86 (s).

Example 56: (1-((((2S,3S,4R,5R)-5-(6-amino-9H-purin-9-yl)-3,4-dihydroxytetrahydrofuran-2-yl)methyl)thio)-2-methoxy-2-oxoethyl)phosphonic Acid

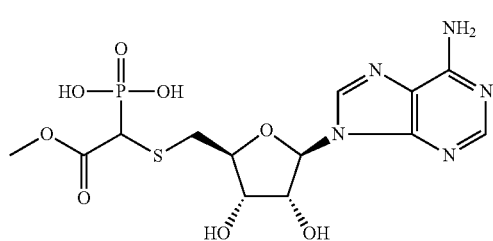 [SMILES: COC(=O)C(SC[C@H]1O[C@@H](n2cnc3c(N)ncnc32)[C@H](O)[C@@H]1O)P(=O)(O)O]

The title compound was synthesized by the method described in Example 1, starting from tert-butyl (2-cyano-9-((3aR,4R,6S,6aS)-6-(mercaptomethyl)-2,2-dimethyltetrahydrofuro[3,4-d][1,3]dioxol-4-yl)-9H-purin-6-yl)carbamate. The final compound was purified by reverse phase HPLC Method A and isolated as mixture of diastereomers.

Example 56 (mixt. of diastereomers). LCMS Method 3: $t_R$=1.02 min, m/z 436 (M+H$^+$).

Example 57: ((R)-1-(((2R,3S,4R,5R)-5-(6-amino-9H-purin-9-yl)-3,4-dihydroxytetrahydrofuran-2-yl)methoxy)-2-hydroxyethyl)phosphonic Acid and Example 57a: ((S)-1-(((2R,3S,4R,5R)-5-(6-amino-9H-purin-9-yl)-3,4-dihydroxytetrahydrofuran-2-yl)methoxy)-2-hydroxyethyl)phosphonic Acid Example 57

139
-continued

Example 57a

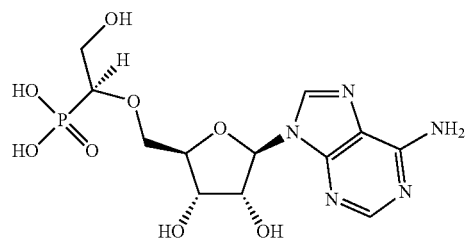

Scheme V

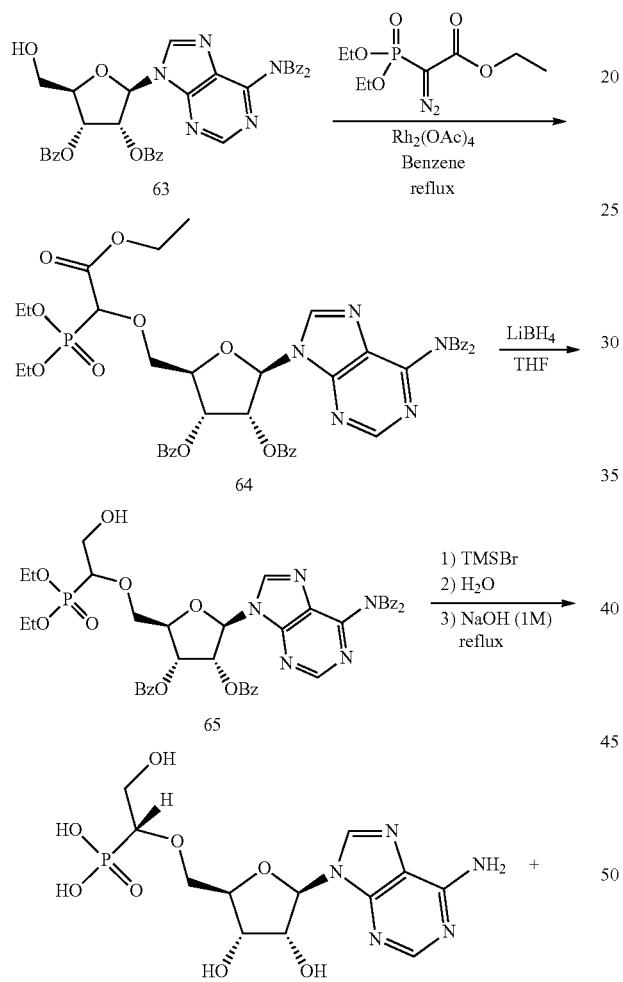

140

Step 1: (2R,3R,4R,5R)-2-(6-(N-benzoylbenzamido)-9H-purin-9-yl)-5-((1-(diethoxyphosphoryl)-2-ethoxy-2-oxoethoxy)methyl)tetrahydrofuran-3,4-diyl Dibenzoate (64)

Rhodium (II) acetate dimer (3 mg, 0.007 mmol) was added to a solution of N6-dibenzoyl-adenosine-2',3'-dibenzoate (63, 518 mg, 0.76 mmol) and ethyl 2-diazo-2-(diethoxyphosphoryl)acetate (379 mg, 1.52 mmol) in benzene (2.5 mL) and heated to reflux overnight. The volatiles were removed in vacuo and the crude purified by flash chromatography on silica gel column using hexane-EtOAc as eluent to yield compound 64 (370 mg) as a colorless oil.

Step 2: (2R,3R,4R,5R)-2-(6-(N-benzoylbenzamido)-9H-purin-9-yl)-5-((1-(diethoxyphosphoryl)-2-hydroxyethoxy)methyl)tetrahydrofuran-3,4-diyl Dibenzoate (65)

LiBH$_4$ (42 mL, 0.084 mmol) was added to a solution of compound 64 (77 mg, 0.085 mmol) in THF (1 mL) and allowed to stir at RT for 2 h. The reaction was diluted with EtOAc and partitioned with 1M HCl. The combined organic phase was washed with water, brine and dried over Na$_2$SO$_4$. The crude product (77 mg) was used as in the next reaction.

Step 3: ((R)-1-(((2R,3S,4R,5R)-5-(6-amino-9H-purin-9-yl)-3,4-dihydroxytetrahydrofuran-2-yl)methoxy)-2-hydroxyethyl)phosphonic acid and ((S)-1-(((2R,3S,4R,5R)-5-(6-amino-9H-purin-9-yl)-3,4-dihydroxytetrahydrofuran-2-yl)methoxy)-2-hydroxyethyl)phosphonic Acid TMSBr (200 μL) was added to a solution of compound 65 (77 mg) in DCM (2 mL). The mixture was refluxed for 2 h and allowed to cool to RT. Water (2 mL) was added and the mixture was stirred 10 minutes at RT followed by 1M NaOH (2 mL). The reaction was refluxed overnight. The final product was purified by RP HPLC Method B to give 1$^{st}$ eluting isomer Example 57 and 2$^{nd}$ eluting isomer Example 57a.

Example 57: LCMS Method 3: $t_R$=1.02 min, m/z=392.4 (M+H$^+$); $^1$H NMR (D$_2$O) δ 8.74 (s, 1H), 8.42 (s, 1H), 6.19 (d, 1H), 4.80 (m, 1H), 4.54 (t, 1H), 4.38 (m, 1H), 4.20 (s, 1H), 3.93 (m, 2H), 3.77 (dd, 1H), 3.71 (dd, 1H) ppm.

Example 57a: LCMS Method 3: $t_R$=1.02 min, m/z=392.4 (M+H$^+$); $^1$H NMR (D$_2$O) δ 8.75 (s, 1H), 8.42 (s, 1H), 6.19 (d, 1H), 4.80 (m, 1H), 4.57 (t, 1H), 4.39 (m, 1H), 4.02 (bs, 2H), 3.98 (m, 1H), 3.67-3.80 (m, 2H) ppm.

Example 58: 2-(((2R,3S,4R,5R)-5-(6-benzamido-2-iodo-9H-purin-9-yl)-3,4-dihydroxytetrahydrofuran-2-yl)methoxy)-2-phosphonoacetic acid

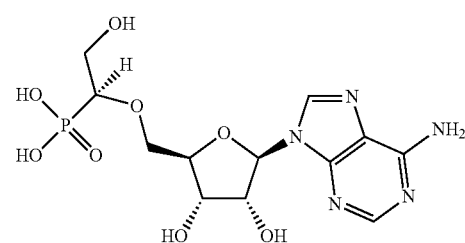

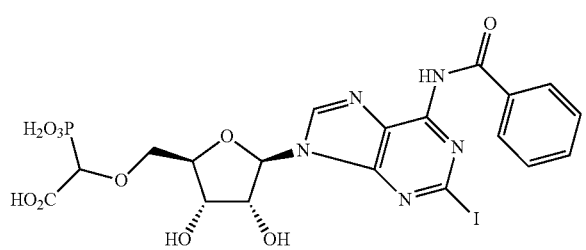

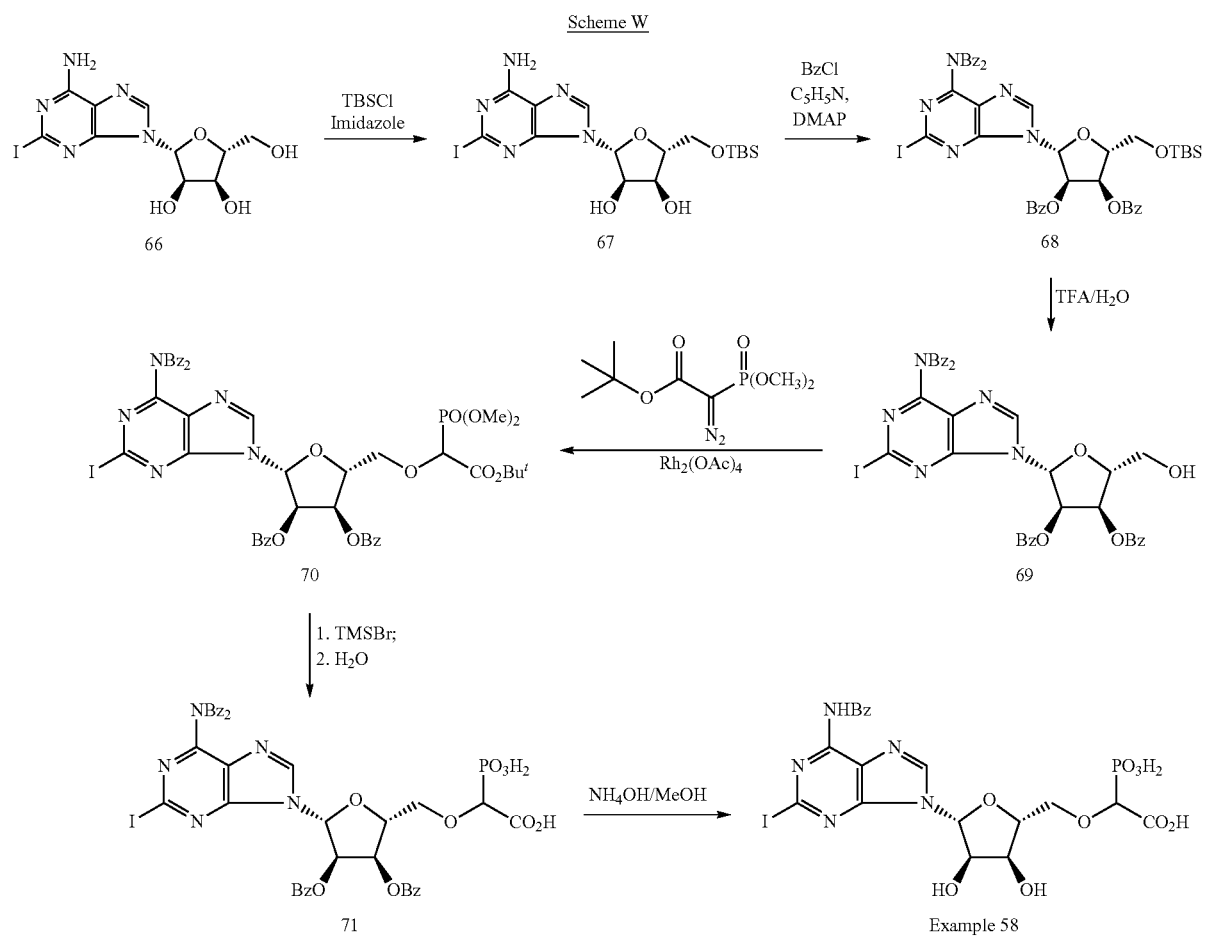

Scheme W

Step 1: (2R,3R,4S,5R)-2-(6-amino-2-iodo-9H-purin-9-yl)-5-(((tert-butyldimethylsilyl)oxy)methyl) tetrahydrofuran-3,4-diol (67)

A mixture of compound 66 (2.60 g, 6.62 mmol), Im (1.03 g, 15.06 mmol), and TBDMSCl (1.27 g, 8.42 mmol) in DMF (15 mL) was stirred at RT for 1.5 h. The reaction was then quenched with ice water and extracted with DCM (3×). The combined organic phase was dried over Na$_2$SO$_4$ and the solvent was removed under reduced pressure, the crude product was used in the next step without further purification. LCMS Method 1: $t_R$=1.42 min, m/z 508 (MH$^+$).

Step 2: (2R,3R,4R,5R)-2-(6-(N-benzoylbenzamido-2-iodo-9H-purin-9-yl)-5-(((tert-butyldimethylsilyl)oxy)methyl)tetrahydrofuran-3,4-diyl Dibenzoate (68)

Benzoyl chloride (8 mL, 68.3 mmol) was added dropwise to an ice cold mixture of compound 67 (6.62 mmol) and DMAP (1.25 g, 10.2 mmol) in pyridine (30 mL). The reaction mixture was stirred at RT for 24 h, after which time, an additional benzoyl chloride (4 mL) was added. The resulting mixture was stirred at RT for another 67 h. The reaction mixture was then cooled with ice bath, and quenched with methanol (24 mL). After 3 h, the solvents were removed under reduced pressure; sat. brine was added to the residue and extracted with DCM (20 mL×3). The combined organic phase was dried over Na$_2$SO$_4$ and solvent was removed under reduced pressure, the residue was purified by chromatography on silica gel (120 g column eluted with 0 to 2% MeOH in DCM over 30 min) to compound 68. LCMS Method 1: $t_R$=2.39 min, m/z 924 (MH$^+$).

Step 3: (2R,3R,4R,5R)-2-(6-(N-benzoylbenzamido)-2-iodo-9H-purin-9-yl)-5-(hydroxymethyl)tetrahydrofuran-3,4-diyl Dibenzoate (69)

Aqueous acid (TFA/H$_2$O, 1:1, 12 mL) was added to an ice cold solution of compound 68 in THF (65 mL), The reaction mixture was stirred for 19 h at RT and then quenched with a solution of NaHCO$_3$ (6.70 g) in water (100 mL). The mixture was extracted with EtOAc (2×). The combined organic phase was dried over Na$_2$SO$_4$, solvent was evaporated under reduced pressure and the residue was purified by chromatography on silica gel (330 g column eluted with 20 to 50% ethyl acetate in hexanes over 40 min) to afford (2R,3R,4R,5R)-2-(6-(N-benzoylbenzamido)-2-iodo-9H-purin-9-yl)-5-(hydroxymethyl)tetrahydrofuran-3,4-diyl dibenzoate (69). LCMS Method 1: $t_R$=1.90 min, m/z 810 (M+H$^+$).

Step 4: (2R,3R,4R,5R)-2-(6-(N-benzoylbenzamido)-2-iodo-9H-purin-9-yl)-5-((2-(tert-butoxy)-1-(dimethoxyphosphoryl)-2-oxoethoxy)methyl)tetrahydrofuran-3,4-diyl Dibenzoate (70)

Rhodium acetate dimer (60 mg, 0.0135 mmol) was added to a solution of compound 69 (0.28 g, 0.35 mmol) and tert-butyl 2-diazo-2-(dimethoxyphosphoryl)acetate (0.216 g, 0.86 mmol) in benzene (10 mL). The reaction mixture was degassed and then stirred for 24 h at 100° C. under nitrogen. After cooling to RT, the solvent was evaporated under reduced pressure, the residue was purified by chromatography on silica gel (40 g column eluted with 30 to 80% ethyl acetate in hexanes over 40 min) to give compound 70 (0.289 g). LCMS Method 1: $t_R$=2.02 min, m/z 1032 (M+H$^+$).

Step 5: 2-(((2R,3S,4R,5R)-5-(6-benzamido-2-iodo-9H-purin-9-yl)-3,4-dihydroxytetrahydrofuran-2-yl)methoxy)-2-phosphonoacetic acid (71)

TMSBr (1 mL) was added to a solution of compound 70 (0.1003 g, 0.097 mmol) in dry ACN (2 mL). The reaction mixture was stirred at RT for 16 h and then quenched with water (1.5 mL). After 2 h, the solvents were removed under reduced pressure and the residue was dissolved in methanol (6 mL) and NH$_4$OH (1.1 mL) was added. The resulting mixture was stirred for 1 h at 60° C. After the solvents were removed under reduced pressure, the crude product was purified by RP HPLC Method A to afford Example 58, as mixture of diastereomers.

Example 58: LCMS Method 3: $t_R$=3.00, 3.15 min, m/z 636 (M+H$^+$).

Example 59: (S)-2-(((2R,3S,4R,5R)-5-(6-amino-2-iodo-9H-purin-9-yl)-3,4-dihydroxytetrahydrofuran-2-yl)methoxy)-2-phosphonoacetic Acid and Example 59a: (R)-2-(((2R,3S,4R,5R)-5-(6-amino-2-iodo-9H-purin-9-yl)-3,4-dihydroxytetrahydrofuran-2-yl)methoxy)-2-phosphonoacetic Acid and Example 59b: 2-(((2R,3S,4R,5R)-3,4-dihydroxy-5-(6-(hydroxyamino)-2-iodo-9H-purin-9-yl)tetrahydrofuran-2-yl)methoxy)-2-phosphonoacetic acid Example 59

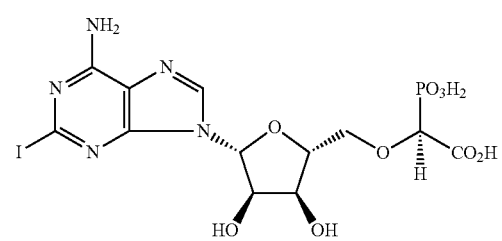

Example 59a

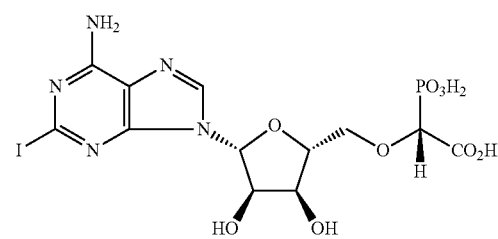

Example 59b

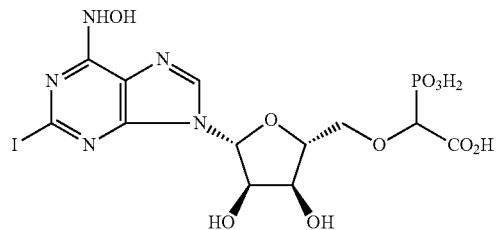

Scheme X

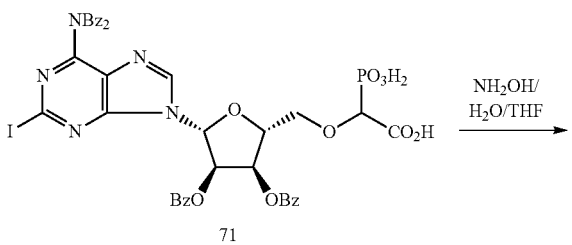

Examples 59, 59a, 59b

Crude compound compound 71 was dissolved in THF (2 mL) and 50% NH$_2$OH in water (2.5 mL) was added and the resulting mixture was stirred for 17 h at RT. The solvents were removed under reduced pressure, the crude product was purified by RP HPLC Method A to afford three products which eluted in following order: Example 59, Example 59a, and Example 59b. These were re-dissolved in 5 mL of distilled water and then lyophilized to yield TFA salts as white fluffy solids.

Example 59: LCMS Method 3: $t_R$=1.28 min, m/z 532 (M+H$^+$).

Example 59a: LCMS Method 3: $t_R$=1.35 min, m/z 532 (M+H$^+$).

Example 59b: LCMS Method 3: $t_R$=1.17 min, m/z 547 (M+H$^+$).

Example 60: (R)-2-(((2R,3S,4R,5R)-3,4-dihydroxy-5-(3-methyl-2,4-dioxo-3,4-dihydropyrimidin-1(2H)-yl)tetrahydrofuran-2-yl)methoxy)-2-phosphonoacetic Acid and Example 60a: (S)-2-(((2R,3S,4R,5R)-3,4-dihydroxy-5-(3-methyl-2,4-dioxo-3,4-dihydropyrimidin-1(2H)-yl)tetrahydrofuran-2-yl)methoxy)-2-phosphonoacetic acid Example 60a

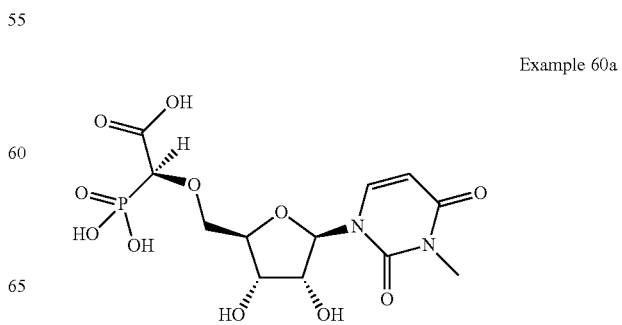

Example 60

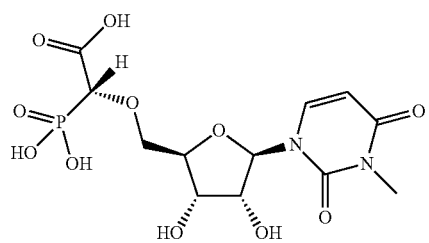

The title compounds were synthesized by the method described in Example 59 starting from 1-((3aR,4R,6R,6aR)-6-(hydroxymethyl)-2,2-dimethyltetrahydrofuro[3,4-d][1,3]dioxol-4-yl)-3-methylpyrimidine-2,4(1H,3H)-dione and following Steps 4 through 6. The final product was purified by RP HPLC Method B to give 1$^{st}$ eluting isomer Example 60 and 2$^{nd}$ eluting isomer Example 60a as white solids.

Example 60: LCMS Method 2: $t_R$=1.05 min, m/z=397 (M+H$^+$).

Example 60a: LCMS Method 2: $t_R$=0.94 min, m/z=397 (M+H$^+$). $^1$H NMR (DMSO) δ 8.26 (d, 1H), 5.86 (d, 1H), 5.61 (d, 1H), 4.16 (d, 1H), 4.12 (m, 1H), 4.07 (m, 1H), 3.97 (m, 1H), 3.70 (m, 2H), 3.14 (s, 3H).

Example 61: (R)-2-(((2R,3S,4R,5R)-5-(6-amino-2-chloro-9H-purin-9-yl)-3,4-dihydroxytetrahydrofuran-2-yl)methoxy)-2-phosphonoacetic Acid and Example 61a: (S)-2-(((2R,3S,4R,5R)-5-(6-amino-2-chloro-9H-purin-9-yl)-3,4-dihydroxytetrahydrofuran-2-yl)methoxy)-2-phosphonoacetic acid Example 61

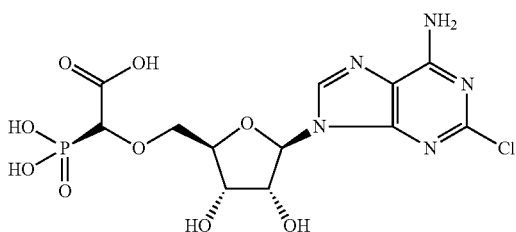

Example 61a

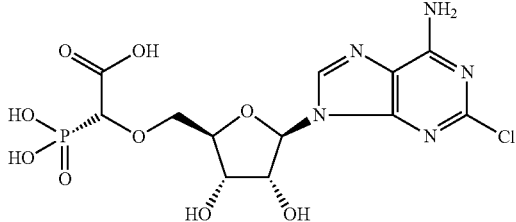

Scheme Y

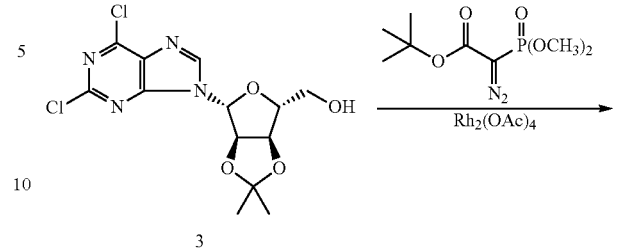

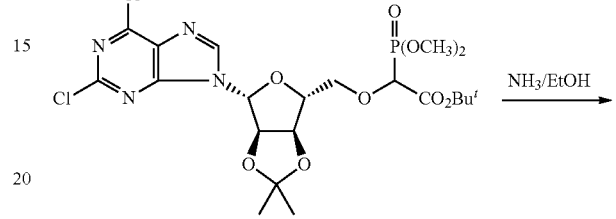

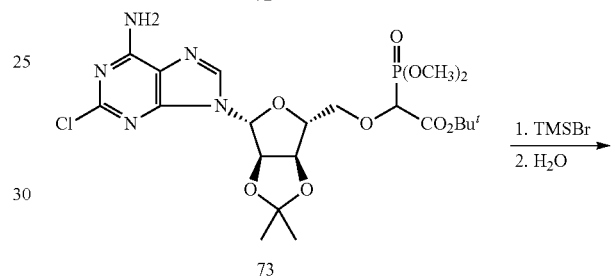

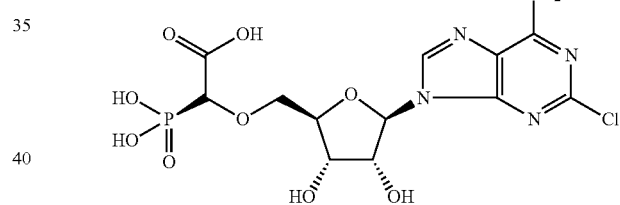

Example 61

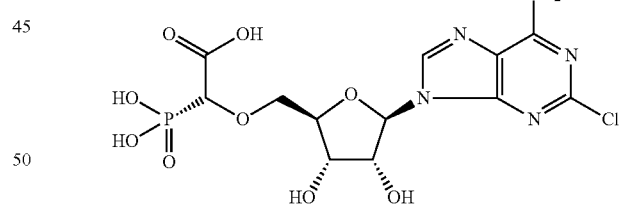

Example 61a

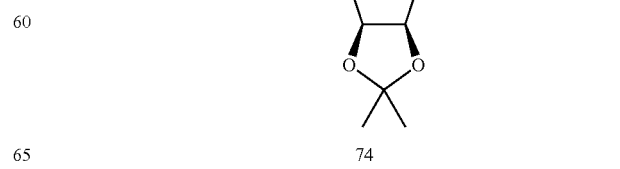

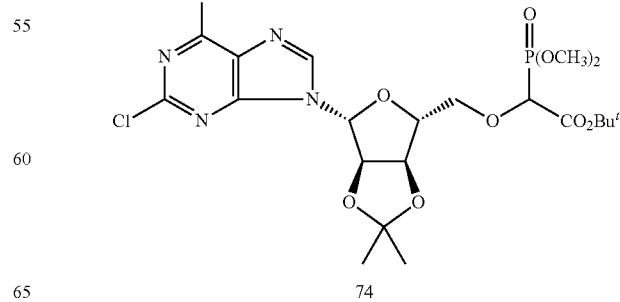

Step 1: tert-Butyl 2-(((3aR,4R,6R,6aR)-6-(2,6-di-chloro-9H-purin-9-yl)-2,2-dimethyltetrahydrofuro[3,4-d][1,3]dioxol-4-yl)methoxy)-2-(dimethoxyphosphoryl)acetate (72)

To a solution of compound 3 (2.43 g, 6.73 mmol) and tert-butyl 2-diazo-2-(dimethoxyphosphoryl)acetate (2.56 g, 10.23 mmol) in benzene (100 mL) was added rhodium acetate dimer (0.0626 g, 0.14 mmol) stirred at 100° C. for 17 h under N$_2$. After cooling to RT, the solvent was evaporated under reduced pressure, the residue was purified by chromatography on silica gel (80 g column eluted with 30 to 80% ethyl acetate/hexanes over 40 min) to give compound 72 (2.14 g). LCMS Method 1: $t_R$=1.54 min, m/z=583, 585 (M+H$^+$).

Step 2: tert-Butyl 2-(((3aR,4R,6R,6aR)-6-(6-amino-2-chloro-9H-purin-9-yl)-2,2-dimethyltetrahydrofuro[3,4-d][1,3]dioxol-4-yl)methoxy)-2-(dimethoxyphosphoryl)acetate (73)

To a solution of compound 72 (1.07 g, 1.84 mmol) in dry THF (20 mL) was added 7 N NH$_3$/methanol (17 mL) and stirred at RT for 15 h. The solvents were removed under reduced pressure at RT and the residue was purified by chromatography on silica gel (120 g column eluted with 0 to 5% methanol in DCM over 40 min) to afford compound 73 as a solid (0.51 g). LCMS Method 1: $t_R$=1.29 min, m/z=564, 566 (M+H$^+$).

Step 3: 2-(((2R,3S,4R,5R)-5-(6-amino-2-chloro-9H-purin-9-yl)-3,4-dihydroxytetrahydrofuran-2-yl)methoxy)-2-phosphonoacetic acid TMSBr (1.4 mL) was added to a solution of compound 73 (0.0977 g, 0.17 mmol) in dry ACN (2 mL). The reaction mixture was stirred at RT for 22 h and then quenched with water (1.5 mL). It was then stirred at RT for 24 h and then treated with NH$_4$OH (2 mL). After an additional 2 h, the solvents were removed under reduced pressure at RT and the residue was purified by RP HPLC Method A to separate two diastereomers. The 1$^{st}$ eluting isomer corresponds to Example 61 and 2$^{nd}$ eluting isomer corresponds to Example 61a.

Example 61: LCMS Method 3: $t_R$=1.09 min, m/z=440, 442 (M+H$^+$).

Example 61a: LCMS Method 3: $t_R$=1.09 min, m/z=440, 442 (M+H$^+$).

Example 62: 2-(((2R,3S,4R,5R)-5-(2,6-dichloro-9H-purin-9-yl)-3,4-dihydroxytetrahydrofuran-2-yl)methoxy)-2-phosphonoacetic acid Scheme Z

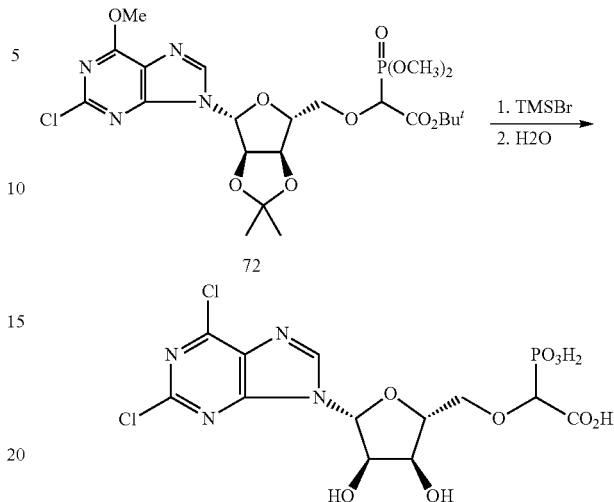

TMSBr (1.4 mL) was added to a solution of tert-butyl 2-(((3aR,4R,6R,6aR)-6-(2,6-dichloro-9H-purin-9-yl)-2,2-dimethyltetrahydrofuro[3,4-d][1,3]dioxol-4-yl)methoxy)-2-(dimethoxyphosphoryl)acetate (72, 0.0908 g, 0.16 mmol) in dry CH$_3$CN (2 mL). The reaction mixture was stirred at RT for 24 h and then quenched with water (2 mL). After stirring at RT for 4 h, the solvents were removed under reduced pressure at RT and the residue was purified by RP HPLC Method A to give 2-(((2R,3S,4R,5R)-5-(2,6-dichloro-9H-purin-9-yl)-3,4-dihydroxytetrahydrofuran-2-yl)methoxy)-2-phosphonoacetic acid as a mixture of diastereomers.

Example 62: LCMS Method 3: $t_R$=1.65 min, m/z=459, 461 (M+H$^+$).

Example 63: 2-(((2R,3S,4R,5R)-5-(2-chloro-6-ethoxy-9H-purin-9-yl)-3,4-dihydroxytetrahydrofuran-2-yl)methoxy)-2-phosphonoacetic acid

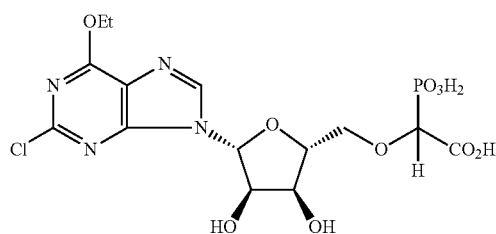

Scheme AA

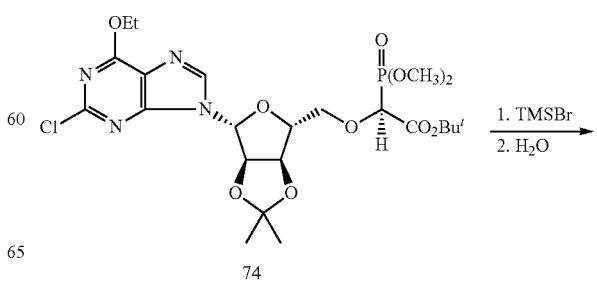

-continued

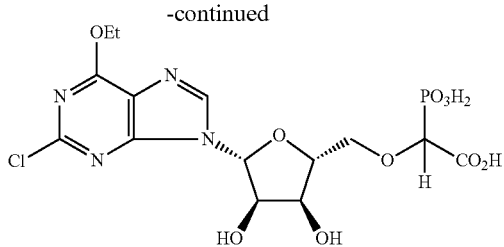

Compound 74 was treated with TMSBr as described in Example 62. The crude product was purified by RP HPLC Method A to afford 2-(((2R,3S,4R,5R)-5-(2-chloro-6-methoxy-9H-purin-9-yl)-3,4-dihydroxytetrahydrofuran-2-yl)methoxy)-2-phosphonoacetic acid as mixture of diastereomers, which was dissolved in water (5 mL) and then lyophilized to yield a white fluffy solid.

Example 63: LCMS Method 3: $t_R$=1.54 min, m/z=454, 456 (M+H$^+$); $^1$H NMR (D$_2$O) δ 9.15, 8.90 (s, 1H), 5.88-5.85 (m, 1H), 4.41 (m, 1H), 4.22 (m, 2H), 3.92-3.86 (m, 1H), 3.76-3.70 (m, 1H), 2.87 (s, 3H).

Example 64: 2-(((2R,3S,4R,5R)-3,4-dihydroxy-5-(6-(isopropylamino)-9H-purin-9-yl)tetrahydrofuran-2-yl)methoxy)-2-phosphonoacetic acid

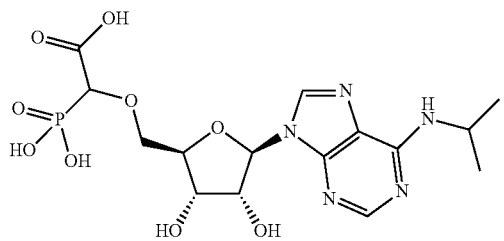 [SMILES: CC(C)Nc1ncnc2c1ncn2[C@@H]1O[C@H](COC(C(=O)O)P(=O)(O)O)[C@@H](O)[C@H]1O]

The title compound was synthesized by the method described in Example 61 starting with ((3aR,4R,6R,6aR)-6-(6-chloro-9H-purin-9-yl)-2,2-dimethyltetrahydrofuro[3,4-d][1,3]dioxol-4-yl)methanol. In Step 2, isopropyl amine was utilized. The final compound was purified by RP HPLC Method B and isolated as a mixture of diastereomers.

Example 64: LCMS Method 2: $t_R$=0.98 min, m/z=448 (M+H$^+$).

Example 65: 2-(((2R,3S,4R,5R)-3,4-dihydroxy-5-(6-(phenylamino)-9H-purin-9-yl)tetrahydrofuran-2-yl)methoxy)-2-phosphonoacetic acid

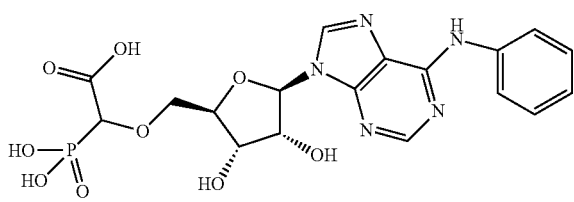 [SMILES: O=C(O)C(OC[C@H]1O[C@@H](n2cnc3c(Nc4ccccc4)ncnc32)[C@H](O)[C@@H]1O)P(=O)(O)O]

The title compound was synthesized by the method described in Example 61 starting with ((3aR,4R,6R,6aR)-6-(6-chloro-9H-purin-9-yl)-2,2-dimethyltetrahydrofuro[3,4-d][1,3]dioxol-4-yl)methanol. In Step 2, aniline was utilized.

The final compound was purified by RP HPLC Method A and isolated as mixture of diastereomers.

Example 65: LCMS Method 2: $t_R$=1.87 min, m/z=482 (M+H$^+$). $^1$H NMR (DMSO-d$_6$) δ 9.93 (s, 1H), 8.72 (s, 1H), 8.38 (s, 1H), 7.92 (d, 2H), 7.3 (m, 2H), 7.01 (m, 1H), 5.98 (d, 1H), 4.66 (m, 1H), 4.24-4.16 (m, 3H), 4.07 (ap s, 1H), 3.74 (m, 2H). $^{31}$P NMR (DMSO-d$_6$) δ 12.13, 11.88.

Example 66: 2-(((2R,3S,4R,5R)-3,4-dihydroxy-5-(6-(4-hydroxypiperidin-1-yl)-9H-purin-9-yl)tetrahydrofuran-2-yl)methoxy)-2-phosphonoacetic acid

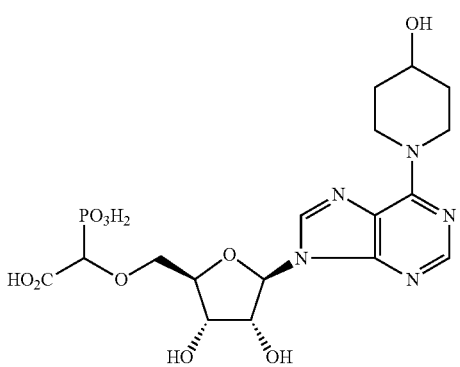

The title compound was synthesized by the method described in Example 61 starting with ((3aR,4R,6R,6aR)-6-(6-chloro-9H-purin-9-yl)-2,2-dimethyltetrahydrofuro[3,4-d][1,3]dioxol-4-yl)methanol. In Step 2, 4-hydroxypiperidine was utilized. The final compound was purified by RP HPLC Method A and isolated as mixture of diastereomers.

Example 66: LCMS Method 2: $t_R$=1.09, 1.13 min, m/z=490 (M+H$^+$).

Example 67: 2-(((2R,3S,4R,5R)-3,4-dihydroxy-5-(6-(methylamino)-9H-purin-9-yl)tetrahydrofuran-2-yl)methoxy)-2-phosphonoacetic acid

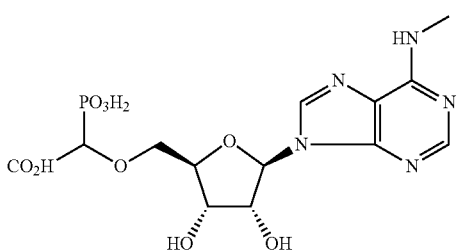

The title compound was synthesized by the method described in Example 61 starting with ((3aR,4R,6R,6aR)-6-(6-chloro-9H-purin-9-yl)-2,2-dimethyltetrahydrofuro[3,4-d][1,3]dioxol-4-yl)methanol. In Step 2, methylamine was utilized. The final compound was purified by RP HPLC Method A and isolated as a mixture of diastereomers.

Example 67: LCMS Method 2: $t_R$=1.02 min, m/z=420 (M+H$^+$). $^1$H NMR (DMSO-d$_6$) δ 8.61 (s, 1H), 8.28 (s, 1H), 5.92 (d, 1H), 4.61 (m, 1H) 4.21-4.14 (m, 2H), 4.05 (ap s, 1H), 3.77-3.64 (m, 2H), 2.47 (s, 3H). $^{31}$P NMR (DMSO-d$_6$) δ 12.11, 11.9.

Example 68: 2-(((2R,3S,4R,5R)-5-(2-chloro-6-
(((R)-tetrahydrofuran-3-yl)amino)-9H-purin-9-yl)-3,
4-dihydroxytetrahydrofuran-2-yl)methoxy)malonic
acid

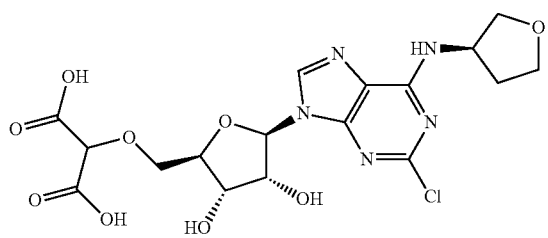 [SMILES: O=C(O)C(OC[C@H]1O[C@@H](n2cnc3c(N[C@@H]4CCOC4)nc(Cl)nc32)[C@H](O)[C@@H]1O)C(=O)O]

The title compound was synthesized by the method described in Example 2 (Step 2 was skipped). In Step 3, (R)-tetrahydrofuran-3-amine was utilized. The final compound was purified by RP HPLC Method A.

Example 68: LCMS Method 2: $t_R$=1.17 min, m/z=474.2 & 476.2 (M+H$^+$).

Example 69: (R)-2-(((2R,3S,4R,5R)-5-(2-chloro-6-
(((R)-tetrahydrofuran-3-yl)amino)-9H-purin-9-yl)-3,
4-dihydroxytetrahydrofuran-2-yl)methoxy)malonic
Acid and Example 69a: (S)-2-(((2R,3S,4R,5R)-5-(6-amino-2-
methyl-9H-purin-9-yl)-3,4-dihydroxytetrahydro-
furan-2-yl)methoxy)-2-phosphonoacetic acid Example 69

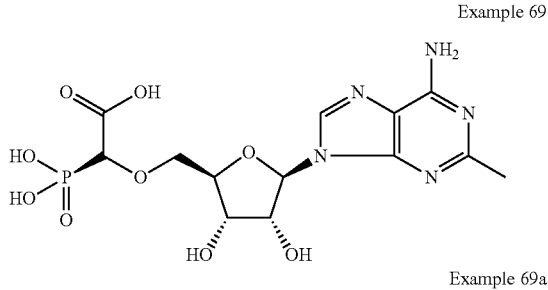

Example 69a

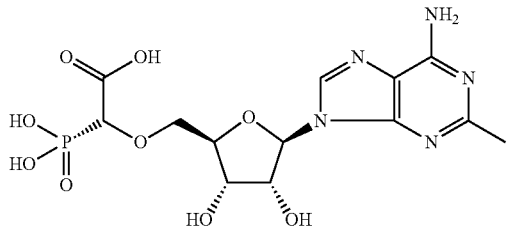

The title compound was synthesized by the method described in Example 1 starting from ((3aR,4R,6R,6aR)-6-(6-amino-2-methyl-9H-purin-9-yl)-2,2-dimethyltetrahydro-furo[3,4-d][1,3]dioxol-4-yl)methanol. The final compound was purified by RP HPLC Method A to separate the two diastereomers. The 1$^{st}$ eluting isomer corresponds to Example 69 and the 2$^{nd}$ eluting isomer corresponds to Example 69a.

Example 69: LCMS Method 2: $t_R$=0.94 min, m/z=420.1 (M+H$^+$).

Example 69a: LCMS Method 2: $t_R$=0.94 min, m/z=420.1 (M+H$^+$).

Example 70: ((R)-1-(((1R,2R,3S,4R)-4-(5-chloro-4-
oxoquinazolin-3(4H)-yl)-2,3-dihydroxycyclopentyl)
methoxy)-2-ethoxy-2-oxoethyl)phosphonic Acid and Example 70a: ((S)-1-(((1R,2R,3S,4R)-4-(5-chloro-
4-oxoquinazolin-3(4H)-yl)-2,3-dihydroxycyclopen-
tyl)methoxy)-2-ethoxy-2-oxoethyl)phosphonic Acid Example 70

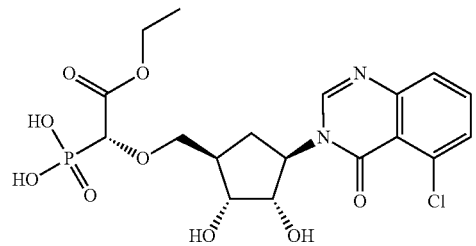

Example 70a

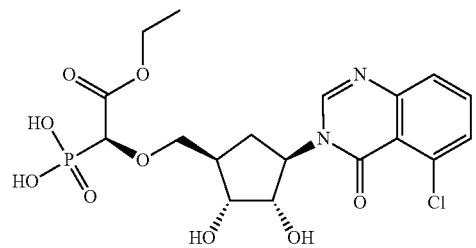

Scheme BB

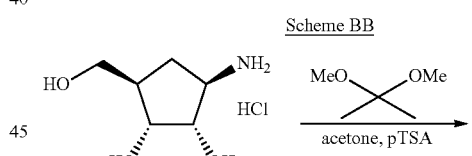

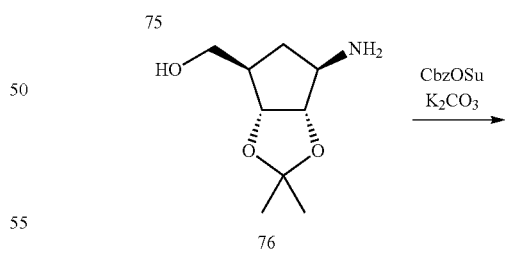

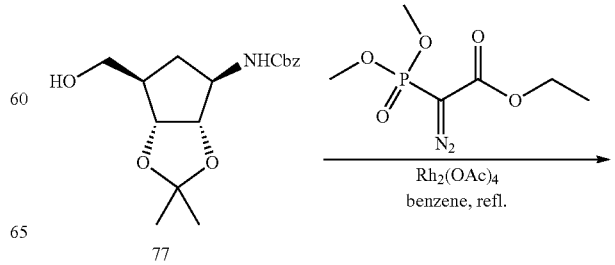

153
-continued

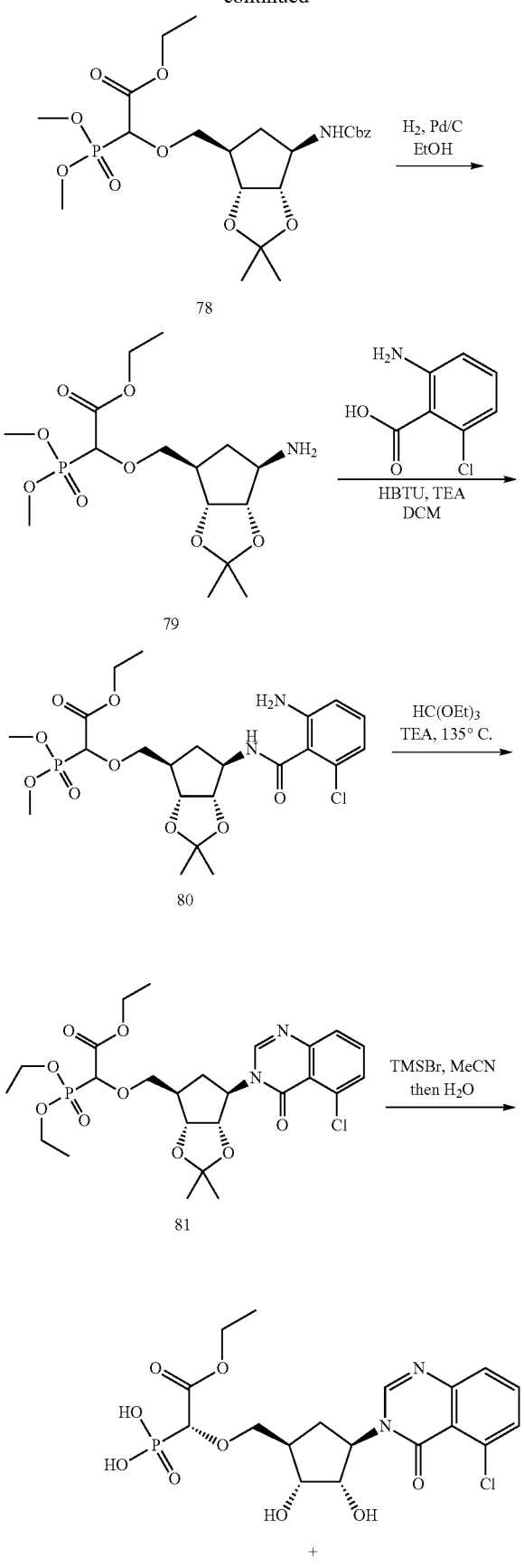

154
-continued

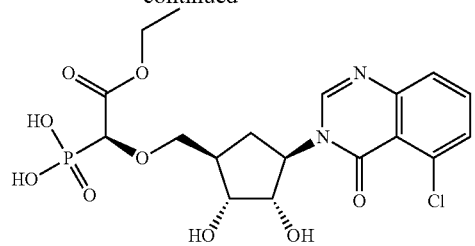

Step 1: Preparation of ((3aR,4R,6R,6aS)-6-amino-2,
2-dimethyltetrahydro-4H-cyclopenta[d][1,3]dioxol-
4-yl)methanol (76)

2,2-Dimethoxypropane (13.8 mL, 111.65 mmol) and TsOH (3. g, 2.23 mmol) were added to the solution of (1R,2S,3R,5R)-3-amino-5-(hydroxymethyl)cyclopentane-1, 2-diol hydrochloride (75) (4.10 g, 22.33 mmol) in acetone (40 mL) and stirred overnight at RT. TEA (6.5 mL) was added and the reaction mixture was stirred another 5 min before solvent was removed under reduced pressure. Brine was added to the residue and the mixture was extracted with EtOAc (2×) and DCM (8×). The combined organic phases were dried over anhydrous $Na_2SO_4$, and filtered, and concentrated under reduced pressure to yield crude product 76 (4.47 g). LCMS Method 2: $t_R$=1.94 min m/z=188 (M+H$^+$). $^1$H NMR: (DMSO-d$_6$): δ 4.47-4.49 (d, J=5.6 Hz, 1H), 4.11-4.13 (d, J=6.0 Hz, 1H), 3.39-3.43 (m, 2H), 3.22-3.24 (m, 1H), 2.10-2.14 (m, 2H), 1.33 (s, 3H), 1.23-1.25 (m, 1H), 1.19 (s, 3H).

Step 2: Preparation of benzyl ((3aS,4R,6R,6aR)-6-
(hydroxymethyl)-2,2-dimethyltetrahydro-4H-cyclo-
penta[d][1,3]dioxol-4-yl)carbamate (77)

To a solution of compound 76 (978 mg, 5.23 mmol) in THF (25 mL) was added CbzOSu (1.563 g, 6.27 mmol) and $K_2CO_3$ (2.788 g, 11.51 mmol). The mixture was stirred for 1.5 h at RT and then diluted with EtOAc (60 mL). The reaction mixture was washed with $H_2O$, followed by brine, and dried over anhydrous $Na_2SO_4$, and concentrated under reduced pressure. The residue was purified by silica gel chromatography with hexane-EtOAc as an eluent to yield compound 77 (1.347 g) which was used directly in the next step.

Step 3: Preparation of ethyl 2-(((3aR,4R,6R,6aS)-6-
(((benzyloxy)carbonyl)amino)-2,2-dimethyltetra-
hydro-4H-cyclopenta[d][1,3]dioxol-4-yl)methoxy)-
2-(dimethoxyphosphoryl)acetate (78)

To a solution of compound 77, $Rh_2(OAc)_4$ (54 mg, 0.12 mmol) in benzene (37 mL), was added ethyl 2-(bis (methoxy)phosphoryl)-2-diazoacetate (742 mg, 3.34 mmol) under $N_2$ atmosphere. The mixture was refluxed for 4 h, cooled down to RT and then washed with $H_2O$ after. The separated organic layer was dried over anhydrous $Na_2SO_4$, and filtered, and evaporated to dryness. The residue was purified by silica gel chromatography with hexane-EtOAc to yield compound 78 (1.077 g). LCMS Method 2: $t_R$=1.36 min, m/z=516 (M+H)$^+$.

Step 4: Preparation of ethyl 2-(((3aR,4R,6R,6aS)-6-
amino-2,2-dimethyltetrahydro-4H-cyclopenta[d][1,
3]dioxol-4-yl)methoxy)-2-(dimethoxyphosphoryl)
acetate (79)

A mixture of compound 78 (1.077 g, 2.09 mmol), 10% Pd/C (107 mg) and EtOH (15 mL) was stirred under $H_2$ atmosphere (balloon) for 30 min. The reaction mixture was filtered and concentrated to yield compound 79 (759 mg). LCMS Method 1: $t_R$=0.62 min, m/z=382 (M+H)⁺.

Step 5: Preparation of ethyl 2-(((3aR,4R,6R,6aS)-6-(2-amino-6-chlorobenzamido)-2,2-dimethyltetrahydro-4H-cyclopenta[d][1,3]dioxol-4-yl)methoxy)-2-(dimethoxyphosphoryl)acetate (80)

A mixture of compound 79 (140 mg, 0.37 mmol), 2-amino-6-chlorobenzoic acid (69 mg, 0.40 mmol), HBTU (167 mg, 0.44 mmol) and TEA (0.15 mL, 1.11 mmol) in DCM (2 mL) was stirred for 1 h at RT. The crude reaction mixture was purified by silica gel chromatography with hexane-EtOAc as an eluent to yield compound 80 (196 mg). LCMS: m/z=535.1 & 537.1 (M+H)⁺.

Step 6: Preparation of ethyl 2-(((3aR,4R,6R,6aS)-6-(5-chloro-4-oxoquinazolin-3(4H)-yl)-2,2-dimethyltetrahydro-4H-cyclopenta[d][1,3]dioxol-4-yl)methoxy)-2-(diethoxyphosphoryl)acetate (81)

A mixture of compound 80 (200 mg, 0.37 mmol), TEA (1 mL) and triethyl orthoformate (5 mL) was heated to 135° C. for 7 days. The reaction mixture was concentrated to dryness, and the residue was purified by reverse phase preparative HPLC to yield compound 81 (32 mg).

Step 7: Preparation of ((R)-1-(((1R,2R,3S,4R)-4-(5-chloro-4-oxoquinazolin-3 (4H)-yl)-2,3-dihydroxycyclopentyl)methoxy)-2-ethoxy-2-oxoethyl)phosphonic acid (Example 70) and ((S)-1-(((1R,2R,3S,4R)-4-(5-chloro-4-oxoquinazolin-3(4H)-yl)-2,3-dihydroxycyclopentyl)methoxy)-2-ethoxy-2-oxoethyl)phosphonic Acid (Example 70a)

TMSBr was added to a solution of compound 81 (32 mg, 0.86 mmol) in anhydrous MeCN (2 mL) (0.113 mL). The mixture was stirred for 1.5 h at RT, then H₂O (1 mL) was add. The mixture was stirred for another 30 min. It was directly purified by RP HPLC Method A to separate two diastereomers. The 1ˢᵗ eluting isomer corresponds to Example 70 (9.4 mg) and the 2ⁿᵈ eluting isomer corresponds to Example 70a (9.2 mg).

Example 70: ¹H NMR (CD₃OD): δ (ppm) 8.72 (s, 1H), 7.76 (t, J=8.0 Hz, 1H), 7.66 (d, J=7.2 Hz, 1H), 7.62 (d, J=7.6 Hz, 1H), 5.15 (m, 1H), 4.57 (m, 1H), 4.36 (d, J=18.8 Hz, 1H), 4.29 (q J=7.0 Hz, 2H), 4.16 (m, 1H), 3.81 (m, 1H), 3.70 (m, 1H), 2.48 (m, 1H), 2.35 (m, 1H), 1.90 (m, 1H), 1.33 (t, J=6.8 Hz, 3H); LCMS Method 2: $t_R$=2.02 min, m/z=477 (M+H⁺).

Example 70a: ¹H NMR (CD₃OD): δ (ppm) 8.90 (s, 1H), 7.77 (t, J=8.0 Hz, 1H), 7.65 (d, J=6.8 Hz, 1H), 7.62 (d, J=7.6 Hz, 1H), 5.08 (m, 1H), 4.58 (m, 1H), 4.37 (d, J=18.8 Hz, 1H), 4.29 (q, J=7.2 Hz, 2H), 4.18 (m, 1H), 3.78 (m, 1H), 3.67 (m, 1H), 2.51 (m, 1H), 2.35 (m, 1H), 1.95 (m, 1H), 1.32 (t, J=7.2 Hz, 3H); LCMS Method 2: $t_R$=2.05 min, m/z=477 (M+H⁺).

Example 71: 2-(((1R,2R,3S,4R)-4-(5-chloro-4-oxoquinazolin-3(4H)-yl)-2,3-dihydroxycyclopentyl)methoxy)-2-phosphonoacetic acid

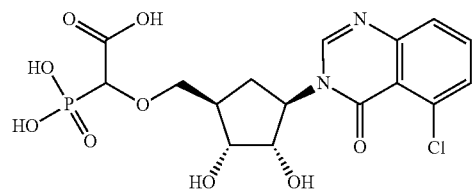

Scheme CC

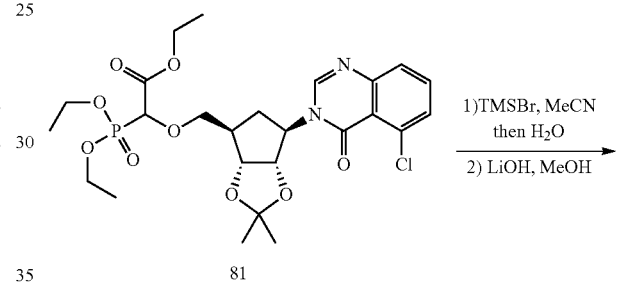

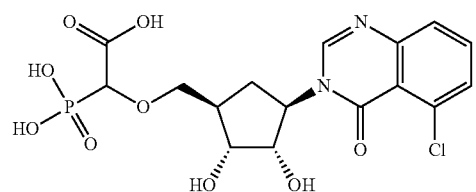 [SMILES: O=C(O)C(OC[C@H]1C[C@@H](n2cnc3cccc(Cl)c3c2=O)[C@H](O)[C@@H]1O)P(=O)(O)O]

TMSBr (0.05 mL) was added to a solution of compound 81 (4.5 mg, 0.86 mmol) in anhydrous ACN (1 mL). The mixture was stirred for 1.5 h at RT, then H₂O (0.5 mL) was added. The mixture was stirred for another 30 min before being concentrated to dryness under reduced pressure. The residue was dissolved in MeOH (1 mL) and 2 M LiOH (3 drops) was added to the solution. The resulting mixture was stirred for 30 min before 50% HCO₂H (2 drops) was added. The crude reaction mixture was purified by preparative RP HPLC Method A to yield Example 71 (9.4 mg) as mixture of diastereomers. LCMS Method 2: $t_R$=1.91 min, m/z=449 (M+H⁺).

Example 72: ((R)-1-(((1R,2R,3S,4R)-4-(5-bromo-4-oxoquinazolin-3(4H)-yl)-2,3-dihydroxycyclopentyl)methoxy)-2-ethoxy-2-oxoethyl)phosphonic Acid and

Example 72a: ((S)-1-(((1R,2R,3S,4R)-4-(5-bromo-4-oxoquinazolin-3(4H)-yl)-2,3-dihydroxycyclopentyl)methoxy)-2-ethoxy-2-oxoethyl)phosphonic Acid

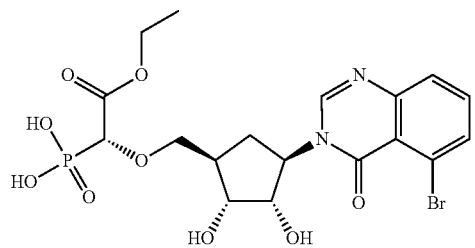

Example 72

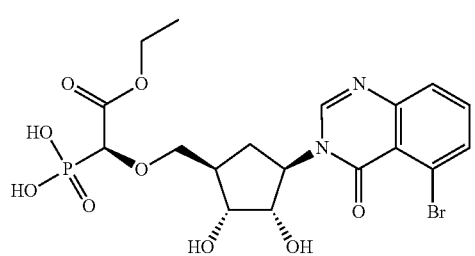

Example 72a

The title compounds were synthesized by the method described in Example 70. In Step 5, 2-amino-6-bromobenzoic acid was utilized instead of 2-amino-6-chlorobenzoic acid. The final product was purified by RP HPLC Method A to separate the two diastereomers. The 1$^{st}$ eluting isomer corresponds to Example 72 (9.4 mg) and the 2$^{nd}$ eluting isomer corresponds to Example 72a (9.2 mg).

Example 72: LCMS Method 2: $t_R$=2.15 min, m/z=477 (M+H$^+$).

Example 72a: LCMS Method 2: $t_R$=2.15 min, m/z=477 (M+H$^+$).

Example 73: ((R)-1-(((1R,2R,3S,4R)-4-(5-cyano-4-oxoquinazolin-3(4H)-yl)-2,3-dihydroxycyclopentyl)methoxy)-2-ethoxy-2-oxoethyl)phosphonic Acid and

Example 73a: ((S)-1-(((1R,2R,3S,4R)-4-(5-cyano-4-oxoquinazolin-3(4H)-yl)-2,3-dihydroxycyclopentyl)methoxy)-2-ethoxy-2-oxoethyl)phosphonic Acid

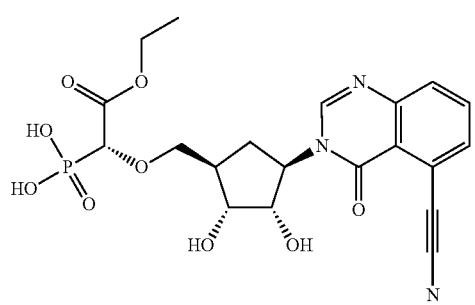

Example 73

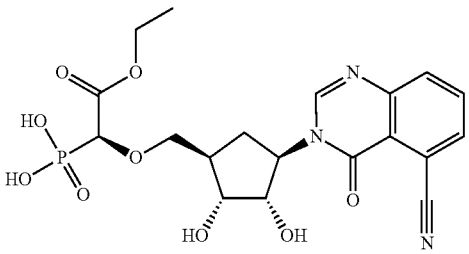

Example 73a

The title compounds were synthesized by the method described in Example 70. In Step 5, 2-amino-6-bromobenzoic acid was utilized instead of 2-amino-6-chlorobenzoic acid. The intermediate from Step 6 was further subjected to the reaction below.

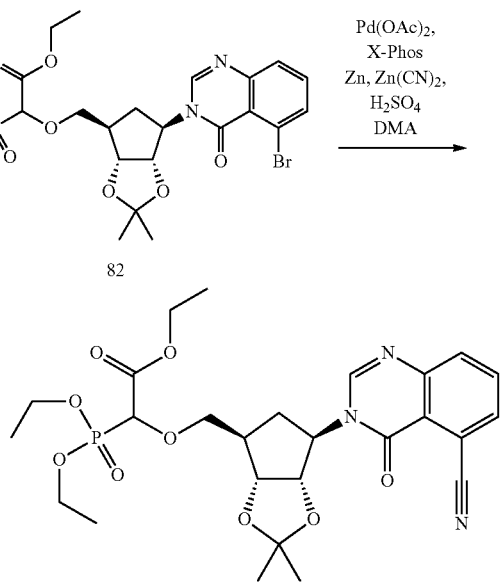

A mixture of Pd(OAc)$_2$ (15 mg, 0.067 mmol), X-Phos (64 mg, 0.13 mmol) in 50 mM H$_2$SO$_4$/DMA (2 mL) charged in a 5 mL vial was degassed for 5 min and filled with N$_2$. The mixture was heated to 80° C. for 30 min. In a separate flask charged with ethyl 2-(((3aR,4R,6R,6aS)-6-(5-bromo-4-oxoquinazolin-3 (4H)-yl)-2,2-dimethyltetrahydro-4H-cyclopenta[d][1,3]dioxol-4-yl)methoxy)-2-(diethoxyphosphoryl)acetate (82) (40 mg, 0.068 mmol), Zn(CN)$_2$, (8 mg, 0.068 mmol), Zn dust (0.8 mg) and DMA (3 mL), the system was degassed for 5 min and filled with N$_2$. To this mixture was canulated about half of prepared catalyst. The resulting mixture was heated to 90° C. for 2 h. Solvent was removed under reduced pressure. EA was added and filtered through a plug of Celite. The filtrate was concentrated to dryness. The crude product (83) (ethyl 2-(((3aR,4R,6R,6aS)-6-(5-cyano-4-oxoquinazolin-3(4H)-yl)-2,2-dimethyltetrahydro-4H-cyclopenta[d][1,3]dioxol-4-yl)methoxy)-2-(diethoxyphosphoryl)acetate) was used in the method described in Step 7 of Example 70. The final product was purified by RP HPLC Method A to separate the two diastereomers. The 1$^{st}$ eluting isomer corresponds to Example 73 and the 2$^{nd}$ eluting isomer corresponds to Example 73a.

Example 73: LCMS Method 2: $t_R$=2.15 min, m/z=468.1 (M+H$^+$).

Example 73a: LCMS Method 2: $t_R$=2.15 min, m/z=469.1 (M+H$^+$).

Example 74: 2-(((1R,2R,3S,4R)-4-(5-chloro-4-oxo-quinazolin-3(4H)-yl)-2,3-dihydroxycyclopentyl)methoxy)malonic acid

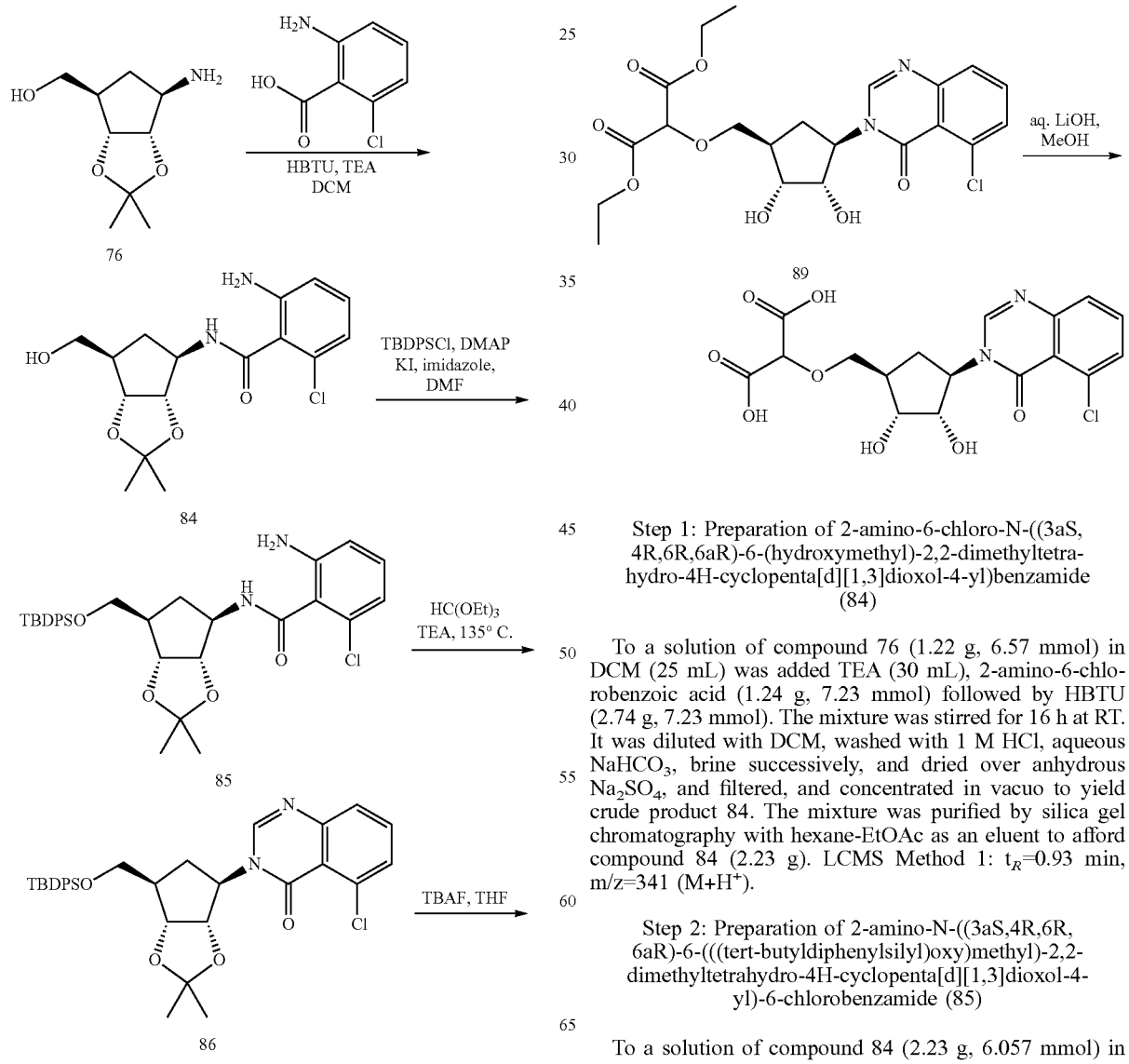

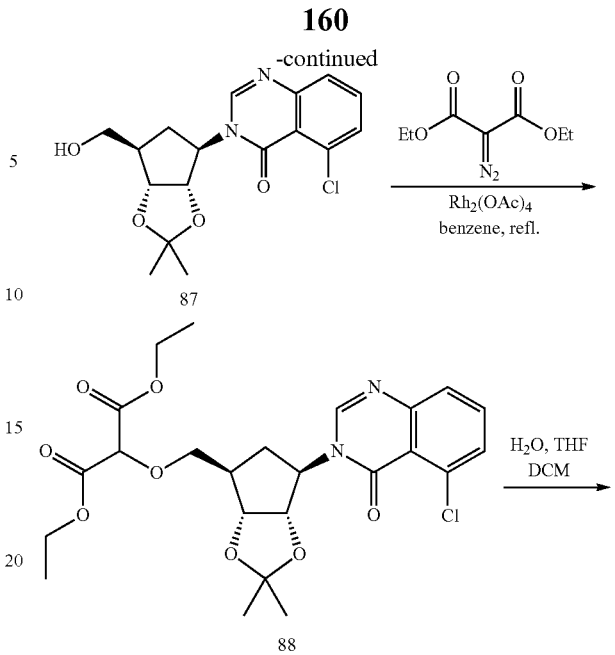

Step 1: Preparation of 2-amino-6-chloro-N-((3aS, 4R,6R,6aR)-6-(hydroxymethyl)-2,2-dimethyltetrahydro-4H-cyclopenta[d][1,3]dioxol-4-yl)benzamide (84)

To a solution of compound 76 (1.22 g, 6.57 mmol) in DCM (25 mL) was added TEA (30 mL), 2-amino-6-chlorobenzoic acid (1.24 g, 7.23 mmol) followed by HBTU (2.74 g, 7.23 mmol). The mixture was stirred for 16 h at RT. It was diluted with DCM, washed with 1 M HCl, aqueous NaHCO$_3$, brine successively, and dried over anhydrous Na$_2$SO$_4$, and filtered, and concentrated in vacuo to yield crude product 84. The mixture was purified by silica gel chromatography with hexane-EtOAc as an eluent to afford compound 84 (2.23 g). LCMS Method 1: $t_R$=0.93 min, m/z=341 (M+H$^+$).

Step 2: Preparation of 2-amino-N-((3aS,4R,6R,6aR)-6-(((tert-butyldiphenylsilyl)oxy)methyl)-2,2-dimethyltetrahydro-4H-cyclopenta[d][1,3]dioxol-4-yl)-6-chlorobenzamide (85)

To a solution of compound 84 (2.23 g, 6.057 mmol) in DMF (5 mL) containing imidazole (893 mg, 13.4 mmol)

was added TBDPSCl (1.88 mL, 7.22 mmol). The mixture was stirred for 16 h at RT. It was diluted with DCM, washed with 1 M HCl, aqueous NaHCO$_3$, brine successively, and dried over anhydrous Na$_2$SO$_4$, filtered and concentrated in vacuo to yield crude product. The mixture was purified by silica gel chromatography with hexane-EtOAc as an eluent to afford compound 85 (1.117 g) as off white foam. LCMS Method 2: $t_R$=3.94 min, m/z=579 (M+H$^+$).

Step 3: Preparation of 3-((3aS,4R,6R,6aR)-6-(((tert-butyldiphenylsilyl)oxy)methyl)-2,2-dimethyltetrahydro-4H-cyclopenta[d][1,3]dioxol-4-yl)-5-chloroquinazolin-4(3H)-one (86)

A mixture of compound 85 (1.01 g, 1.74 mmol), TEA (2 mL) and triethyl orthoformate (12 mL) was heated at 135° C. for 7 days. The reaction mixture was concentrated to dryness, and the residue was purified by preparative HPLC to yield compound 86 (411 mg). LCMS Method 2: $t_R$=2.32 min, m/z=589 (M+H$^+$).

Step 4: Preparation of 5-chloro-3-((3aS,4R,6R,6aR)-6-(hydroxymethyl)-2,2-dimethyltetrahydro-4H-cyclopenta[d][1,3]dioxol-4-yl)quinazolin-4(3H)-one (87)

TMAF (195 mg, 2.1 mmol) was added to a solution of compound 86 (411 mg, 0.7 mmol) in ACN (4 mL). The mixture was stirred at RT for 1 h. Brine was added to the reaction mixture and extracted with EA (3×). The combined organic phases were dried over anhydrous Na$_2$SO$_4$, and filtered, and concentrated in vacuo to yield crude product. It was purified by silica gel chromatography with hexane-EtOAc to afford compound 87 (260 mg). LCMS Method 1: $t_R$=1.08 min, m/z=351 (M+H$^+$).

Step 5: Preparation of diethyl 2-(((3aR,4R,6R,6aS)-6-(5-chloro-4-oxoquinazolin-3(4H)-yl)-2,2-dimethyltetrahydro-4H-cyclopenta[d][1,3]dioxol-4-yl)methoxy)malonate (88)

Diethyl 2-diazomalonate (138 mg 0.81 mmol) was added to a solution of compound 87 (260 mg, 0.74 mmol) and Rh$_2$(OAc)$_4$ (7 mg, 0.015 mmol) in anhydrous benzene (12 mL) under N$_2$ atmosphere. The mixture was heated at reflux for 16 h. The reaction mixture was cooled to RT, washed with water, and dried over anhydrous Na$_2$SO$_4$, filtered, and evaporated to dryness. The residue was purified by silica gel chromatography to yield compound 88 (186 mg). LCMS Method 1: $t_R$=1.54 min, m/z=509 (M+H$^+$).

Step 6: 2-(((1R,2R,3S,4R)-4-(5-chloro-4-oxoquinazolin-3(4H)-yl)-2,3-dihydroxycyclopentyl)methoxy)malonic acid A mixture of compound 88 (57 mg, 0.11 mmol), DCM (0.5 mL), TFA (0.5 mL) and H$_2$O (3 drops) was stirred for 20 min. The reaction mixture was concentrated to dryness to yield compound 89. The residue was dissolved in MeOH (2 mL) and a solution 2 M aq. LiOH solution (5 drops) was added. The mixture was stirred for 3 h before being neutralized by 50% HCO$_2$H. The mixture was purified by preparative RP HPLC Method A to yield Example 74 (15 mg) as a TFA salt. $^1$H NMR (CD$_3$OD): δ (ppm) 8.79 (s, 1H), 7.73 (t, J=8.0 Hz, 1H), 7.62 (d, J=8.0 Hz, 1H), 7.59 (d, J=8.0 Hz, 1H), 5.16 (q, J=7.2 Hz, 1H), 4.61 (m, 2H), 4.13 (m, 1H), 3.75 (dd, J=8.8, 4.4 Hz, 1H), 3.75 (dd, J=8.8, 4.8 Hz, 1H), 2.50 (m, 1H), 2.36 (m, 1H), 1.88 (m, 1H); LCMS Method 2: $t_R$=1.94 min, m/z=413 (M+H$^+$).

Example 75: (2-(ethylamino)-1-(((1R,2R,3S,4R)-4-(6-(ethylamino)-9H-purin-9-yl)-2,3-dihydroxycyclopentyl)methoxy)-2-oxoethyl)phosphonic Acid

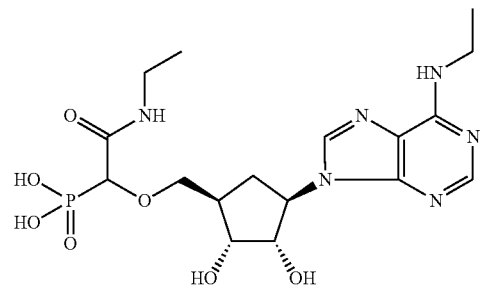 [SMILES: CCNC(=O)C(OC[C@H]1C[C@@H](n2cnc3c(NCC)ncnc32)[C@H](O)[C@@H]1O)P(=O)(O)O]

Scheme EE

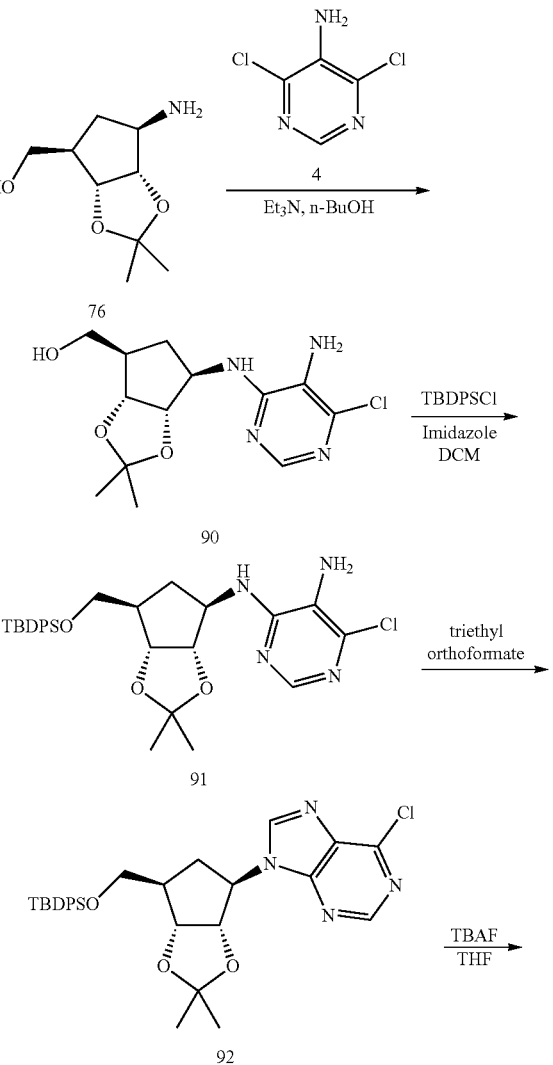

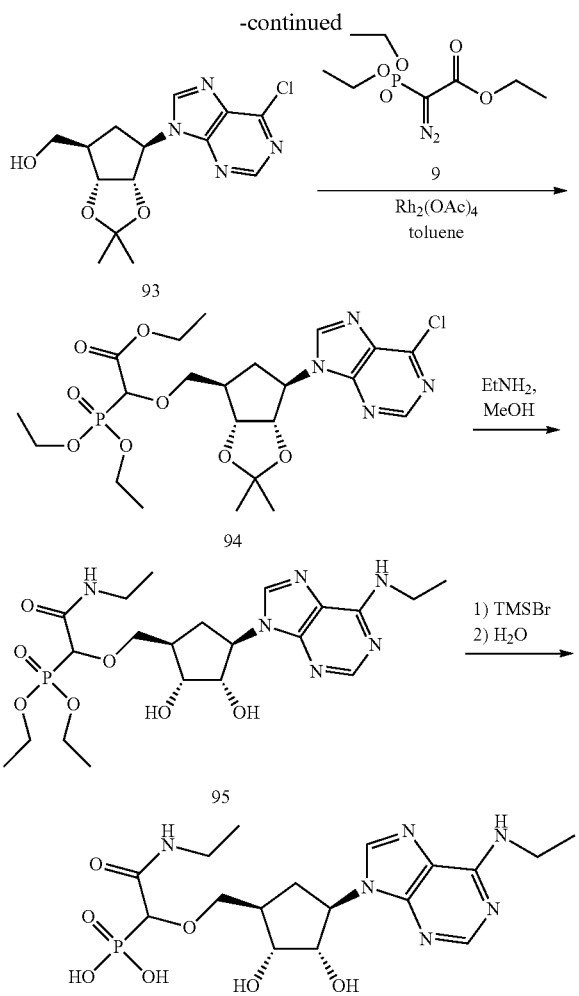

Step 1: ((3aR,4R,6R,6aS)-6-((5-amino-6-chloropyrimidin-4-yl)amino)-2,2-dimethyltetrahydro-3aH-cyclopenta[d][1,3]dioxol-4-yl)methanol (90)

4,6-Dichloropyrimidin-5-amine (1.40 g, 8.55 mmol) and Et$_3$N (2.59 g, 25.65 mmol) were added to a solution of compound 76 (1.60 g, 8.55 mmol, crude) in n-BuOH (20 mL). The mixture was stirred overnight at 100° C. The solvent was removed in vacuo and the resulting residue was purified by via reverse phase-HPLC method 2 to give compound 90 (1.2 g). LCMS Method 2: R$_t$=0.50 min, m/z=314.9 (M+H$^+$). $^1$H NMR: (CDCl$_3$): δ 8.03 (s, 1H), 6.73-6.76 (d, J=8.0 Hz, 1H), 4.60-4.62 (m, 2H), 4.40-4.42 (m, 1H), 3.88-3.93 (m, 1H), 3.70-3.75 (m, 1H), 3.60 (s, 1H), 3.49 (s, 2H), 2.62-2.71 (m, 1H), 2.38-2.41 (m, 1H), 1.59-1.64 (d, J=10.4 Hz, 1H), 1.47 (s, 3H), 1.26 (s, 3H).

Step 2: N4-((3aS,4R,6R,6aR)-6-(((tert-butyldiphenylsilyl)oxy)methyl)-2,2-dimethyltetrahydro-3aH-cyclopenta[d][1,3]dioxol-4-yl)-6-chloropyrimidine-4,5-diamine (91)

TBDPSCl (176 mg, 064 mmol) and imidazole (44 mg, 0.64 mmol) were added to the solution of compound 90 in DCM (10 mL). The mixture was stirred overnight at RT. The reaction mixture was poured into H$_2$O (20 mL), extracted with DCM (3×20 mL). The combined organic layer was dried over Na$_2$SO$_4$, concentrated and then purified by column chromatography on silica gel (petroleum ether:ethyl acetate=3:1) to give N4-((3aS,4R,6R,6aR)-6-(((tert-butyldiphenylsilyl)oxy)methyl)-2,2-dimethyltetrahydro-3aH-cyclopenta[d][1,3]dioxol-4-yl)-6-chloropyrimidine-4,5-diamine (91, 120 mg) as white oil. $^1$H NMR: (CDCl$_3$): δ 8.11 (s, 1H), 7.60-7.68 (m, 4H), 7.35-7.44 (m, 6H), 4.99-5.01 (d, J=6.0 Hz, 1H), 4.45-4.55 (m, 2H), 4.37-4.39 (m, 1H), 3.78-3.82 (m, 1H), 3.68-3.73 (m, 1H), 2.99 (s, 2H), 2.42-2.52 (m, 2H), 1.73-1.80 (m, 1H), 1.50 (s, 3H), 1.29-3.26 (m, H), 1.09 (s, 9H).

Step 3: 9-((3aS,4R,6R,6aR)-6-(((tert-butyldiphenylsilyl)oxy)methyl)-2,2-dimethyltetrahydro-3aH-cyclopenta[d][1,3]dioxol-4-yl)-6-chloro-9H-purine (92)

The solution of compound 91 (1.4 g, 2.53 mmol) in triethyl orthofomate (20 mL) was stirred overnight at 110° C. The solvent was removed in vacuo and the residue was purified by column chromatography on silica gel (petroleum ether:ethyl acetate=3:1) to give 9-((3aS,4R,6R,6aR)-6-(((tert-butyldiphenylsilyl)oxy)methyl)-2,2-dimethyltetrahydro-3aH-cyclopenta[d][1,3]dioxol-4-yl)-6-chloro-9H-purine (92, 900 mg) as yellow oil. LCMS Method 2: R$_t$=0.99 min, m/z=563.1 (M+H$^+$). $^1$H NMR: (CDCl$_3$): δ 8.62-8.64 (d, J=3.2 Hz, 1H), 8.07-8.09 (s, 1H), 7.56-7.61 (m, 4H), 7.31-7.38 (m, 6H), 5.01-5.15 (m, 1H), 4.94-4.98 (m, 1H), 4.75-4.79 (m, 1H), 4.63-4.67 (m, 1H), 3.76-3.79 (m, 1H), 2.55-2.62 (m, 2H), 2.32-2.37 (m, 1H), 1.49 (s, 3H), 1.22 (s, 3H), 1.02 (s, 9H).

Step 4: ((3aR,4R,6R,6aS)-6-(6-chloro-9H-purin-9-yl)-2,2-dimethyltetrahydro-3aH-cyclopenta[d][1,3]dioxol-4-yl)methanol (93)

TBAF (1.46 mL, 1M in THF, 1.46 mmol) was added to a solution of compound 92 (823 mg, 1.46 mmol) in THF (20 mL) and stirred for 2 h at RT. The solvent was removed in vacuo and the crude residue was purified by column chromatography on silica gel (petroleum ether:ethyl acetate=3:1) to give compound 93, (350 mg) as yellow oil. LCMS Method 2: R$_t$=0.597 min, m/z=324.8. (M+H$^+$). $^1$H NMR: (CDCl$_3$): δ 8.73 (s, 1H), 8.22 (s, 1H), 5.01-5.05 (t, J=6.4 Hz, 1H), 4.80-4.90 (m, 1H), 4.65-4.75 (m, 1H), 3.80-3.90 (m, 2H), 2.40-2.59 (m, 3H), 2.25-2.35 (m, 1H), 1.58 (s, 3H), 1.31 (s, 3H).

Step 5: (ethyl 2-(((3aR,4R,6R,6aS)-6-(6-chloro-9H-purin-9-yl)-2,2-dimethyltetrahydro-3aH-cyclopenta[d][1,3]dioxol-4-yl)methoxy)-2-(diethoxyphosphoryl)acetate) (94)

Ethyl 2-diazo-2-(diethoxyphosphoryl)acetate (540 mg, 2.16 mmol) and Rh$_2$(OAc)$_4$ (48 mg, 0.11 mmol) were added to the solution of compound 93 (350 mg, 1.08 mmol) in toluene (20 mL). The resulting mixture was stirred overnight at 90° C. under N$_2$. The solvent was removed in vacuo and the residue was purified via RP HPLC Method B to give ethyl 2-(((3aR,4R,6R,6aS)-6-(6-chloro-9H-purin-9-yl)-2,2-dimethyltetrahydro-3aH cyclopenta[d][1,3]dioxol-4-yl)methoxy)-2-(diethoxyphosphoryl)acetate (94) (320 mg) as a white solid. LCMS Method 2: R$_t$=0.717 min, m/z=546.9 (M+H$^+$). $^1$H NMR: (CDCl$_3$): δ 8.71 (s, 1H), 8.29-8.33 (d, J=11.2 Hz, 1H), 4.98-5.03 (m, 1H), 4.85-4.95 (m, 1H), 4.65-4.75 (m, 1H), 4.15-4.35 (m, 7H), 3.70-3.85 (m, 2H), 2.55-2.60 (m, 2H), 1.72 (s, 1H), 1.57 (s, 3H), 1.29-1.36 (m, 12H).

Step 6: Preparation of diethyl (2-(ethylamino)-1-(((3aR,4R,6R,6aS)-6-(6-(ethylamino)-9H-purin-9-yl)-2,2-dimethyltetrahydro-4H-cyclopenta[d][1,3]dioxol-4-yl)methoxy)-2-oxoethyl)phosphonate. (95)

Compound 94 (75 mg, 0.137 mmol) in 2.0 M EtNH$_2$/MeOH (3 mL) solution was heated for 60 minutes at 90° C. in CEM reactor. The solvent was removed under reduced pressure to afford the crude product 95, which was used in the next step without further purification.

Step 7: Preparation of (2-(ethylamino)-1-(((1R,2R,3S,4R)-4-(6-(ethylamino)-9H-purin-9-yl)-2,3-dihydroxycyclopentyl)methoxy)-2-oxoethyl)phosphonic acid. (96)

TMSBr (0.2 mL) was added to a solution of crude product 95 in anhydrous ACN (3 mL) and stirred for 16 h at RT, then H$_2$O (0.2 mL) was added. The mixture was stirred for another 30 min and then concentrated to dryness under reduced pressure. The residue was purified by RP HPLC Method A to yield Example 76 (55 mg) as a TFA salt and as a mixture of diastereomers. $^1$H NMR (CD$_3$OD): δ 8.36 (s, 1H), 8.24 (s, 1H), 4.88-4.75 (m, 3H), 4.46 (m, 1H), 4.07 (m, 1H), 3.98 (m, 1H), 3.68-3.50 (m, 2H), 3.23-3.09 (m, 2H), 2.43 (m, 1H), 2.31 (m, 1H), 1.86 (m, 1H), 1.25 (t, J=6.8 Hz, 3H), 1.00 (t, J=7.2 Hz, 3H); LCMS Method 2: $t_R$=1.17 min, m/z=459 (M+H$^+$).

Example 76: ((R)-1-(((1R,2R,3S,4R)-4-(6-amino-2-chloro-9H-purin-9-yl)-2,3-dihydroxycyclopentyl)methoxy)-2-ethoxy-2-oxoethyl)phosphonic Acid and Example 76a: ((S)-1-(((1R,2R,3S,4R)-4-(6-amino-2-chloro-9H-purin-9-yl)-2,3-dihydroxycyclopentyl)methoxy)-2-ethoxy-2-oxoethyl)phosphonic Acid The title compounds were synthesized by the method described in Example 75. In Step 1: 2,4,6-dichloropyrimidin-5-amine was utilized. In Step 6, ammonia in isopropanol was utilized and the reaction stirred at RT for 24 h. The final compound was purified was purified by RP HPLC Method A to separate the two diastereomers. The 1$^{st}$ eluting isomer corresponds to Example 76 and the 2$^{nd}$ eluting isomer corresponds to Example 76a.

Example 76: LCMS Method 2: $t_R$=1.17 min, m/z=466.2 & 468.2 (M+H$^+$).

Example 76a: LCMS Method 2: $t_R$=1.27 min m/z=466.2 & 468.2 (M+H$^+$).

Example 77: (1-(((1R,2R,3S,4R)-4-(7-amino-5-chloro-3H-[1,2,3]triazolo[4,5-d]pyrimidin-3-yl)-2,3-dihydroxycyclopentyl)methoxy)-2-ethoxy-2-oxoethyl)phosphonic Acid and Example 77a: (1-(((1R,2R,3S,4R)-4-(7-amino-5-bromo-3H-[1,2,3]triazolo[4,5-d]pyrimidin-3-yl)-2,3-dihydroxycyclopentyl)methoxy)-2-ethoxy-2-oxoethyl)phosphonic Acid Example 77

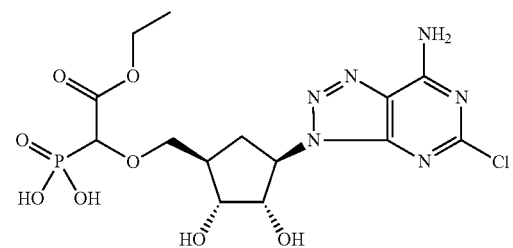

Example 77a

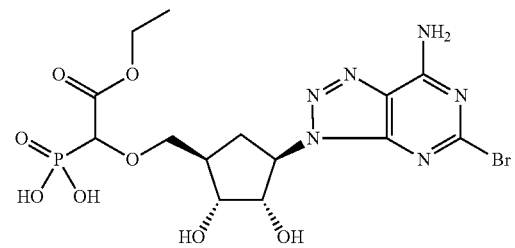

Example 76

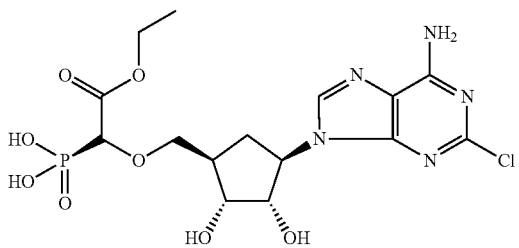

Example 76a

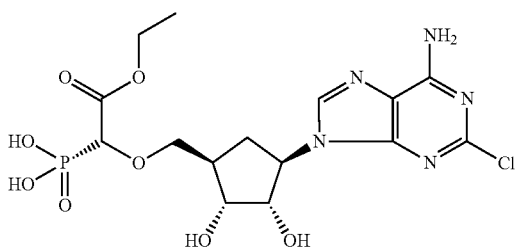

Scheme FF

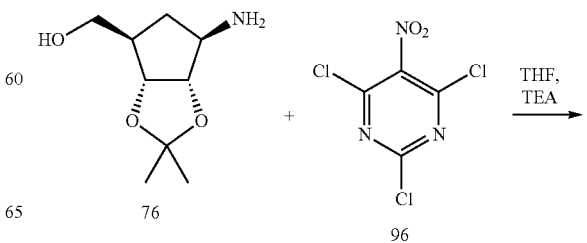

167

-continued

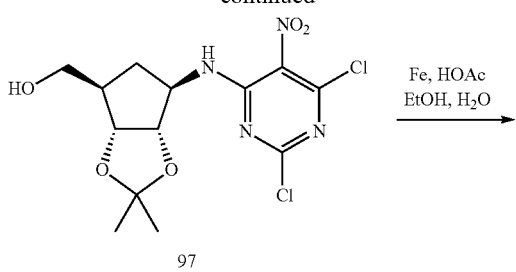

97

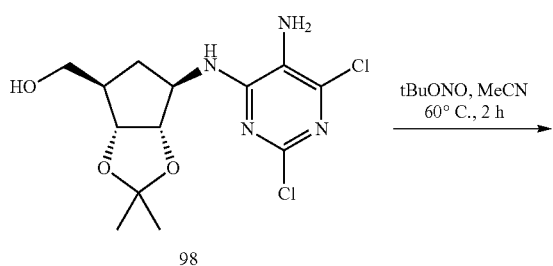

98

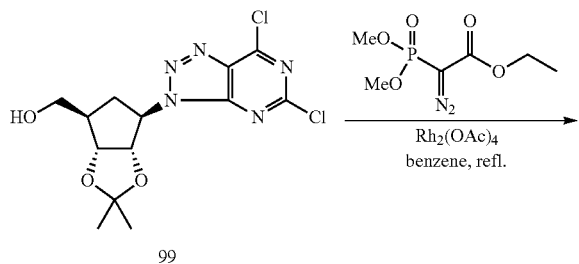

99

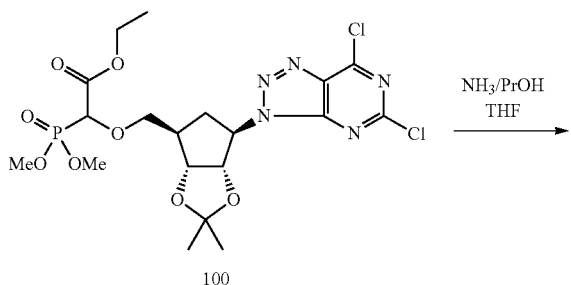

100

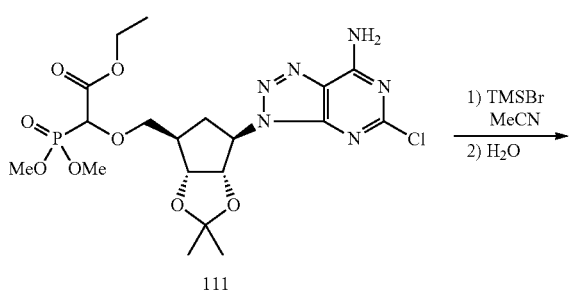

111

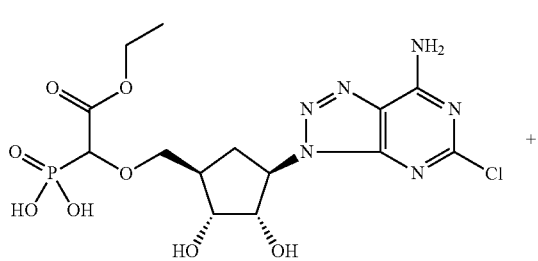

168

-continued

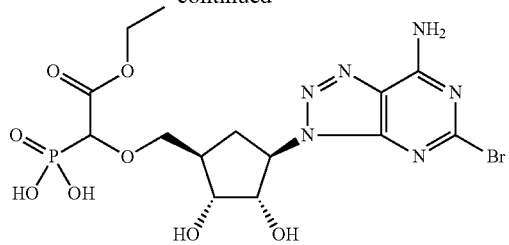

Step 1: Preparation of ((3aR,4R,6R,6aS)-6-((2,6-dichloro-5-nitropyrimidin-4-yl)amino)-2,2-dimethyl-tetrahydro-4H-cyclopenta[d][1,3]dioxol-4-yl)methanol (97)

2,4,6-Trichloro-5-nitropyrimidine (283 mg, 1.24 mmol), followed by TEA (0.172 mL, 1.24 mmol) were added to a solution of ((3aR,4R,6R,6aS)-6-amino-2,2-dimethyltetrahydro-4H-cyclopenta[d][1,3]dioxol-4-yl)methanol (232 mg, 1.24 mmol) in THF (6 mL) and stirred for 5 min at RT. The reaction mixture was diluted with EA/Et$_2$O (1:1), and washed with 10% citric acid, brine successively, and dried over anhydrous Na$_2$SO$_4$. The solvent was removed under reduced pressure. The residue was purified by silica gel chromatography (eluted with MeOH/DCM, 0-20%) to yield compound 97 (293 mg). LCMS Method 1: t$_R$=1.50 min, m/z=379 (M+H$^+$).

Step 2: Preparation of ((3aR,4R,6R,6aS)-6-((5-amino-2,6-dichloropyrimidin-4-yl)amino)-2,2-dimethyltetrahydro-4H-cyclopenta[d][1,3]dioxol-4-yl)methanol (98)

Iron powder (346 mg, 6.19 mmol), and HOAc (0.352 mL, 6.19 mmol) were added to a solution of compound 97 (293 mg, 0.77 mmol) in EtOH (4 mL) and H$_2$O (3 mL) and heated at 60° C. for 15 min. The reaction mixture was filtered through a short pad of Celite, and the solids washed with EA/Et$_2$O (1:1). The filtrate was washed with H$_2$O. The aqueous phase was extracted with EA/Et$_2$O (1:1). The combined organic phases were washed with brine, and dried over anhydrous Na$_2$SO$_4$, and filtered, and concentrated in vacuo to afford compound 98 (303) mg as an off-white foam which was used in the next step without further purification. LCMS Method 1: t$_R$=1.12 min, m/z=349 (M+H$^+$).

Step 3: Preparation of ((3aR,4R,6R,6aS)-6-(5,7-dichloro-3H-[1,2,3]triazolo[4,5-d]pyrimidin-3-yl)-2,2-dimethyltetrahydro-4H-cyclopenta[d][1,3]dioxol-4-yl)methanol (99)

tert-Butyl nitrite (138 µL, 1.16 mmol) was added to a solution of crude product obtained in previous step in anhydrous MeCN (4 mL) under a N$_2$ atmosphere and heated for 2 h at 60° C. The reaction mixture was concentrated in vacuo to dryness. The residue was purified by silica gel chromatography and eluted with MeOH/DCM to afford compound 99 (217 mg) as a light yellow solid. LCMS Method 1: t$_R$=1.30 min, m/z=360 (M+H$^+$).

Step 4: Preparation of ethyl 2-(((3aR,4R,6R,6aS)-6-(5,7-dichloro-3H-[1,2,3]triazolo[4,5-d]pyrimidin-3-yl)-2,2-dimethyltetrahydro-4H-cyclopenta[d][1,3]dioxol-4-yl)methoxy)-2-(dimethoxyphosphoryl)acetate (100)

Ethyl 2-(bis(methoxy)phosphoryl)-2-diazoacetate (160 mg 0.72 mmol). was added to a solution of compound 99

(217 mg, 0.60 mmol) and Rh$_2$(OAc)$_4$ (11 mg, 0.024 mmol) in anhydrous benzene (8 mL) under N$_2$ atmosphere. The mixture was heated at reflux for 3 h. The reaction mixture was washed with water after being cooled down to RT, and dried over anhydrous Na$_2$SO$_4$, and filtered, and evaporated to dryness. The residue was purified by silica gel chromatography to yield compound 100 (261 mg). LCMS Method 1: $t_R$=1.48 min, m/z=554 (M+H$^+$).

Step 5: Preparation ethyl 2-(((3aR,4R,6R,6aS)-6-(7-amino-5-chloro-3H-[1,2,3]triazolo[4,5-d]pyrimidin-3-yl)-2,2-dimethyltetrahydro-4H-cyclopenta[d][1,3]dioxol-4-yl)methoxy)-2-(dimethoxyphosphoryl)acetate (101)

3 M NH$_3$/i-PrOH (3 mL) was added to a solution of compound 100 (87 mg, 0.157 mmol) in THF (2 mL). The mixture was stirred for 5 min at RT and then concentrated in vacuo to afford 96 mg product 101 (96 mg). The product was used in the next step without further purification. LC/MS Method 2: $t_R$=1.18 min, 535 (M+H$^+$).

Step 6: Preparation of ethyl 2-(((3aR,4R,6R,6aS)-6-(7-amino-5-chloro-3H-[1,2,3]triazolo[4,5-d]pyrimidin-3-yl)-2,2-dimethyltetrahydro-4H-cyclopenta[d][1,3]dioxol-4-yl)methoxy)-2-(dimethoxyphosphoryl)acetate and (1-(((1R,2R,3S,4R)-4-(7-amino-5-bromo-3H-[1,2,3]triazolo[4,5-d]pyrimidin-3-yl)-2,3-dihydroxycyclopentyl)methoxy)-2-ethoxy-2-oxoethyl)phosphonic Acid TMSBr (0.15 mL) was added to a solution of crude product 101 in anhydrous ACN (3 mL) and stirred at RT for 1 h. H$_2$O (0.1 mL) was added and stirred for another 8 h and then concentrated in vacuo. The residue was purified by RP HPLC Method A to separate the two diastereomers. The 1$^{st}$ eluting isomer corresponds to Example 77 (29 mg) and the 2$^{nd}$ eluting isomer corresponds to Example 77a (7 mg).

Example 77a: $^1$H NMR (CD$_3$OD): 5.14 (m, 1H), 4.60 (m, 1H), 4.39-4.15 (m, 4H), 3.83-3.66 (m, 2H), 2.55-2.46 (m, 2H), 2.03 (m, 1H), 1.31 (t, J=7.2 Hz, 3H); LCMS Method 2: $t_R$=1.65 min, m/z=467 (M+H$^+$).

Example 77a $^1$H NMR (CD$_3$OD): 5.14 (m, 1H), 4.59 (m, 1H), 4.38-4.15 (m, 4H), 3.81-3.66 (m, 2H), 2.55-2.45 (m, 2H), 2.02 (m, 1H), 1.31 (t, J=7.2 Hz, 3H); LCMS Method 2: $t_R$=2.05 min, m/z=511 (M+H$^+$).

Example 78: ((R)-1-(((1R,2R,3S,4R)-4-(6-amino-2-chloro-9H-purin-9-yl)-2,3-dihydroxycyclopentyl)methoxy)-2-(tert-butoxy)-2-oxoethyl)phosphonic Acid and Example 78a: ((S)-1-(((1R,2R,3S,4R)-4-(6-amino-2-chloro-9H-purin-9-yl)-2,3-dihydroxycyclopentyl)methoxy)-2-(tert-butoxy)-2-oxoethyl)phosphonic Acid Example 78

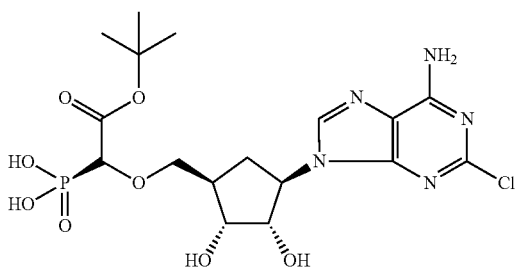

Example 78a

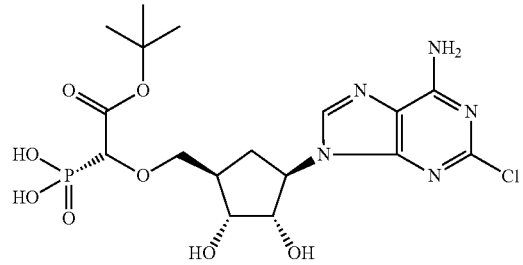

The title compounds were synthesized by the method described in Example 75. In Step 1, the reagent 2,4,6-dichloropyrimidin-5-amine was utilized. In Step 5, tert-butyl 2-diazo-2-(diethoxyphosphoryl)acetate was used. In Step 6, ammonia in isoproponal was utilized and stirred at RT for 24 h. The final product was purified by RP HPLC Method A to separate the two diastereomers. The 1$^{st}$ eluting isomer corresponds to Example 78 and the 2$^{nd}$ eluting isomer corresponds to Example 78a.

Example 78: LCMS Method 2: $t_R$=1.27 min, m/z=494.2 & 496.2 (M+H$^+$).

Example 78a: LCMS Method 2: $t_R$=1.31 min, m/z=494.2 & 496.2 (M+H$^+$).

Example 79: (R)-3-(((2R,3S,4R,5R)-5-(6-amino-2-fluoro-9H-purin-9-yl)-3,4-dihydroxytetrahydrofuran-2-yl)methoxy)-4-ethoxy-4-oxo-3-phosphonobutanoic Acid and Example 79a: (S)-3-(((2R,3S,4R,5R)-5-(6-amino-2-fluoro-9H-purin-9-yl)-3,4-dihydroxytetrahydrofuran-2-yl)methoxy)-4-ethoxy-4-oxo-3-phosphonobutanoic acid Example 79

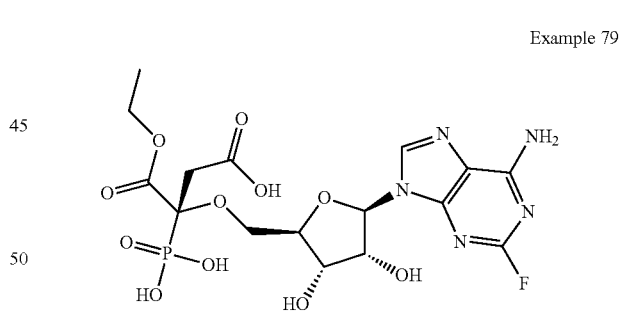

Example 79a

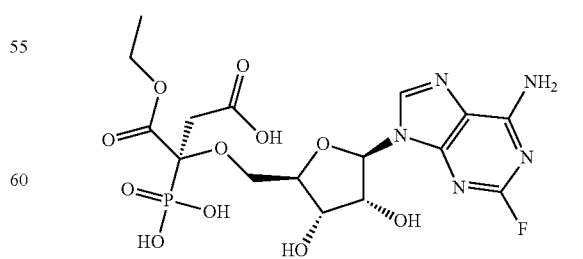

The title compounds were synthesized by the method described in Examples 8 & 9. ((3aR,4R,6R,6aR)-6-(6-amino-2-fluoro-9H-purin-9-yl)-2,2-dimethyltetrahydrofuro

[3,4-d][1,3]dioxol-4-yl)methanol was utilized as starting material. The first step involved use of ethyl 2-diazo-2-(diethoxyphosphoryl)acetate according to the procedure described in Step 1 of Example 1. The product from this reaction was further alkylated with ethyl-2-bromoacetate as described Step 1 of Example 9. Further elaboration of this intermediate by Step 3 in Example 9 gave the desired final product which was purified by RP HPLC Method A to separate the two diastereomers. The 1$^{st}$ eluting isomer corresponds to Example 79 and 2$^{nd}$ eluting isomer corresponds to Example 79a.

Example 79: LCMS Method 2: $t_R$=1.17 min, m/z=466.2 & 468.2 (M+H$^+$).

Example 79a: LCMS Method 2: $t_R$=1.17 min, m/z=510.2 & 511.2 (M+H$^+$).

Example 80: (2R)-ethyl 2-(((2R,3S,4R,5R)-5-(2-chloro-6-(ethylamino)-9H-purin-9-yl)-3,4-dihydroxytetrahydrofuran-2-yl)methoxy)-2-(ethoxy(hydroxy)phosphoryl)propanoate and Example 80a: (2S)-ethyl 2-(((2R,3S,4R,5R)-5-(2-chloro-6-(ethylamino)-9H-purin-9-yl)-3,4-dihydroxytetrahydrofuran-2-yl)methoxy)-2-(ethoxy(hydroxy)phosphoryl)propanoate Example 80

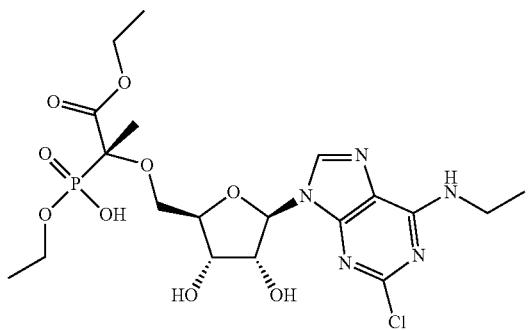

Example 80a

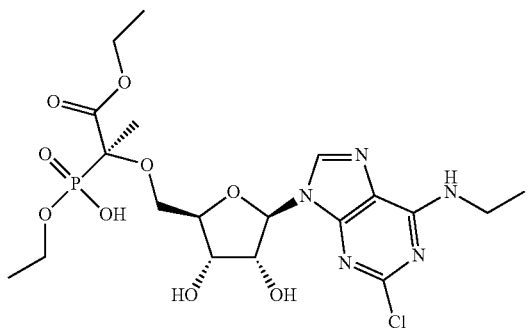

The title compounds were synthesized by the method described in Example 9. In Step 2, ethylamine was utilized instead of ammonia. The product was purified by RP HPLC Method A to separate the two diastereomers. The 1$^{st}$ eluting isomer corresponds to Example 80 and the 2$^{nd}$ eluting isomer corresponds to Example 80a.

Example 80: $^1$H NMR (CD$_3$OD): 8.24 (s, 1H), 4.88-4.75 (m, 3H), 4.46 (m, 1H), 4.07 (m, 1H), 3.98 (m, 1H), 3.68-3.50 (m, 2H), 3.23-3.09 (m, 2H), 2.43 (m, 1H), 2.31 (m, 1H), 1.86 (m, 1H), 1.25 (t, J=6.8 Hz, 3H), 1.00 (t, J=7.2 Hz, 3H); LCMS Method 2: $t_R$=1.17 min, m/z=466.2 & 468.2 (M+H$^+$).

Example 80a: $^1$H NMR (CD$_3$OD): 8.24 (s, 1H), 4.88-4.75 (m, 3H), 4.46 (m, 1H), 4.07 (m, 1H), 3.98 (m, 1H), 3.68-3.50 (m, 2H), 3.23-3.09 (m, 2H), 2.43 (m, 1H), 2.31 (m, 1H), 1.86 (m, 1H), 1.25 (t, J=6.8 Hz, 3H), 1.00 (t, J=7.2 Hz, 3H); LCMS Method 2: $t_R$=1.17 min, m/z=510.2 & 511.2 (M+H$^+$).

Example 81: ((R)-1-(((2R,3S,4R,5R)-5-(5,6-dichloro-1H-benzo[d]imidazol-1-yl)-3,4-dihydroxytetrahydrofuran-2-yl)methoxy)-2-ethoxy-2-oxoethyl) phosphonic Acid and Example 81a: ((S)-1-(((2R,3S,4R,5R)-5-(5,6-dichloro-1H-benzo[d]imidazol-1-yl)-3,4-dihydroxytetrahydrofuran-2-yl)methoxy)-2-ethoxy-2-oxoethyl) phosphonic Acid Example 81

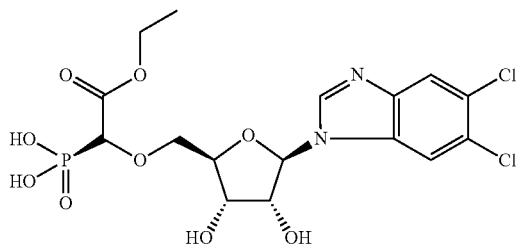

Example 81a

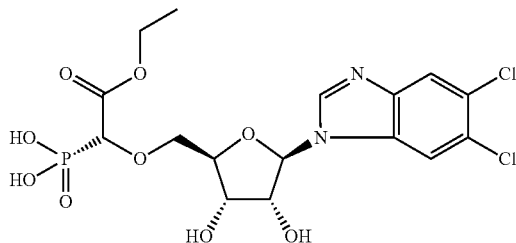

(2R,3R,4S,5R)-2-(5,6-Dichloro-3H-imidazo[4,5-b]pyridin-3-yl)-5-(hydroxymethyl)tetrahydrofuran-3,4-diol was synthesized from 5,6-dichloro-1H-benzo[d]imidazole and (2S,3R,4R)-4-(acetoxymethyl)cyclopentane-1,2,3-triyl triacetate by method described in *Nucleosides & Nucleotides*, 4(5), 625-39; 1985. The acetonide group was introduced by method described in Step 1 of Example 70. The product from this reaction was further elaborated as described in Steps 2 and 4 in Example 1. The crude product was purified by RP HPLC Method A to separate the two diastereomers. The 1$^{st}$ eluting isomer corresponds to Example 81 and 2$^{nd}$ eluting isomer corresponds to Example 81a.

Example 81: $^1$H NMR (CD$_3$OD): 8.24 (s, 1H), 4.88-4.75 (m, 3H), 4.46 (m, 1H), 4.07 (m, 1H), 3.98 (m, 1H), 3.68-3.50 (m, 2H), 3.23-3.09 (m, 2H), 2.43 (m, 1H), 2.31 (m, 1H), 1.86 (m, 1H), 1.25 (t, J=6.8 Hz, 3H), 1.00 (t, J=7.2 Hz, 3H); LCMS Method 2: $t_R$=1.17 min, m/z=485.2 & 487.2 (M+H$^+$).

Example 81a: $^1$H NMR (CD$_3$OD): 8.24 (s, 1H), 4.88-4.75 (m, 3H), 4.46 (m, 1H), 4.07 (m, 1H), 3.98 (m, 1H), 3.68-3.50 (m, 2H), 3.23-3.09 (m, 2H), 2.43 (m, 1H), 2.31 (m, 1H), 1.86 (m, 1H), 1.25 (t, J=6.8 Hz, 3H), 1.00 (t, J=7.2 Hz, 3H); LCMS Method 2: $t_R$=1.17 min, m/z=485.2 & 487.2 (M+H$^+$).

Example 82: ((S)-1-(((2R,3S,4R,5R)-5-(6-amino-2-chloro-9H-purin-9-yl)-3,4-dihydroxytetrahydrofuran-2-yl)methoxy)-2-(diethylamino)-2-oxoethyl) phosphonic Acid and

Example 82a: ((R)-1-(((2R,3S,4R,5R)-5-(6-amino-2-chloro-9H-purin-9-yl)-3,4-dihydroxytetrahydrofuran-2-yl)methoxy)-2-(diethylamino)-2-oxoethyl) phosphonic Acid Example 82

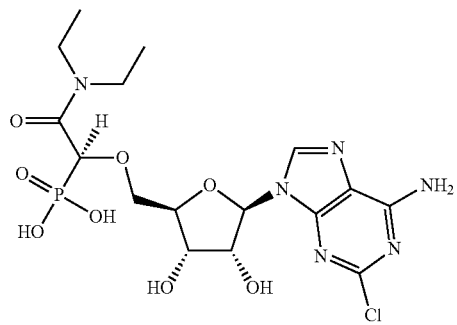

Example 82a

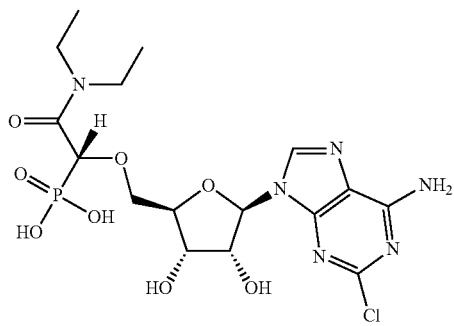

The title compounds were synthesized by the method described in Example 1. In Step 3, diethyl amine was used instead of isobutyl amine. The final compound was purified by RP HPLC Method A to separate the two diastereomers. The 1st eluting isomer corresponds to Example 82 and 2nd eluting isomer corresponds to Example 82a.

Example 82: $^1$H NMR (CD$_3$OD) δ 8.66 (s, 1H), 6.05 (d, 1H), 4.70 (m, 1H), 4.51 (m, 1H), 4.26 (m, 1H), 3.86 (m, 2H), 3.73 (m, 2H), 3.59 (m, 2H), 1.20 (m, 6H). $^{19}$F NMR (CD$_3$OD) δ −77.25. LCMS Method 2: $t_R$=1.27 min, m/z=495.2 & 497.2 (M+H$^+$).

Example 82a: $^1$H NMR (CD$_3$OD) δ 8.86 (s, 1H), 6.06 (d, 1H), 4.70 (m, 1H), 4.51 (m, 1H), 4.28 (m, 1H), 3.95 (d, 1H), 3.81 (m, 1H), 3.72 (m, 2H), 3.61 (m, 2H), 1.18 (m, 6H). $^{19}$F NMR (CD$_3$OD) δ −77.11. LCMS Method 2: $t_R$=1.32 min, m/z=466.2 & 468.2 (M+H$^+$).

Example 83: 2-(((2R,3S,4R,5R)-5-(2-chloro-6-(((S)-tetrahydrofuran-3-yl)amino)-9H-purin-9-yl)-3,4-dihydroxytetrahydrofuran-2-yl)methoxy)malonic acid

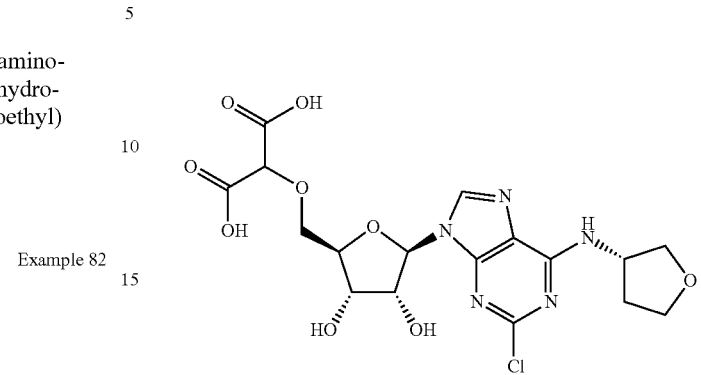

The title compound was synthesized by the method described in Example 2. The procedures of Step 2 were skipped. In Step 3, (S)-tetrahydrofuran-3-amine was utilized. The final compound was purified by RP HPLC Method A.

Example 83: LCMS Method 2: $t_R$=1.27 min, m/z=474.2 & 476.2 (M+H$^+$).

Example 84: 2-(((2R,3S,4R,5R)-5-(6-amino-2-chloro-9H-purin-9-yl)-3,4-dihydroxytetrahydrofuran-2-yl)methoxy)-2-(2,6-difluorobenzyl)malonic acid

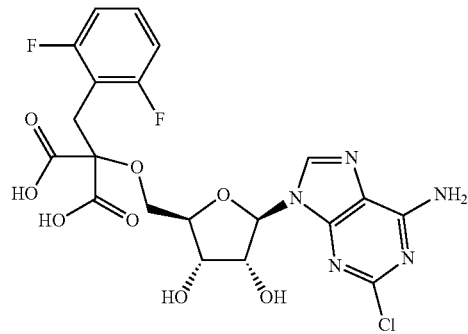 [SMILES: Nc1nc(Cl)nc2c1ncn2[C@@H]1O[C@H](COC(Cc2c(F)cccc2F)(C(=O)O)C(=O)O)[C@@H](O)[C@H]1O]

The title compound was synthesized by the method described in Example 1. In Step 2, 2,6-difluorobenzylbromide was used. In Step 3, ammonia was utilized. The final compound was purified by RP HPLC Method A.

Example 84: LCMS Method 2: $t_R$=1.25 min, m/z=530.2 & 532.2 (M+H$^+$).

Example 85: 2-(((2R,3S,4R,5R)-5-(6-amino-2-chloro-9H-purin-9-yl)-3,4-dihydroxytetrahydrofuran-2-yl)methoxy)-2-(2,6-difluorobenzyl)malonic acid

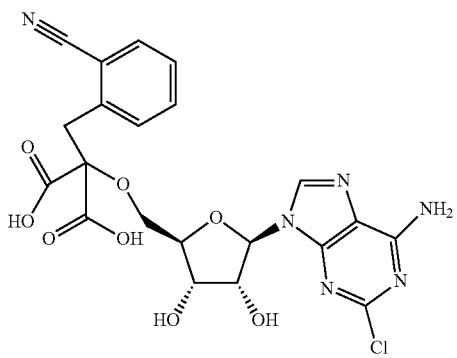 [SMILES: N#Cc1ccccc1CC(OC[C@H]1O[C@@H](n2cnc3c(N)nc(Cl)nc32)[C@H](O)[C@@H]1O)(C(=O)O)C(=O)O]

The title compound was synthesized by the method described in Example 2. In Step 2, 2-cyano-benzylbromide was used. In Step 3, ammonia was utilized. The final compound was purified by RP HPLC Method A.

Example 85: LCMS Method 2: $t_R$=1.15 min, m/z=519.2 & 521.2 (M+H$^+$).

Example 86: 2-(((2R,3S,4R,5R)-5-(6-amino-2-chloro-9H-purin-9-yl)-3,4-dihydroxytetrahydrofuran-2-yl)methoxy)-2-(2-(methylsulfonyl)benzyl)malonic acid

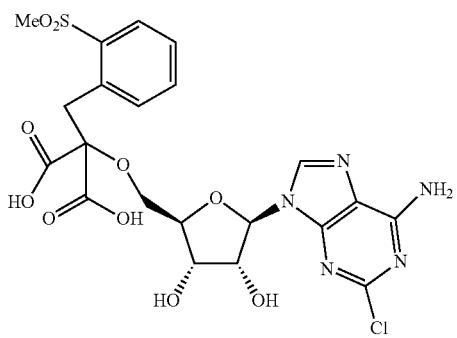 [SMILES: CS(=O)(=O)c1ccccc1CC(OC[C@H]1O[C@@H](n2cnc3c(N)nc(Cl)nc32)[C@H](O)[C@@H]1O)(C(=O)O)C(=O)O]

The title compound was synthesized by the method described in Example 2. In Step 2, 2-methylsulfone benzylbromide was used. In Step 3, ammonia was utilized. The final compound was purified by RP HPLC Method A.

Example 86: LCMS Method 2: $t_R$=1.16 min, m/z=572.2 & 574.2 (M+H$^+$).

Example 87: ((R)-1-(((2R,3S,4R,5R)-5-(5-chloro-3H-imidazo[4,5-b]pyridin-3-yl)-3,4-dihydroxytetrahydrofuran-2-yl)methoxy)-2-ethoxy-2-oxoethyl)phosphonic Acid and

Example 87a: ((S)-1-(((2R,3S,4R,5R)-5-(5-chloro-3H-imidazo[4,5-b]pyridin-3-yl)-3,4-dihydroxytetrahydrofuran-2-yl)methoxy)-2-ethoxy-2-oxoethyl)phosphonic Acid Example 87

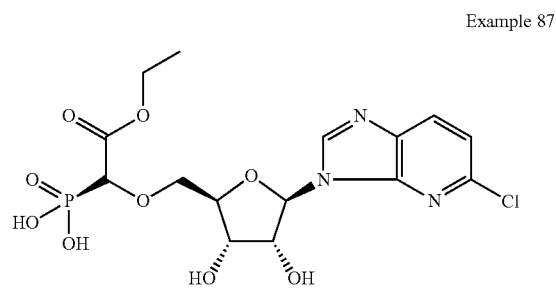

Example 87a

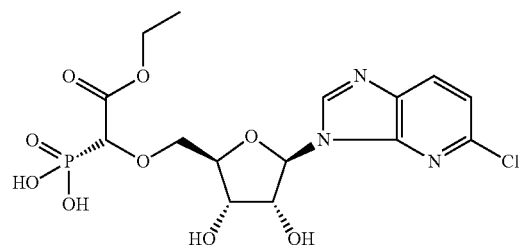

(2R,3R,4S,5R)-2-(5-Chloro-3H-imidazo[4,5-b]pyridin-3-yl)-5-(hydroxymethyl)tetrahydrofuran-3,4-diol was prepared by the method described in *Nucleosides & Nucleotides,* 4(5), 625-39; 1985 starting from 5-chloro-3H-imidazo[4,5-b]pyridine and (2S,3R,4R)-4-(acetoxymethyl)cyclopentane-1,2,3-triyl triacetate. The acetonide group was introduced by the method described in Step 1 of Example 70. The product from this reaction was further elaborated as described in Steps 2 and 4 of Example 1 and was purified by RP HPLC Method A to separate the two diastereomers. The 1$^{st}$ eluting isomer corresponds to Example 87 and the 2$^{nd}$ eluting isomer corresponds to Example 87a.

Example 87: LCMS Method 2: $t_R$=1.17 min, m/z=452.1 & 454.1 (M+H$^+$).

Example 87a: LCMS Method 2: $t_R$=1.17 min, m/z=452.1 & 454.2 (M+H$^+$).

Example 88: (1-(((1R,2R,3S,4R)-4-(5-chloro-7-((((S)-tetrahydrofuran-3-yl)methyl)amino)-3H-[1,2,3]triazolo[4,5-d]pyrimidin-3-yl)-2,3-dihydroxycyclopentyl)methoxy)-2-ethoxy-2-oxoethyl) phosphonic Acid

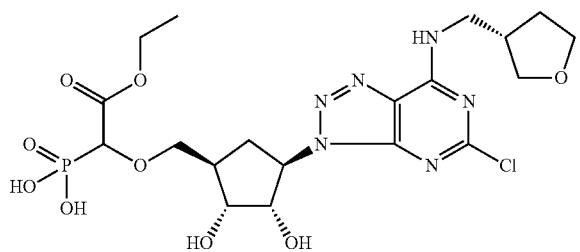 [SMILES: CCOC(=O)C(OC[C@H]1C[C@@H](n2nnc3c(NC[C@@H]4CCOC4)nc(Cl)nc32)[C@H](O)[C@@H]1O)P(=O)(O)O]

The title compound was synthesized by the method described in Example 77. In Step 5, (S)-(tetrahydrofuran-3-yl)methanamine was utilized. The final compound was purified by RP HPLC Method A and isolated as mixture of diastereomers.

Example 88: LCMS Method 2: $t_R$=1.16 min, m/z=551.2 & 553.2 (M+H$^+$). $^1$H NMR (CD$_3$OD): 5.13 (m, 1H), 4.91-4.69 (m, 4H), 4.58 (m, 1H) 4.36-4.16 (m, 3H), 3.94-3.58 (m, 5H), 2.71-2.24 (m, 2H), 2.15-1.93 (m, 2H), 1.76 (m, 1H), 1.44-1.25 (m, 4H), 0.93 (m, 1H).

Example 89: (1-(((1R,2R,3S,4R)-4-(5-chloro-7-((((R)-tetrahydrofuran-3-yl)methyl)amino)-3H-[1,2,3]triazolo[4,5-d]pyrimidin-3-yl)-2,3-dihydroxycyclopentyl)methoxy)-2-ethoxy-2-oxoethyl) phosphonic Acid

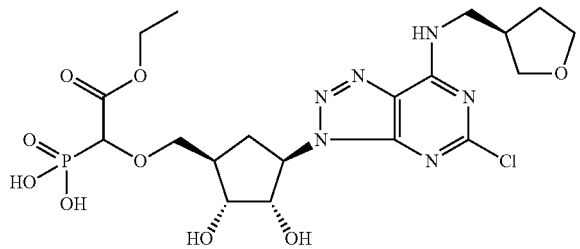 [SMILES: CCOC(=O)C(OC[C@H]1C[C@@H](n2nnc3c(NC[C@H]4CCOC4)nc(Cl)nc32)[C@H](O)[C@@H]1O)P(=O)(O)O]

The title compound was synthesized by the method described in Example 77. In Step 5, (R)-(tetrahydrofuran-3-yl)methanamine was utilized. The final compound was purified by RP HPLC Method A and isolated as mixture of diastereomers.

Example 89: LCMS Method 2: $t_R$=1.17 min, m/z=551.2 & 553.2 (M+H$^+$). $^1$H NMR (CD$_3$OD): 5.13 (m, 1H), 4.94-4.65 (m, 4H), 4.58 (m, 1H) 4.36-4.16 (m, 3H), 3.98-3.57 (m, 5H), 2.71-2.48 (m, 2H), 2.17-1.93 (m, 2H), 1.75 (m, 1H), 1.41-1.25 (m, 4H), 0.92 (m, 1H).

Example 90: (1-(((1R,2R,3S,4R)-4-(5-chloro-7-(((R)-tetrahydrofuran-3-yl)amino)-3H-[1,2,3]triazolo[4,5-d]pyrimidin-3-yl)-2,3-dihydroxycyclopentyl)methoxy)-2-ethoxy-2-oxoethyl)phosphonic Acid

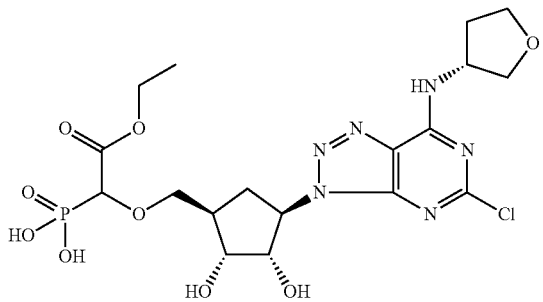 [SMILES: CCOC(=O)C(OC[C@H]1C[C@@H](n2nnc3c(N[C@@H]4CCOC4)nc(Cl)nc32)[C@H](O)[C@@H]1O)P(=O)(O)O]

The title compound was synthesized by the method described in Example 77. In Step 5, (s)-(tetrahydrofuran-3-yl) amine was utilized. The final compound was purified by RP HPLC Method A and isolated as mixture of diastereomers.

Example 90: LCMS Method 2: $t_R$=1.17 min, 537.2 & 539.2 (M+H$^+$). $^1$H NMR (CD$_3$OD): 5.13 (m, 1H), 4.96-4.60 (m, 6H), 4.27-3.67 (m, 6H), 2.52-2.34 (m, 2H), 2.03 (m, 1H), 1.44-1.25 (m, 5H).

Example 91: (1-(((1R,2R,3S,4R)-4-(5-chloro-7-(((S)-tetrahydrofuran-3-yl)amino)-3H-[1,2,3]triazolo[4,5-d]pyrimidin-3-yl)-2,3-dihydroxycyclopentyl)methoxy)-2-ethoxy-2-oxoethyl)phosphonic Acid

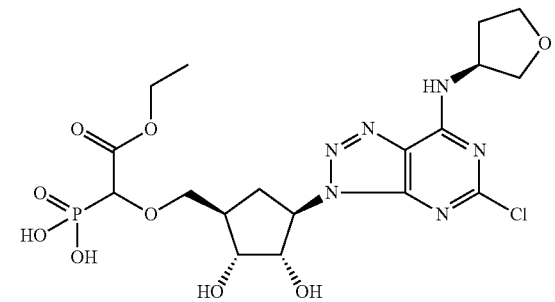 [SMILES: CCOC(=O)C(OC[C@H]1C[C@@H](n2nnc3c(N[C@H]4CCOC4)nc(Cl)nc32)[C@H](O)[C@@H]1O)P(=O)(O)O]

The title compound was synthesized by the method described in Example 77. In Step 5, (R)-(tetrahydrofuran-3-yl) amine was utilized. The final compound was purified by RP HPLC Method A and isolated as mixture of diastereomers.

Example 91: LCMS Method 2: $t_R$=1.14 min, m/z=537.2 & 539.2 (M+H$^+$). $^1$H NMR (CD$_3$OD): δ (ppm) 5.14 (m, 1H), 4.96-4.79 (m, 6H), 4.61-4.16 (m, 6H), 2.53-1.98 (m, 4H), 1.41-1.27 (m, 4H).

Example 92: (1-(((1R,2R,3S,4R)-4-(5-chloro-7-(cyclopentylamino)-3H-[1,2,3]triazolo[4,5-d]pyrimidin-3-yl)-2,3-dihydroxycyclopentyl)methoxy)-2-ethoxy-2-oxoethyl)phosphonic Acid

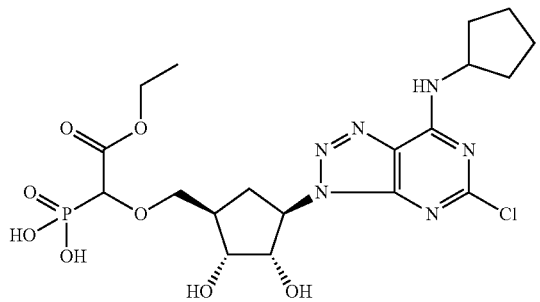 [SMILES: CCOC(=O)C(OC[C@H]1C[C@@H](n2nnc3c(NC4CCCC4)nc(Cl)nc32)[C@H](O)[C@@H]1O)P(=O)(O)O]

The title compound was synthesized by the method described in Example 77. In Step 5, cyclopentylamine was utilized. The final compound was purified by RP HPLC Method A and isolated as mixture of diastereomers.

Example 92: LCMS Method 2: $t_R$=1.17 min, m/z=535.2 & 537.2 (M+H$^+$). $^1$H NMR (CD$_3$OD): 5.12 (m, 1H), 4.57 (m, 1H), 4.38-4.16 (m, 5H), 3.81-3.63 (m, 2H), 2.50 (m, 1H), 2.18-2.00 (m, 2H), 1.80-1.65 (m, 7H), 1.32-1.27 (m, 4H).

Example 93: 2-(((2R,3S,4R,5R)-5-(6-amino-2-chloro-9H-purin-9-yl)-3,4-dihydroxytetrahydrofuran-2-yl)methoxy)-2-(pyridin-2-ylmethyl)malonic acid

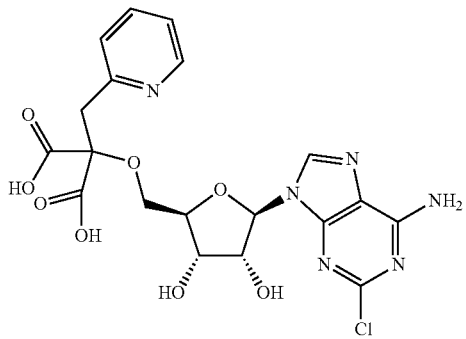 [SMILES: Nc1nc(Cl)nc2c1ncn2[C@@H]1O[C@H](COC(Cc2ccccn2)(C(=O)O)C(=O)O)[C@@H](O)[C@H]1O]

The title compound was synthesized by the method described in Example 2. In Step 2, 2-pyridylmethylbromide was used. In Step 3, ammonia was utilized. The final compound was purified by reverse phase HPLC.

Example 92: LCMS Method 2: $t_R$=1.17 min, m/z=495.2 & 497.2 (M+H$^+$). $^1$H NMR (D$_2$O): δ 8.35 (d, J=5.4 Hz, 1H), 8.17-8.34 (m, 1H), 8.06-8.12 (m, 1H), 7.60-7.2 (m, 3H), 5.93 (d, J=5.6 Hz, 1H), 4.38-4.40 (m, 1H), 3.91-3.93 (m, 1H), 3.79-3.81 (m, 1H), 3.68 (br. s., 2H), 3.28-3.31 (m, 2H).

Example 94: 2-(((2R,3S,4R,5R)-5-(6-amino-2-chloro-9H-purin-9-yl)-3,4-dihydroxytetrahydrofuran-2-yl)methoxy)-2-(thiazol-2-ylmethyl)malonic acid

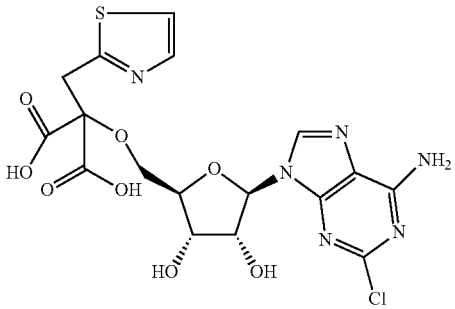 [SMILES: Nc1nc(Cl)nc2c1ncn2[C@@H]1O[C@H](COC(Cc2nccs2)(C(=O)O)C(=O)O)[C@@H](O)[C@H]1O]

The title compound was synthesized by the method described in Example 1. In Step 2, 2-bromomethylthiazole was used. In Step 3, ammonia was utilized. The final compound was purified by RP HPLC Method A.

LCMS Method 2: $t_R$=1.17 min, m/z=501.2 & 503.2 (M+H$^+$). $^1$H NMR (MeOD): δ 8.98 (s, 1H), 7.91 (d, 1H, J=4.0 Hz), 7.71 (d, 1H, J=4.0 Hz), 6.09 (d, 1H, J=4.8 Hz), 4.73-4.76 (m, 1H), 4.44 (t, 1H, J=4.0 Hz), 4.35 (d, 1H, J=4.0 Hz), 4.13 (d, 1H, J=10.0 Hz), 4.01-4.04 (m, 3H).

Example 95: 2-(((2R,3S,4R,5R)-5-(2-chloro-6-(((R)-tetrahydrofuran-3-yl)amino)-9H-purin-9-yl)-3,4-dihydroxytetrahydrofuran-2-yl)methoxy)malonic acid

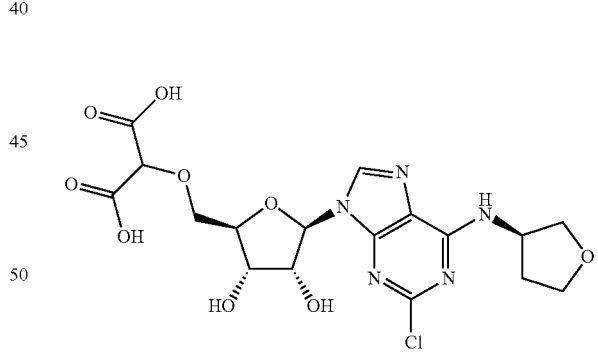

The title compound was synthesized by the method described in Example 1. Step 3 was skipped and in Step 4, (R)-aminotetrahydrofuran was utilized.

$^1$H NMR (MeOH-d$_4$): δ 8.71 (s, 1H), 6.06-6.09 (d, J=5.6 Hz, 1H), 4.74-4.76 (m, 1H), 4.65-4.70 (s, 2H), 4.40-4.50 (m, 1H), 4.20-4.30 (m, 1H), 4.01-4.05 (m, 2H), 3.75-3.95 (m, 4H), 2.35-2.44 (m, 1H), 2.01-2.08 (m, 1H). LCMS Method 2: $t_R$=0.855 min, m/z=474.1 [M+H]$^+$.

Example 96: 2-(((2R,3S,4R,5R)-5-(6-amino-2-chloro-9H-purin-9-yl)-3,4-dihydroxytetrahydrofuran-2-yl)methoxy)-2-(3,5-difluorobenzyl)malonic acid

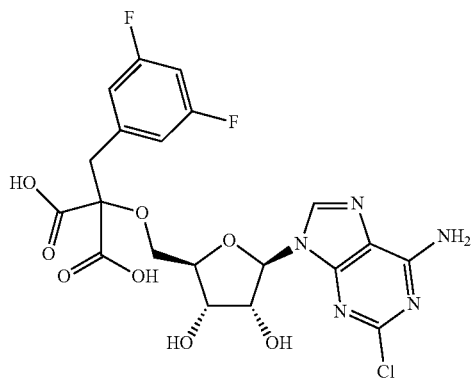 [SMILES: Nc1nc(Cl)nc2c1ncn2[C@@H]1O[C@H](COC(Cc2cc(F)cc(F)c2)(C(=O)O)C(=O)O)[C@@H](O)[C@H]1O]

The title compound was synthesized by the method described in Example 1. In Step 2, 3,5-difluorobromomethyl benzene was used. In Step 3, ammonia was utilized. The final compound was purified by RP HPLC Method A.

$^1$H NMR (CD$_3$CN): δ 8.68 (s, 1H), 6.69-6.83 (m, 3H), 5.97-5.98 (d, J=4.0 Hz, 1H), 4.54 (s, 1H), 4.27-4.33 (m, 2H), 3.83-3.96 (m, 2H), 3.42 (s, 2H). $^{19}$F NMR (CD3CN): δ −112.133. LCMS Method 2: $t_R$=1.024 min, MS (ESI) m/z=530.0 [M+H]$^+$.

Example 97: 2-(((2R,3S,4R,5R)-5-(2-chloro-6-(cyclopentylamino)-9H-purin-9-yl)-3,4-dihydroxytetrahydrofuran-2-yl)methoxy)-2-(4-fluorobenzyl)malonic acid

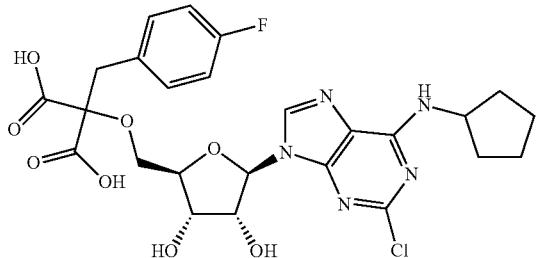 [SMILES: O=C(O)C(Cc1ccc(F)cc1)(OC[C@H]1O[C@@H](n2cnc3c(NC4CCCC4)nc(Cl)nc32)[C@H](O)[C@@H]1O)C(=O)O]

The title compound was synthesized according to Example 2. In Step 3, 4-fluorobenzyl bromide was used instead of MeI. In Step 4, cyclopentylamine was used instead of methyl amine. The final compound was purified by RP-HPLC Method B.

$^1$H NMR (Methanol-d$_4$): δ 8.55 (s, 1H), 7.24-7.28 (dd, J=8.8, 5.6 Hz, 2H), 6.99-7.04 (t, J=8.8 Hz, 2H), 6.09-6.11 (d, J=6.0 Hz, 1H), 4.76-4.78 (m, 1H), 4.66 (s, 1H), 4.43-4.46 (dd, J=4.8, 2.8 Hz, 1H), 4.26-4.27 (m, 1H), 3.90-3.91 (m, 1H), 3.81-3.84 (m, 1H), 3.33-3.34 (m, 2H), 1.85-1.95 (m, 2H), 1.64-1.78 (m, 6H). $^{19}$F NMR (MeOD 400 MHz 19F): −118.593. LCMS Method 2: $t_R$=1.055 min, m/z=580.1 [M+H]$^+$.

Example 98: 2-(((2R,3S,4R,5R)-5-(6-amino-2-chloro-9H-purin-9-yl)-3,4-dihydroxytetrahydrofuran-2-yl)methoxy)-2-(cyclopropylmethyl)malonic acid

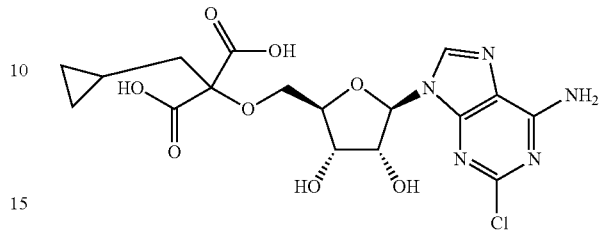

The title compound was synthesized according to Example 2. In Step 3, cyclopropylmethyl bromide was used instead of MeI. In Step 4, ammonia in methanol was used instead of methyl amine. The final compound was purified by RP-HPLC Method B.

$^1$H NMR (Methanol-d$_4$): δ 8.56 (s, 1H), 7.32 (brs, 2H), 7.01-7.07 (m, 2H), 6.09-6.11 (d, J=6.4 Hz, 1H), 4.76-4.79 (m, 1H), 4.66 (s, 1H), 4.44-4.47 (dd, J=5.2, 3.2 Hz, 1H), 4.27 (q, J=2.8 Hz, 1H), 3.91 (m, 1H), 3.83-3.84 (m, 1H), 3.32-3.34 (m, 2H), 2.39-2.47 (m, 1H), 1.68-1.70 (m, 4H), 1.53-1.55 (m, 2H), 1.28-1.33 (m, 2H). $^{19}$F NMR (Methanol): −117.483. LCMS Method 2: $t_R$=1.163 min, m/z=594.1 [M+H]$^+$.

Example 99: (1-(((((2S,3S,4R,5R)-5-(6-amino-2-chloro-9H-purin-9-yl)-3,4-dihydroxytetrahydrofuran-2-yl)methyl)thio)-2-ethoxy-2-oxoethyl)phosphonic Acid

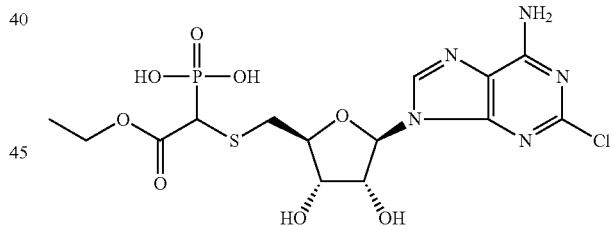

The starting material ((3aS,4S,6R,6aR)-6-(2,6-dichloro-9H-purin-9-yl)-2,2-dimethyltetrahydrofuro[3,4-d][1,3]dioxol-4-yl)methanthiol was synthesized from ((3aS,4S,6R,6aR)-6-(2,6-dichloro-9H-purin-9-yl)-2,2-dimethyltetrahydrofuro[3,4-d][1,3]dioxol-4-yl)methanol by the method described in Pignot et al., 2000, Eur. J. Org. Chem., 3:549-555. The title compound was synthesized from this thiol intermediate by the method described in Example 1. The final compound was purified by reverse phase HPLC Method A and isolated as a mixture of diastereomers.

Example 99 (mixture of diastereomers). LCMS Method 3: $t_R$=1.12 min, m/z 483, 485 (M+H$^+$).

Example 100: ((R)-1-(((2R,3S,4R,5R)-5-(2-chloro-6-(methylamino)-9H-purin-9-yl)-3,4-dihydroxytetrahydrofuran-2-yl)methoxy)-2,2,2-trifluoroethyl)phosphonic Acid and Example 100a: ((S)-1-(((2R,3S,4R,5R)-5-(2-chloro-6-(methylamino)-9H-purin-9-yl)-3,4-dihydroxytetrahydrofuran-2-yl)methoxy)-2,2,2-trifluoroethyl)phosphonic Acid

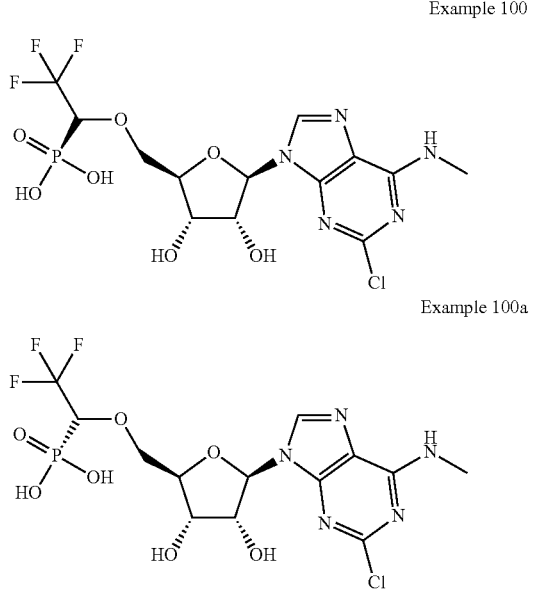

The title compounds were synthesized by the method described in Example 1, starting from (2R,3R,4S,5R)-2-(2,6-dichloro-9H-purin-9-yl)-5-(hydroxymethyl)tetrahydrofuran-3,4-diol and diethyl (1-diazo-2,2,2-trifluoroethyl) phosphonate. In Step 3, methylamine was utilized instead of ammonia. The final compounds were purified by RP HPLC Method B to separate the two diastereomers. The $1^{st}$ eluting isomer was Example 100 and $2^{nd}$ eluting isomer was Example 100a.

Example 100: LCMS Method 3: $t_R$=1.22 min, m/z 478, 480 (M+H+).

Example 100a: LCMS Method 3: $t_R$=1.28 min, m/z 478, 480 (M+H+).

Biological Assays

Inhibition of 5'-Nucleotidase Activity of CD73 (Assay 1)

Compounds of the present invention were tested for the ability to inhibit CD73 enzyme activity. Tested compounds were dissolved in DMSO (50× final concentration), and 3.2 µL of the solutions added to 96-well polystyrene plates. To these wells were added, 100 µL of human CD73 (R&D Systems Cat. No. 5795-EN-010) and 57 µL of cytidine-5'-monophosphate (CMP) solutions in assay buffer (25 mM Tris-HCl, pH 7.4, 0.005% Brij-35) were added to achieve final concentrations in the assay of 4 ng/ml CD73 and 50 µM of CMP. The assay mixture was incubated for 20 min at RT. The reaction was stopped by addition of 40 µL of malachite green reagent which was prepared by mixing together 10 ml 2M $H_2SO_4$, 2.5 ml of 15% ammonium molybdate and 0.2 ml of 11% Tween-20. The mixture was agitated vigorously for 10 min at RT, and absorbance at 620 nm was determined on a microplate spectrophotometer. Percent inhibition values were calculated as the difference between optical densities of uninhibited controls (incubation with 3.2 µL of DMSO) and the assay wells normalized by the assay window (the difference between the uninhibited controls and fully inhibited control incubations containing 5 µM adenosine 5'-(α,β-methylene)diphosphate (APCP), Sigma-Aldrich Cat. No. M3763). The $IC_{50}$ values were derived using a non-linear 4 parameter logistic model (XLFit software, IDBS) and correspond to the inflection points on dose-response curves.

Inhibition of Ecto-5'-Nucleotidase Activity in U138 Neuroglioma Cells (Assay 2)

The ability of compounds of the invention to inhibit CD73 enzyme activity in a cell-based assay was demonstrated using U138 neuroglioma cells, which express CD73 on their surface. U138 cells were obtained from the American Type Culture Collection (ATCC) (Manassas, Va.), and cultured in complete growth media (DMEM, 10% FBS, 1 mM L-glutamine, 100 U penicillin-streptomycin) at 37° C., 5% $CO_2$. The day before the experiment, cells were seeded at 2,500 cells/well in 100 µL of complete media into 96-well plates. Cells were washed twice with 200 µL of assay buffer (20 mM HEPES, pH 7.4, 137 mM NaCl, 5.4 mM KCl, 1.3 mM $CaCl_2$, 4.2 mM $NaHCO_3$, 1 mg/mL glucose) to remove residual inorganic phosphate. After washing, assays contained serial dilutions of test compounds and 50 µM of cytidine-5'-monophosphate (CMP) in a total volume of 200 µL of assay buffer, with a final DMSO concentration ≤0.1%. After 2 hr at 37° C., 5% CO2, 100 µL of supernatant was removed from the cells and the concentration of inorganic phosphate was determined using malachite green reagent. $IC_{50}$ values for test compounds were determined from non-linear regression fits of the data using XLfit (IDBS). Adenosine-(αβ-methylene)-diphosphate (APCP) was used as a standard in each experiment, and the $IC_{50}$ value for APCP typically ranged between 12-25 nM.

The results of assays 1 and 2 are shown in Table 1 (+ means >1000 nM; ++ means 100 nM to 1000 nM; and +++ means <100 nM).

TABLE 1

| Example No. | Assay 1 | Assay 2 |
|---|---|---|
| 1, isomer 1 | +++ | +++ |
| 1, isomer 2 | ++ | ++ |
| 2 | ++ | ++ |
| 3 | +++ | ++ |
| 4 | +++ | +++ |
| 5 | +++ | +++ |
| 6 | +++ | +++ |
| 7 | +++ | +++ |
| 8 | + | |
| 9 | +++ | ++ |
| 9a | ++ | ++ |
| 10 | ++ | ++ |
| 10a | + | |
| 11 | +++ | ++ |
| 11a | ++ | + |
| 12 | +++ | ++ |
| 12a | + | |
| 13 | +++ | ++ |
| 13a | + | |
| 14 | +++ | +++ |
| 14a | ++ | ++ |
| 15 | +++ | +++ |
| 15a | ++ | ++ |
| 16 | +++ | +++ |
| 16a | ++ | + |
| 17 | +++ | +++ |
| 17a | ++ | +++ |
| 18 | +++ | ++ |

TABLE 1-continued

| Example No. | Assay 1 | Assay 2 |
|---|---|---|
| 18a | ++ | +++ |
| 19 | +++ | +++ |
| 19a | ++ | ++ |
| 20 | +++ | ++ |
| 21 | +++ | ++ |
| 21a | ++ | + |
| 22 | +++ | +++ |
| 22a | ++ | ++ |
| 23 | +++ | +++ |
| 23a | ++ | ++ |
| 24 | +++ | +++ |
| 24a | ++ | ++ |
| 25 | +++ | +++ |
| 25a | +++ | +++ |
| 26 | +++ | +++ |
| 26a | ++ | ++ |
| 27 | +++ | ++ |
| 27a | ++ | ++ |
| 28 | +++ | +++ |
| 28a | ++ | + |
| 29 | +++ | +++ |
| 29a | ++ | ++ |
| 30 | ++ | + |
| 30a | + | |
| 31 | + | |
| 32 | + | |
| 33 | ++ | ++ |
| 33a | ++ | + |
| 34 | +++ | ++ |
| 34a | +++ | +++ |
| 35 | + | |
| 36 | +++ | ++ |
| 36a | ++ | + |
| 37 | +++ | ++ |
| 37a | + | |
| 38 | ++ | + |
| 39 | +++ | ++ |
| 39a | + | + |
| 40 | +++ | ++ |
| 40a | +++ | |
| 41 | ++ | + |
| 41a | + | |
| 42 | +++ | ++ |
| 42a | + | |
| 43 | ++ | + |
| 44 | + | + |
| 45 | +++ | +++ |
| 45a | ++ | ++ |
| 46 | ++ | ++ |
| 46a | + | |
| 47 | +++ | +++ |
| 48 | +++ | +++ |
| 49 | +++ | ++ |
| 49a | ++ | + |
| 50 | ++ | + |
| 50a | + | |
| 51 | ++ | + |
| 51a | ++ | + |
| 51b | + | |
| 52 | +++ | ++ |
| 52a | ++ | + |
| 53 | +++ | ++ |
| 53a | + | + |
| 54 | +++ | +++ |
| 54a | ++ | + |
| 54b | +++ | ++ |
| 55 | + | |
| 55a | + | |
| 56 | + | |
| 57 | + | |
| 57a | + | |
| 58 | +++ | ++ |
| 59 | +++ | ++ |
| 59a | +++ | ++ |
| 59b | +++ | ++ |
| 60 | + | |
| 60a | + | |
| 61 | +++ | +++ |
| 61a | +++ | +++ |
| 62 | +++ | ++ |
| 63 | +++ | ++ |
| 64 | + | |
| 65 | ++ | ++ |
| 66 | ++ | + |
| 67 | ++ | + |
| 68 | +++ | ++ |
| 69 | ++ | + |
| 69a | ++ | + |
| 70 | ++ | + |
| 70a | + | |
| 71 | + | |
| 72 | ++ | + |
| 72a | + | |
| 73 | +++ | ++ |
| 73a | + | |
| 74 | + | |
| 75 | + | |
| 76 | +++ | +++ |
| 76a | ++ | ++ |
| 77 | +++ | ++ |
| 77a | +++ | ++ |
| 78 | +++ | ++ |
| 78a | ++ | + |
| 79 | ++ | + |
| 79a | ++ | |
| 80 | + | |
| 80a | + | |
| 81 | + | |
| 81a | + | |
| 82 | +++ | ++ |
| 82a | +++ | ++ |
| 83 | ++ | + |
| 84 | +++ | +++ |
| 85 | +++ | +++ |
| 86 | +++ | ++ |
| 87 | +++ | ++ |
| 87a | + | |
| 88 | +++ | +++ |
| 89 | +++ | +++ |
| 90 | +++ | +++ |
| 91 | +++ | +++ |
| 92 | +++ | +++ |
| 93 | +++ | +++ |
| 94 | +++ | +++ |
| 95 | +++ | ++ |
| 96 | +++ | +++ |
| 97 | ++ | ++ |
| 98 | +++ | +++ |
| 99 | ++ | ++ |
| 100 | ++ | +++ |
| 100a | +++ | +++ |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

What is claimed is:
1. A compound of Formula Ia:

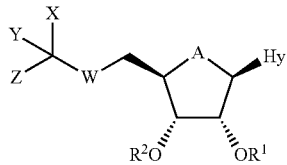

or a pharmaceutically acceptable salt thereof, wherein:
Hy is selected from:

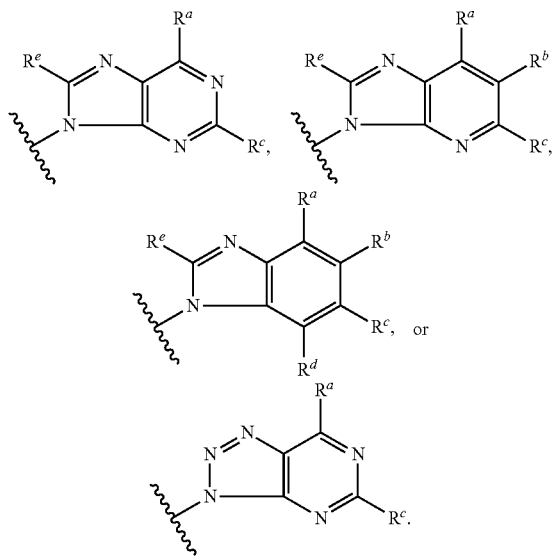

A is O, S, $NR^f$, or $CH_2$;
W is O or S;
X is $C_{1-4}$ haloalkyl, —C(O)OR$^3$, —C(O)NR$^4$R$^5$, —CH$_2$OR$^3$, —S(O)$_2$R$^6$, —P(O)(OR$^7$)(OR$^8$), or a 5-6 membered heteroaryl group optionally substituted with 1, 2, or 3 substituents independently selected from halo, CN, OH, $C_{1-4}$ alkyl, $C_{1-4}$ alkoxy, $NH_2$, NH($C_{1-4}$ alkyl), N($C_{1-4}$ alkyl)$_2$, C(O)($C_{1-4}$ alkyl), C(O)NH$_2$, C(O)NH($C_{1-4}$ alkyl), C(O) N($C_{1-4}$ alkyl)$_2$, C(O)OH, or C(O)O ($C_{1-4}$ alkyl);
Y is H, Cy$^1$, $C_{1-4}$ alkyl, or —C(O)OR$^9$, wherein said $C_{1-4}$ alkyl is optionally substituted by 1, 2, or 3 substituents independently selected from Cy$^1$, halo, $C_{1-4}$ haloalkyl, CN, NO$_2$, OR$^{a1}$, SR$^{a1}$, C(O)R$^{b1}$, C(O)NR$^{c1}$R$^{d1}$, C(O) OR$^{a1}$, OC(O)R$^{b1}$, OC(O)NR$^{c1}$R$^{d1}$, NR$^{c1}$R$^{d1}$, NR$^{c1}$C (O)R$^{b1}$, NR$^{c1}$C(O)OR$^{a1}$, NR$^{c1}$C(O)NR$^{c1}$R$^{d1}$, NR$^{c1}$S (O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, or S(O)$_2$NR$^{c1}$R$^{d1}$;
Z is —C(O)OR$^{10}$ or —P(O)(OR$^{11}$)(OR$^{12}$);
R$^1$ and R$^2$ are both H;
R$^3$ is H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl are each optionally substituted with 1, 2, 3, or 4 substituents independently selected from halo, $C_{1-4}$ alkyl, $C_{1-4}$ haloalkyl, CN, NO$_2$, OR$^{a2}$, SR$^{a2}$, C(O)R$^{b2}$, C(O) NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O) NR$^{c2}$R$^{d2}$, NR$^{c2}$S(O)R$^{b2}$, NR$^{c2}$S(O)$_2$R$^{b2}$ NR$^{c2}$S(O)$_2$ NR$^{c2}$R$^{d2}$, S(O)R$^{b2}$, S(O)NR$^{c2}$R$^{d2}$, S(O)$_2$R$^{b2}$, or S(O)$_2$ NR$^{c2}$R$^{d2}$;
R$^4$ and R$^5$ are each independently selected from H, —NR$^4$R$^B$, —OR$^C$, $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl are each optionally substituted with 1, 2, 3, or 4 substituents independently selected from halo, $C_{1-4}$ alkyl, $C_{1-4}$ haloalkyl, CN, NO$_2$, OR$^{a3}$, SR$^{a3}$, C(O)R$^{b3}$, C(O) NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)OR, NR$^{c3}$C(O) NR$^{c3}$R$^{d3}$, NR$^{c3}$S(O)R$^{b3}$, NR$^{c3}$S(O)$_2$R$^{b3}$, NR$^{c3}$S(O)$_2$ NR$^{c3}$R$^{d3}$, S(O)R$^{b3}$, S(O)NR$^{c3}$R$^{d3}$, S(O)$_2$R$^{b3}$, or S(O)$_2$ NR$^{c3}$R$^{d3}$;
R$^6$ is $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl;
R$^7$ and R$^8$ are each independently selected from H or $C_{1-6}$ alkyl optionally substituted by 1, 2, or 3 substituents independently selected from halo, CN, OR$^4$, SR$^4$, C(O) R$^{b4}$, C(O)NR$^{c4}$R$^{d4}$, C(O)OR$^{a4}$, OC(O)R$^{b4}$, OC(O) NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$ R$^{b4}$, or S(O)$_2$NR$^{c4}$R$^{d4}$;
R$^9$ is H or $C_{1-4}$ alkyl;
R$^{10}$ is H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl are each optionally substituted with 1, 2, 3, or 4 substituents independently selected from halo, $C_{1-4}$ alkyl, $C_{1-4}$ haloalkyl, CN, NO$_2$, OR$^{a5}$, SR$^{a5}$, C(O)R$^{b5}$, C(O) NR$^{c5}$R$^{d5}$, C(O)OR$^{a5}$, OC(O)R$^{b5}$, OC(O)NR$^{c5}$R$^{d5}$, NR$^{c5}$R$^{d5}$ NR$^{c5}$C(O)R$^{b5}$, NR$^{c5}$C(O)OR$^{a5}$, NR$^{c5}$C(O) NR$^{c5}$R$^{d5}$, NR$^{c5}$S(O)R$^{b5}$, NR$^{c5}$S(O)$_2$R$^{b5}$, NR$^{c5}$S(O)$_2$ NR$^{c5}$R$^{d5}$, S(O)R$^{b5}$, S(O)NR$^{c5}$R$^{d5}$, S(O)$_2$R$^{b5}$, or S(O)$_2$ NR$^{c5}$R$^{d5}$;
R$^{11}$ and R$^{12}$ are each independently selected from H or $C_{1-6}$ alkyl optionally substituted by 1, 2, or 3 substituents independently selected from halo, CN, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)OR$^{a6}$, NR$^{c6}$C(O)NR$^{c6}$R$^{d6}$, NR$^{c6}$S(O)R$^{b6}$, NR$^{c6}$S(O)$_2$R$^{b6}$, NR$^{c6}$S(O)$_2$NR$^{c6}$R$^{d6}$, S(O)R$^{b6}$, S(O)NR$^{c6}$R$^{d6}$, S(O)$_2$R$^{b6}$, or S(O)$_2$NR$^{c6}$R$^{d6}$;

R$^A$ is H or C$_{1-6}$ alkyl;

R$^B$ is C$_{1-6}$ alkyl or —C(O)(C$_{1-6}$ alkyl);

R$^C$ is H or C$_{1-6}$ alkyl;

R$^a$ is Cy$^2$, H, halo, C$_{1-4}$ alkyl, NR$^{c7}$R$^{d7}$, or NR$^{c7}$C(O)R$^{b7}$, wherein said C$_{1-4}$ alkyl is optionally substituted by Cy$^2$;

R$^b$ is H or halo;

R$^c$ is Cy$^2$, halo, C$_{1-4}$ alkyl, C$_{1-4}$ haloalkyl, CN, OR$^{a7}$, SR$^{a7}$, C(O)R$^{b7}$, C(O)NR$^{c7}$R$^{d7}$, C(O)OR$^{a7}$, OC(O)R$^{b7}$, OC(O)NR$^{c7}$R$^{d7}$, NR$^{c7}$R$^{d7}$, NR$^{c7}$C(O)R$^{b7}$, NR$^{c7}$C(O)OR$^{a7}$, NR$^{c7}$C(O)NR$^{c7}$R$^{d7}$, NR$^{c7}$S(O)R$^{b7}$, NR$^{c7}$S(O)$_2$R$^{b7}$, NR$^{c7}$S(O)$_2$NR$^{c7}$R$^{d7}$, S(O)R$^{b7}$, S(O)NR$^{c7}$R$^{d7}$, S(O)$_2$R$^{b7}$, or S(O)$_2$NR$^{c7}$R$^{d7}$, wherein said C$_{1-4}$ alkyl is optionally substituted by 1, 2, or 3 substituents independently selected from Cy$^2$, H, halo, C$_{1-4}$ haloalkyl, CN, OR$^{a7}$, SR$^{a7}$, C(O)R$^{b7}$, C(O)NR$^{c7}$R$^{d7}$, C(O)OR$^{a7}$, OC(O)R$^{b7}$, OC(O)NR$^{c7}$R$^{d7}$, NR$^{c7}$R$^{d7}$, NR$^{c7}$C(O)R$^{b7}$, NR$^{c7}$C(O)OR$^{a7}$, NR$^{c7}$C(O)NR$^{c7}$R$^{d7}$ NR$^{c7}$S(O)R$^{b7}$, NR$^{c7}$S(O)$_2$R$^{b7}$, NR$^{c7}$S(O)$_2$NR$^{c7}$R$^{d7}$, S(O)R$^{b7}$, S(O)NR$^{c7}$R$^{d7}$, S(O)$_2$R$^{b7}$, or S(O)$_2$NR$^{c7}$R$^{d7}$;

R$^d$ is halo or CN;

R$^e$ selected from H, halo, or C$_{1-4}$ alkyl;

R$^f$ is H, C$_{1-4}$ alkyl, or —C(O)(C$_{1-4}$ alkyl);

each Cy$^1$ and Cy$^2$ are independently selected from C$_{6-10}$ aryl, C$_{3-10}$ cycloalkyl, 5-10 membered heteroaryl, or 4-10 membered heterocycloalkyl, each of which is substituted with 1, 2, 3, or 4 substituents independently selected from halo, C$_{1-4}$ alkyl, C$_{1-4}$ haloalkyl, C$_{1-4}$ cyanoalkyl, CN, NO$_2$, OR$^{a8}$, SR$^{a8}$, C(O)R$^{b8}$, C(O)NR$^{c8}$R$^{d8}$, C(O)OR$^{a8}$, OC(O)R$^{b8}$, OC(O)NR$^{c8}$R$^{d8}$, NR$^{c8}$R$^{d8}$, NR$^{c8}$C(O)R$^{b8}$, NR$^{c8}$C(O)OR$^{a8}$, NR$^{c8}$C(O)NR$^{c8}$R$^{d8}$, NR$^{c8}$S(O)R$^{b8}$, NR$^{c8}$S(O)$_2$R$^{b8}$, NR$^{c8}$S(O)$_2$NR$^{c8}$R$^{d8}$, S(O)R$^{b8}$, S(O)NR$^{c8}$R$^{d8}$, S(O)$_2$R$^{b8}$, or S(O)$_2$NR$^{c8}$R$^{d8}$;

each R$^{a1}$, R$^{b1}$, R$^{c1}$, R$^{d1}$, R$^{a2}$, R$^{b2}$, R$^{c2}$, R$^{d2}$, R$^{a3}$, R$^{b3}$, R$^{c3}$, R$^{d3}$, R$^{a4}$, R$^{b4}$, R$^{c4}$, R$^{d4}$, R$^{a5}$, R$^{b5}$, R$^{c5}$, R$^{d5}$, R$^{a6}$, R$^{b6}$, R$^{c6}$, R$^{d6}$, R$^{a7}$, R$^{b7}$, R$^{c7}$, R$^{d7}$, R$^{a8}$, R$^{b8}$, R$^{c8}$, and R$^{d8}$ is independently selected from H, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, or (4-10 membered heterocycloalkyl)-C$_{1-4}$ alkyl-, wherein said C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl- is optionally substituted with 1, 2, 3, 4, or 5 substituents independently selected from C$_{1-4}$ alkyl, C$_{1-4}$ haloalkyl, C$_{1-4}$ cyanoalkyl, halo, CN, OR$^{a9}$, SR$^{a9}$, C(O)R$^{b9}$, C(O)NR$^{c9}$R$^{d9}$, C(O)OR$^{a9}$, OC(O)R$^{b9}$, OC(O)NR$^{c9}$R$^{d9}$, NR$^{c9}$R$^{d9}$, NR$^{c9}$C(O)R$^{b9}$, NR$^{c9}$C(O)NR$^{c9}$R$^{d9}$, NR$^{c9}$C(O)OR$^{a9}$, S(O)R$^{b9}$, S(O)NR$^{c9}$R$^{d9}$, S(O)$_2$R$^{b9}$, NR$^{c9}$S(O)$_2$R$^{b9}$, NR$^{c9}$S(O)$_2$NR$^{c9}$R$^{d9}$, or S(O)$_2$NR$^{c9}$R$^{d9}$;

or any R$^{c1}$ and R$^{d1}$ together with the N atom to which they are attached form a 4-, 5-, 6-, or 7-membered heterocycloalkyl group optionally substituted with 1, 2, or 3 substituents independently selected from C$_{1-6}$ alkyl, C$_{3-7}$ cycloalkyl, 4-7 membered heterocycloalkyl, C$_{6-10}$ aryl, 5-6 membered heteroaryl, C$_{1-6}$ haloalkyl, halo, CN, OR$^{a9}$, SR$^{a9}$, C(O)R$^{b9}$, C(O)NR$^{c9}$R$^{d9}$, C(O)OR$^{a9}$, OC(O)R$^{b9}$, OC(O)NR$^{c9}$R$^{d9}$, NR$^{c9}$R$^{d9}$, NR$^{c9}$C(O)R$^{b9}$, NR$^{c9}$C(O)NR$^{c9}$R$^{d9}$, NR$^{c9}$C(O)OR$^{a9}$, S(O)R$^{b9}$, S(O)NR$^{c9}$R$^{d9}$, S(O)$_2$R$^{b9}$, NR$^{c9}$S(O)$_2$R$^{b9}$, NR$^{c9}$S(O)$_2$NR$^{c9}$R$^{d9}$, or S(O)$_2$NR$^{c9}$R$^{d9}$, wherein said C$_{1-6}$ alkyl, C$_{3-7}$ cycloalkyl, 4-7 membered heterocycloalkyl, C$_{6-10}$ aryl, and 5-6 membered heteroaryl are optionally substituted by 1, 2, or 3 substituents independently selected from halo, C$_{1-4}$ alkyl, C$_{1-4}$ haloalkyl, C$_{1-4}$ cyanoalkyl, CN, OR$^{a9}$, SR$^{a9}$, C(O)R$^{b9}$, C(O)NR$^{c9}$R$^{d9}$, C(O)OR$^{a9}$, OC(O)R$^{b9}$, OC(O)NR$^{c9}$R$^{d9}$, NR$^{c9}$R$^{d9}$, NR$^{c9}$C(O)R$^{b9}$, NR$^{c9}$C(O)NR$^{c9}$R$^{d9}$, NR$^{c9}$C(O)OR$^{a9}$, S(O)R$^{b9}$, S(O)NR$^{c9}$R$^{d9}$, S(O)$_2$R$^{b9}$, NR$^{c9}$S(O)$_2$R$^{b9}$, NR$^{c9}$S(O)$_2$NR$^{c9}$R$^{d9}$, or S(O)$_2$NR$^{c9}$R$^{d9}$;

or any R$^{c2}$ and R$^{d2}$ together with the N atom to which they are attached form a 4-, 5-, 6-, or 7-membered heterocycloalkyl group optionally substituted with 1, 2, or 3 substituents independently selected from C$_{1-6}$ alkyl, C$_{3-7}$ cycloalkyl, 4-7 membered heterocycloalkyl, C$_{6-10}$ aryl, 5-6 membered heteroaryl, C$_{1-6}$ haloalkyl, halo, CN, OR$^{a9}$, SR$^{a9}$, C(O)R$^{b9}$, C(O)NR$^{c9}$R$^{d9}$, C(O)OR$^{a9}$, OC(O)R$^{b9}$, OC(O)NR$^{c9}$R$^{d9}$, NR$^{c9}$R$^{d9}$, NR$^{c9}$C(O)R$^{b9}$, NR$^{c9}$C(O)NR$^{c9}$R$^{d9}$, NR$^{c9}$C(O)OR$^{a9}$, S(O)R$^{b9}$, S(O)NR$^{c9}$R$^{d9}$, S(O)$_2$R$^{b9}$, NR$^{c9}$S(O)$_2$R$^{b9}$, NR$^{c9}$S(O)$_2$NR$^{c9}$R$^{d9}$, or S(O)$_2$NR$^{c9}$R$^{d9}$, wherein said C$_{1-6}$ alkyl, C$_{3-7}$ cycloalkyl, 4-7 membered heterocycloalkyl, C$_{6-10}$ aryl, and 5-6 membered heteroaryl are optionally substituted by 1, 2, or 3 substituents independently selected from halo, C$_{1-4}$ alkyl, C$_{1-4}$ haloalkyl, C$_{1-4}$ cyanoalkyl, CN, OR$^{a9}$, SR$^{a9}$, C(O)R$^{b9}$, C(O)NR$^{c9}$R$^{d9}$, C(O)OR$^{a9}$, OC(O)R$^{b9}$, OC(O)NR$^{c9}$R$^{d9}$, NR$^{c9}$R$^{d9}$, NR$^{c9}$C(O)R$^{b9}$, NR$^{c9}$C(O)NR$^{c9}$R$^{d9}$, NR$^{c9}$C(O)OR$^{a9}$, S(O)R$^{b9}$, S(O)NR$^{c9}$R$^{d9}$, S(O)$_2$R$^{b9}$, NR$^{c9}$S(O)$_2$R$^{b9}$, NR$^{c9}$S(O)$_2$NR$^{c9}$R$^{d9}$, or S(O)$_2$NR$^{c9}$R$^{d9}$;

or any R$^{c3}$ and R$^{d3}$ together with the N atom to which they are attached form a 4-, 5-, 6-, or 7-membered heterocycloalkyl group optionally substituted with 1, 2, or 3 substituents independently selected from C$_{1-6}$ alkyl, C$_{3-7}$ cycloalkyl, 4-7 membered heterocycloalkyl, C$_{6-10}$ aryl, 5-6 membered heteroaryl, C$_{1-6}$ haloalkyl, halo, CN, OR$^{a9}$, SR$^{a9}$, C(O)R$^{b9}$, C(O)NR$^{c9}$R$^{d9}$, C(O)OR$^{a9}$, OC(O)R$^{b9}$, OC(O)NR$^{c9}$R$^{d9}$, NR$^{c9}$R$^{d9}$, NR$^{c9}$C(O)R$^{b9}$, NR$^{c9}$C(O)NR$^{c9}$R$^{d9}$, NR$^{c9}$C(O)OR$^{a9}$, S(O)R$^{b9}$, S(O)NR$^{c9}$R$^{d9}$, S(O)$_2$R$^{b9}$, NR$^{c9}$S(O)$_2$R$^{b9}$, NR$^{c9}$S(O)$_2$NR$^{c9}$R$^{d9}$, or S(O)$_2$NR$^{c9}$R$^{d9}$, wherein said C$_{1-6}$ alkyl, C$_{3-7}$ cycloalkyl, 4-7 membered heterocycloalkyl, C$_{6-10}$ aryl, and 5-6 membered heteroaryl are optionally substituted by 1, 2, or 3 substituents independently selected from halo, C$_{1-4}$ alkyl, C$_{1-4}$ haloalkyl, C$_{1-4}$ cyanoalkyl, CN, OR$^{a9}$, SR$^{a9}$, C(O)R$^{b9}$, C(O)NR$^{c9}$R$^{d9}$, C(O)OR$^{a9}$, OC(O)R$^{b9}$, OC(O)NR$^{c9}$R$^{d9}$, NR$^{c9}$R$^{d9}$, NR$^{c9}$C(O)R$^{b9}$, NR$^{c9}$C(O)NR$^{c9}$R$^{d9}$, NR$^{c9}$C(O)OR$^{a9}$, S(O)R$^{b9}$, S(O)NR$^{c9}$R$^{d9}$, S(O)$_2$R$^{b9}$, NR$^{c9}$S(O)$_2$R$^{b9}$, NR$^{c9}$S(O)$_2$NR$^{c9}$R$^{d9}$, or S(O)$_2$NR$^{c9}$R$^{d9}$;

or any R$^{c4}$ and R$^{d4}$ together with the N atom to which they are attached form a 4-, 5-, 6-, or 7-membered heterocycloalkyl group optionally substituted with 1, 2, or 3 substituents independently selected from C$_{1-6}$ alkyl, C$_{3-7}$ cycloalkyl, 4-7 membered heterocycloalkyl, C$_{6-10}$ aryl, 5-6 membered heteroaryl, C$_{1-6}$ haloalkyl, halo, CN, OR$^{a9}$, SR$^{a9}$, C(O)R$^{b9}$, C(O)NR$^{c9}$R$^{d9}$, C(O)OR$^{a9}$, OC(O)R$^{b9}$, OC(O)NR$^{c9}$R$^{d9}$, NR$^{c9}$R$^{d9}$, NR$^{c9}$C(O)R$^{b9}$, NR$^{c9}$C(O)NR$^{c9}$R$^{d9}$, NR$^{c9}$C(O)OR$^{a9}$, S(O)R$^{b9}$, S(O)NR$^{c9}$R$^{d9}$, S(O)$_2$R$^{b9}$, NR$^{c9}$S(O)$_2$R$^{b9}$, NR$^{c9}$S(O)$_2$NR$^{c9}$R$^{d9}$, or S(O)$_2$NR$^{c9}$R$^{d9}$, wherein said C$_{1-6}$ alkyl, C$_{3-7}$ cycloalkyl, 4-7 membered heterocycloalkyl, C$_{6-10}$ aryl, and 5-6 membered heteroaryl are optionally substituted by 1, 2, or 3 substituents independently selected from halo, $C_{1-4}$ alkyl, $C_{1-4}$ haloalkyl, $C_{1-4}$ cyanoalkyl, CN, $OR^{a9}$, $SR^{a9}$, $C(O)R^{b9}$, $C(O)NR^{c9}R^{d9}$, $C(O)OR^{a9}$, $OC(O)R^{b9}$, $OC(O)NR^{c9}R^{d9}$, $NR^{c9}R^{d9}$, $NR^{c9}C(O)R^{b9}$, $NR^{c9}C(O)NR^{c9}R^{d9}$, $NR^{c9}C(O)OR^{a9}$, $S(O)R^{b9}$, $S(O)NR^{c9}R^{d9}$, $S(O)_2R^{b9}$, $NR^{c9}S(O)_2R^{b9}$, $NR^{c9}S(O)_2NR^{c9}R^{d9}$, or $S(O)_2NR^{c9}R^{d9}$;

or any $R^{c5}$ and $R^{d5}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a9}$, $SR^{a9}$, $C(O)R^{b9}$, $C(O)NR^{c9}R^{d9}$, $C(O)OR^{a9}$, $OC(O)R^{b9}$, $OC(O)NR^{c9}R^{d9}$, $NR^{c9}R^{d9}$, $NR^{c9}C(O)R^{b9}$, $NR^{c9}C(O)NR^{c9}R^{d9}$, $NR^{c9}C(O)OR^{a9}$, $S(O)R^{b9}$, $S(O)NR^{c9}R^{d9}$, $S(O)_2R^{b9}$, $NR^{c9}S(O)_2R^{b9}$, $NR^{c9}S(O)_2NR^{c9}R^{d9}$, or $S(O)_2NR^{c9}R^{d9}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, $C_{1-4}$ alkyl, $C_{1-4}$ haloalkyl, $C_{1-4}$ cyanoalkyl, CN, $OR^{a9}$, $SR^{a9}$, $C(O)R^{b9}$, $C(O)NR^{c9}R^{d9}$, $C(O)OR^{a9}$, $OC(O)R^{b9}$, $OC(O)NR^{c9}R^{d9}$, $NR^{c9}R^{d9}$, $NR^{c9}C(O)R^{b9}$, $NR^{c9}C(O)NR^{c9}R^{d9}$, $NR^{c9}C(O)OR^{a9}$, $S(O)R^{b9}$, $S(O)NR^{c9}R^{d9}$, $S(O)_2R^{b9}$, $NR^{c9}S(O)_2R^{b9}$, $NR^{c9}S(O)_2NR^{c9}R^{d9}$, or $S(O)_2NR^{c9}R^{d9}$;

or any $R^{c6}$ and $R^{d6}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a9}$, $SR^{a9}$, $C(O)R^{b9}$, $C(O)NR^{c9}R^{d9}$, $C(O)OR^{a9}$, $OC(O)R^{b9}$, $OC(O)NR^{c9}R^{d9}$, $NR^{c9}R^{d9}$, $NR^{c9}C(O)R^{b9}$, $NR^{c9}C(O)NR^{c9}R^{d9}$, $NR^{c9}C(O)OR^{a9}$, $S(O)R^{b9}$, $S(O)NR^{c9}R^{d9}$, $S(O)_2R^{b9}$, $NR^{c9}S(O)_2R^{b9}$, $NR^{c9}S(O)_2NR^{c9}R^{d9}$, or $S(O)_2NR^{c9}R^{d9}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, $C_{1-4}$ alkyl, $C_{1-4}$ haloalkyl, $C_{1-4}$ cyanoalkyl, CN, $OR^{a9}$, $SR^{a9}$, $C(O)R^{b9}$, $C(O)NR^{c9}R^{d9}$, $C(O)OR^{a9}$, $OC(O)R^{b9}$, $OC(O)NR^{c9}R^{d9}$, $NR^{c9}R^{d9}$, $NR^{c9}C(O)R^{b9}$, $NR^{c9}C(O)NR^{c9}R^{d9}$, $NR^{c9}C(O)OR^{a9}$, $S(O)R^{b9}$, $S(O)NR^{c9}R^{d9}$, $S(O)_2R^{b9}$, $NR^{c9}S(O)_2R^{b9}$, $NR^{c9}S(O)_2NR^{c9}R^{d9}$, or $S(O)_2NR^{c9}R^{d9}$;

or any $R^{c7}$ and $R^{d7}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a9}$, $SR^{a9}$, $C(O)R^{b9}$, $C(O)NR^{c9}R^{d9}$, $C(O)OR^{a9}$, $OC(O)R^{b9}$, $OC(O)NR^{c9}R^{d9}$, $NR^{c9}R^{d9}$, $NR^{c9}C(O)R^{b9}$, $NR^{c9}C(O)NR^{c9}R^{d9}$, $NR^{c9}C(O)OR^{a9}$, $S(O)R^{b9}$, $S(O)NR^{c9}R^{d9}$, $S(O)_2R^{b9}$, $NR^{c9}S(O)_2R^{b9}$, $NR^{c9}S(O)_2NR^{c9}R^{d9}$, or $S(O)_2NR^{c9}R^{d9}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, $C_{1-4}$ alkyl, $C_{1-4}$ haloalkyl, $C_{1-4}$ cyanoalkyl, CN, $OR^{a9}$, $SR^{a9}$, $C(O)R^{b9}$, $C(O)NR^{c9}R^{d9}$, $C(O)OR^{a9}$, $OC(O)R^{b9}$, $OC(O)NR^{c9}R^{d9}$, $NR^{c9}R^{d9}$, $NR^{c9}C(O)R^{b9}$, $NR^{c9}C(O)NR^{c9}R^{d9}$, $NR^{c9}C(O)OR^{a9}$, $S(O)R^{b9}$, $S(O)NR^{c9}R^{d9}$, $S(O)_2R^{b9}$, $NR^{c9}S(O)_2R^{b9}$, $NR^{c9}S(O)_2NR^{c9}R^{d9}$, or $S(O)_2NR^{c9}R^{d9}$;

or any $R^{c8}$ and $R^{d8}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a9}$, $SR^{a9}$, $C(O)R^{b9}$, $C(O)NR^{c9}R^{d9}$, $C(O)OR^{a9}$, $OC(O)R^{b9}$, $OC(O)NR^{c9}R^{d9}$, $NR^{c9}R^{d9}$, $NR^{c9}C(O)R^{b9}$, $NR^{c9}C(O)NR^{c9}R^{d9}$, $NR^{c9}C(O)OR^{a9}$, $S(O)R^{b9}$, $S(O)NR^{c9}R^{d9}$, $S(O)_2R^{b9}$, $NR^{c9}S(O)_2R^{b9}$, $NR^{c9}S(O)_2NR^{c9}R^{d9}$, or $S(O)_2NR^{c9}R^{d9}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, $C_{1-4}$ alkyl, $C_{1-4}$ haloalkyl, $C_{1-4}$ cyanoalkyl, CN, $OR^{a9}$, $SR^{a9}$, $C(O)R^{b9}$, $C(O)NR^{c9}R^{d9}$, $C(O)OR^{a9}$, $OC(O)R^{b9}$, $OC(O)NR^{c9}R^{d9}$, $NR^{c9}R^{d9}$, $NR^{c9}C(O)R^{b9}$, $NR^{c9}C(O)NR^{c9}R^{d9}$, $NR^{c9}C(O)OR^{a9}$, $S(O)R^{b9}$, $S(O)NR^{c9}R^{d9}$, $S(O)_2R^{b9}$, $NR^{c9}S(O)_2R^{b9}$, $NR^{c9}S(O)_2NR^{c9}R^{d9}$, or $S(O)_2NR^{c9}R^{d9}$; and each $R^{a9}$, $R^{b9}$, $R^{c9}$, and $R^{d9}$ is independently selected from H, $C_{1-4}$ alkyl, $C_{1-4}$ haloalkyl, $C_{2-4}$ alkenyl, and $C_{2-4}$ alkynyl, wherein said $C_{1-4}$ alkyl, $C_{2-4}$ alkenyl, and $C_{2-4}$ alkynyl, is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, or $C_{1-4}$ haloalkoxy.

2. The compound of claim 1, or a pharmaceutically acceptable salt thereof, wherein X is —C(O)OR$^3$, —C(O)NR$^4$R$^5$, —CH$_2$OR$^3$, —S(O)$_2$R$^6$, or a 5-membered heteroaryl group optionally substituted with halo, CN, OH, $C_{1-4}$ alkyl, $C_{1-4}$ alkoxy, NH$_2$, NH($C_{1-4}$ alkyl), N($C_{1-4}$ alkyl)$_2$, C(O)($C_{1-4}$ alkyl), C(O)NH$_2$, C(O)NH($C_{1-4}$ alkyl), C(O)N($C_{1-4}$ alkyl)$_2$, C(O)OH, or C(O)O($C_{1-4}$ alkyl).

3. The compound of claim 1, or a pharmaceutically acceptable salt thereof, wherein Y is H or $C_{1-4}$ alkyl, wherein said $C_{1-4}$ alkyl is optionally substituted by Cy$^1$, OR$^{a1}$, or C(O)OR$^{a1}$.

4. The compound of claim 1, or a pharmaceutically acceptable salt thereof, wherein Z is —C(O)OR$^{10}$.

5. The compound of claim 1, or a pharmaceutically acceptable salt thereof, wherein Z is —P(O)(OR$^{11}$)(OR$^{12}$).

6. The compound of claim 1, or a pharmaceutically acceptable salt thereof, wherein R$^3$ is H, $C_{1-6}$ alkyl, or $C_{6-10}$ aryl-$C_{1-4}$ alkyl.

7. The compound of claim 1, or a pharmaceutically acceptable salt thereof, wherein R$^4$ and R$^5$ are each independently selected from H, —NR$^A$R$^B$, —OR$^C$, or $C_{1-6}$ alkyl.

8. The compound of claim 1, or a pharmaceutically acceptable salt thereof, wherein R$^6$ is $C_{1-6}$ alkyl.

9. The compound of claim 1, or a pharmaceutically acceptable salt thereof, wherein R$^{11}$ and R$^{12}$ are each independently selected from H or $C_{1-4}$ alkyl.

10. The compound of claim 1, or a pharmaceutically acceptable salt thereof, wherein R$^e$ is H.

11. The compound of claim 1, or a pharmaceutically acceptable salt thereof, having Formula IIIa, IIIb, IIIc, IIId, or IIIe:

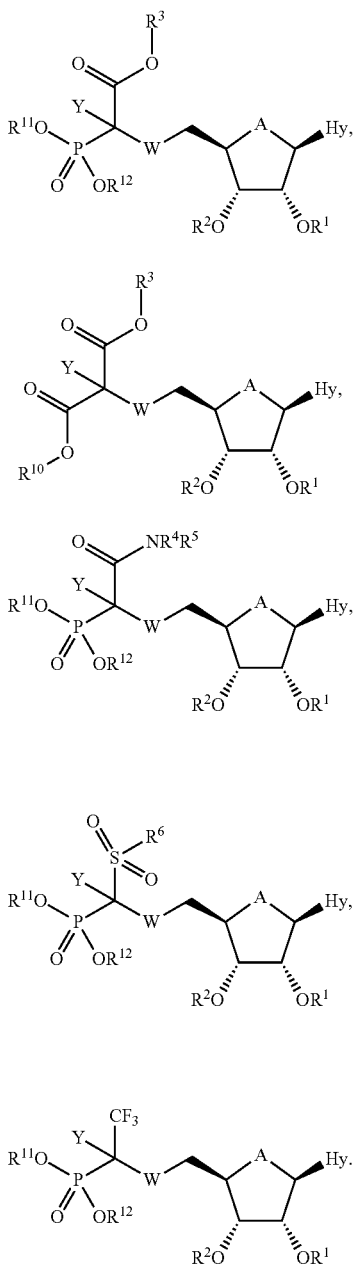

12. The compound of claim 1, or a pharmaceutically acceptable salt thereof, having Formula Va, Vb, Vc, Vd, or Ve:

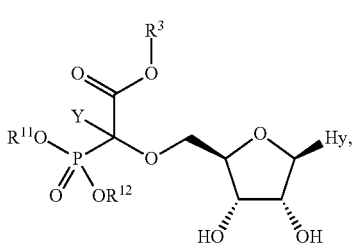

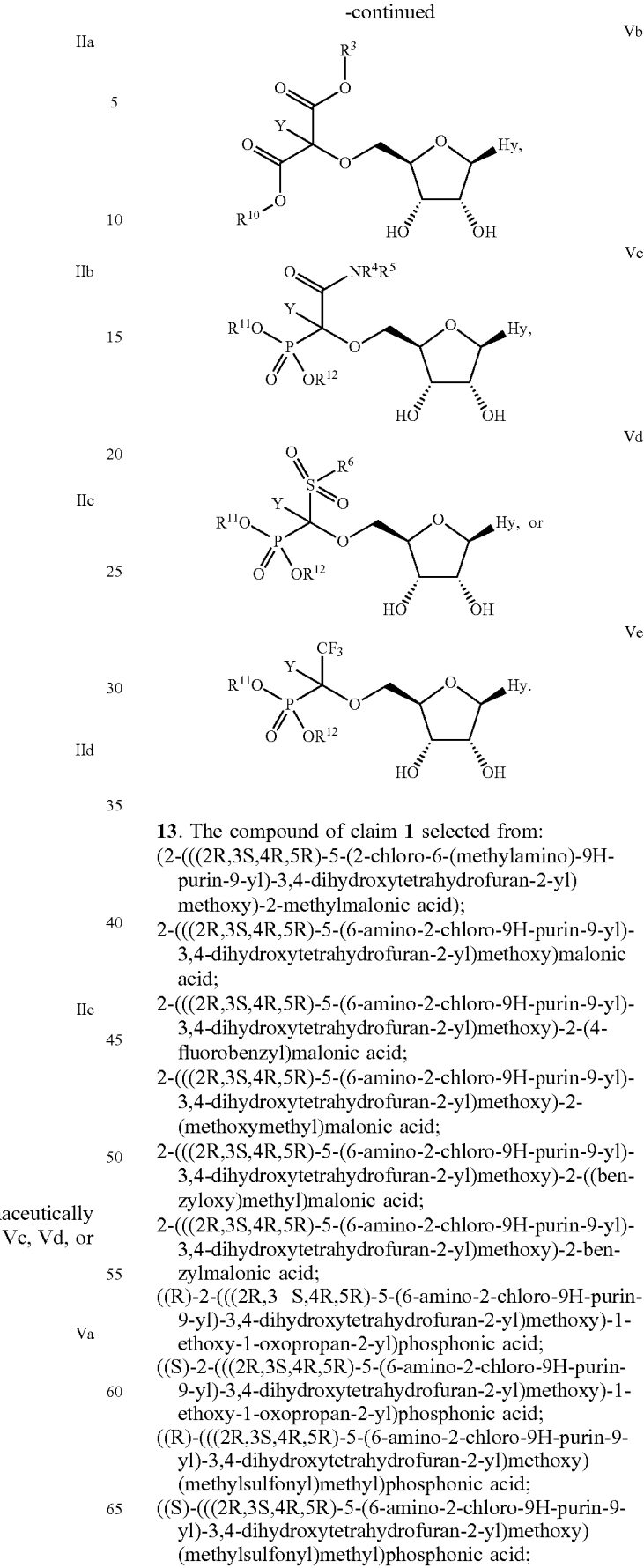

13. The compound of claim 1 selected from:
(2-(((2R,3S,4R,5R)-5-(2-chloro-6-(methylamino)-9H-purin-9-yl)-3,4-dihydroxytetrahydrofuran-2-yl) methoxy)-2-methylmalonic acid);
2-(((2R,3S,4R,5R)-5-(6-amino-2-chloro-9H-purin-9-yl)-3,4-dihydroxytetrahydrofuran-2-yl)methoxy)malonic acid;
2-(((2R,3S,4R,5R)-5-(6-amino-2-chloro-9H-purin-9-yl)-3,4-dihydroxytetrahydrofuran-2-yl)methoxy)-2-(4-fluorobenzyl)malonic acid;
2-(((2R,3S,4R,5R)-5-(6-amino-2-chloro-9H-purin-9-yl)-3,4-dihydroxytetrahydrofuran-2-yl)methoxy)-2-(methoxymethyl)malonic acid;
2-(((2R,3S,4R,5R)-5-(6-amino-2-chloro-9H-purin-9-yl)-3,4-dihydroxytetrahydrofuran-2-yl)methoxy)-2-((benzyloxy)methyl)malonic acid;
2-(((2R,3S,4R,5R)-5-(6-amino-2-chloro-9H-purin-9-yl)-3,4-dihydroxytetrahydrofuran-2-yl)methoxy)-2-benzylmalonic acid;
((R)-2-(((2R,3S,4R,5R)-5-(6-amino-2-chloro-9H-purin-9-yl)-3,4-dihydroxytetrahydrofuran-2-yl)methoxy)-1-ethoxy-1-oxopropan-2-yl)phosphonic acid;
((S)-2-(((2R,3S,4R,5R)-5-(6-amino-2-chloro-9H-purin-9-yl)-3,4-dihydroxytetrahydrofuran-2-yl)methoxy)-1-ethoxy-1-oxopropan-2-yl)phosphonic acid;
((R)-(((2R,3S,4R,5R)-5-(6-amino-2-chloro-9H-purin-9-yl)-3,4-dihydroxytetrahydrofuran-2-yl)methoxy) (methylsulfonyl)methyl)phosphonic acid;
((S)-(((2R,3S,4R,5R)-5-(6-amino-2-chloro-9H-purin-9-yl)-3,4-dihydroxytetrahydrofuran-2-yl)methoxy) (methylsulfonyl)methyl)phosphonic acid;

((S)-(((2R,3S,4R,5R)-5-(6-amino-2-chloro-9H-purin-9-yl)-3,4-dihydroxytetrahydrofuran-2-yl)methoxy)(ethylsulfonyl)methyl)phosphonic acid;
((R)-(((2R,3S,4R,5R)-5-(6-amino-2-chloro-9H-purin-9-yl)-3,4-dihydroxytetrahydrofuran-2-yl)methoxy)(ethylsulfonyl)methyl)phosphonic acid;
((R)-(((2R,3S,4R,5R)-5-(6-amino-2-chloro-9H-purin-9-yl)-3,4-dihydroxytetrahydrofuran-2-yl)methoxy)(propylsulfonyl)methyl)phosphonic acid;
((S)-(((2R,3S,4R,5R)-5-(6-amino-2-chloro-9H-purin-9-yl)-3,4-dihydroxytetrahydrofuran-2-yl)methoxy)(propylsulfonyl)methyl)phosphonic acid;
((R)-(((2R,3S,4R,5R)-5-(6-amino-2-chloro-9H-purin-9-yl)-3,4-dihydroxytetrahydrofuran-2-yl)methoxy)(isobutylsulfonyl)methyl)phosphonic acid;
((S)-(((2R,3S,4R,5R)-5-(6-amino-2-chloro-9H-purin-9-yl)-3,4-dihydroxytetrahydrofuran-2-yl)methoxy)(isobutylsulfonyl)methyl)phosphonic acid;
((R)-1-(((2R,3 S,4R,5R)-5-(6-amino-2-chloro-9H-purin-9-yl)-3,4-dihydroxytetrahydrofuran-2-yl)methoxy)-2-isobutoxy-2-oxoethyl)phosphonic acid;
((S)-1-(((2R,3S,4R,5R)-5-(6-amino-2-chloro-9H-purin-9-yl)-3,4-dihydroxytetrahydrofuran-2-yl)methoxy)-2-isobutoxy-2-oxoethyl)phosphonic acid;
((R)-1-(((2R,3 S,4R,5R)-5-(6-amino-2-chloro-9H-purin-9-yl)-3,4-dihydroxytetrahydrofuran-2-yl)methoxy)-2-(tert-butoxy)-2-oxoethyl)phosphonic acid;
((S)-1-(((2R,3S,4R,5R)-5-(6-amino-2-chloro-9H-purin-9-yl)-3,4-dihydroxytetrahydrofuran-2-yl)methoxy)-2-(tert-butoxy)-2-oxoethyl)phosphonic acid;
((R)-1-(((2R,3 S,4R,5R)-5-(6-amino-2-chloro-9H-purin-9-yl)-3,4-dihydroxytetrahydrofuran-2-yl)methoxy)-2-(benzyloxy)-2-oxoethyl)phosphonic acid;
((S)-1-(((2R,3S,4R,5R)-5-(6-amino-2-chloro-9H-purin-9-yl)-3,4-dihydroxytetrahydrofuran-2-yl)methoxy)-2-(benzyloxy)-2-oxoethyl)phosphonic acid;
((R)-1-(((2R,3 S,4R,5R)-5-(6-amino-2-chloro-9H-purin-9-yl)-3,4-dihydroxytetrahydrofuran-2-yl)methoxy)-2-(isobutylamino)-2-oxoethyl)phosphonic acid;
((S)-1-(((2R,3S,4R,5R)-5-(6-amino-2-chloro-9H-purin-9-yl)-3,4-dihydroxytetrahydrofuran-2-yl)methoxy)-2-(isobutylamino)-2-oxoethyl)phosphonic acid;
((R)-1-(((2R,3S,4R,5R)-5-(6-amino-2-chloro-9H-purin-9-yl)-3,4-dihydroxytetrahydrofuran-2-yl)methoxy)-2-(ethylamino)-2-oxoethyl)phosphonic acid;
((S)-1-(((2R,3S,4R,5R)-5-(6-amino-2-chloro-9H-purin-9-yl)-3,4-dihydroxytetrahydrofuran-2-yl)methoxy)-2-(ethylamino)-2-oxoethyl)phosphonic acid;
((R)-1-(((2R,3 S,4R,5R)-5-(6-amino-2-chloro-9H-purin-9-yl)-3,4-dihydroxytetrahydrofuran-2-yl)methoxy)-2-(tert-butylamino)-2-oxoethyl)phosphonic acid;
((S)-1-(((2R,3S,4R,5R)-5-(6-amino-2-chloro-9H-purin-9-yl)-3,4-dihydroxytetrahydrofuran-2-yl)methoxy)-2-(tert-butylamino)-2-oxoethyl)phosphonic acid;
(2-(2-acetylhydrazinyl)-1-(((2R,3 S,4R,5R)-5-(6-amino-2-chloro-9H-purin-9-yl)-3,4-dihydroxytetrahydrofuran-2-yl)methoxy)-2-oxoethyl)phosphonic acid;
((R)-(((2R,3S,4R,5R)-5-(6-amino-2-chloro-9H-purin-9-yl)-3,4-dihydroxytetrahydrofuran-2-yl)methoxy)(5-methyl-1,3,4-oxadiazol-2-yl)methyl)phosphonic acid;
((S)-(((2R,3S,4R,5R)-5-(6-amino-2-chloro-9H-purin-9-yl)-3,4-dihydroxytetrahydrofuran-2-yl)methoxy)(5-methyl-1,3,4-oxadiazol-2-yl)methyl)phosphonic acid;
((R)-1-(((2R,3S,4R,5R)-5-(2-chloro-6-(cyclopropylamino)-9H-purin-9-yl)-3,4-dihydroxytetrahydrofuran-2-yl)methoxy)-2-ethoxy-2-oxoethyl)phosphonic acid;
((S)-1-(((2R,3S,4R,5R)-5-(2-chloro-6-(cyclopropylamino)-9H-purin-9-yl)-3,4-dihydroxytetrahydrofuran-2-yl)methoxy)-2-ethoxy-2-oxoethyl)phosphonic acid;
((R)-1-(((2R,3 S,4R,5R)-5-(2-chloro-6-(methylamino)-9H-purin-9-yl)-3,4-dihydroxytetrahydrofuran-2-yl)methoxy)-2-ethoxy-2-oxoethyl)phosphonic acid;
((S)-1-(((2R,3S,4R,5R)-5-(2-chloro-6-(methylamino)-9H-purin-9-yl)-3,4-dihydroxytetrahydrofuran-2-yl)methoxy)-2-ethoxy-2-oxoethyl)phosphonic acid;
((R)-1-(((2R,3S,4R,5R)-5-(6-(benzylamino)-2-chloro-9H-purin-9-yl)-3,4-dihydroxytetrahydrofuran-2-yl)methoxy)-2-ethoxy-2-oxoethyl)phosphonic acid;
((S)-1-(((2R,3S,4R,5R)-5-(6-(benzylamino)-2-chloro-9H-purin-9-yl)-3,4-dihydroxytetrahydrofuran-2-yl)methoxy)-2-ethoxy-2-oxoethyl)phosphonic acid;
((R)-1-(((2R,3S,4R,5R)-5-(2-chloro-6-(cyclopentylamino)-9H-purin-9-yl)-3,4-dihydroxytetrahydrofuran-2-yl)methoxy)-2-ethoxy-2-oxoethyl)phosphonic acid;
((S)-1-(((2R,3S,4R,5R)-5-(2-chloro-6-(cyclopentylamino)-9H-purin-9-yl)-3,4-dihydroxytetrahydrofuran-2-yl)methoxy)-2-ethoxy-2-oxoethyl)phosphonic acid;
((R)-1-(((2R,3S,4R,5R)-5-(2-chloro-6-methyl-9H-purin-9-yl)-3,4-dihydroxytetrahydrofuran-2-yl)methoxy)-2-ethoxy-2-oxoethyl)phosphonic acid;
((S)-1-(((2R,3S,4R,5R)-5-(2-chloro-6-methyl-9H-purin-9-yl)-3,4-dihydroxytetrahydrofuran-2-yl)methoxy)-2-ethoxy-2-oxoethyl)phosphonic acid;
((R)-1-(((2R,3S,4R,5R)-5-(2-chloro-6-methyl-9H-purin-9-yl)-3,4-dihydroxytetrahydrofuran-2-yl)methoxy)-2-ethoxy-2-oxoethyl)phosphonic acid;
((S)-1-(((2R,3S,4R,5R)-5-(2-chloro-6-methyl-9H-purin-9-yl)-3,4-dihydroxytetrahydrofuran-2-yl)methoxy)-2-ethoxy-2-oxoethyl)phosphonic acid;
((R)-2-(((2R,3S,4R,5R)-5-(2-chloro-6-(ethylamino)-9H-purin-9-yl)-3,4-dihydroxytetrahydrofuran-2-yl)methoxy)-1-ethoxy-1-oxopropan-2-yl)phosphonic acid;
((S)-2-(((2R,3S,4R,5R)-5-(2-chloro-6-(ethylamino)-9H-purin-9-yl)-3,4-dihydroxytetrahydrofuran-2-yl)methoxy)-1-ethoxy-1-oxopropan-2-yl)phosphonic acid;
((R)-1 (((2R,3S4R,5R)-5-(2-chloro-6-(ethylamino)-9H-purin-9-yl)-3,4-dihydroxytetrahydro furan-2-yl)methoxy)-2-(ethylamino)-2-oxoethyl)phosphonic acid;
((S)-1-(((2R,3S,4R,5R)-5-(2-chloro-6-(ethylamino)-9H-purin-9-yl)-3,4-dihydroxytetrahydrofuran-2-yl)methoxy)-2-(ethylamino)-2-oxoethyl)phosphonic acid;
((R)-1-(((2R,3S,4R,5R)-5-(6-benzamido-2-chloro-9H-purin-9-yl)-3,4-dihydroxytetrahydrofuran-2-yl)methoxy)-2-(ethylamino)-2 oxoethyl)phosphonic acid;
((S)-1-(((24R3S,4R,5R)-5-(6-benzamido-2-chloro-9H-purin-9-yl)-3,4-dihydroxytetrahydrofuran-2-yl)methoxy)-2-ethoxy-2-oxoethyl)phosphonic acid;
((R)-1-(((2S,3R,4S,5)-5-(6-amino-2-methyl-9H-purin-9-yl)-3,4-dihydroxytetrahydrofuran-2-yl)methoxy)-2-ethoxy-2-oxoethyl)phosphonic acid;
((S)-1-(((2S,3R,4S,5S)-5-(6-amino-2-methyl-9H-purin-9-yl)-3,4-dihydroxytetrahydrofuran-2-yl)methoxy)-2-ethoxy-2-oxoethyl)phosphonic acid;
2-(((2R,3S,4R,5R)-5-(2,6-dimethyl-9H-purin-9-yl)-3,4-dihydroxytetrahydrofuran 2-yl)methoxy)-2-phosphonoacetic acid;
((R)-1-(((2R,3 S,4R,5R)-5-(6-amino-2-benzyl-9H-purin-9-yl)-3,4-dihydroxytetrahydrofuran-2-yl)methoxy)-2-ethoxy-2-oxoethyl)phosphonic acid;

((S)-1-(((2R,3S,4R,5R)-5-(6-amino-2-benzyl-9H-purin-9-yl)-3,4-dihydroxytetrahydrofuran-2-yl)methoxy)-2-ethoxy-2-oxoethyl)phosphonic acid;
((R)-1-(((2R,3S,4R,5R)-5-(6-amino-2-phenyl-9H-purin-9-yl)-3,4-dihydroxytetrahydrofuran-2-yl)methoxy)-2-ethoxy-2-oxoethyl)phosphonic acid;
((S)-1-(((2R,3S,4R,5R)-5-(6-amino-2-phenyl-9H-purin-9-yl)-3,4-dihydroxytetrahydrofuran-2-yl)methoxy)-2-ethoxy-2-oxoethyl)phosphonic acid;
((R)-1-(((2R,3S,4R,5R)-5-(6-amino-2-(3,5-difluorophenyl)-9H-purin-9-yl)-3,4 dihydroxytetrahydrofuran-2-yl)methoxy)-2-ethoxy-2-oxoethyl)phosphonic acid;
((S)-1-(((2R,3S,4R,5R)-5-(6-amino-2-(3,5-difluorophenyl)-9H-purin-9-yl)-3,4 dihydroxytetrahydrofuran-2-yl)methoxy)-2-ethoxy-2-oxoethyl)phosphonic acid;
((R)-1-(((2R,3S,4R,5R)-5-(6-amino-2-(trifluoromethyl)-9H-purin-9-yl)-3,4-dihydroxytetrahydrofuran-2-yl)methoxy)-2-ethoxy-2-oxoethyl)phosphonic acid;
((S)-1-(((2R,3S,4R,5R)-5-(6-amino-2-(trifluoromethyl)-9H-purin-9-yl)-3,4-dihydroxytetrahydrofuran-2-yl)methoxy)-2-ethoxy-2-oxoethyl)phosphonic acid;
(1-(((2R,3S,4R,5R)-5-(6-amino-2-(methylthio)-9H-purin-9-yl)-3,4-dihydroxytetrahydrofuran-2-yl)methoxy)-2-ethoxy-2-oxoethyl)phosphonic acid;
((R)-1-(((2R,3S,4R,5R)-5-(6-amino-2-(ethylthio)-9H-purin-9-yl)-3,4-dihydroxytetrahydrofuran-2-yl)methoxy)-2-ethoxy-2-oxoethyl)phosphonic acid;
((S)-1-(((2R,3S,4R,5R)-5-(6-amino-2-(ethylthio)-9H-purin-9-yl)-3,4-dihydroxytetrahydrofuran-2-yl)methoxy)-2-ethoxy-2-oxoethyl)phosphonic acid;
((R)-1-(((2R,3S,4R,5R)-5-(6-amino-2-cyano-9H-purin-9-yl)-3,4-dihydroxytetrahydrofuran-2-yl)methoxy)-2-ethoxy-2-oxoethyl)phosphonic acid;
((S)-1-(((2R,3S,4R,5R)-5-(6-amino-2-cyano-9H-purin-9-yl)-3,4-dihydroxytetrahydrofuran-2-yl)methoxy)-2-ethoxy-2-oxoethyl)phosphonic acid;
((R)-1-(((2R,3S,4R,5R)-5-(6-amino-2-isobutyl-9H-purin-9-yl)-3,4-dihydroxytetrahydrofuran-2-yl)methoxy)-2-ethoxy-2-oxoethyl)phosphonic acid;
((S)-1-(((2R,3S,4R,5R)-5-(6-amino-2-isobutyl-9H-purin-9-yl)-3,4-dihydroxytetrahydrofuran-2-yl)methoxy)-2-ethoxy-2-oxoethyl)phosphonic acid;
2-(((2R,3S,4R,5R)-5-(6-amino-2-chloro-9H-purin-9-yl)-3,4-dihydroxytetrahydrofuran-2-yl)methoxy)-2-(4-chlorobenzyl)malonic acid;
2-(((2R,3S,4R,5R)-5-(6-amino-2-chloro-9H-purin-9-yl)-3,4-dihydroxytetrahydrofuran-2-yl)methoxy)-2-(4-cyanobenzyl)malonic acid;
((R)-1-(((2R,3S,4R,5R)-5-(6-amino-2-(oxazol-2-yl)-9H-purin-9-yl)-3,4-dihydroxytetrahydrofuran-2-yl)methoxy)-2-ethoxy-2-oxoethyl)phosphonic acid;
((S)-1-(((2R,3S,4R,5R)-5-(6-amino-2-(oxazol-2-yl)-9H-purin-9-yl)-3,4-dihydroxytetrahydrofuran-2-yl)methoxy)-2-ethoxy-2-oxoethyl)phosphonic acid;
((R)-1-(((2R,3S,4R,5R)-5-(6-amino-2-cyclopropyl-9H-purin-9-yl)-3,4-dihydroxytetrahydrofuran-2-yl)methoxy)-2-ethoxy-2-oxoethyl)phosphonic acid;
((S)-1-(((2R,3S,4R,5R)-5-(6-amino-2-cyclopropyl-9H-purin-9-yl)-3,4-dihydroxytetrahydrofuran-2-yl)methoxy)-2-ethoxy-2-oxoethyl)phosphonic acid;
((R)-1-(((2R,3S,4R,5R)-5-(6-amino-2-((R)-oxazolidin-2-yl)-9H-purin-9-yl)-3,4-dihydroxytetrahydrofuran-2-yl)methoxy)-2-ethoxy-2-oxoethyl)phosphonic acid;
((R)-1-(((2R,3S,4R,5R)-5-(6-amino-2-((S)-oxazolidin-2-yl)-9H-purin-9-yl)-3,4-dihydroxytetrahydrofuran-2-yl)methoxy)-2-ethoxy-2-oxoethyl)phosphonic acid;
((1S)-1-(((2R,3S,4R,5R)-5-(6-amino-2-(oxazolidin-2-yl)-9H-purin-9-yl)-3,4-dihydroxytetrahydrofuran-2-yl)methoxy)-2-ethoxy-2-oxoethyl)phosphonic acid;
((S)-1-(((2R,3S,4R,5R)-5-(6-amino-2-fluoro-9H-purin-9-yl)-3,4-dihydroxytetrahydrofuran-2-yl)methoxy)-2-ethoxy-2-oxoethyl)phosphonic acid;
((R)-1-(((2R,3S,4R,5R)-5-(6-amino-2-fluoro-9H-purin-9-yl)-3,4-dihydroxytetrahydrofuran-2-yl)methoxy)-2-ethoxy-2-oxoethyl)phosphonic acid;
(R)-2-(((2R,3S,4R,5R)-5-(6-amino-2-fluoro-9H-purin-9-yl)-3,4-dihydroxytetrahydrofuran-2-yl)methoxy)-2-phosphonoacetic acid;
(S)-2-(((2R,3S,4R,5R)-5-(6-amino-2-fluoro-9H-purin-9-yl)-3,4-dihydroxytetrahydrofuran-2-yl)methoxy)-2-phosphonoacetic acid;
(1-(((2R,3S,4R,5R)-5-(6-amino-2-cyano-9H-purin-9-yl)-3,4-dihydroxytetrahydrofuran-2-yl)methoxy)-2-(tert-butoxy)-2-oxoethyl)phosphonic acid;
((R)-1-(((2R,3S,4R,5R)-5-(6-amino-2-cyano-9H-purin-9-yl)-3,4-dihydroxytetrahydrofuran-2-yl)methoxy)-2-(tert-butoxy)-2-oxoethyl)phosphonic acid;
((S)-1-(((2R,3S,4R,5R)-5-(6-amino-2-cyano-9H-purin-9-yl)-3,4-dihydroxytetrahydrofuran-2-yl)methoxy)-2-(tert-butoxy)-2-oxoethyl)phosphonic acid;
((R)-1-(((2R,3S,4R,5R)-5-(6-amino-2-(aminomethyl)-9H-purin-9-yl)-3,4-dihydroxytetrahydrofuran-2-yl)methoxy)-2-(tert-butoxy)-2-oxoethyl)phosphonic acid;
((S)-1-(((2R,3S,4R,5R)-5-(6-amino-2-(aminomethyl)-9H-purin-9-yl)-3,4-dihydroxytetrahydrofuran-2-yl)methoxy)-2-(tert-butoxy)-2-oxoethyl)phosphonic acid;
2-(((2R,3 S,4R,5R)-5-(6-benzamido-2-iodo-9H-purin-9-yl)-3,4-dihydroxytetrahydrofuran-2-yl)methoxy)-2-phosphonoacetic acid;
(S)-2-(((2R,3S,4R,5R)-5-(6-amino-2-iodo-9H-purin-9-yl)-3,4-dihydroxytetrahydrofuran-2-yl)methoxy)-2-phosphonoacetic acid;
(R)-2-(((2R,3S,4R,5R)-5-(6-amino-2-iodo-9H-purin-9-yl)-3,4-dihydroxytetrahydrofuran-2-yl)methoxy)-2-phosphonoacetic acid;
2-(((2R,3S,4R,5R)-3,4-dihydroxy-5-(6-(hydroxyamino)-2-iodo-9H-purin-9-yl)tetrahydrofuran-2-yl)methoxy)-2-phosphonoacetic acid;
(R)-2-(((2R,3S,4R,5R)-5-(6-amino-2-chloro-9H-purin-9-yl)-3,4-dihydroxytetrahydrofuran-2-yl)methoxy)-2-phosphonoacetic acid;
(S)-2-(((2R,3S,4R,5R)-5-(6-amino-2-chloro-9H-purin-9-yl)-3,4-dihydroxytetrahydrofuran-2-yl)methoxy)-2-phosphonoacetic acid;
2-(((2R,3S,4R,5R)-5-(2,6-dichloro-9H-purin-9-yl)-3,4-dihydroxytetrahydrofuran-2-yl)methoxy)-2-phosphonoacetic acid;
2-(((2R,3S,4R,5R)-5-(2-chloro-6-(((R)-tetrahydrofuran-3-yl)amino)-9H-purin-9-yl)-3,4-dihydroxytetrahydrofuran-2-yl)methoxy)malonic acid;
(R)-2-(((2R,3S,4R,5R)-5-(2-chloro-6-(((R)-tetrahydrofuran-3-yl)amino)-9H-purin-9-yl)-3,4-dihydroxytetrahydrofuran-2-yl)methoxy)malonic acid;
(S)-2-(((2R,3S,4R,5R)-5-(6-amino-2-methyl-9H-purin-9-yl)-3,4-dihydroxytetrahydrofuran-2-yl)methoxy)-2-phosphonoacetic acid;
((R)-1-(((1R,2R,3S,4R)-4-(6-amino-2-chloro-9H-purin-9-yl)-2,3-dihydroxycyclopentyl)methoxy)-2-(tert-butoxy)-2-oxoethyl)phosphonic acid;
((S)-1-(((1R,2R,3S,4R)-4-(6-amino-2-chloro-9H-purin-9-yl)-2,3-dihydroxycyclopentyl)methoxy)-2-(tert-butoxy)-2-oxoethyl)phosphonic acid;

(1-(((1R,2R,3S,4R)-4-(7-amino-5-chloro-3H-[1,2,3]triazolo[4,5-d]pyrimidin-3-yl)-2,3-dihydroxycyclopentyl)methoxy)-2-ethoxy-2-oxoethyl)phosphonic acid;
(1-(((1R,2R,3S,4R)-4-(7-amino-5-bromo-3H-[1,2,3]triazolo[4,5-d]pyrimidin-3-yl)-2,3-dihydroxycyclopentyl)methoxy)-2-ethoxy-2-oxoethyl)phosphonic acid;
((R)-1-(((1R,2R,3S,4R)-4-(6-amino-2-chloro-9H-purin-9-yl)-2,3-dihydroxycyclopentyl)methoxy)-2-(tert-butoxy)-2-oxoethyl)phosphonic acid;
((S)-1-(((1R,2R,3S,4R)-4-(6-amino-2-chloro-9H-purin-9-yl)-2,3-dihydroxycyclopentyl)methoxy)-2-(tert-butoxy)-2-oxoethyl)phosphonic acid;
(R)-3-(((2R,3S,4R,5R)-5-(6-amino-2-fluoro-9H-purin-9-yl)-3,4-dihydroxytetrahydrofuran-2-yl)methoxy)-4-ethoxy-4-oxo-3-phosphonobutanoic acid;
(S)-3-(((2R,3S,4R,5R)-5-(6-amino-2-fluoro-9H-purin-9-yl)-3,4-dihydroxytetrahydrofuran-2-yl)methoxy)-4-ethoxy-4-oxo-3-phosphonobutanoic acid;
(2R)-ethyl 2-(((2R,3S,4R,5R)-5-(2-chloro-6-(ethylamino)-9H-purin-9-yl)-3,4-dihydroxytetrahydrofuran-2-yl)methoxy)-2-(ethoxy(hydroxy)phosphoryl)propanoate;
(2S)-ethyl 2-(((2R,3S,4R,5R)-5-(2-chloro-6-(ethylamino)-9H-purin-9-yl)-3,4-dihydroxytetrahydrofuran-2-yl)methoxy)-2-(ethoxy(hydroxy)phosphoryl)propanoate;
((R)-1-(((2R,3S,4R,5R)-5-(5,6-dichloro-1H-benzo[d]imidazol-1-yl)-3,4-dihydroxytetrahydrofuran-2-yl)methoxy)-2-ethoxy-2-oxoethyl)phosphonic acid;
((S)-1-(((2R,3S,4R,5R)-5-(5,6-dichloro-1H-benzo[d]imidazol-1-yl)-3,4-dihydroxytetrahydrofuran-2-yl)methoxy)-2-ethoxy-2-oxoethyl)phosphonic acid;
((S)-1-(((2R,3S,4R,5R)-5-(6-amino-2-chloro-9H-purin-9-yl)-3,4-dihydroxytetrahydrofuran-2-yl)methoxy)-2-(diethylamino)-2-oxoethyl)phosphonic acid;
((R)-1-(((2R,3 S,4R,5R)-5-(6-amino-2-chloro-9H-purin-9-yl)-3,4-dihydroxytetrahydrofuran-2-yl)methoxy)-2-(diethylamino)-2-oxoethyl)phosphonic acid;
2-(((2R,3S,4R,5R)-5-(2-chloro-6-(((S)-tetrahydrofuran-3-yl)amino)-9H-purin-9-yl)-3,4-dihydroxytetrahydrofuran-2-yl)methoxy)malonic acid;
2-(((2R,3S,4R,5R)-5-(6-amino-2-chloro-9H-purin-9-yl)-3,4-dihydroxytetrahydrofuran-2-yl)methoxy)-2-(2,6-difluorobenzyl)malonic acid;
2-(((2R,3S,4R,5R)-5-(6-amino-2-chloro-9H-purin-9-yl)-3,4-dihydroxytetrahydrofuran-2-yl)methoxy)-2-(2,6-difluorobenzyl)malonic acid;
2-(((2R,3S,4R,5R)-5-(6-amino-2-chloro-9H-purin-9-yl)-3,4-dihydroxytetrahydrofuran-2-yl)methoxy)-2-(2-(methylsulfonyl)benzyl)malonic acid;
((R)-1-(((2R,3S,4R,5R)-5-(5-chloro-3H-imidazo[4,5-b]pyridin-3-yl)-3,4-dihydroxytetrahydrofuran-2-yl)methoxy)-2-ethoxy-2-oxoethyl)phosphonic acid;
((S)-1-(((2R,3S,4R,5R)-5-(5-chloro-3H-imidazo[4,5-b]pyridin-3-yl)-3,4-dihydroxytetrahydrofuran-2-yl)methoxy)-2-ethoxy-2-oxoethyl)phosphonic acid;
(1-(((1R,2R,3S,4R)-4-(5-chloro-7-((((S)-tetrahydrofuran-3-yl)methyl)amino)-3H-[1,2,3]triazolo[4,5-d]pyrimidin-3-yl)-2,3-dihydroxycyclopentyl)methoxy)-2-ethoxy-2-oxoethyl)phosphonic acid;
(1-(((1R,2R,3S,4R)-4-(5-chloro-7-((((R)-tetrahydrofuran-3-yl)methyl)amino)-3H-[1,2,3]triazolo[4,5-d]pyrimidin-3-yl)-2,3-dihydroxycyclopentyl)methoxy)-2-ethoxy-2-oxoethyl)phosphonic acid;
(1-(((1R,2R,3S,4R)-4-(5-chloro-7-(((R)-tetrahydrofuran-3-yl)amino)-3H-[1,2,3]triazolo[4,5-d]pyrimidin-3-yl)-2,3-dihydroxycyclopentyl)methoxy)-2-ethoxy-2-oxoethyl)phosphonic acid;
(1-(((1R,2R,3S,4R)-4-(5-chloro-7-(((S)-tetrahydrofuran-3-yl)amino)-3H-[1,2,3]triazolo[4,5-d]pyrimidin-3-yl)-2,3-dihydroxycyclopentyl)methoxy)-2-ethoxy-2-oxoethyl)phosphonic acid;
(1-(((1R,2R,3S,4R)-4-(5-chloro-7-(cyclopentylamino)-3H-[1,2,3]triazolo[4,5-d]pyrimidin-3-yl)-2,3-dihydroxycyclopentyl)methoxy)-2-ethoxy-2-oxoethyl)phosphonic acid;
2-(((2R,3S,4R,5R)-5-(6-amino-2-chloro-9H-purin-9-yl)-3,4-dihydroxytetrahydrofuran-2-yl)methoxy)-2-(pyridin-2-ylmethyl)malonic acid;
2-(((2R,3S,4R,5R)-5-(6-amino-2-chloro-9H-purin-9-yl)-3,4-dihydroxytetrahydrofuran-2-yl)methoxy)-2-(thiazol-2-ylmethyl)malonic acid;
2-(((2R,3S,4R,5R)-5-(2-chloro-6-(((R)-tetrahydrofuran-3-yl)amino)-9H-purin-9-yl)-3,4-dihydroxytetrahydrofuran-2-yl)methoxy)malonic acid;
2-(((2R,3S,4R,5R)-5-(6-amino-2-chloro-9H-purin-9-yl)-3,4-dihydroxytetrahydrofuran-2-yl)methoxy)-2-(3,5-difluorobenzyl)malonic acid;
2-(((2R,3S,4R,5R)-5-(2-chloro-6-(cyclopentylamino)-9H-purin-9-yl)-3,4-dihydroxytetrahydrofuran-2-yl)methoxy)-2-(4-fluorobenzyl)malonic acid;
2-(((2R,3S,4R,5R)-5-(6-amino-2-chloro-9H-purin-9-yl)-3,4-dihydroxytetrahydrofuran-2-yl)methoxy)-2-(cyclopropylmethyl)malonic acid;
(1-((((2S,3S,4R,5R)-5-(6-amino-2-chloro-9H-purin-9-yl)-3,4-dihydroxytetrahydrofuran-2-yl)methyl)thio)-2-ethoxy-2-oxoethyl)phosphonic acid;
((R)-1-(((2R,3 S,4R,5R)-5-(2-chloro-6-(methylamino)-9H-purin-9-yl)-3,4-dihydroxytetrahydrofuran-2-yl)methoxy)-2,2,2-trifluoroethyl)phosphonic acid;
((S)-1-(((2R,3S,4R,5R)-5-(2-chloro-6-(methylamino)-9H-purin-9-yl)-3,4-dihydroxytetrahydrofuran-2-yl)methoxy)-2,2,2-trifluoroethyl)phosphonic acid;
(1-(((2R,3S,4R,5R)-5-(6-amino-2-chloro-9H-purin-9-yl)-3,4-dihydroxytetrahydrofuran-2-yl)methoxy)-2-ethoxy-2-oxoethyl)phosphonic acid; and
((R)-1-(((2R,3 S,4R,5R)-5-(6-amino-2-chloro-9H-purin-9-yl)-3,4-dihydroxytetrahydrofuran-2-yl)methoxy)-2-ethoxy-2-oxoethyl)phosphonic acid;
or a pharmaceutically acceptable salt of any of the aforementioned.

14. A pharmaceutical composition comprising the compound of claim 1, or a pharmaceutically acceptable salt thereof, and a pharmaceutically acceptable carrier.

* * * * *